US012643887B2

(12) United States Patent
Chen et al.

(10) Patent No.: US 12,643,887 B2
(45) Date of Patent: Jun. 2, 2026

(54) HETEROCYCLIC DERIVATIVES WITH CARDIOMYOCYTE PROLIFERATION ACTIVITY FOR TREATMENT OF HEART DISEASES

(71) Applicant: Tongji University, Shanghai (CN)

(72) Inventors: Yihan Chen, Shanghai (CN); Dandan Liang, Shanghai (CN); Yi Liu, Shanghai (CN); Subas Man Sakya, Shanghai (CN); Xiang Li, Shanghai (CN); Li Li, Shanghai (CN); Huixing Zhou, Shanghai (CN); Fulei Zhang, Shanghai (CN); Xiaoyu He, Shanghai (CN); Jinhua Yang, Shanghai (CN)

(73) Assignee: Tongji University, Shanghai (CN)

( * ) Notice: Subject to any disclaimer, the term of this patent is extended or adjusted under 35 U.S.C. 154(b) by 1029 days.

(21) Appl. No.: 17/755,401

(22) PCT Filed: Dec. 14, 2020

(86) PCT No.: PCT/CN2020/136230
§ 371 (c)(1),
(2) Date: Apr. 28, 2022

(87) PCT Pub. No.: WO2021/115489
PCT Pub. Date: Jun. 17, 2021

(65) Prior Publication Data

US 2023/0025301 A1 Jan. 26, 2023

(30) Foreign Application Priority Data

Dec. 14, 2019 (WO) ................ PCT/CN2019/125454

(51) Int. Cl.

| | |
|---|---|
| ***C07D 405/06*** | (2006.01) |
| ***A61P 9/10*** | (2006.01) |
| ***C07D 401/06*** | (2006.01) |
| ***C07D 401/14*** | (2006.01) |
| ***C07D 403/06*** | (2006.01) |
| ***C07D 405/14*** | (2006.01) |
| ***C07D 409/06*** | (2006.01) |
| ***C07D 413/06*** | (2006.01) |
| ***C07D 417/06*** | (2006.01) |
| ***C07D 417/14*** | (2006.01) |
| ***C12N 5/077*** | (2010.01) |

(52) U.S. Cl.
CPC .............. *C07D 405/06* (2013.01); *A61P 9/10* (2018.01); *C07D 401/06* (2013.01); *C07D 401/14* (2013.01); *C07D 403/06* (2013.01); *C07D 405/14* (2013.01); *C07D 409/06* (2013.01); *C07D 413/06* (2013.01); *C07D 417/06* (2013.01); *C07D 417/14* (2013.01); *C12N 5/0657* (2013.01)

(58) Field of Classification Search
CPC .. C07D 401/06; C07D 401/14; C07D 403/06; C07D 405/06; C07D 405/14; C07D 409/06; C07D 413/06; C07D 417/06; C07D 417/14; A61P 9/10
See application file for complete search history.

(56) References Cited

FOREIGN PATENT DOCUMENTS

| | | | |
|---|---|---|---|
| CN | 103214422 | A | 7/2013 |
| CN | 101784542 | A | 7/2020 |
| JP | 2010535180 | A | 11/2010 |
| WO | 2009050352 | A2 | 4/2009 |
| WO | 2014188193 | A1 | 11/2014 |
| WO | 2018081401 | A1 | 5/2018 |
| WO | 2019136320 | A1 | 7/2019 |

OTHER PUBLICATIONS

Jansco, Attila, et al., “Synthesis and spectroscopic characterization of novel GFP chromophore analogues based on aminoimidazolone derivatives,” Spectrochimica Acta Part A: Molecular and Biomolecular Spectroscopy, vol. 218, pp. 161-170 (2019).
Wangngae, Sirilak, et al., “Ph3P/12-Mediated Synthesis of N,N', N''-Substituted Guanidines and 2-Iminoimidazolin-4-ones from Aryl Isothiocyanates,” Journal of Organic Chemistry, vol. 82, pp. 10331-10341 (2017).
Selvaraju, Manikandan, et al., “Unprecedented One-Pot Chemocontrolled Entry to Thioxoimidazolidinones and Aminoimidazolones: Synthesis of Kinase Inhibitor Leucettamine B,” ACS Cominatorial Science, vol. 17, pp. 182-189 (2015).
Evindar, Ghotas, et al., “Peptide Heterocycle Conjugates: A Diverted Edman Degradation Protocol for the Synthesis of N-Terminal 2-Iminohydantoins,” Organic Letters, vol. 5, No. 8, pp. 1201-1204 (2003).
Yu, Yongping, et al., “Solid-phase parallel synthesis of 2-aminoimidazolidin-4-ones,” Tetrahedron, vol. 58, pp. 3349-3353 (2002).
Porello, Enzo R., et al., “Transient Regenerative Potential of the Neonatal Mouse Heart,” Science, vol. 331, pp. 1078-1080, Feb. 25, 2011.
Zhu, Wuqiang, et al., “Regenerative Potential of Neonatal Porcine Hearts,” Circulation, vol. 24, pp. 2809-2816, Dec. 11, 2018.
Schade, Dennis, et al., “Medicinal Chemistry Approaches to Heart Regeneration,” Journal of Medicinal Chemistry, vol. 58, pp. 9451-9479, 2015.
Tzahor, Eldad, et al., “Cardiac regeneration strategies: Staying young at heart,” Science, vol. 356, pp. 1035-1039, Jun. 9, 2017.
Fiedler, Loma R., et al., “MAP4K4 Inhibition Promotes Survival of Human Stem Cell-Derived Cardiomyocytes and Reduces Infarct Size In Vivo,” Cell Stem Cell, vol. 24, pp. 579-591, Apr. 4, 2019.
Saulnier, Mark, G., et al., “An Efficient Method for The Synthesis of Guanidino Prodrugs,” Bioorganic & Medicinal Chemistry Letters, vol. 4, No. 16, pp. 1985-1990, 1994.

(Continued)

*Primary Examiner* — Rebecca L Anderson
(74) *Attorney, Agent, or Firm* — ICE MILLER LLP

(57) ABSTRACT

Provided are novel heterocyclic derivatives with cardiomyocyte proliferation activity for treatment of heart diseases. Specifically, provided are the compounds of formula (I) or pharmaceutically acceptable salts, stereoisomers, solvates or prodrugs, preparation method thereof, application thereof and pharmaceutical composition useful for treatment of heart diseases.

11 Claims, No Drawings

(56) References Cited

OTHER PUBLICATIONS

Greenwald, Richard B., et al., "Drug Delivery Systems Based on Trimethyl Lock Lactonization: Poly(ethylene glycol) Prodrugs of Amino-Containing Compounds," J. Med. Chem, vol. 43, pp. 475-487, 2000.
Roue, Nathalie, et al., "Synthesis of the Marine Alkaloid Leucettamine B," Tetrahedron, vol. 55, pp. 14729-14738, 1999.
Debdab, Mansour, et al., "Leucettines, a Class of Potent Inhibitors of cdc2-Like Kinases and Dual Specificty, Tyrosine Phosphorylation Regulated Kinases Derived from the Marine Sponge Leucettamine B: Modulation of Alternative Pre-RNA Splicing," Journal of Medicinal Chemistry, vol. 54, pp. 4172-4186, 2011.
Papeo, Gianluca, et al., "Discovery of 2-[1-(4,4-Difluorocyclohexyl)piperidin-4-yl]-6-fluoro-3-oxo-2,3-dihydro-1H-isoindole-4-carboxamide (NMS-P118): A Potent, Orally Available, and Highly Selective PARP-1 Inhibitor for Cancer Therapy," Journal of Medicinal Chemistry, vol. 58 pp. 6875-6898, 2015.
Chen, Jinghai, et al., "mir-17-92 Cluster is Required for and Sufficient to Induce Cardiomyocyte Proliferation in Postnatal and Adult Hearts," Circulation Research, vol. 112, pp. 1557-1566, Jun. 7, 2013.
Andersson, Olov, et al., "Adenosine Signaling Promotes Regeneration of Pancreatic B Cells in Vivo," Cell Matabolism, vol. 15, pp. 885-894, Jun. 6, 2012.
Dogra, Deepika, et al., "Opposite effects of Activin type 2 receptor ligands on cardiomyocyte poliferation during development and repair," Nature Communications, 8:1902 doi: 10.1038/s41467-017-109501, 2017.
Hirose, Kentaro, et al., "Evidence for hormonal control of heart regenerative capacity during endothermy acquisition," Science 364, pp. 184-188, Downloaded from https://science.sciencemag.org/on Mar. 7, 2019.
Liin, Zhiqiang, et al., "Pi3kcb Links Hippo-YAP and P13K-AKT Signaling Pathways to Promote Cardiomyocyte Proliferation and Survival," Circulation Research, Downloaded from http://circres.ahajournals.org/content/early/2014/09/23/CIRCRESAHA.115.304457 on Sep. 27, 2014.
Wang, Jinhu, et al., "Epicardial regeneration is guided by cardiac outflow tract and Hedgehog signalling," Nature, pp. 226-230, 2015.
Salic, Adrian, et al., "A chemical method for fast and sensitive detection of DNA synthesis in vivo," PNAS, vol. 105, No. 7, pp. 2415-2420, Feb. 19, 2008.
Wang Qian, et al., "Bioconjugation by Copper(I)-Catalyzed Azide-Alkyne [3 +2] Cycloaddition," JACS, vol. 125, pp. 3192-3193, Feb. 22, 2003.
Registry RN 2309381-26-6 Enter STN: May 16, 2019, pp. 1-258, and other structures mentioned in ISR.
Heallen, T., et al., "Hippo signaling impedes adult heart regeneration," Development. Dec. 2013; 140(23):4683-90. doi: 10.1242/dev.102798. PMID: 24255096; PMCID: PMC3833428.
Tahtouh, Tania, et al., "Selectivity, Cocrystal Structures, and Neuroprotective Properties of Leucettines, a Family of Protein Kinase Inhibitors Derived from the Marine Sponge Alkaloid Leucettamine B," Journal of Medicinal Chemistry, No. 21, vol. 55, pp. 9312-9330, Sep. 21, 2012.
Hille, Susanne, et al., "Dyrk1a regulates the cardiomyocyte cell cycle via D-cyclin-dependent Rb/E2f-signalling," Cardiovascular Research, vol. 110, pp. 381-394, 2016.
Wang, Yong, et al., "Synthesis of novel 2-(arylamino)-3-aryl-5-arylidene-4H-imidazolin-4-one derivatives," Wuhan Gongcheng Daxue Xuebao, No. 3, vol. 32, pp. 37-39, Mar. 31, 2010.
Khalifa, N.M., et al., "Synthesis of Some Novel 2-Thioxoimidazolidin-4-one Substituted Glycosyl Hydrazone Derivatives," Russian Journal of General Chemistry, vol. 87, No. 3, pp. 523-529, 2017.
Li, Zhigang, et al., "GSK-3B inhibition protects the rat heart from the lipopolysaccharide-induced inflammation injury via suppressing FOXO3A activity," J. Cell Mol. Med. vol. 23, pp. 7796-7809, 2019.
Singh, Anand Prakash, et al., Inhibition of GSK-3 to induce cardiomyocyte proliferation: a receipt for in situ cardiac regeneration, Cardiovascular Research, vol. 115, pp. 20-30, 2019.
International Search Report issued Mar. 11, 2021 in PCT/CN2020/136230.
Kouichi Hasegawa, et al., "Wnt Signaling Orchestration with a Small Molecule DYRK Inhibitor Provides Long-Term Xeno-Free Human Pluripotent Cell Expansion," Stem Cells Translational Medicine, vol. 1, No. 1, pp. 18-28, Dec. 7, 2011.
Dennis Schade, et al., "Medicinal Chemistry Approaches to Heart Regeneration," Journal of Medicinal Chemistry, vol. 58, No. 24, pp. 9451-9479, Sep. 3, 2015.

HETEROCYCLIC DERIVATIVES WITH CARDIOMYOCYTE PROLIFERATION ACTIVITY FOR TREATMENT OF HEART DISEASES

CROSS-REFERENCE TO RELATED APPLICATION

This application is a Section 371 of International Application No. PCT/CN2020/136230, filed on Dec. 14, 2020, that published in the English language on Jun. 17, 2021, under International Publication No. WO2021/115489 A1, which claims priority to Chinse Patent Application No. PCT/CN2019/125454, filed on Dec. 14, 2019.

FIELD OF INVENTION

The present invention belongs to the field of medical technology and pharmaceuticals, and specifically, relates to novel heterocyclic derivatives with cardiomyocyte proliferation activity for treatment of heart diseases.

BACKGROUND

A variety of factors can lead to cardiomyocyte death and/or disfunction of the cardiac muscle cells, causing numerous heart diseases. However, adult cardiomyocytes almost lose their ability to undergo cell division and proliferation after a narrow proliferative window at the neonatal stages (Science 2011; 331: 1078-1080; *Circulation* 2018; 24: 2809-2816). This almost complete loss of regeneration capability of the adult cardiomyocytes severely limits the repair of myocardial injury. Adult mammalian hearts form fibrotic scars in response to injury, which can lead to heart failure, arrhythmia and death. Current treatments can temporarily improve heart function but do not replace lost cardiomyocytes. Thus, multiple research areas have focused on agents that might regenerate heart cardiomyocytes via drug treatment or stem cell treatment.

Recent review article (J. Med. Chem. 2015, 58: 9451-9479*; Science.* 2017, 356: 1035-1039) highlights many different approaches to treating heart disease related cardiomyocyte growth and proliferation. Number of kinase inhibitors, such as GSK b inhibitors are known to activate the WnT pathway leading to cell growth. Some of these compounds are also activators for stem cell differentiation. Another publication (Cell Stem Cell 2019, 24: 579-591.e12) highlighted a MAP4K4 inhibitors that protect heart in acute myocardial infarction. Other kinase inhibitors, such as DYRK and CLK kinesis inhibitors, are also known to help with cell growth as described in several other literature references especially pancreatic cell growth (WO 2018081401 and WO 2019136320). Others include CLK2 kinase inhibitors that have been shown to show growth of osteoclasts for osteoarthritis and have been shown to be useful for treatment of osteoarthritis.

It is an urgent need in the art to develop new compounds which can efficiently promote the proliferation of myocardial cells and myocardial regeneration.

SUMMARY OF INVENTION

The object of the present invention is to provide compounds with completely new structures that modulate entirely new targets, which can strongly promote the proliferation of myocardial cells and myocardial regeneration, and thus prevent and treat the occurrence and development of major cardiovascular diseases (such as myocardial infarction, heart failure, dilated cardiomyopathy and congenital heart disease). Further, the compound can effectively and quickly promote cardiomyocyte proliferation or regeneration and treat heart attacks and heart infarction.

In the first aspect of the present invention, it provides a compound of formula (I); or a pharmaceutically acceptable salt, a solvate, a stereoisomer or a prodrug thereof;

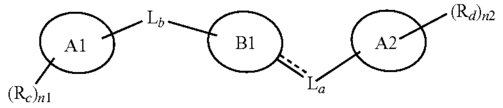

(I)

wherein each of ring A1 and ring A2 is independently selected from the group consisting of substituted or unsubstituted C3-C10 heterocyclic group, C4-C10 heteroaryl, C6-C10 aryl, wherein heterocycle and heteroaryl have 1-4 heteroatoms selected from N, O, S;

ring B is substituted 5-membered heteroaryl having two N heteroatoms or one N heteroatom and one S or O heteroatom, wherein 1 or 2 ring C atoms have an oxo (=O) substituent;

---- is a single or double bond;

La is absent, or a substituted or unsubstituted divalent or trivalent linkage group, and the number of skeleton linkage atom (N, C, O) is 1, 2 or 3, wherein La is a trivalent linkage group when ---- is a double bond; and La is a divalent linkage group, when ---- is a single bond;

Lb is a substituted or unsubstituted divalent linkage group, and the number of skeleton linkage atoms (N, C, O) is 1, 2 or 3;

$R_c$ and $R_d$ are independently selected from the group consisting of halogen (preferably, F, Cl, Br, I), —OH, nitro, cyano, sulfonyl, R", —N(R")$_2$—, R"—O—, R"—S—, R"—S(O)$_2$—, R"—S(O)—, R"—C(O), R"—C(O)O—, R"—OC(O)—; wherein R" is each independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, —C1-C4 alkylene-C3-C6 cycloalkyl, —C1-C4 alkylene-C6-C10 aryl, —C1-C4 alkylene-4 to 7-membered heterocycloalkyl, and —C1-C4 alkylene-5 to 7-membered heteroaryl;

wherein two adjacent Rc may together form a substituted or unsubstituted C4-C8 heterocyclic ring, substituted or unsubstituted C4-C7 heteroaryl, substituted or unsubstituted C6 aryl;

wherein two adjacent Rd may together form a substituted or unsubstituted C4-C8 heterocyclic ring, substituted or unsubstituted C4-C7 heteroaryl, substituted or unsubstituted C6 aryl;

n1 and n2 are independently 0, 1, 2, 3, 4 or 5;

unless otherwise specified, the term "substituted" refers to one or more (preferably 1, 2, 3, 4 or 5) hydrogens in the group are replaced with an R' group;

each R' is independently selected from the group consisting of D, halogen (preferably F, Cl, Br, I), —OH, nitro, cyano, sulfonyl, R", —N(R"), R"—O—, R"—S—, R"—S(O)$_2$—, R"—S(O)—, R"—C(O), R"—C(O)O—, R"—OC(O)—, where R" is each independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, C1-C4 alkylene-C3-C6 cycloalkyl, —C1-C4 alkylene-C6-C10 aryl, —C1-C4 alkylene-(4 to 7-membered heterocycloalkyl), —C1-C4 alkylene-(5 to 7-membered heteroaryl);

and in R', the alkyl, alkenyl, alkynyl, cycloalkyl, aryl, heterocycloalkyl and heteroaryl, as a whole group or a partial group, can be optionally substituted by a substituent selected from the group consisting of: halogen (preferably F, Cl, Br, I), C1-C4 alkyl, C1-C4 alkoxy, C1-C4 haloalkyl, —OH, nitro, cyano, sulfonyl, and amino;

with the proviso that:

(A) when Lb, ring B and La together form

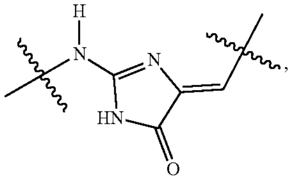 [SMILES: */C=C1\N=C(N*)NC1=O]

then (P1) ring A1 is not a substituted or unsubstituted phenyl; or (P2) ring A2 is not selected from the group consisting of:

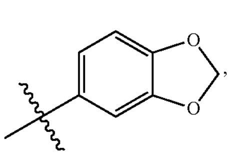, 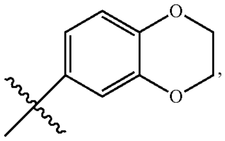,

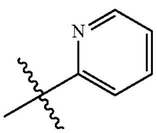, 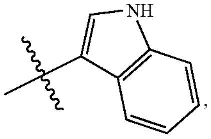,

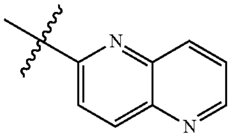

and substituted or unsubstituted phenyl; or, (P3) ring A1 and/or ring A2 is selected from the group consisting of:

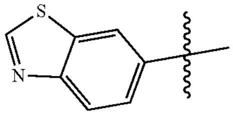 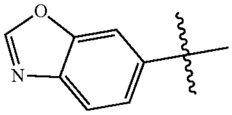

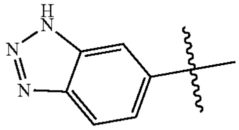 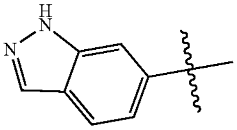

-continued

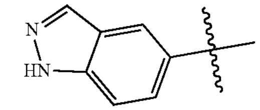 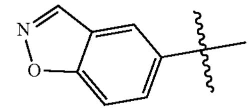

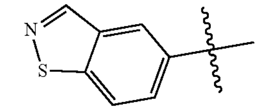 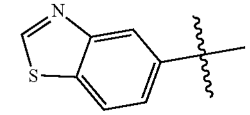

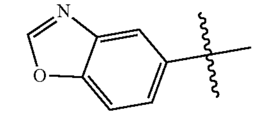 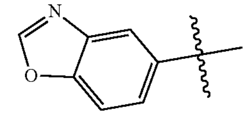

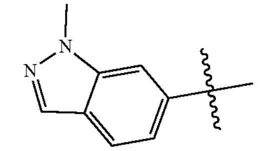 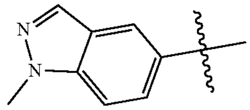

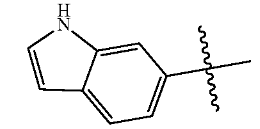 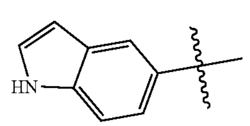

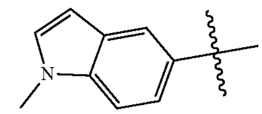 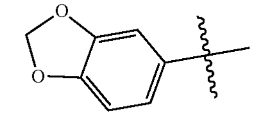

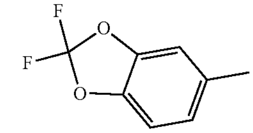 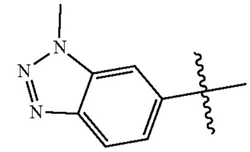

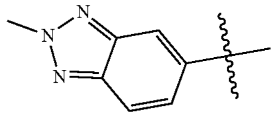 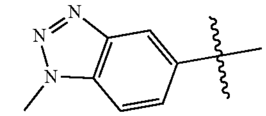

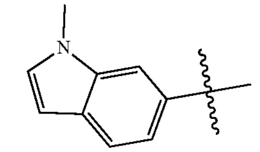 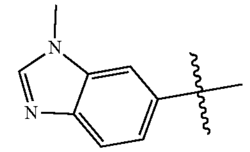

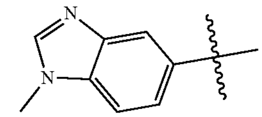 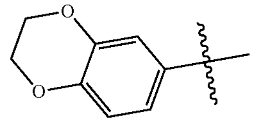

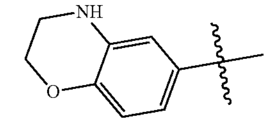 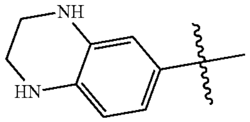

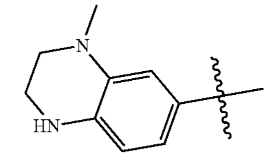 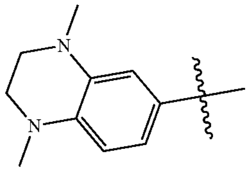

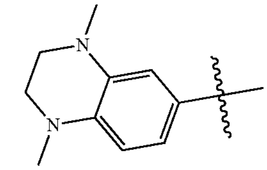 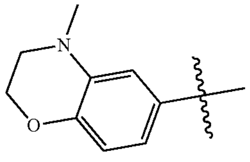

-continued

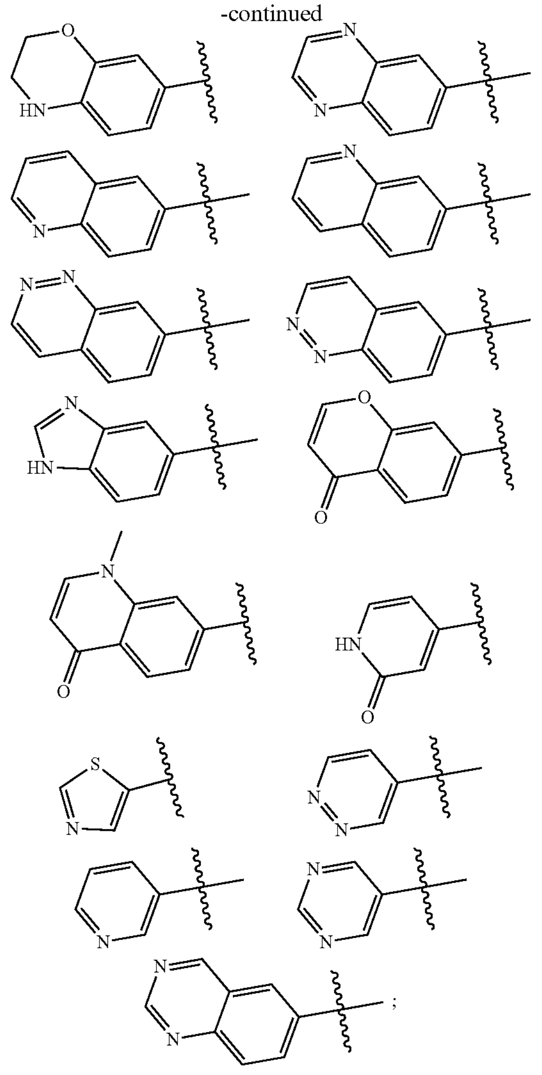

or (B) both ring A1 and ring A2 are not a substituted or unsubstituted phenyl; or (C) ring A2 is not

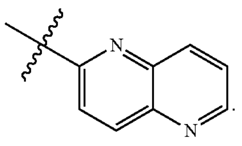 [SMILES: *c1ccc2ncccc2n1]

In another preferred embodiment, (D) ring B1 is not

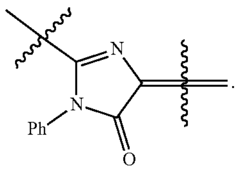 [SMILES: *C1=NC(=*)C(=O)N1c1ccccc1]

In another preferred embodiment, Lb and La are linked at two different positions of ring B1, which are separated by at least one ring atom (or not neighboring).

In another preferred embodiment, none of Lb and La has —CO—O— moiety or fragment.

In another preferred embodiment, none of Ring A1 and Ring A2 is

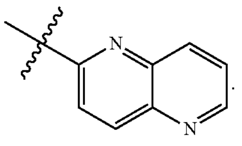 [SMILES: *c1ccc2ncccc2n1]

Unless otherwise defined, the term "a substituted or unsubstituted phenyl" means a phenyl with a single ring structure having none or one or more substituent.

In another preferred embodiment, in (P2), the substituted phenyl is

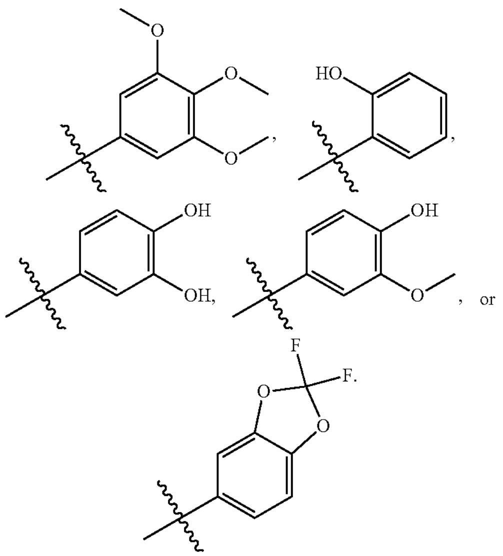

In another preferred embodiment, "substituted" in ring B refers to one or more (preferably 1, 2, 3, 4 or 5) hydrogens in the group are replaced with the substituents selected from the group consisting of D, halogen (preferably F, Cl, Br, I), —OH, nitro, cyano, sulfonyl, R", —N(R"), R"—O—, R"—S—, R"—$S(O)_2$—, R"—S(O)—, R"—C(O), R"—C(O)O—, R"—OC(O)—, and wherein R" is each independently selected from the group consisting of H, C1-C6 alkyl, C2-C6 alkenyl, C2-C6 alkynyl.

In another preferred embodiment, ring B1 has a structure selected from the group consisting of:

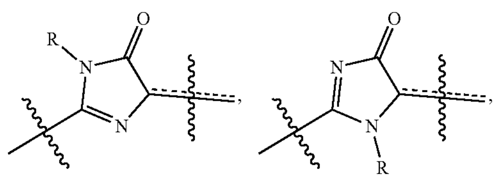

-continued

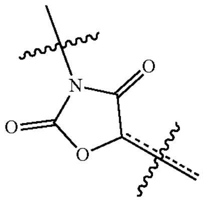, 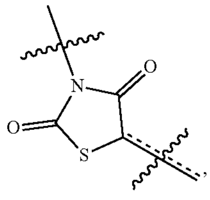,

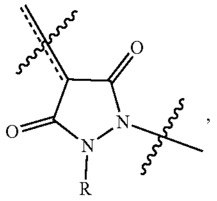, 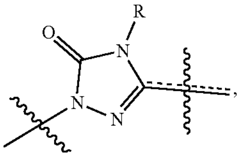, and

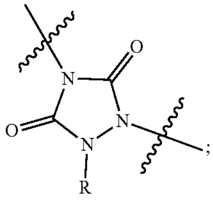;

wherein R is H or C1-C4 alkyl, C3-C4 cycloalkyl or C1-C4 haloalkyl.

In another preferred embodiment, wherein ring B1 has a structure selected from the group consisting of:

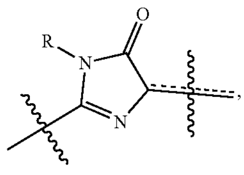, 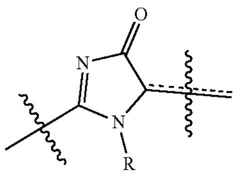 and

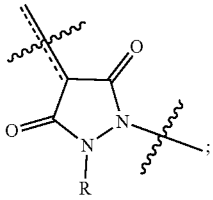;

wherein R is H or C1-C4 alkyl.

In another preferred embodiment, Lb is -Lb1-Lb2-Lb3-, wherein each of Lb1 and Lb2 is independently selected from the group consisting of: absent, —S—, —O—, —NRa—, —N(CORa)—, —N(COORa)—, or —C($R_b$)$_2$—, and Lb3 is selected from the group consisting of: —S—, —O—, —NRa—, —N(CORa)—, —N(COORa)—, and —C($R_b$)$_2$—;

each of $R_a$ and $R_b$ is independently selected from the group consisting of: H, substituted or unsubstituted C1-C8 alkyl; substituted or unsubstituted C2-C6 alkenyl, substituted or unsubstituted C2-C8 alkynyl, substituted or unsubstituted C3-C10 cycloalkyl, substituted or unsubstituted C3-C10 heterocycloalkyl, substituted or unsubstituted C6-C10 aryl, substituted or unsubstituted C3-C7 heteroaryl, substituted or unsubstituted C1-C3 alkylene-C6-C10 aryl, substituted or unsubstituted C1-C3 alkylene-C3-C10 cycloalkyl, substituted or unsubstituted C1-C3 alkylene-C3-C10 heterocycloalkyl.

In another preferred embodiment, Lb is —NRa—, —N(CORa)—, —N(COORa)—, or —C($R_b$)$_2$—.

In another preferred embodiment, Lb is —NH—, —$CH_2$—, or —$CH_2$—$CH_2$—.

In another preferred embodiment, Lb is absent.

In another preferred embodiment, La is -La1-La2-La3-, wherein La1 is selected from the group consisting of: =CRb—, —CRb=, —S—, —O—, —NRa—, —N(CORa)—, —N(COORa)—, —N(S(O)$_2$Ra)—, —N=, and —C($R_b$)$_2$—; and each of La2 and La3 is independently selected from the group consisting of: absent, =CRb—, —CRb=, —S—, —O—, —NRa—, —N(CORa)—, —N(COORa)—, —N(S(O)$_2$Ra)—, —N=, and —C($R_b$)$_2$—;

each of $R_a$ and $R_b$ is independently selected from the group consisting of: H, substituted or unsubstituted C1-C8 alkyl; substituted or unsubstituted C2-C6 alkenyl, substituted or unsubstituted C2-C8 alkynyl, substituted or unsubstituted C3-C10 cycloalkyl, substituted or unsubstituted C3-C10 heterocycloalkyl, substituted or unsubstituted C6-C10 aryl, substituted or unsubstituted C3-C7 heteroaryl, substituted or unsubstituted C1-C3 alkylene-C6-C10 aryl, substituted or unsubstituted C1-C3 alkylene-C3-C10 cycloalkyl, substituted or unsubstituted C1-C3 alkylene-C3-C10 heterocycloalkyl.

In another preferred embodiment, La is =CRb—, =CRb—C(Rb)$_2$—, —C(Rb)$_2$—, —C(Rb)$_2$—C(Rb)$_2$—, or —NRa—.

In another preferred embodiment, La is =$CH_2$—, =CH—$CH_2$—, —$CH_2$—, —$CH_2$—$CH_2$—, —C($CH_3$)H—, or —C($CH_3$)$_2$—.

In another preferred embodiment, La is =$CH_2$—, —$CH_2$—, —C($CH_3$)H—, or —C($CH_3$)$_2$—.

In another preferred embodiment, ---- is a double bond.

In another preferred embodiment, ---- is a single bond.

In another preferred embodiment, each of ring A1 and ring A2 is independently selected from the group consisting of: single ring, fused ring (or bicyclic ring) or tricyclic ring.

In another preferred embodiment, at least one of ring A1 and ring A2 is selected from the group consisting of: substituted or unsubstituted fused ring (or bicyclic ring) or tricyclic ring, wherein each of the fused ring (or bicyclic ring) or tricyclic ring has 0-5 heteroatoms selected from N, O, S.

In another preferred embodiment, both of ring A1 and ring A2 are selected from the group consisting of: substituted or unsubstituted fused ring (or bicyclic ring) or tricyclic ring.

In another preferred embodiment, ring A1 and/or ring A2 is a bicyclic ring with 6-membered ring plus 6-membered ring structure, or a bicyclic ring with 6-membered ring plus 5-membered ring structure.

In another preferred embodiment, ring A1 and/or ring A2 is a bicyclic ring with 6-membered aromatic ring plus 6-membered aromatic or non-aromatic ring structure, or a bicyclic ring with 6-membered aromatic ring plus 5-membered aromatic or non-aromatic ring structure.

In another preferred embodiment, the 5-membered aromatic or non-aromatic ring structure has 0, 1, 2, or 3 heteroatoms (N, S or O).

In another preferred embodiment, the 6-membered aromatic or non-aromatic ring structure has 0, 1, 2, or 3 heteroatoms (N, S or O).

In another preferred embodiment, ring A1 and/or ring A2 is selected from the group consisting of:

-continued
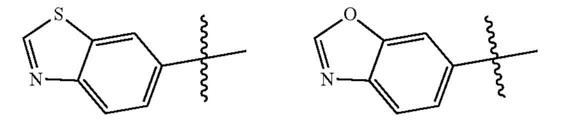
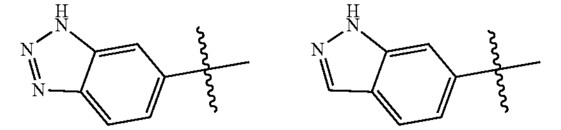
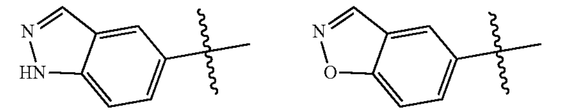
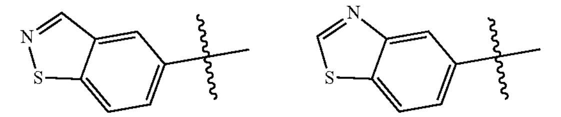
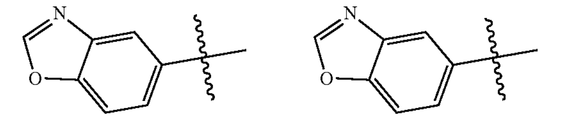
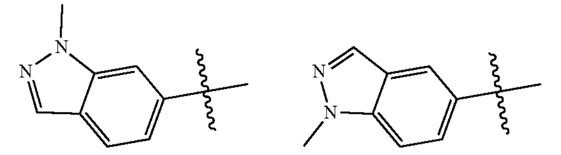
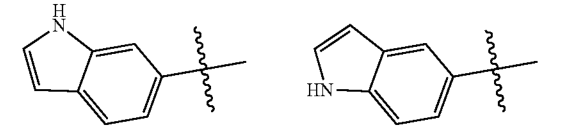
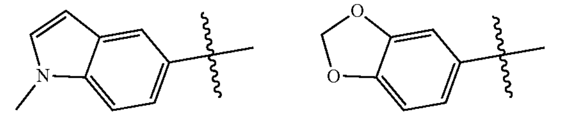
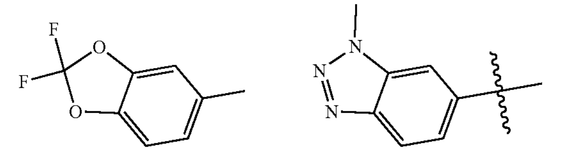
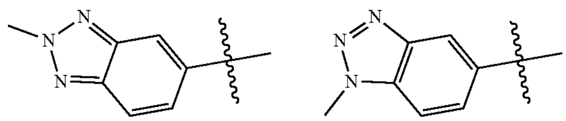
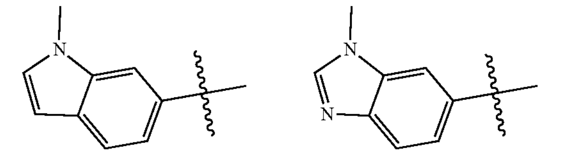
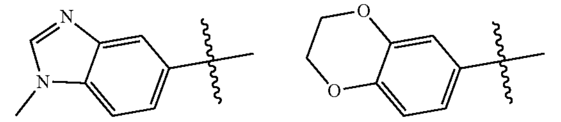
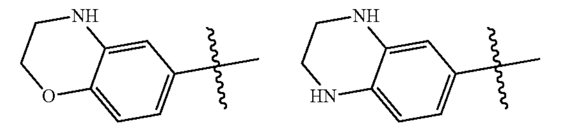
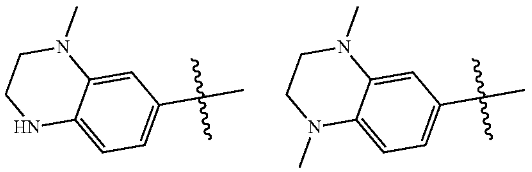
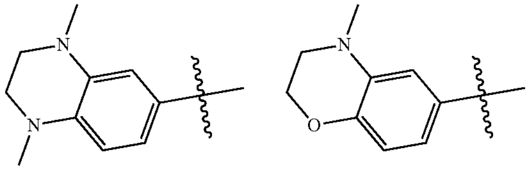
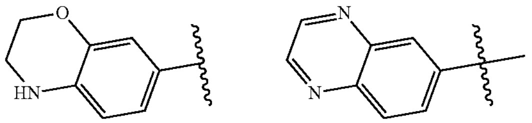
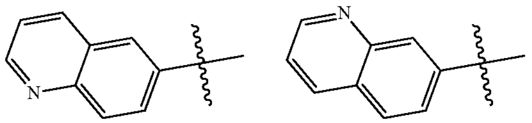
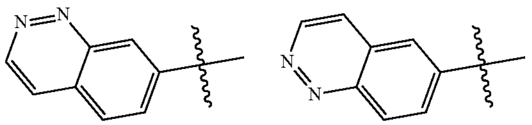
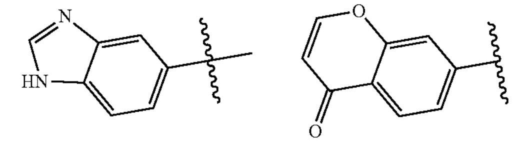
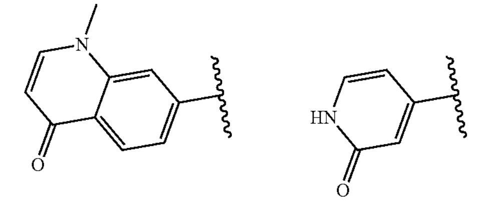
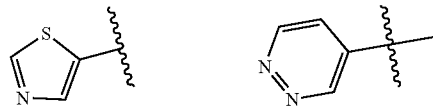
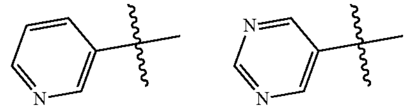
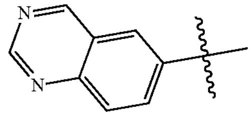
.
In another preferred embodiment, the fused ring (or bicyclic ring) is selected from the group consisting of:
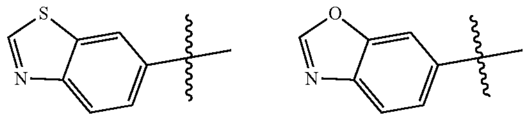

-continued
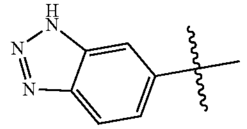 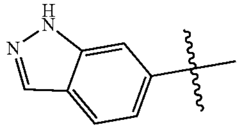
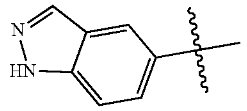 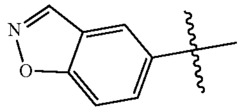
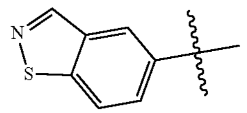 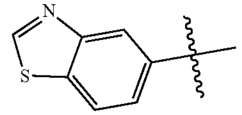
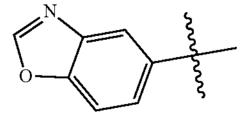 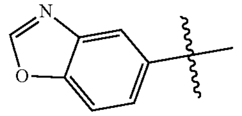
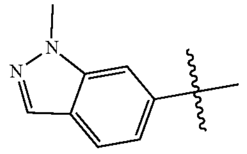 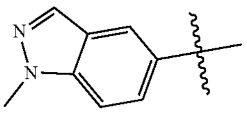
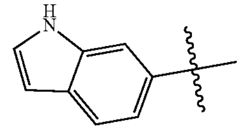 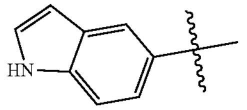
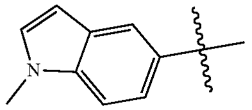 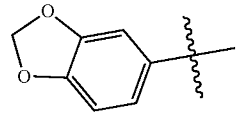
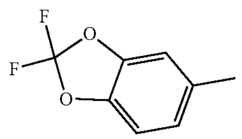 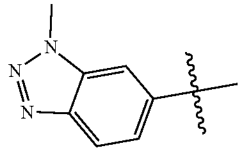
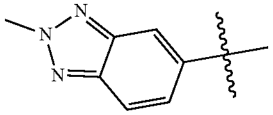 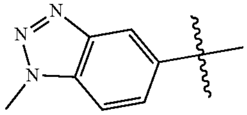
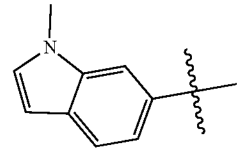 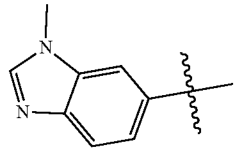
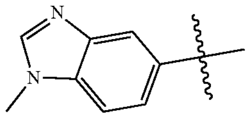 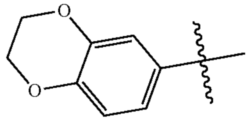
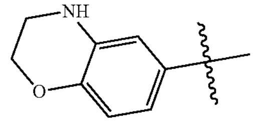 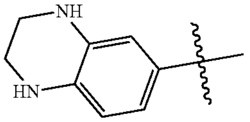
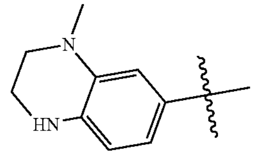 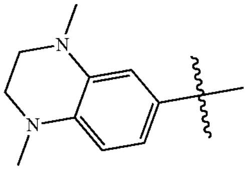
-continued
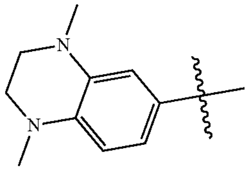 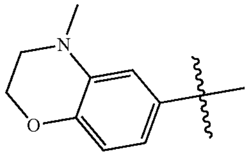
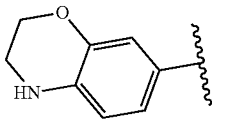 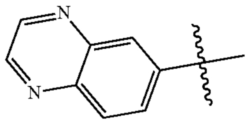
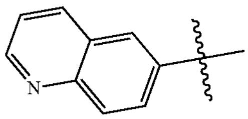 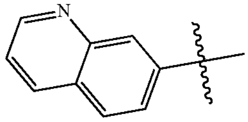
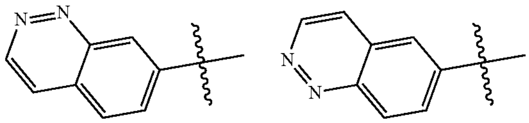
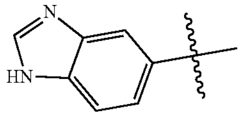 .
In another preferred embodiment, ring A2 is selected from the group consisting of:
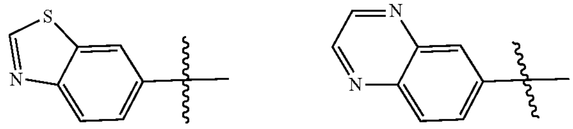
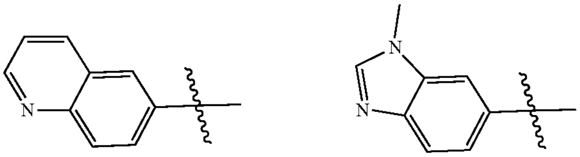
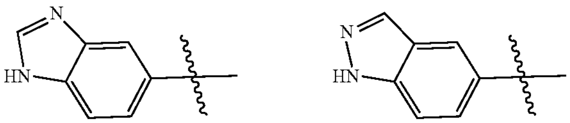
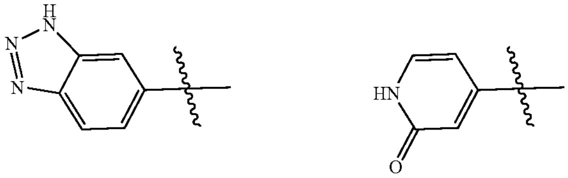
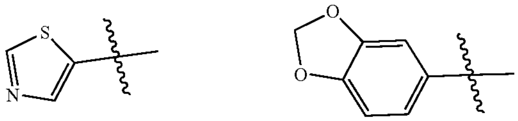
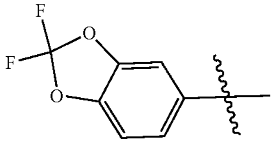

-continued

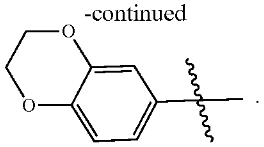

In another preferred embodiment, unless otherwise specified, the heteroaryl group refers to an aromatic ring group containing 1, 2, or 3 heteroatoms selected from: O, N, and S.

In another preferred embodiment, unless otherwise specified, the heterocycloalkyl group refers to a cycloalkyl group containing 1, 2, or 3 heteroatoms selected from: O, N, and S.

In another preferred embodiment, wherein the compound is the compound has a structure of formula A or formula B Formula (A)

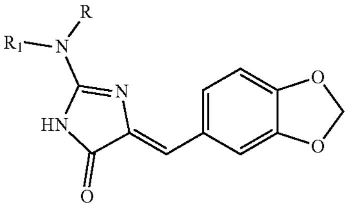

Formula (B)

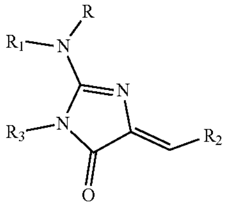

R is Alkyl, Aryl, $SO_2$Alkyl, COAlkyl;

$R_1$ is Alkyl, Aryl, Hetero aryl;

$R_3$ is alkyl, aryl, hetero-aryl;

$R_2$ is heteroaryl.

In another preferred embodiment, each of A1, A2, B1, La, Lb, ----, R, $R_1$, $R_2$, $R_3$, $R_c$, $R_d$ n1 and n2 are the corresponding groups in the compounds as prepared in the Examples.

In another preferred embodiment, the compound of formula (I) is any of compounds as prepared in Examples 1 to 105.

In another preferred embodiment, the compound is any selected from Table A, Table 1 or Table 2.

In another preferred embodiment, the compound is selected from Table A:

TABLE A

| Compound | Name |
|---|---|
| Example 1: | (4Z)-4-[(2H-1,3-benzodioxol-5-yl)methylidene]-2-[methyl(phenyl)amino]-4,5-dihydro-1H-imidazol-5-one |
| Example 2: | (4Z)-4-[(2H-1,3-benzodioxol-5-yl)methylidene]-1-benzyl-2-[benzyl(phenyl)amino]-4,5-dihydro-1H-imidazol-5-one |
| Example 3: | (4Z)-4-[(2H-1,3-benzodioxol-5-yl)methylidene]-1-methyl-2-[methyl(phenyl)amino]-4,5-dihydro-1H-imidazol-5-one |

TABLE A-continued

| Compound | Name |
|---|---|
| Example 4: | (4Z)-4-[(2H-1,3-benzodioxol-5-yl)methylidene]-2-[ethyl(phenyl)amino]-4,5-dihydro-1H-imidazol-5-one |
| Example 5: | N-[(4Z)-4-[(2H-1,3-benzodioxol-5-yl)methylidene]-5-oxo-4,5-dihydro-1H-imidazol-2-yl]-N-phenylacetamide |
| Example 6: | (4Z)-4-[(1,3-benzothiazol-6-yl)methylidene]-2-(phenylamino)-4,5-dihydro-1H-imidazol-5-one |
| Example 7: | (4Z)-4-[(1,3-benzothiazol-6-yl)methylidene]-2-[methyl(phenyl)amino]-4,5-dihydro-1H-imidazol-5-one |
| Example 8: | (4Z)-4-[(2,3-dihydro-1,4-benzodioxin-6-yl)methylidene]-2-[methyl(phenyl)amino]-4,5-dihydro-1H-imidazol-5-one |
| Example 9: | 5-{[(4Z)-5-oxo-2-(phenylamino)-4,5-dihydro-1H-imidazol-4-ylidene]methyl}-1,2-dihydropyridin-2-one |
| Example 10: | (4Z)-4-[(2H-1,3-benzodioxol-5-yl)methylidene]-2-[(cyclopropylmethyl)(phenyl)amino]-4,5-dihydro-1H-imidazol-5-one |
| Example 11: | (4Z)-4-[(2H-1,3-benzodioxol-5-yl)methylidene]-2-[(cyclopropylmethyl)(methyl)amino]-4,5-dihydro-1H-imidazol-5-one |
| Example 12: | (4Z)-4-[(2H-1,3-benzodioxol-5-yl)methylidene]-2-[(4-methoxyphenyl)(methyl)amino]-4,5-dihydro-1H-imidazol-5-one |
| Example 13: | (4Z)-4-[(2H-1,3-benzodioxol-5-yl)methylidene]-2-[(2-hydroxyethyl)(phenyl)amino]-4,5-dihydro-1H-imidazol-5-one |
| Example 14: | (4Z)-4-[(1,3-benzothiazol-5-yl)methylidene]-2-(phenylamino)-4,5-dihydro-1H-imidazol-5-one |
| Example 15: | (4Z)-2-(phenylamino)-4-[(1,3-thiazol-5-yl)methylidene]-4,5-dihydro-1H-imidazol-5-one |
| Example 16: | (4Z)-2-(phenylamino)-4-[(quinoxalin-6-yl)methylidene]-4,5-dihydro-1H-imidazol-5-one |
| Example 17: | (4Z)-4-[(2,2-difluoro-2H-1,3-benzodioxol-5-yl)methylidene]-2-[methyl(phenyl)amino]-4,5-dihydro-1H-imidazol-5-one |
| Example 18: | (4Z)-4-[(2H-1,3-benzodioxol-5-yl)methylidene]-2-[methyl(pyridin-3-yl)amino]-4,5-dihydro-1H-imidazol-5-one |
| Example 19: | (4Z)-2-[(cyclopropylmethyl)(methyl)amino]-4-[(2,3-dihydro-1,4-benzodioxin-6-yl)methylidene]-4,5-dihydro-1H-imidazol-5-one |
| Example 20: | (4Z)-4-[(2H-1,3-benzodioxol-5-yl)methylidene]-2-{methyl[2-(morpholin-4-yl)ethyl]amino}-4,5-dihydro-1H-imidazol-5-one |
| Example 21: | (4Z)-4-[(2H-1,3-benzodioxol-5-yl)methylidene]-2-[(2-methoxyphenyl)(methyl)amino]-4,5-dihydro-1H-imidazol-5-one; formic acid |
| Example 22: | (4Z)-4-[(2H-1,3-benzodioxol-5-yl)methylidene]-2-[benzyl(phenyl)amino]-4,5-dihydro-1H-imidazol-5-one |
| Example 23: | (4Z)-4-[(2H-1,3-benzodioxol-5-yl)methylidene]-2-[benzyl(methyl)amino]-4,5-dihydro-1H-imidazol-5-one |
| Example 24: | (4Z)-4-[(1,3-benzothiazol-6-yl)methylidene]-2-[(4-chlorophenyl)(methyl)amino]-4,5-dihydro-1H-imidazol-5-one |
| Example 25: | (4Z)-4-[(1,3-benzothiazol-6-yl)methylidene]-2-[(4-methoxyphenyl)amino]-4,5-dihydro-1H-imidazol-5-one |
| Example 26: | (4Z)-4-[(1H-1,3-benzodiazol-5-yl)methylidene]-2-(phenylamino)-4,5-dihydro-1H-imidazol-5-one |
| Example 27: | 3-{[(4Z)-4-[(2H-1,3-benzodioxol-5-yl)methylidene]-5-oxo-4,5-dihydro-1H-imidazol-2-yl](phenyl)amino}propanoic acid |
| Example 28: | (4Z)-4-[(1,3-benzothiazol-6-yl)methylidene]-2-[benzyl(methyl)amino]-4,5-dihydro-1H-imidazol-5-one |
| Example 29: | (4Z)-4-[(1,3-benzothiazol-6-yl)methylidene]-2-{[2-(morpholin-4-yl)ethyl]amino}-4,5-dihydro-1H-imidazol-5-one |
| Example 30: | (4Z)-4-[(1H-1,3-benzodiazol-5-yl)methylidene]-2-[methyl(phenyl)amino]-4,5-dihydro-1H-imidazol-5-one |
| Example 31: | (4Z)-4-[(1,3-benzothiazol-6-yl)methylidene]-2-(benzylamino)-4,5-dihydro-1H-imidazo 1-5-one |

TABLE A-continued

| Compound | Name |
| --- | --- |
| Example 32: | (4Z)-4-[(1,3-benzothiazol-6-yl)methylidene]-2-{methyl[2-(morpholin-4-yl)ethyl]amino}-4,5-dihydro-1H-imidazol-5-one |
| Example 33: | (4Z)-4-[(1,3-benzothiazol-6-yl)methylidene]-2-[(cyclopropylmethyl)(methyl)amino]-4,5-dihydro-1H-imidazol-5-one |
| Example 34: | (4Z)-4-[(1,3-benzothiazol-6-yl)methylidene]-2-[(cyclopropylmethyl)amino]-4,5-dihydro-1H-imidazol-5-one |
| Example 35: | (4Z)-4-[(1H-1,3-benzodiazol-5-yl)methylidene]-2-[benzyl(phenyl)amino]-4,5-dihydro-1H-imidazol-5-one |
| Example 36: | 3-{[(4Z)-4-[(2H-1,3-benzodioxol-5-yl)methylidene]-5-oxo-4,5-dihydro-1H-imidazol-2-yl](phenyl)amino}propanamide |
| Example 37: | (4Z)-2-[(4-aminophenyl)(methyl)amino]-4-[(2H-1,3-benzodioxol-5-yl)methylidene]-4,5-dihydro-1H-imidazol-5-one |
| Example 38: | (4Z)-4-[(1,3-benzothiazol-6-yl)methylidene]-2-[(4-methoxyphenyl)(methyl)amino]-4,5-dihydro-1H-imidazol-5-one |
| Example 39: | (4Z)-2-[(cyclopropylmethyl)(phenyl)amino]-4-[(2,3-dihydro-1,4-benzodioxin-6-yl)methylidene]-4,5-dihydro-1H-imidazol-5-one |
| Example 40: | (4Z)-4-[(1,3-benzothiazol-6-yl)methylidene]-2-[(4-chlorophenyl)amino]-4,5-dihydro-1H-imidazol-5-one |
| Example 41: | (4Z)-4-[(1,3-benzothiazol-6-yl)methylidene]-2-[benzyl(phenyl)amino]-4,5-dihydro-1H-imidazol-5-one |
| Example 42: | (4Z)-4-[(1,3-benzothiazol-6-yl)methylidene]-1-benzyl-2-[benzyl(phenyl)amino]-4,5-dihydro-1H-imidazol-5-one |
| Example 43: | (4Z)-4-[(1,3-benzothiazol-6-yl)methylidene]-2-[methyl(4-nitrophenyl)amino]-4,5-dihydro-1H-imidazol-5-one |
| Example 44: | (4Z)-2-[(4-aminophenyl)(methyl)amino]-4-[(1,3-benzothiazol-6-yl)methylidene]-4,5-dihydro-1H-imidazol-5-one |
| Example 45: | (4Z)-4-[(1,3-benzothiazol-6-yl)methylidene]-1-methyl-2-[(propan-2-yl)amino]-4,5-dihydro-1H-imidazol-5-one |
| Example 46: | (4Z)-4-[(1-methyl-1H-1,3-benzodiazol-6-yl)methylidene]-2-(phenylamino)-4,5-dihydro-1H-imidazol-5-one |
| Example 47: | (4Z)-4-[(2H-1,3-benzodioxol-5-yl)methylidene]-2-[(1,3-benzothiazol-6-yl)amino]-4,5-dihydro-1H-imidazol-5-one |
| Example 48: | (4Z)-2-[(1,3-benzothiazol-6-yl)amino]-4-[(1,3-benzothiazol-6-yl)methylidene]-4,5-dihydro-1H-imidazol-5-one |
| Example 49: | (4Z)-4-[(1,3-benzothiazol-5-yl)methylidene]-2-[(propan-2-yl)amino]-4,5-dihydro-1H-imidazol-5-one; formic acid |
| Example 50: | (4Z)-2-[(adamantan-1-yl)amino]-4-[(1,3-benzothiazol-5-yl)methylidene]-4,5-dihydro-1H-imidazol-5-one; formic acid |
| Example 51: | (4Z)-4-[(1H-indol-5-yl)methylidene]-2-(phenylamino)-4,5-dihydro-1H-imidazol-5-one; formic acid |
| Example 52: | (4Z)-4-[(1-benzofuran-5-yl)methylidene]-2-(phenylamino)-4,5-dihydro-1H-imidazol-5-one |
| Example 53: | (4Z)-2-(phenylamino)-4-[(quinolin-6-yl)methylidene]-4,5-dihydro-1H-imidazol-5-one; formic acid |
| Example 53: | (4Z)-2-(phenylamino)-4-[(quinolin-6-yl)methylidene]-4,5-dihydro-1H-imidazol-5-one |
| Example 54: | (4Z)-4-[(1H-indazol-6-yl)methylidene]-2-(phenylamino)-4,5-dihydro-1H-imidazol-5-one |
| Example 55: | (4Z)-4-[(1H-indazol-5-yl)methylidene]-2-(phenylamino)-4,5-dihydro-1H-imidazol-5-one |
| Example 56: | (4Z)-4-[(1H-1,2,3-benzotriazol-6-yl)methylidene]-2-(phenylamino)-4,5-dihydro-1H-imidazol-5-one |
| Example 57: | (4Z)-4-[(1,3-benzothiazol-5-yl)methylidene]-2-[(1,3-benzothiazol-6-yl)amino]-4,5-dihydro-1H-imidazol-5-one |
| Example 57: | (4Z)-4-[(1,3-benzothiazol-5-yl)methylidene]-2-[(1,3-benzothiazol-6-yl)amino]-4,5-dihydro-1H-imidazol-5-one hydrochloride |

TABLE A-continued

| Compound | Name |
| --- | --- |
| Example 58: | (4Z)-2-[(1,3-benzothiazol-6-yl)amino]-4-[(1H-indol-5-yl)methylidene]-4,5-dihydro-1H-imidazol-5-one; formic acid |
| Example 59: | (4Z)-4-[(1-benzofuran-5-yl)methylidene]-2-[(1,3-benzothiazol-6-yl)amino]-4,5-dihydro-1H-imidazol-5-one |
| Example 60: | (4Z)-2-[(1,3-benzothiazol-6-yl)amino]-4-[(quinolin-6-yl)methylidene]-4,5-dihydro-1H-imidazol-5-one |
| Example 61: | (4Z)-4-[(1,3-benzothiazol-6-yl)methylidene]-2-[(1-methyl-1H-1,3-benzodiazol-5-yl)amino]-4,5-dihydro-1H-imidazol-5-one; formic acid |
| Example 63: | (4Z)-2-[(1,3-benzothiazol-6-yl)amino]-4-[(1H-indol-6-yl)methylidene]-4,5-dihydro-1H-imidazol-5-one; formic acid |
| Example 69: | (4Z)-4-[(1,3-benzothiazol-6-yl)methylidene]-2-[(1H-indol-5-yl)amino]-4,5-dihydro-1H-imidazol-5-one |
| Example 70: | (4Z)-4-[(2H-1,3-benzodioxol-5-yl)methylidene]-2-[(1,3-benzothiazol-6-yl)(methyl)amino]-4,5-dihydro-1H-imidazol-5-one |
| Example 71: | (4Z)-4-[(1-methyl-1H-1,3-benzodiazol-5-yl)methylidene]-2-(phenylamino)-4,5-dihydro-1H-imidazol-5-one |
| Example 72: | (4Z)-4-[(1-benzothiophen-5-yl)methylidene]-2-(phenylamino)-4,5-dihydro-1H-imidazol-5-one |
| Example 73: | (4Z)-4-[(1H-indol-6-yl)methylidene]-2-(phenylamino)-4,5-dihydro-1H-imidazol-5-one |
| Example 74: | (4Z)-2-[(1,3-benzothiazol-6-yl)amino]-4-[(2,3-dihydro-1,4-benzodioxin-6-yl)methylidene]-4,5-dihydro-1H-imidazol-5-one |
| Example 75: | (4Z)-2-[(1,3-benzothiazol-6-yl)amino]-4-[(1-methyl-1H-1,3-benzodiazol-6-yl)methylidene]-4,5-dihydro-1H-imidazol-5-one |
| Example 76: | (4Z)-4-[(1H-1,3-benzodiazol-6-yl)methylidene]-2-[(1,3-benzothiazol-6-yl)amino]-4,5-dihydro-1H-imidazol-5-one |
| Example 77: | (4Z)-4-[(1-methyl-1H-indazol-5-yl)methylidene]-2-(phenylamino)-4,5-dihydro-1H-imidazol-5-one |
| Example 78: | (4Z)-2-[(1,3-benzothiazol-6-yl)amino]-4-[(1-methyl-1H-indazol-5-yl)methylidene]-4,5-dihydro-1H-imidazol-5-one |
| Example 79: | (4Z)-4-[(1-methyl-1H-indazol-6-yl)methylidene]-2-(phenylamino)-4,5-dihydro-1H-imidazol-5-one |
| Example 80: | (4Z)-2-[(1,3-benzothiazol-6-yl)amino]-4-[(1-methyl-1H-indazol-6-yl)methylidene]-4,5-dihydro-1H-imidazol-5-one |
| Example 81: | (4Z)-4-[(1,3-benzothiazol-6-yl)methylidene]-2-[(2,3-dihydro-1,4-benzodioxin-6-yl)amino]-4,5-dihydro-1H-imidazol-5-one |
| Example 82: | (4Z)-4-[(1,3-benzothiazol-6-yl)methylidene]-2-[(quinoxalin-6-yl)amino]-4,5-dihydro-1H-imidazol-5-one |
| Example 83: | (4Z)-2-[(1,3-benzothiazol-6-yl)(methyl)amino]-4-[(1,3-benzothiazol-6-yl)methylidene]-4,5-dihydro-1H-imidazol-5-one |
| Example 84: | (4Z)-2-[(1,3-benzothiazol-6-yl)(methyl)amino]-4-[(2,3-dihydro-1,4-benzodioxin-6-yl) methylidene]-4,5-dihydro-1H-imidazol-5-one |
| Example 85: | (4Z)-2-[(1,3-benzothiazol-6-yl)(methyl)amino] -4-[(quinolin-6-yl)methylidene]-4,5-dihydro-1H-imidazol-5-one; formic acid |
| Example 86: | (4Z)-4-[(1,3-benzothiazol-6-yl)methylidene]-2-[methyl(1-methyl-1H-1,3-benzodiazol-5-yl)amino]-4,5-dihydro-1H-imidazol-5-one |
| Example 87: | (4E)-2-[(1,3-benzothiazol-6-yl)(methyl)amino]-4-[(1H-indol-5-yl)methylidene]-4,5-dihydro-1H-imidazol-5-one |
| Example 88: | (4Z)-2-[(1,3-benzothiazol-6-yl)amino]-4-[(1,3-benzothiazol-6-yl)methylidene]-1-methyl-4,5-dihydro-1H-imidazol-5-one |
| Example 89: | (4Z)-2-[(1,3-benzothiazol-6-yl)(2-methoxyethyl)amino]-4-[(1,3-benzothiazol-6-yl)methylidene]-4,5-dihydro-1H-imidazol-5-one |
| Example 90: | (4Z)-4-[(1,3-benzothiazol-6-yl)methylidene]-2-[(2-methyl-1,3-benzothiazol-6-yl)amino]-4,5-dihydro-1H-imidazol-5-one |

TABLE A-continued

| Compound | Name |
| --- | --- |
| Example 91: | N-(1,3-benzothiazol-6-yl)-N-[(4Z)-4-[(1,3-benzothiazol-6-yl)methylidene]-5-oxo-4,5-dihydro-1H-imidazol-2-yl]acetamide |
| Example 92: | (4Z)-2-[(1,3-benzothiazol-6-yl)amino]-4-[(1,3-thiazol-5-yl)methylidene]-4,5-dihydro-1H-imidazol-5-one; formic acid |
| Example 93: | (4Z)-4-[(1,3-benzothiazol-6-yl)methylidene]-2-[(1-methyl-1H-1,3-benzodiazol-6-yl)amino]-4,5-dihydro-1H-imidazol-5-one |
| Example 94: | (4Z)-2-[(1,3-benzothiazol-6-yl)amino]-4-[(quinoxalin-6-yl)methylidene]-4,5-dihydro-1H-imidazol-5-one |
| Example 95: | (4Z)-2-[(1,3-benzothiazol-6-yl)amino]-4-[(1H-indazol-6-yl)methylidene]-4,5-dihydro-1H-imidazol-5-one |
| Example 96: | (5Z)-5-[(1-benzothiophen-5-yl)methylidene]-2-sulfanylideneimidazolidin-4-one |
| Example 97: | (4Z)-2-[(1H-1,3-benzodiazol-6-yl)amino]-4-[(1,3-benzothiazol-6-yl)methylidene]-4,5-dihydro-1H-imidazol-5-one |
| Example 98: | (4Z)-2-[(4-aminophenyl)amino]-4-[(1,3-benzothiazol-6-yl)methylidene]-4,5-dihydro-1H-imidazol-5-one |
| Example 99: | (4Z)-2-[(1,3-benzothiazol-6-yl)(benzyl)amino]-4-[(1,3-benzothiazol-6-yl)methylidene]-4,5-dihydro-1H-imidazol-5-one |
| Example 100: | (4Z)-4-[(1,3-benzothiazol-6-yl)methylidene]-2-({2-[(propan-2-yl)amino]-1,3-benzothiazol-6-yl}amino)-4,5-dihydro-1H-imidazol-5-one |
| Example 101: | (4Z)-4-[(1,3-benzothiazol-6-yl)methylidene]-2-[(1-benzothiophen-5-yl)amino]-4,5-dihydro-1H-imidazol-5-one |
| Example 102: | 2-[(1,3-benzothiazol-6-yl)amino]-4-[(1,3-benzothiazol-6-yl)methyl]-4,5-dihydro-1H-imidazol-5-one hydrochloride |
| Example 103: | (4Z)-2-amino-4-[(1,3-benzothiazol-6-yl)methylidene]-4,5-dihydro-1H-imidazol-5-one |
| Example 104: | (4Z)-4-[(1,3-benzothiazol-6-yl)methylidene]-2-{[2-(phenylamino)-1,3-benzothiazol-6-yl]amino}-4,5-dihydro-1H-imidazol-5-one |
| Example 105: | (4Z)-2-[(1,3-benzothiazol-6-yl)(cyclopropylmethyl)amino]-4-[(1,3-benzothiazol-6-yl)methylidene]-4,5-dihydro-1H-imidazol-5-one |

In the second aspect of the present invention, it provides a pharmaceutical composition, which comprises the compound of the first aspect of the present invention, or a pharmaceutically acceptable salt, solvate, stereoisomer, or prodrug thereof, and a pharmaceutically acceptable carrier.

In the third aspect of the present invention, it provides a use of a compound of the first aspect of the present invention, or a pharmaceutically acceptable salt, a solvate, a stereoisomer or a prodrug thereof for manufacture of a medicament for treating or preventing a cardiovascular disease.

In another preferred embodiment, the cardiovascular disease is a heart disease.

In another preferred embodiment, the heart disease is selected from the group consisting of heart infarct, heart failure, atrial fibrillation, coronary heart disease, myocardial infarction, atrial septal defect, coronary artery disease, and combinations thereof.

In another preferred embodiment, the cardiovascular disease is treated or prevented via the inhibition of the activity of one or more kinases selected from the group consisting of DYRK1A, DYRK2, CLK1, CIT, HIPK1, and CK2 alpha 2 (CK2a2).

In another preferred embodiment, the cardiovascular disease is treated or prevented via the inhibition of the activity of one or more kinases selected from the group consisting of DYRK1A, DYRK2, CLK1, CIT, HIPK1, CK2 alpha 2 (CK2a2) (preferably, the group consisting of DYRK1A, CLK1, and CK2 alpha 2 (CK2a2)) and not via the inhibition of GSK3b kinase activity.

In the fourth aspect of the present invention, it provides a method for promoting growth of cardiomyocytes in vitro, which comprises a step of:

culturing cardiomyocyte in the present of a compound of formula I, or a pharmaceutically acceptable salt, a solvate, a stereoisomer or a prodrug.

In the fifth aspect of the present invention, it provides a method for promoting cardiomyocyte proliferation and/or regeneration in vitro, which comprises a step of:

contacting cardiomyocyte with a compound of the first aspect of the present invention, or a pharmaceutically acceptable salt, a solvate, a stereoisomer or a prodrug, thereby promoting cardiomyocyte proliferation and/or regeneration.

In the sixth aspect of the present invention, it provides a method for treating a cardiovascular disease, which comprises a step of: administering a compound according to the first aspect of the present invention or a pharmaceutically acceptable salt, a solvate, a stereoisomer or a prodrug to a subject in need.

In another preferred embodiment, the subjects comprises human and non-human mammal.

In the seventh aspect of the present invention, it provides a method of inhibiting DYRK1A kinase activity, wherein the method comprises step of: contacting cells with a compound of the first aspect of the present invention, or a pharmaceutically acceptable salt, a solvate, a stereoisomer or a prodrug, thereby inhibiting DYRK1A kinase activity.

In another preferred embodiment, the ratio of the IC50 value of the compound for DYRK1A to that for GSK3 beta is less than 1/5, preferably less than 1/10, more preferably less than 1/20.

In the eighth aspect of the present invention, it provides a method of inhibiting DYRK2 kinase activity, wherein the method comprises step of: contacting cells with a compound of the first aspect of the present invention, or a pharmaceutically acceptable salt, a solvate, a stereoisomer or a prodrug, thereby inhibiting DYRK2 kinase activity.

In the ninth aspect of the present invention, it provides a method of inhibiting CLK1 kinase activity, wherein the method comprises step of: contacting cells with a compound of the first aspect of the present invention, or a pharmaceutically acceptable salt, a solvate, a stereoisomer or a prodrug, thereby inhibiting the activity of said kinase.

In another preferred embodiment, the ratio of IC50 value of the compound for CLK1 to that for GSK3 beta is less than 1/5, preferably less than 1/10, more preferably less than 1/20.

In the tenth aspect of the present invention, it provides a method of inhibiting CIT kinase activity, wherein the method comprises step of: contacting cells with a compound of the first aspect of the present invention, or a pharmaceutically acceptable salt, a solvate, a stereoisomer or a prodrug, thereby inhibiting the activity of CIT kinase activity.

In the 11th aspect of the present invention, it provides a method of inhibiting the HIPK1 kinase activity, wherein the method comprises step of: contacting cells with a compound of the first aspect of the present invention, or a pharmaceutically acceptable salt, a solvate, a stereoisomer or a prodrug, thereby inhibiting the activity of HIPK1 kinase activity.

In the 12th aspect of the present invention, it provides a method of inhibiting HIPK2 kinase activity, wherein the method comprises step of: contacting cells with a compound of the first aspect of the present invention, or a pharmaceutically acceptable salt, a solvate, a stereoisomer or a prodrug, thereby inhibiting the activity of HIPK2 kinase activity.

In the 13th aspect of the present invention, it provides a method of inhibiting CK2 alpha 2 (CK2a2) kinase activity, wherein the method comprises step of: contacting cells with a compound of the first aspect of the present invention, or a pharmaceutically acceptable salt, a solvate, a stereoisomer or a prodrug, thereby inhibiting the activity of CK2 alpha 2 (CK2a2) kinase.

In another preferred embodiment, the ratio of IC50 value of the compound for CK2 alpha 2 (CK2a2) to that for GSK3 beta is less than 1/5, preferably less than 1/10, more preferably less than 1/20.

In another preferred embodiment, the method in any of the $7^{th}$ to $13^{th}$ aspect is in vivo or in vitro method.

It should be understood that each of the above technical features of the invention and each technical feature specifically described below (such as in Examples) can be combined with each other within the scope of the present invention so as to constitute new or preferred technical solutions.

DETAILED DESCRIPTION OF INVENTION

After extensive and intensive research, the inventors have unexpectedly developed a novel compound of formula I that effectively stimulate proliferation and regeneration of cardiomyocytes. In addition, the inventors also have unexpectedly found these compounds can effectively inhibit certain kinases which are related to proliferation and/or regeneration of cardiomyocytes, such as HIPK1, HIPK2, CK2 alpha 2, and CIT. The present invention is completed on this basis.

Definition of Terms

As used herein, term "C1-6 alkyl" refers to a straight or branched saturated aliphatic hydrocarbon group having 1 to 6 carbon atoms, for example, methyl, ethyl, propyl, isopropyl, n-butyl, iso-butyl, tert-butyl, pentyl, hexyl and the like, and preferably alkyl having 1 to 4 carbon atoms, and more preferably alkyl having 1 to 3 carbon atoms.

As used herein, term "C2-6 alkenyl" refers to a straight or branched unsaturated aliphatic hydrocarbon group having 2 to 6 (preferably 2 to 4) carbon atoms and carbon-carbon double bond (C═C), for example ethenyl, propenyl, isopropenyl, n-butenyl, iso-butenyl, pentenyl, hexenyl and the like.

As used herein, term "C2-6 alkynyl" refers to a straight or branched unsaturated aliphatic hydrocarbon group having 2 to 6 (preferably 2 to 4) carbon atoms and carbon-carbon triple bond, for example ethynyl, propynyl, n-butynyl, isobutynyl, pentynyl, hexynyl and the like.

As used herein, term "C3-8 cycloalkyl" refers to cycloalkyl having 3 to 8 carbon atoms, for example cyclopropyl, cyclobutyl, cyclopentyl, cyclohexyl and the like.

As used herein, term "C1-4 alkoxy" refers to C1-4 alkyl-O—, for example methoxy, ethoxy, propoxy, butoxy and the like.

As used herein, term "C6-10 aryl" refers to aromatic hydrocarbon group having 6 to 10 carbon atoms, for example phenyl, naphthyl and the like. As used herein, term "halogen" refers to fluorine, chlorine, bromine or iodine.

As used herein, term "divalent C1-4 hydrocarbyl" refers to a straight or branched alkylidene(or "alkylene group"), alkenylidene or alkynylidene, wherein, "alkylidene" or "alkylene group" refers to divalent alkyl, for example, methylidene, ethylidene and the like; and "alkenylidene" refers to divalent alkenyl. "Alkylidene is replaced" refers to the methylidene in the divalent straight or branched $C_{1-3}$ hydrocarbyl may be replaced with the groups as defined herein, for example, it is $—CH_2—S(O)—CH_2—$, $—CH_2—C(O)NR^y—CH_2—$, $—C(O)—CH_2—CH_2—$, $—CH_2—C(R^yR^x)—CH_2—$, $—N(R^y)—CH_2—CH_2—$, $—C(R^yR^x)—C(R^yR^x)—CH_2—$ and the like after replacement.

Unless specifically defined, the term "cycloalkyl" is also meant to refer to bicyclic and polycyclic hydrocarbon rings such as, for example, bicyclo[2.2.1]heptane, bicyclo[2.2.2]octane, etc.

Unless specifically defined, the term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

Unless specifically defined, the term "aryl" means, unless otherwise stated, a polyunsaturated, typically aromatic, hydrocarbon group which can be a single ring or multiple rings (up to three rings) which are fused together or linked covalently.

Unless specifically defined, the term "heteroaryl" refers to aryl groups (or rings) that contain from one to five heteroatoms selected from N, O, and S, wherein the nitrogen and sulfur atoms are optionally oxidized, and the nitrogen atom (s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzooxazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, pyrrolopyridyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

Pharmaceutical Composition

Generally, the compound of the present invention or a pharmaceutically acceptable salt solvate, stereoisomer, or prodrug thereof may form a suitable dosage form for administration with one or more pharmaceutically acceptable carriers. These dosage forms are suitable for oral, rectal, topical, intraoral administration, and other parenteral administration (e.g., subcutaneous, intramuscular, intravenous administration, etc.). For example, dosage forms suitable for oral administration include capsules, tablets, granules and syrups. Compounds of the present invention contained in these formulations may be solid powders or granules; solutions or suspensions in aqueous or non-aqueous liquid; water-in-oil or oil-in-water emulsions etc. Such dosage forms may be prepared with active compounds and one or more carriers or excipients through the conventional pharmacy methods. The above-mentioned carriers should be compatible with active compounds or other excipients. For solid formulations, conventional non-toxic carriers include, but not limited to mannitol, lactose, starch, magnesium stearate, cellulose, glucose, sucrose and the like. Carriers used for liquid preparations include water, saline, aqueous dextrose, ethylidene glycol, polyethylidene glycol and the like. The active compounds may form a solution or suspension with the above-mentioned carriers.

The compositions of the present invention are formulated, quantified and administrated in a manner consistent with the practice of medicine. The "effective amount" of the administrated compound depends on the factors such as the specific disease to be treated, the individual being treated, the cause of diseases, the drug targets and the mode of administration, etc.

As used herein, term "pharmaceutically acceptable salt (s)" includes pharmaceutically acceptable acid addition salt (s) and base addition salt(s).

As used herein, term "Pharmaceutically acceptable acid addition salts" refer to salts that are able to retain the biological effectiveness of the free base without other side effects and are formed with inorganic or organic acids. Inorganic acid salts include, but not limited to, hydrochloride, hydrobromide, sulfate, phosphate and the like; organic acid salts include, but not limited to, formate, acetate, propionate, glycolate, gluconate, lactate, oxalate, maleate, succinate, fumarate, tartrate, citrate, glutamate, aspartate, benzoate, methanesulfonate, p-toluenesulfonate, salicylate and the like. These salts can be prepared by the methods known in the art.

"Pharmaceutically acceptable base addition salts" include, but not limited to the salts of inorganic bases such as sodium, potassium, calcium and magnesium salts, and include but not limited to the salts of organic bases, such as ammonium salt, triethylamine salt, lysine salt, arginine salt and the like. These salts can be prepared by the methods known in the art.

As used herein, the compounds of formula (I) may exit in one or more crystalline forms. The active compounds of the present invention include various polymorphs and mixtures thereof.

The "solvate" mentioned in the present invention refers to a complex formed with the compound of the present invention and a solvent. The solvate can be formed either through a reaction in a solvent or precipitated or crystallized from the solvent. For example, a complex formed with water is referred to as "hydrate". The solvates of the compounds of formula (I) are within the scope of the present invention.

The compounds of formula (I) of the invention may contain one or more chiral centers, and may exist in different optically active forms. When the compound contains one chiral center, the compound includes enantiomers. The present invention includes both of two isomers and a mixture thereof, such as racemic mixtures. Enantiomers can be resolved using methods known in the art, such as crystallization and chiral chromatography and the like. When the compound of formula (I) contain more than one chiral centers, the compounds may include diastereomers. The present invention includes specific isomers resolved into optically pure isomers as well as the mixtures of diastereomeric isomers. Diastereomeric isomers can be resolved using methods known in the art, such as crystallization and preparative chromatography.

The present invention includes prodrugs of the above-mentioned compounds. Prodrugs include known amino protecting groups and carboxyl protecting groups which are hydrolyzed under physiologic conditions or released by enzyme reaction to obtain the parent compounds. Specific preparation methods of prodrugs can refer to (Saulnier, M G; Frennesson, D B; Deshpande, M S; Hansel, S B and Vysa, D M Bioorg. Med. Chem Lett. 1994, 4, 1985-1990; and Greenwald, R B; Choe, Y H; Conover, C D; Shum, K.; Wu, D.; Royzen, M. J. Med. Chem. 2000, 43, 475).

As used herein, term "therapeutically effective amount" refers to an amount that yields a function or activity to humans and/or animals and may be tolerated by humans and/or animals.

The pharmaceutical composition provided by the present invention preferably contains the active ingredient in a weight ratio of 1 to 99%. Preferably, the compound of the general formula I accounts for 65 wt % to 99 wt % of the total weight as the active ingredient, and the rest are pharmaceutically acceptable carriers, diluents, solutions or salt solutions.

The compounds and pharmaceutical compositions provided by the present invention may be in various forms, such as tablets, capsules, powders, syrups, solutions, suspensions, aerosols, etc., and may be present in suitable solid or liquid carriers or diluents, and in disinfectors suitable for injection or instillation.

Various dosage forms of the pharmaceutical compositions of the present invention can be prepared according to the conventional preparation methods in the pharmaceutical field. The unit dosage of its formulation formula comprises 0.05-200 mg of the compound of formula I, preferably, the unit dosage of the formulation formula contains 0.1 mg-100 mg of the compound of formula I.

The compounds of the present invention may be administered alone or in combination with other pharmaceutically acceptable compounds (such as other drugs for treating heart diseases).

The compounds and pharmaceutical compositions of the present invention can be used clinically in mammals, including humans and animals, and can be administered via mouth, nose, skin, lung or gastrointestinal tract. Most preferred is oral. The most preferred daily dose is 0.01-200 mg/kg body weight in one dose, or 0.01-100 mg/kg body weight in divided doses. Regardless of the administering method, the individual's optimal dose should be based on the specific treatment. Usually, it starts with a small dose, which is gradually increased until the most suitable dose is found.

Preparation Method

The present invention provides preparation methods of compounds of formula (I). The compounds of the present invention can be easily prepared by a variety of synthetic operations, and these operations are familiar to those skilled in the art. An exemplary preparation of these compounds may include (but not limited to) the processes described below.

Generally, in the preparation process, each reaction is generally conducted in an inert solvent, under room temperature to reflux temperature (such as 0-150° C., preferably from 0-100° C.). The reaction time is usually 0.1 hours-60 hours, preferably 0.5 to 48 hours.

Preferably, Compounds of formula (I) of the present invention can be prepared referring to the following schemes. The procedures of method can be extended or combined as desired in practice.

Scheme 1

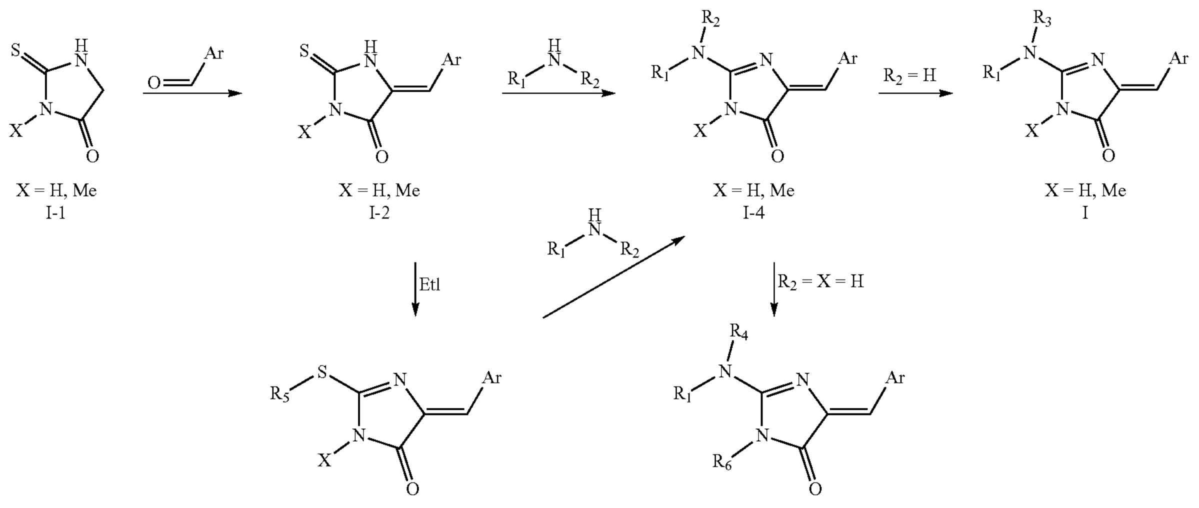

X = H, Me I-1; X = H, Me I-2; X = H, Me I-4; X = H, Me I; I-3; I

Scheme shows one route that can be used to access most of the targets synthesized in this patent. Intermediate I-1 can be made using route described in Rou et al., N.; Bergman, J. Synthesis of the marine alkaloid leucettamine B. Tetrahedron 1999, 55, 14729-14738 and J. Med. Chem. 2011, 54, 4172-((186. Compounds of formula I-1 are available commercially or prepared through methods known to the skilled in the art based on literature reported conditions (J. Med. Chem 2015, 58(17), 6889; WO2014188193, 2014) The reagent aldehyde and amines used to make the targets are also commercially available or can be prepared through methods known to those skilled in the art.

Compound I-1 can be prepared by the following reaction.

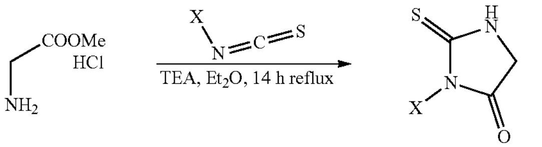

Reaction of I-1 with aldehyde using catalytic base such as Et3N, DIPEA, piperidine, etc in alcoholic or aprotic solvent will provide intermediate 1-2. This intermediate then can be reacted in the presence of an oxidang such as TBHP and amines, either primary or secondary amines, to give the desired targets 1-4. Detailed conditions mentioned have been described in the J. Med, Chem. 2011, 54, 4172-486. In the case of primary amines (R2=H), the product 1-4 can be treated with acid chlorides, sulfonyl chlorides and alkyl halides in the presence of base such as NaH, $K_2CO_3$, $Et_3N$, DIPEA, etc to give the amide, sulfonamide or di-alkyl amino targets I where $R_3$ is $COR_7$, $SO_2R7$ or alkyl groups.

1-2 can also be alkylated with R3X where R3 is alkyl and X is halide or O-sulfones to give 1-3. This can then be reacted with primary or secondary amines in the presence of base (alkyl amines or inorganic base) to give 1-4. This can further be reacted with R6X to give alkylated targets I where $R_4$ is also alkyl. If $R_2$ is H, then both $R_4$ and $R_6$ can be the same after alkylation with $R^6X$.

Compounds of formula (I), preparation methods thereof, pharmaceutical compositions and treatment protocols disclosed in the present invention can be achieved by the person skilled in the art through appropriate improvements of process parameters referring to this disclosure of invention. It should be particularly noted that all such alterations and changes are obvious to the skilled artisan, and they are deemed to be included in the present invention. Preferred embodiments of products, methods and applications of the present invention have been described, and relevant personnel can obviously alter or change and combine the methods and uses of the present invention without departing from the content, spirit and scope of the present invention for implementation and application of the present technology.

Compared with the prior art, the main advantages of the present invention include:

(1) The compounds of the present invention show a high inhibitory activity against CLK1 (such as CLK1A) and DYRK1.

(2) Several of the key compounds with myocyte growth activity also show inhibitory activity against HIPK1, HIPK2, CK2 and/or CIT kinases.

(3) The compounds of the present invention exhibit selectivity against GSKb.

(4) Most importantly, the compounds of the present invention exhibit superior myocyte proliferation activity, and therefore are useful for treating heart diseases relating to cardiomyocyte.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Unless defined otherwise, terms used herein are the same as those familiar to the skilled in the art. Moreover, any method or material similar or equivalent to those recorded in the present invention can be used in the present invention.

Reagents and Instruments

All reactions were conducted under an atmosphere of dry nitrogen unless specified otherwise. Reactions were monitored with TLC plates, which were visualized with u.v. light or appropriate stains. Flash chromatography refers to column chromatography over silica gel (40-60 μm) using glass columns. Alternatively, automated chromatography was performed using ISCO, Biotage SP1 or Biotage Isolera systems with u.v. detection at 220 or 254 nm and employing Biotage normal phase or reverse phase silica cartridges. Further details can be found under the relevant experimental procedure.

The following system was used for LCMS: Agilent 6120 (binary pump), Waters CORTECS column C18, 2.7 μm, 4.6x30 mm, 45° C., 1 μL injection volume, 1.8 mL/min, with a gradient of acetonitrile in 0.05% aqueous formic acid according to the following timings:

| Time(min) | Acetonitrile (0.05% FA) (%) | $H_2O$ (0.05% FA) (%) |
|---|---|---|
| 0.00 | 5 | 95 |
| 0.80 | 95 | 5 |
| 1.60 | 95 | 5 |
| 1.61 | 5 | 95 |
| 2.00 | 5 | 95 |

The following systems were used for UPLC (no mass spectrometry): Waters H-Class (quaternary pump), Waters ACQUITY BEH C18 1.7 μm, 2.1x50 mm, 0.5 mL/min, 45° C.; gradient 5-95% acetonitrile in 0.05% aqueous trifluoroacetic acid over 2 min, then hold 95% acetonitrile 0.5 min. re-equilibrate back to 5% Acetonitrile to 2.7 min, Total 3.5 min. NMR spectra were measured with a Bruker spectrometer operating at 400 MHz (1H), 376 MHz (19F) or 100 MHz (13C). Solvents used for samples are specified in the experimental procedures for each compound.

$^1$HNMR: Bruker AVANCE-400 NMR machine. The internal standard was tetramethylsilane (TMS).

Preparative high performance liquid chromatography (pre-HPLC): Waters PHW007, column XBridge C18, 4.6×150 mm, 3.5 um.

Using ISCO Combiflash-Rf75 or Rf200 automatic eluting column instrument, Agela 4 g, 12 g, 20 g, 40 g, 80 g, 120 g disposable silica gel column.

The known starting materials of the invention are synthesized by the methods known in the art, or are purchased from Bide Chemical ltd., Bridge, Combi Blocks, Wuxi Lab Networks, Acros Organics, Aldrich Chemical Company, Accela ChemBio Inc and Darui Chemical Company etc.

All examples were performed under nitrogen or argon atmosphere and the solution refers to aqueous solution if without special explanation.

In the examples, the reaction process was monitored by thin layer chromatography (TLC), compounds were purified by column chromatography. The eluent used in Column chromatography or TLC were selected from a system of dichloromethane and methanol, n-hexane and ethyl acetate, petroleum ether and ethyl acetate, or acetone and the like, wherein the volume ratio of the solvents might be regulated according to the different polarity of compounds.

DMF refers to dimethylformamide, DMSO refers to dimethylsulfoxide, THF refers to tetrahydrofuran, DIEA refers to N,N-diisopropylethylamine, EA refers to ethyl acetate, PE refers to petroleum ether. BINAP refers to (2R, 3S)-2,2'-bis diphenylphosphino-1,1'-binaphthyl, NBS refers to N-bromosuccinimide, NCS refers to N-chlorosuccinimide, Pd2(dba)3 refers to tris(dibenzylideneacetone)dipalladium, Pd(dppf)Cl2 refers to [1,1'-bis(diphenylphosphino)ferrocene] palladium dichloride.

As used herein, room temperature refers to be about 25° C.

Example 1

(Z)-5-(benzo[d][1,3]dioxol-5-ylmethylene)-2-(methyl(phenyl)amino)-3,5-dihydro-4H-imidazol-4-one

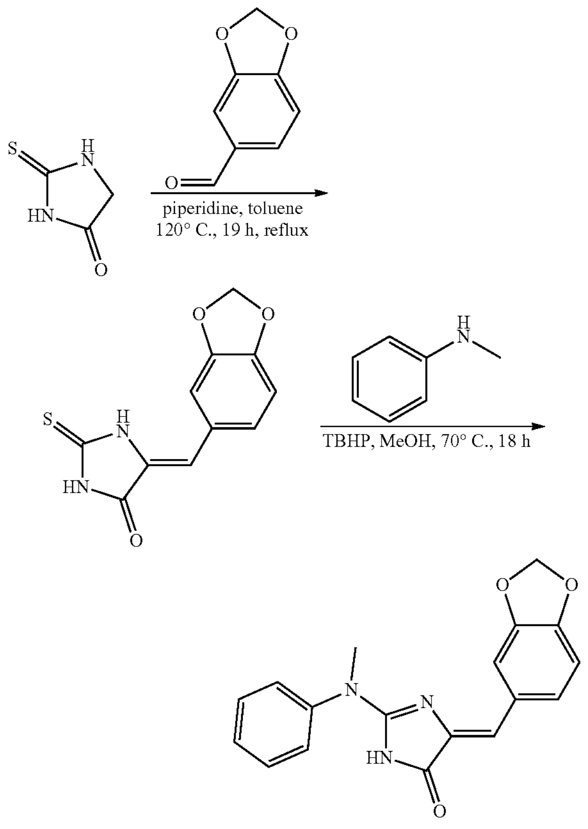

TJU-B115

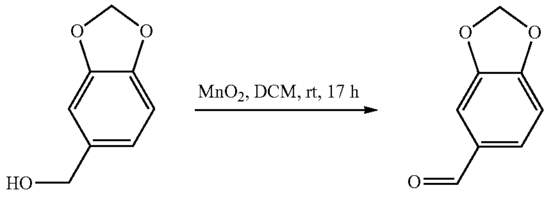

To a solution of benzo[d][1,3]dioxol-5-ylmethanol (10.0 g, 65.7 mmol) in DCM (150 mL) was added activated $MnO_2$ (57.0 g, 657 mmol) and the mixture was stirred at 40° C. for 17 h. After filtration, the filtrate was concentrated to afford benzo[d][1,3]dioxole-5-carbaldehyde (9.8 g, 99%) as a white solid which was used for the next step without further purification. LRMS (M+H$^+$) m/z calculated 151.0, found 151.0.

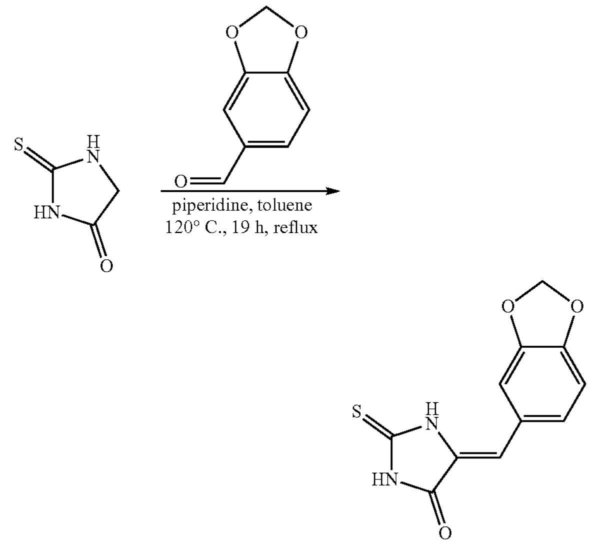

To a mixture of 2-thioxoimidazolidin-4-one (1.9 g, 17 mmol) and benzo[d][1,3]dioxole-5-carbaldehyde (3.0 g, 20.4 mmol) in toluene (30 mL) was added piperidine (71 mg, 0.85 mmol) and the mixture was stirred at 120° C. for 19 h. After concentration, the residue was recrystallized from DCM (30 mL) to afford (Z)-5-(benzo[d][1,3]dioxol-5-ylmethylene)-2-thioxoimidazolidin-4-one (3.8 g, 90%) as a yellow solid which was used for the next step without further purification. LRMS (M+H) m/z calculated 249.0, found 249.0.

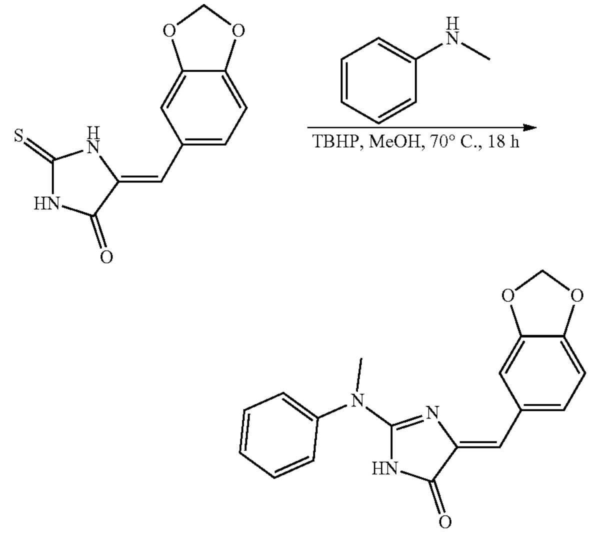

TJU-B115

To a mixture of (Z)-5-(benzo[d][1,3]dioxol-5-ylmethylene)-2-thioxoimidazolidin-4-one (600 mg, 2.4 mmol) and aniline (2235 mg, 24 mmol) in methanol (8 mL) was added a solution of TBHP (70% in water, 649 mg, 7.2 mmol) and the mixture was stirred at room temperature for 17 h. The reaction mixture was concentrated to remove excess aniline and the residue was recrystallized from MeOH (20 mL) to afford (Z)-5-(benzo[d][1,3]dioxol-5-ylmethylene)-2-(methyl(phenyl)amino)-3,5-dihydro-4H-imidazol-4-one (65.0 mg, 35%) as a yellow solid. LRMS (M+H$^+$) m/z calculated 322.1, found 322.1. $^1$H NMR (400 MHz, DMSO-d6) δ 10.96 (s, 1H), 7.93 (d, J=1.4 Hz, 1H), 7.47-7.38 (m, 5H), 7.34-7.27 (m, 1H), 6.91 (d, J=8.0 Hz, 1H), 6.37 (s, 1H), 6.03 (s, 2H), 3.48 (s, 3H).

Example 2

(Z)-5-(benzo[d][1,3]dioxol-5-ylmethylene)-3-benzyl-2-(benzyl(phenyl)amino)-3,5-dihydro-4H-imidazol-4-one

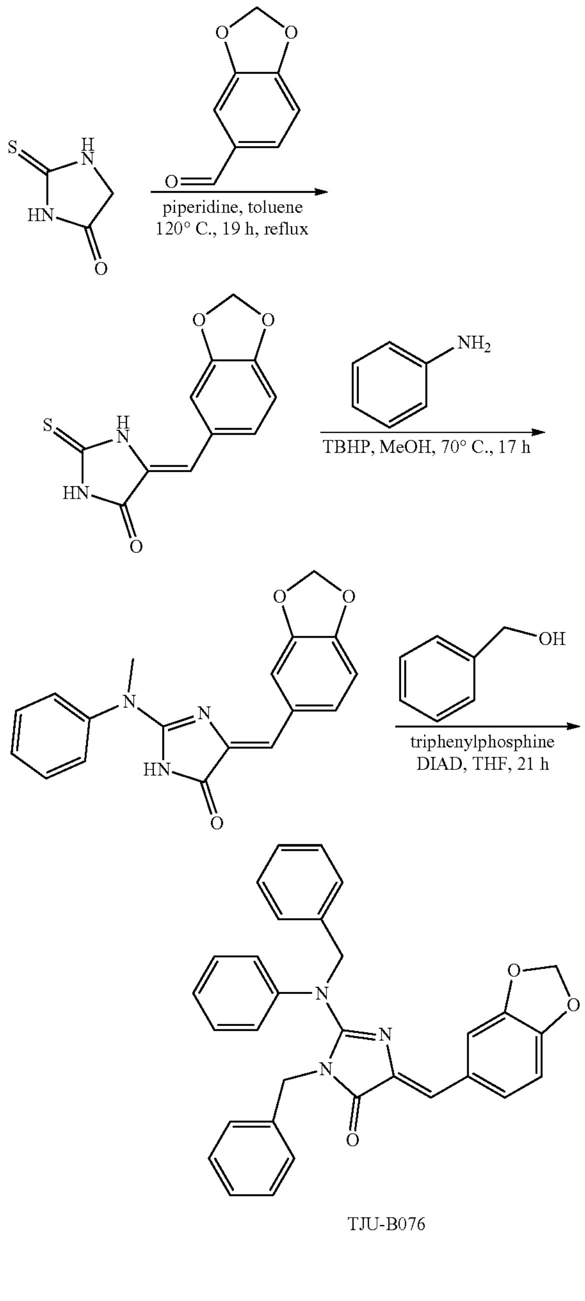

TJU-B076

-continued

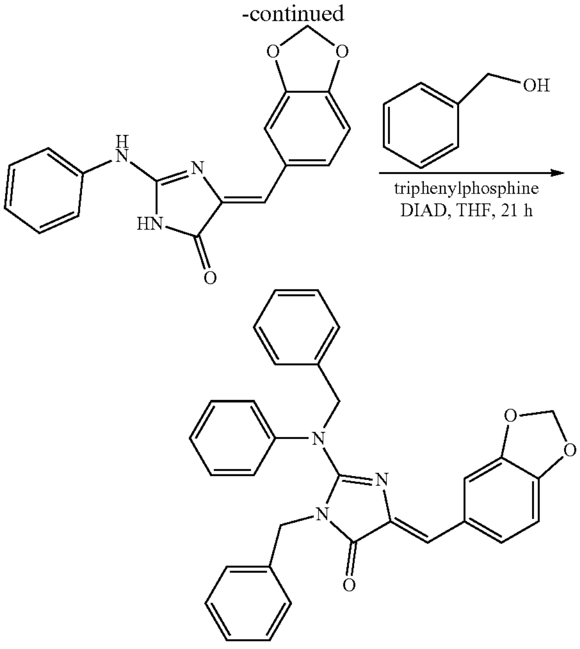

To a mixture of (Z)-5-(benzo[d][1,3]dioxol-5-ylmethylene)-2-(phenylamino)-3,5-dihydro-4H-imidazol-4-one (46 mg, 0.15 mmol), phenylmethanol (21 mg, 0.195 mmol) and triphenylphosphine (59 mg, 0.225 mmol) in THF (1 mL) was added DIAD (46 mg, 0.225 mmol) at room temperature. The mixture was stirred at room temperature for 21 h under $N_2$ protection. The reaction mixture was concentrated and the residue was purified by flash column chromatography on silica gel (EA/PE=1/1, v/v) to afford (Z)-5-(benzo[d][1,3]dioxol-5-ylmethylene)-3-benzyl-2-(benzyl(phenyl)amino)-3,5-dihydro-4H-imidazol-4-one (10 mg, 9%) as a yellow solid.

LRMS ($M+H^+$) m/z calculated 488.2, found 488.2. $^1H$ NMR (400 MHz, DMSO-d6) δ 7.29-6.95 (m, 16H), 6.60 (t, J=20.0 Hz, 3H), 6.08 (s, 2H), 4.79 (s, 2H), 4.34 (s, 2H).

Example 3

(Z)-5-(benzo[d][1,3]dioxol-5-ylmethylene)-3-methyl-2-(methyl(phenyl)amino)-3,5-dihydro-4H-imidazol-4-one

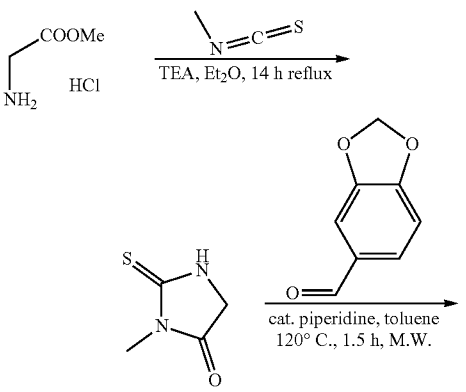

-continued

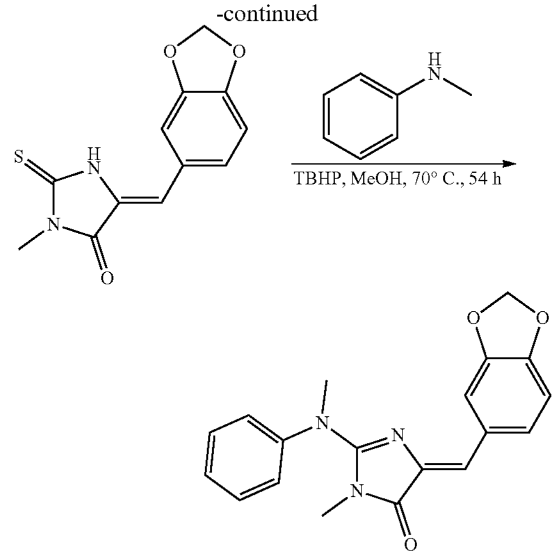

TJU-B116

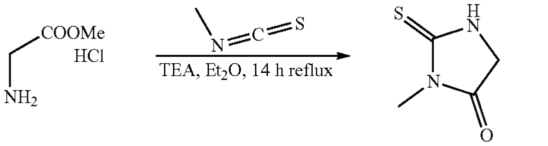

A suspension of methyl glycinate hydrochloride (10 g, 0.08 mol), methyl isothiocyanate (5.84 g, 0.08 mol), and triethylamine (8.08 g, 0.08 mol) in dry ether (150 mL) was stirred 38° C. for 14 h under $N_2$ atmosphere. The solvent was removed in vacuo, then EtOAc (200 mL) was added, the insoluble salt ($Et_3N$. HCl) was filtered off and the filtrate was concentrated and the residue was purified via column chromatography (DCM/MeOH=1/0 to 20/1, v/v) to give 3-methyl-2-thioxoimidazolidin-4-one (6.5 g, 63%) as a yellow solid. LRMS ($M+H^+$) m/z calculated 131.0, found 131.0. $^1H$ NMR (400 MHz, DMSO-d6) δ 7.53 (br, 1H), 4.10 (s, 2H), 3.26 (s, 3H).

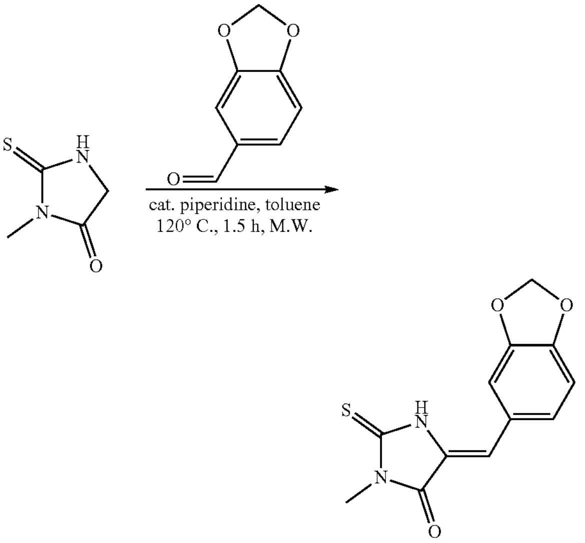

To a suspension of 3-methyl-2-thioxoimidazolidin-4-one (200 mg, 1.538 mmol) and 3,4-dimethoxybenzaldehyde (692 mg, 4.615 mmol) in toluene (5 mL) was added piperidine (7 mg, 0.076 mmol) and the reaction mixture was stirred at 120° C. for 1.5 h under microwave irradiation. The mixture was filtered and the filter cake was washed with $Et_2O$ to afford (Z)-5-(3,4-dimethoxybenzylidene)-3-methyl-2-thioxoimidazolidin-4-one (330 mg, 77%) as a yellow solid. LRMS (M+H$^+$) m/z calculated 263.1, found 263.1.

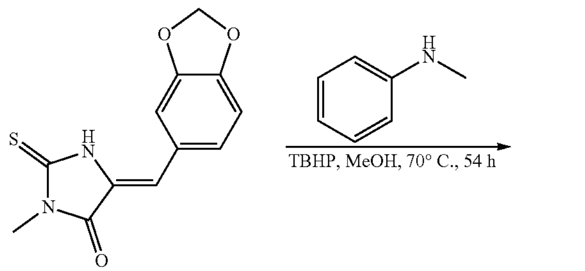

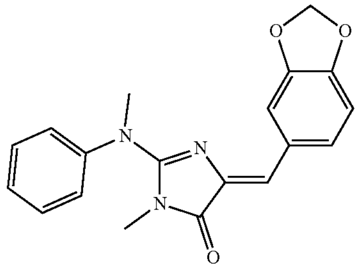

TJU-B116

To a mixture of (Z)-5-(benzo[d][1,3]dioxol-5-ylmethylene)-3-methyl-2-thioxoimidazolidin-4-one (628 mg, 2.4 mmol) and N-methylaniline (2568 mg, 24 mmol) in methanol (8 mL) was added a solution of TBHP (70% in water, 649 mg, 7.2 mmol). The mixture was stirred at room temperature for 17 h. The reaction mixture was concentrated to remove excess aniline and the residue was recrystallized from MeOH (20 mL) to afford (Z)-5-(benzo[d][1,3]dioxol-5-ylmethylene)-3-methyl-2-(methyl(phenyl)amino)-3,5-dihydro-4H-imidazol-4-one (53.0 mg). LRMS (M+H$^+$) m/z calculated 336.1, found 336.1. $^1$H NMR (400 MHz, DMSO-d6) δ 8.02 (d, J=1.5 Hz, 1H), 7.55-7.53 (m, 1H), 7.49-7.45 (m, 2H), 7.36-7.31 (m, 3H), 6.98 (d, J=8.0 Hz, 1H), 6.64 (s, 1H), 6.07 (s, 2H), 3.50 (s, 3H), 2.44 (s, 3H).

Example 4

(Z)-5-(benzo[d][1,3]dioxol-5-ylmethylene)-2-(ethyl (phenyl)amino)-3,5-dihydro-4H-imidazol-4-one

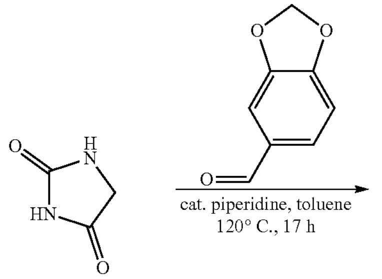

-continued

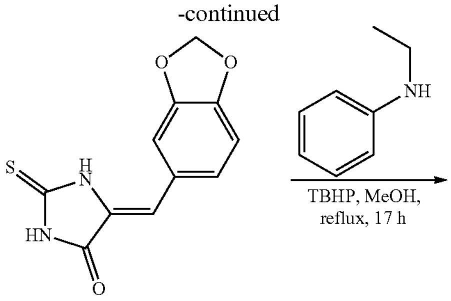

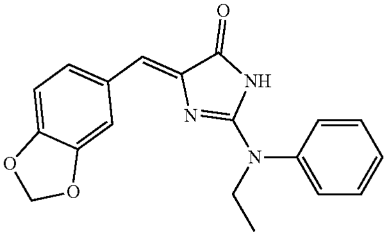

TJU-B182

(Z)-5-(benzo[d][1,3]dioxol-5-ylmethylene)-2-(ethyl(phenyl)amino)-3,5-dihydro-4H-imidazol-4-one (3.9 mg) was prepared in the same procedure as described for Example 1. LRMS (M+H$^+$) m/z calculated 336.1, found 336.2. $^1$H NMR (400 MHz, DMSO-d6) δ 10.82 (s, 1H), 7.92 (s, 1H), 7.49-7.46 (m, 2H), 7.38-7.34 (m, 4H), 6.91 (d, J=8.0 Hz, 1H), 6.34 (s, 1H), 6.02 (s, 2H), 3.95 (q, J=24 Hz, 2H), 1.16 (t, J=12 Hz, 3H).

Example 5

(Z)—N-(4-(benzo[d][1,3]dioxol-5-ylmethylene)-5-oxo-4,5-dihydro-1H-imidazol-2-yl)-N-phenylacetamide

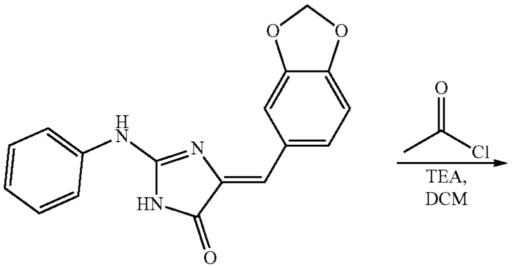

Leucettamine B, $L_{41}$
TJU-B038

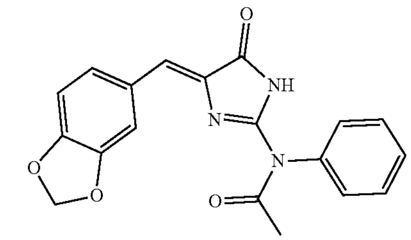

TJU-B183

To a solution of (Z)-5-(benzo[d][1,3]dioxol-5-ylmethylene)-2-(phenylamino)-3,5-dihydro-4H-imidazol-4-one (30 mg, 0.1 mmol, 1.0 equiv.) in DCM were added acetyl chloride (11.7 mg, 0.15 mmol, 1.5 equiv.) and TEA (30.3 mg, 0.3 mmol, 3.0 equiv.) at 0° C. The reaction mixture was stirred for 17 h at room temperature. After concentration, the residue was diluted with water and extracted with DCM (10 mL×3). The combined organic layer was dried over $Na_2SO_4$ and concentrated. The residue was triturated with (1 mL EA) to afford (Z)—N-(4-(benzo[d][1,3]dioxol-5-ylmethylene)-5-oxo-4,5-dihydro-1H-imidazol-2-yl)-N-phenylacetamide (5.3 mg, 17%) as a yellow solid. LRMS ($M+H^+$) m/z calculated 350.1, found 350.1. $^1H$ NMR (400 MHz, DMSO-d6) δ 10.15 (s, 1H), 7.95 (s, 1H), 7.83 (d, J=8.0 Hz, 2H), 7.54 (d, J=8.0 Hz, 1H), 7.43 (t, J=16.0 Hz, 2H), 7.17 (t, J=16.0 Hz, 1H), 7.02 (d, J=8.0 Hz, 1H), 6.76 (s, 1H), 6.10 (s, 2H), 2.63 (s, 3H).

Example 6

(Z)-5-(benzo[d]thiazol-6-ylmethylene)-2-(phenylamino)-3,5-dihydro-4H-imidazol-4-one

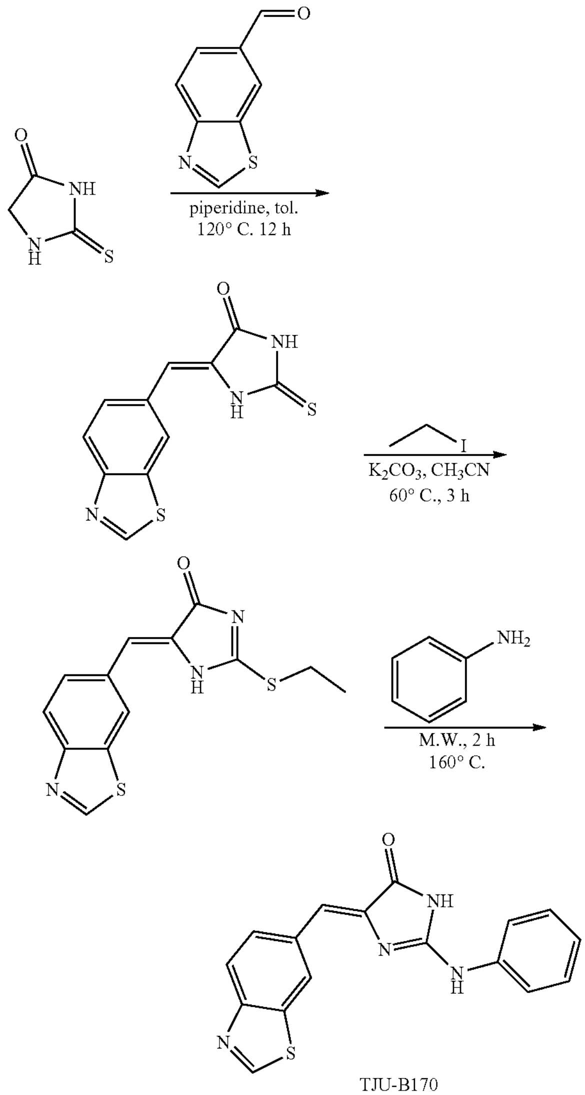

TJU-B170

-continued

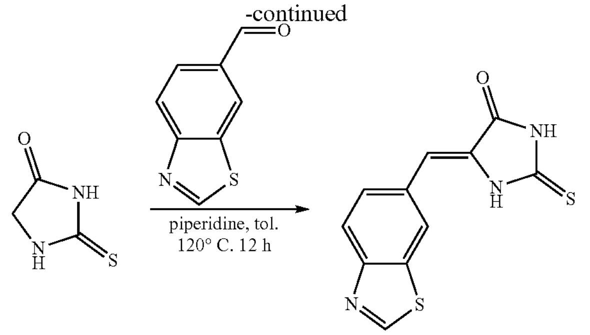

To a mixture of 2-thioxoimidazolidin-4-one (1.9 g, 17 mmol, 1.0 eq.) and benzo[d]thiazole-6-carbaldehyde (3.0 g, 20.4 mmol, 1.2 eq.) in toluene (30 mL) was added piperidine (71 mg, 0.85 mmol, 0.05 eq.) and the reaction mixture was stirred at 120° C. for 19 h. The mixture was concentrated and the residue was recrystallized from DCM (30 mL) to afford (Z)-5-(benzo[d]thiazol-6-ylmethylene)-2-thioxoimidazolidin-4-one (3.8 g, 90%) as a yellow solid which was used for the next step without further purification. LRMS ($M+H^+$) m/z calculated 263.0, found 263.0.

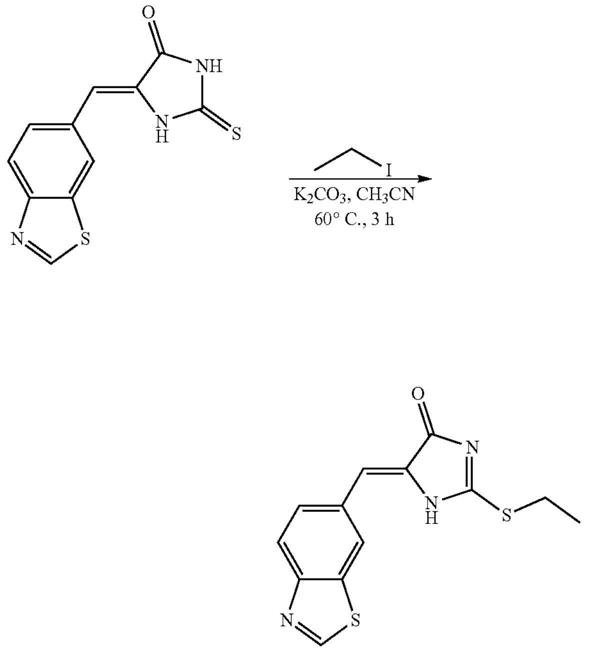

To a mixture of (Z)-5-(benzo[d]thiazol-6-ylmethylene)-2-thioxoimidazolidin-4-one (496 mg, 2.0 mmol, 1.0 eq.) in acetonitrile (6 mL) were added $K_2CO_3$ (138 mg, 1.0 mmol, 0.5 eq.) and EtI (375 mg, 2.4 mmol, 1.2 eq.) at room temperature, the mixture was stirred at 60° C. for 18 h. The mixture was concentrated and the residue was recrystallized from DCM to afford (Z)-5-(benzo[d]thiazol-6-ylmethylene)-2-(ethylthio)-1,5-dihydro-4H-imidazol-4-one (550 mg, 99%) as a yellow solid which was used for the next step. LRMS ($M+H^+$) m/z calculated 290.0, found 290.0.

-continued

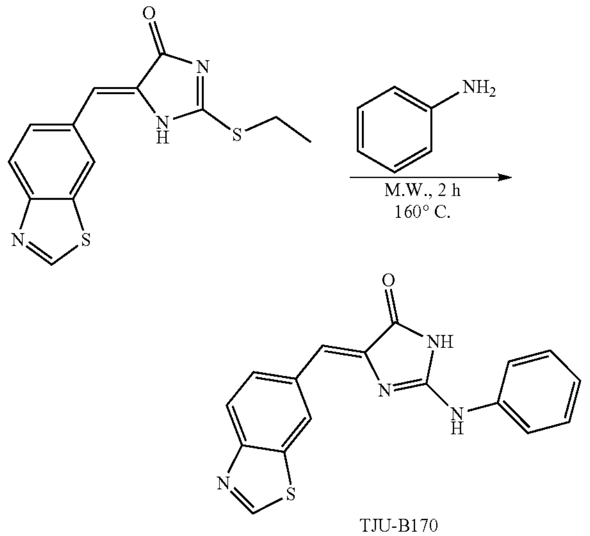

TJU-B170

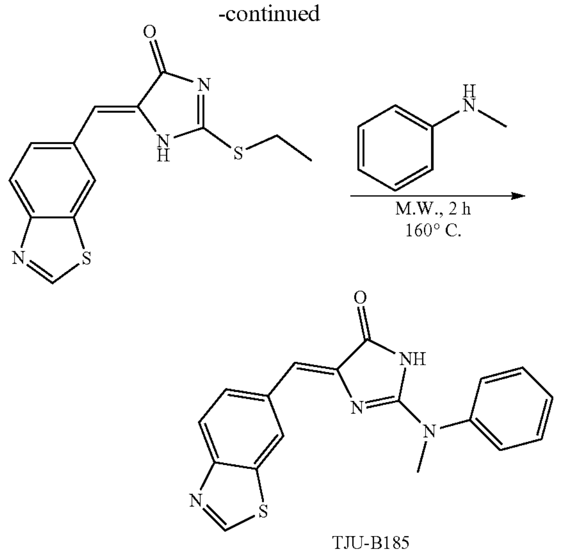

TJU-B185

A mixture of (Z)-5-(benzo[d]thiazol-6-ylmethylene)-2-(ethylthio)-1,5-dihydro-4H-imidazol-4-one (150 mg, 0.54 mmol, 1.0 eq.) and aniline (1.0 g) was stirred at 160° C. for 2 h under microwave irradiation. The reaction mixture was diluted with DCM, then the precipitate was filtered and collected by filtration to afford (Z)-5-(benzo[d]thiazol-6-ylmethylene)-2-(phenylamino)-3,5-dihydro-4H-imidazol-4-one (54 mg, 31%) as a yellow solid. LRMS $(M+H^+)$ m/z calculated 321.1, found 321.1. $^1H$ NMR (400 MHz, DMSO-d6) δ 10.81 (br, 1H), 9.95 (br, 1H), 9.41 (s, 1H), 8.86 (s, 1H), 8.35 (d, J=4.0 Hz, 1H), 8.11 (d, J=8.0 Hz, 1H), 7.82 (d, J=8.0 Hz, 2H), 7.42 (t, J=16.0 Hz, 2H), 7.12 (t, J=16.0 Hz, 1H), 6.65 (s, 1H).

Example 7

(Z)-5-(benzo[d]thiazol-6-ylmethylene)-2-(methyl (phenyl)amino)-3,5-dihydro-4H-imidazol-4-one

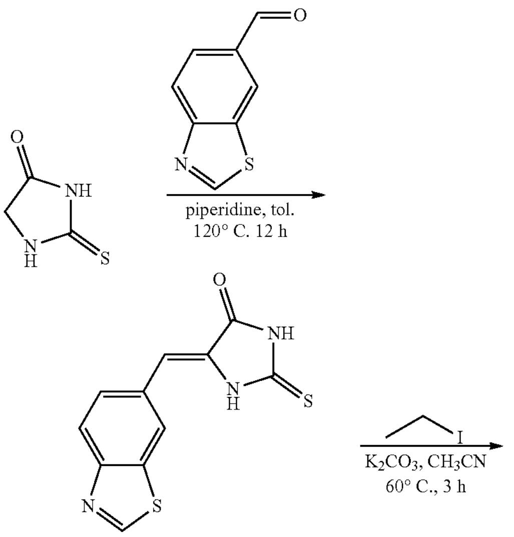

(Z)-5-(benzo[d]thiazol-6-ylmethylene)-2-(methyl(phenyl)amino)-3,5-dihydro-4H-imidazol-4-one (30 mg) was prepared in the same procedure as described for Example 6. LRMS $(M+H^+)$ m/z calculated 335.1, found 335.1. $^1H$ NMR (400 MHz, DMSO-d6) δ 11.07 (s, 1H), 9.37 (s, 1H), 8.86 (d, J=1.3 Hz, 1H), 8.30-8.28 (m, 1H), 8.04 (d, J=8.0 Hz, 1H), 7.51-7.45 (m, 4H), 7.37-7.33 (m, 1H), 6.54 (s, 1H), 3.55 (s, 3H).

Example 8

(Z)-5-((2,3-dihydrobenzo[b][1,4]dioxin-6-yl)methylene)-2-(methyl(phenyl)amino)-3,5-dihydro-4H-imidazol-4-one

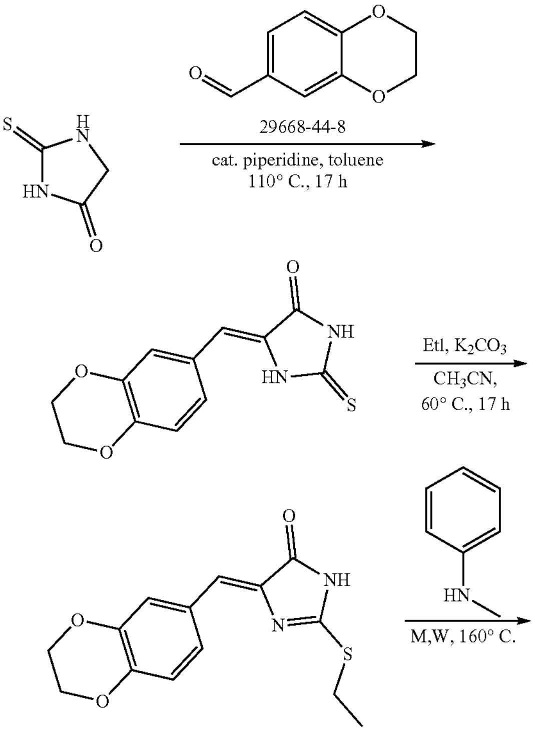

-continued

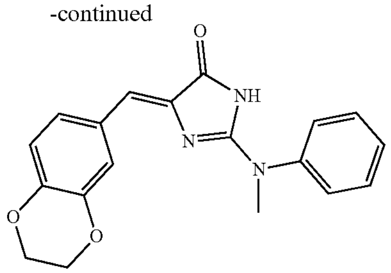

TJU-B180

(Z)-5-((2,3-dihydrobenzo[b][1,4]dioxin-6-yl)methylene)-2-(methyl(phenyl)amino)-3,5-dihydro-4H-imidazol-4-one (9.4 mg) was prepared in the same procedure as described for Example 6. LRMS (M+H) m/z calculated 336.1, found 336.1. $^1$H NMR (400 MHz, $CD_3OD$) δ 7.49 (d, J=7.6 Hz, 3H), 7.39 (d, J=5.9 Hz, 4H), 6.82 (d, J=8.4 Hz, 1H), 6.49 (s, 1H), 4.25 (d, J=2.3 Hz, 4H), 3.56 (s, 3H).

Example 9

(Z)-5-((5-oxo-2-(phenylamino)-1,5-dihydro-4H-imidazol-4-ylidene)methyl)pyridin-2(1H)-one

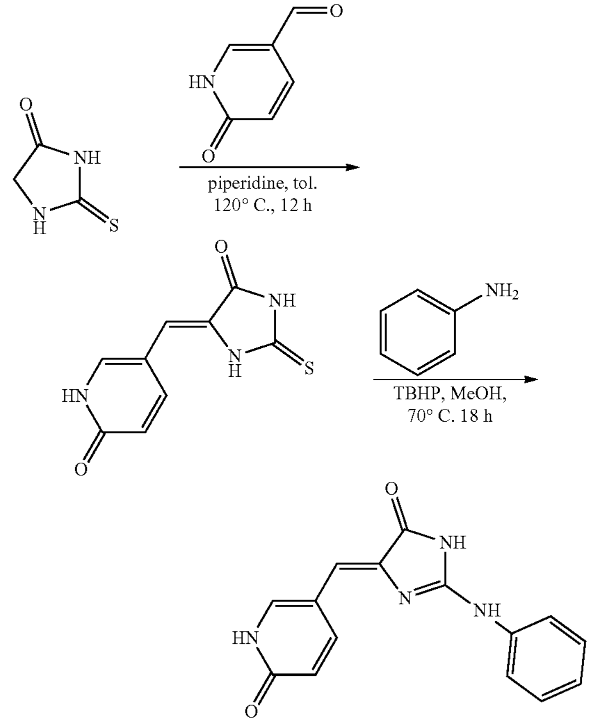

TJU-B181

(Z)-5-((5-oxo-2-(phenylamino)-1,5-dihydro-4H-imidazol-4-ylidene)methyl)pyridin-2(1H)-one (5.87 mg) was prepared in the same procedure as described for Example 1. LRMS (M+H$^+$) m/z calculated 281.1, found 281.1. $^1$H NMR (400 MHz, DMSO-d6) δ 11.90 (br, 1H), 9.72 (br, 1H), 8.30 (d, J=12.0 Hz, 1H), 8.18 (s, 1H), 7.73 (d, J=8.0 Hz, 2H), 7.37 (t, J=16.0 Hz, 2H), 7.06 (t, J=16.0 Hz, 1H), 6.41 (d, J=8.0 Hz, 2H).

Example 10

(Z)-5-(benzo[d][1,3]dioxol-5-ylmethylene)-2-((cyclopropylmethyl)(phenyl)amino)-3,5-dihydro-4H-imidazol-4-one

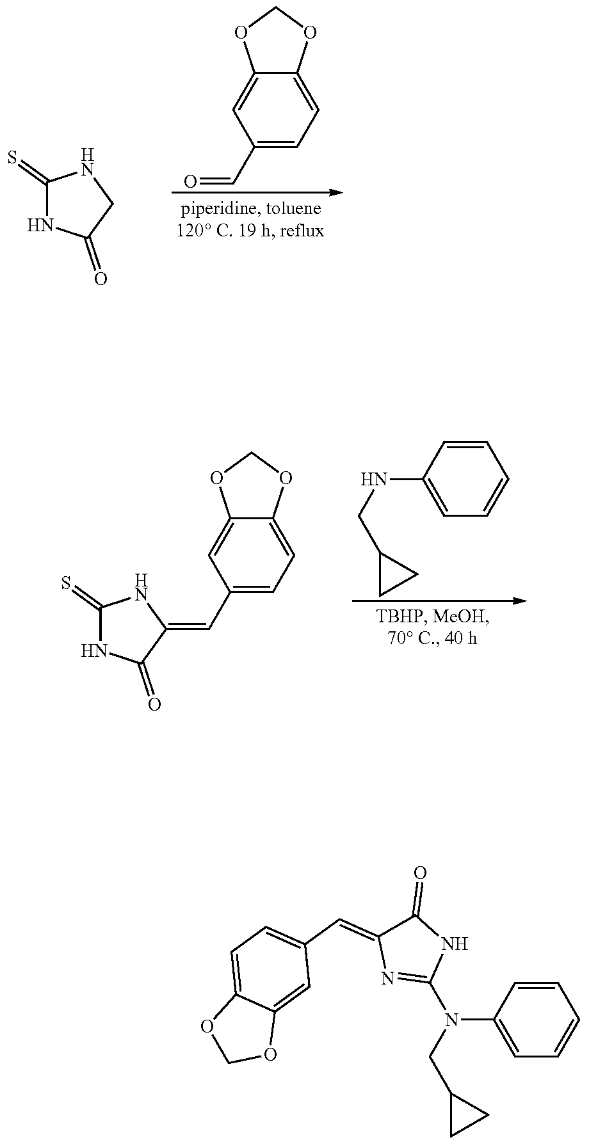

TJU-B207

(Z)-5-(benzo[d][1,3]dioxol-5-ylmethylene)-2-((cyclopropylmethyl)(phenyl)amino)-3,5-dihydro-4H-imidazol-4-one (35 mg) was prepared in the same procedure as described for Example 1. LRMS (M+H$^+$) m/z calculated 362.1, found 362.2. $^1$H NMR (400 MHz, DMSO-d6) δ 10.80 (s, 1H), 7.94 (d, J=1.4 Hz, 1H), 7.49-7.45 (m, 2H), 7.40-7.34 (m, 4H), 6.91 (d, J=8.0 Hz, 1H), 6.34 (s, 1H), 6.03 (s, 2H), 3.81 (d, J=4.0 Hz, 2H), 1.11-1.05 (m, 1H), 0.44-0.40 (m, 2H), 0.18-0.15 (m, 2H).

Example 11

(Z)-5-(benzo[d][1,3]dioxol-5-ylmethylene)-2-((cyclopropylmethyl)(methyl)amino)-3,5-dihydro-4H-imidazol-4-one

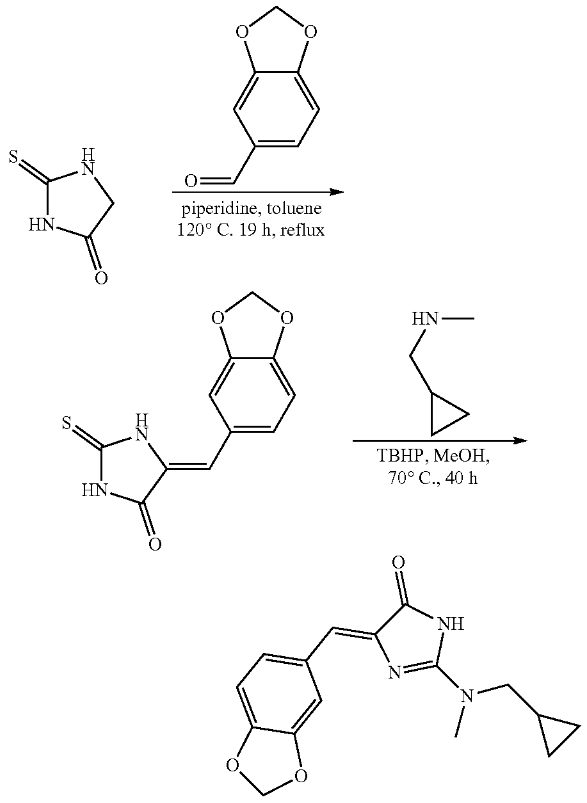

TJU-B210

(Z)-5-(benzo[d][1,3]dioxol-5-ylmethylene)-2-((cyclopropylmethyl)(methyl)amino)-3,5-dihydro-4H-imidazol-4-one (20 mg) was prepared in the same procedure as described for Example 1. LRMS (M+H) m/z calculated 300.1, found 300.1. $^1$H NMR (400 MHz, DMSO-d6) δ 11.19 (s, 1H), 7.92 (d, J=4.0 Hz, 1H), 7.37 (d, J=8.0 Hz, 1H), 6.90 (d, J=12.0 Hz, 1H), 6.24 (s, 1H), 6.02 (s, 2H), 3.36-3.32 (m, 2H), 3.13 (s, 3H), 1.10-1.05 (m, 1H), 0.51-0.48 (m, 2H), 0.32-0.29 (m, 2H).

Example 12

(Z)-5-(benzo[d][1,3]dioxol-5-ylmethylene)-2-((4-methoxyphenyl)(methyl)amino)-3,5-dihydro-4H-imidazol-4-one

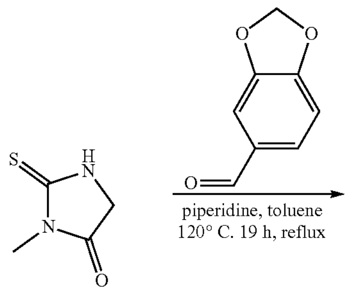

-continued

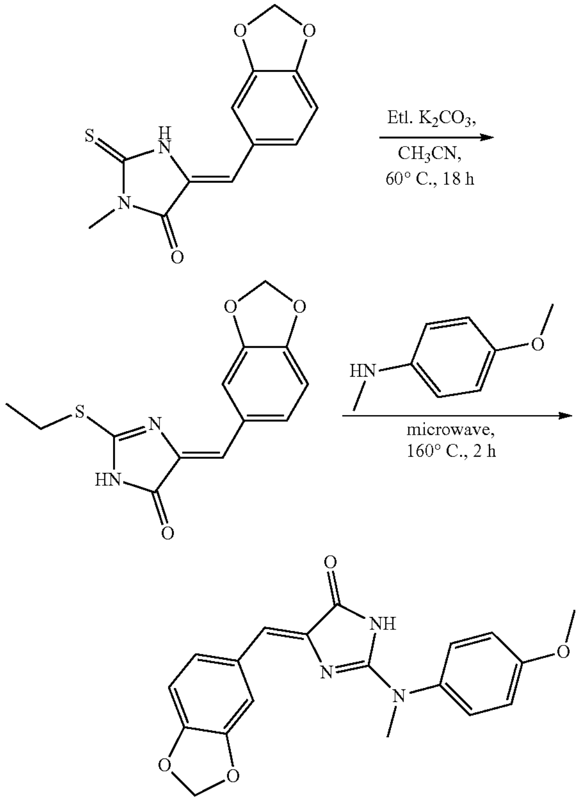

TJU-B215

(Z)-5-(benzo[d][1,3]dioxol-5-ylmethylene)-2-((4-methoxyphenyl)(methyl)amino)-3,5-dihydro-4H-imidazol-4-one (15 mg) was prepared in the same procedure as described for Example 6. LRMS (M+H$^+$) m/z calculated 352.1, found 352.1. $^1$H NMR (400 MHz, DMSO-d6) δ 10.80 (s, 1H), 7.93 (d, J=1.4 Hz, 1H), 7.41-7.38 (m, 1H), 7.35-7.31 (m, 2H), 7.02-6.98 (m, 2H), 6.91 (d, J=8.0 Hz, 1H), 6.33 (s, 1H), 6.03 (s, 2H), 3.79 (s, 3H), 3.43 (s, 3H).

Example 13

(Z)-5-(benzo[d][1,3]dioxol-5-ylmethylene)-2-((2-hydroxyethyl)(phenyl)amino)-3,5-dihydro-4H-imidazol-4-one

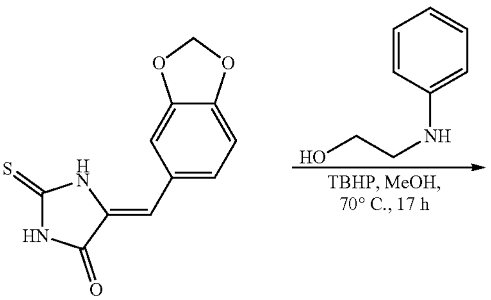

-continued

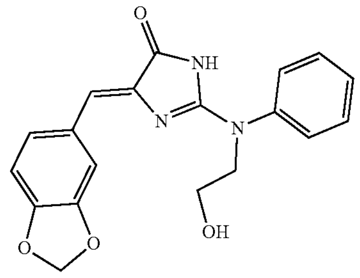

TJU-B218

(Z)-5-(benzo[d][1,3]dioxol-5-ylmethylene)-2-((2-hydroxyethyl) (phenyl)amino)-3,5-dihydro-4H-imidazol-4-one (19.30 mg) was prepared in the same procedure as described for Example 1. LRMS (M+H$^+$) m/z calculated 352.1, found 352.1. $^1$H NMR (400 MHz, DMSO-d6) δ 10.79 (br, 1H), 7.91 (s, 1H), 7.47-7.42 (m, 4H), 7.36-7.32 (m, 2H), 6.91 (d, J=8.0 Hz, 1H), 6.34 (s, 1H), 6.03 (s, 2H), 4.91 (br, 1H), 3.96 (t, J=12.0 Hz, 2H), 3.63 (t, J=12.0 Hz, 2H).

Example 14

(Z)-5-(benzo[d]thiazol-5-ylmethylene)-2-(phenylamino)-3,5-dihydro-4H-imidazol-4-one

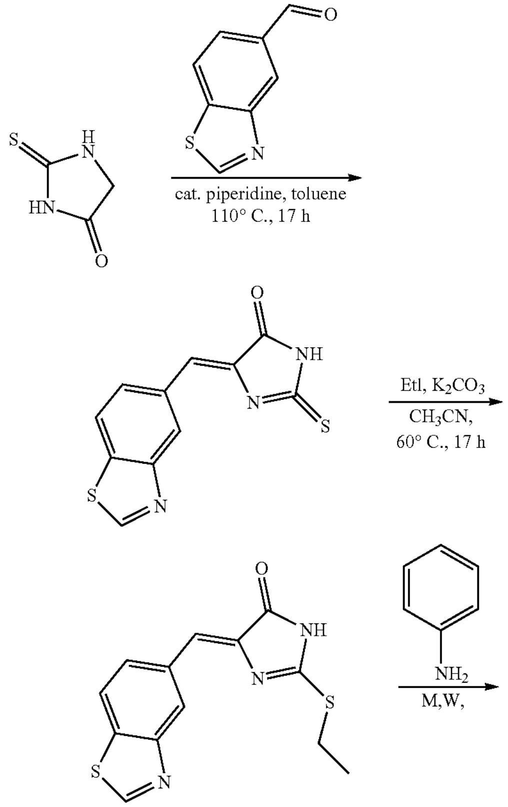

-continued

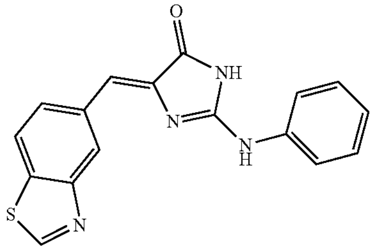

TJU-B171

(Z)-5-(benzo[d]thiazol-5-ylmethylene)-2-(phenylamino)-3,5-dihydro-4H-imidazol-4-one (6.8 mg) was prepared in the same procedure as described for Example 6. LRMS (M+H$^+$) m/z calculated 321.1, found 321.1. $^1$HNMR (400 MHz, DMSO-d6) δ 9.40 (s, 1H), 8.97 (s, 1H), 8.17 (m, 2H), 7.53 (m, 5H), 7.38 (m, 2H), 6.66 (s, 1H).

Example 15: (Z)-2-(phenylamino)-5-(thiazol-5-ylmethylene)-3,5-dihydro-4H-imidazol-4-one

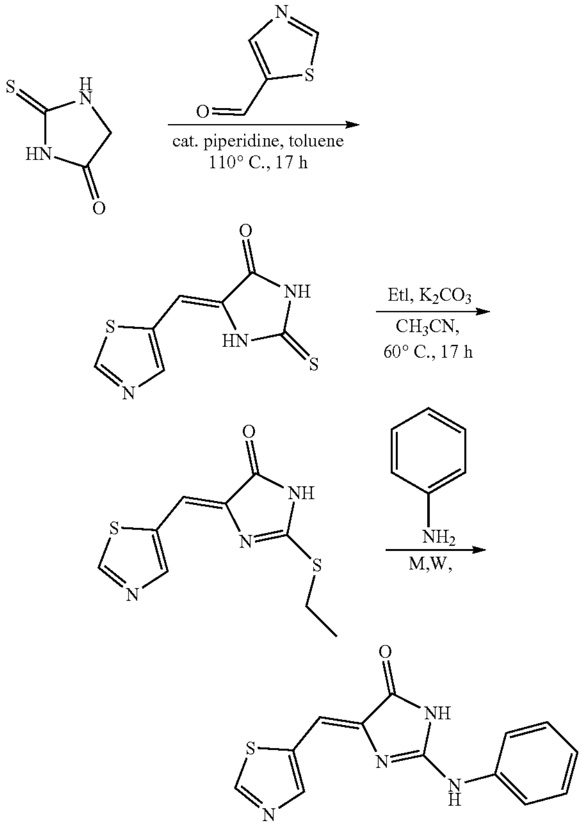

TJU-B179

(Z)-2-(phenylamino)-5-(thiazol-5-ylmethylene)-3,5-dihydro-4H-imidazol-4-one (6.6 mg) was prepared in the same procedure as described for Example 6. LRMS (M+H$^+$) m/z calculated 271.1, found 271.1. $^1$H NMR (400 MHz, DMSO-d6) δ 9.07 (s, 1H), 8.18 (s, 1H), 7.53 (d, J=7.6 Hz, 4H), 7.36-7.34 (m, 2H), 6.88 (s, 1H).

Example 16: (Z)-2-(phenylamino)-5-(quinoxalin-6-ylmethylene)-3,5-dihydro-4H-imidazol-4-one

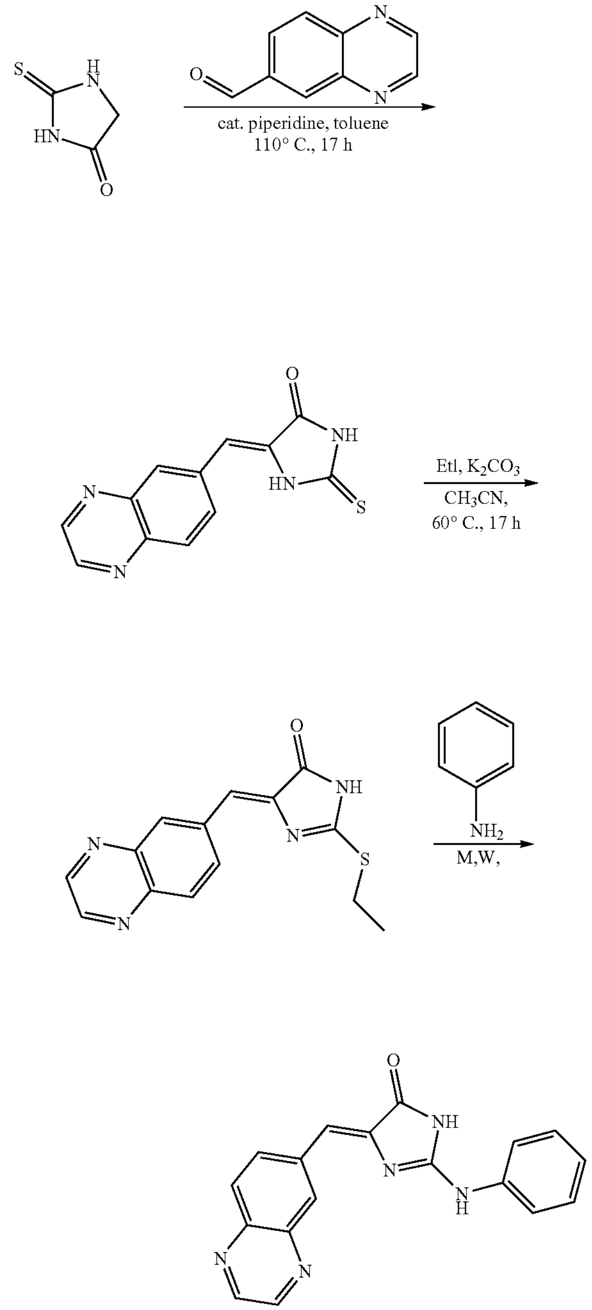

TJU-B200

(Z)-2-(phenylamino)-5-(quinoxalin-6-ylmethylene)-3,5-dihydro-4H-imidazol-4-one (12.8 mg) was prepared in the same procedure as described for Example 6. LRMS ($M+H^+$) m/z calculated 316.1, found 316.1. $^1H$ NMR (400 MHz, DMSO-d6) δ 10.14 (s, 1H), 8.95-8.89 (m, 2H), 8.81 (s, 1H), 8.61 (s, 1H), 8.09 (d, J=8.8 Hz, 1H), 7.85 (d, J=7.3 Hz, 2H), 7.44-7.42 (m, 2H), 7.14 (t, J=7.4 Hz, 1H), 6.74 (s, 1H).

Example 17

(Z)-5-((2,2-difluorobenzo[d][1,3]dioxol-5-yl)methylene)-2-(methyl(phenyl)amino)-3,5-dihydro-4H-imidazol-4-one

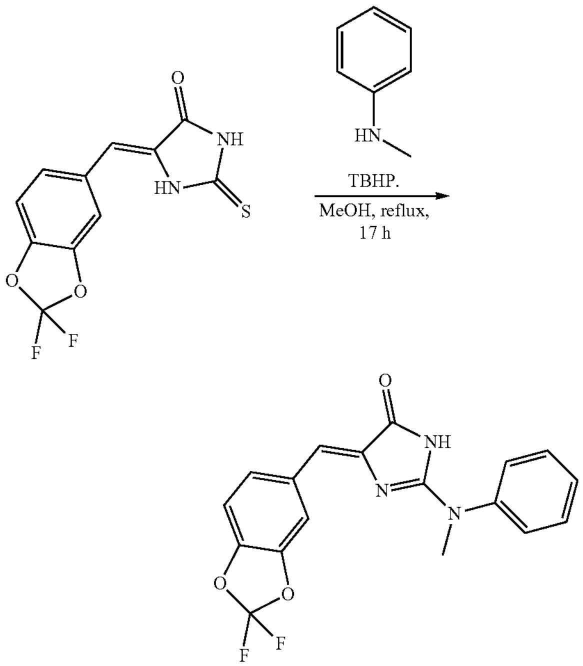

TJU-B205

(Z)-5-((2,2-difluorobenzo[d][1,3]dioxol-5-yl)methylene)-2-(methyl(phenyl)amino)-3,5-dihydro-4H-imidazol-4-one (19.2 mg) was prepared in the same procedure as described for Example 1. LRMS (M+H) m/z calculated 359.1, found 359.1. $^1H$ NMR (400 MHz, $CD_3OD$) δ 8.32 (s, 1H), 7.62 (d, J=7.9 Hz, 1H), 7.50 (t, J=7.8 Hz, 2H), 7.39 (t, J=7.4 Hz, 3H), 7.18 (d, J=8.4 Hz, 1H), 6.52 (s, 1H), 3.58 (s, 3H).

Example 18

(Z)-5-(benzo[d][1,3]dioxol-5-ylmethylene)-2-(methyl(pyridin-3-yl)amino)-3,5-dihydro-4H-imidazol-4-one

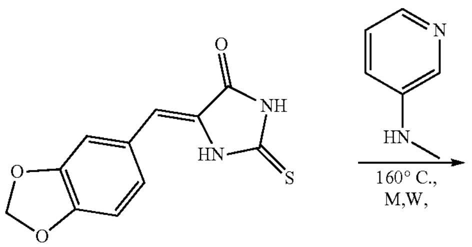

-continued

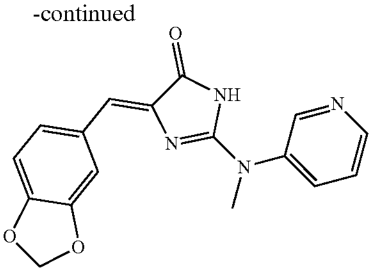

TJU-B214

(Z)-5-(benzo[d][1,3]dioxol-5-ylmethylene)-2-(methyl (pyridin-3-yl)amino)-3,5-dihydro-4H-imidazol-4-one (8.0 mg) was prepared in the same procedure as described for Example 6. LRMS ($M+H^+$) m/z calculated 323.1, found 323.1. $^1H$ NMR (400 MHz, DMSO-d6) δ 11.18 (s, 1H), 8.71 (d, J=2.4 Hz, 1H), 8.50 (s, 1H), 7.91-7.89 (m, 2H), 7.49-7.37 (m, 1H), 7.38 (d, J=7.8 Hz, 1H), 6.91 (d, J=8.1 Hz, 1H), 6.41 (s, 1H), 6.04 (d, J=5.4 Hz, 2H), 3.50 (s, 3H).

Example 19

(Z)-2-((cyclopropylmethyl)(methyl)amino)-5-((2,3-dihydrobenzo[b][1,4]dioxin-6-yl)methylene)-3,5-di hydro-4H-imidazol-4-one

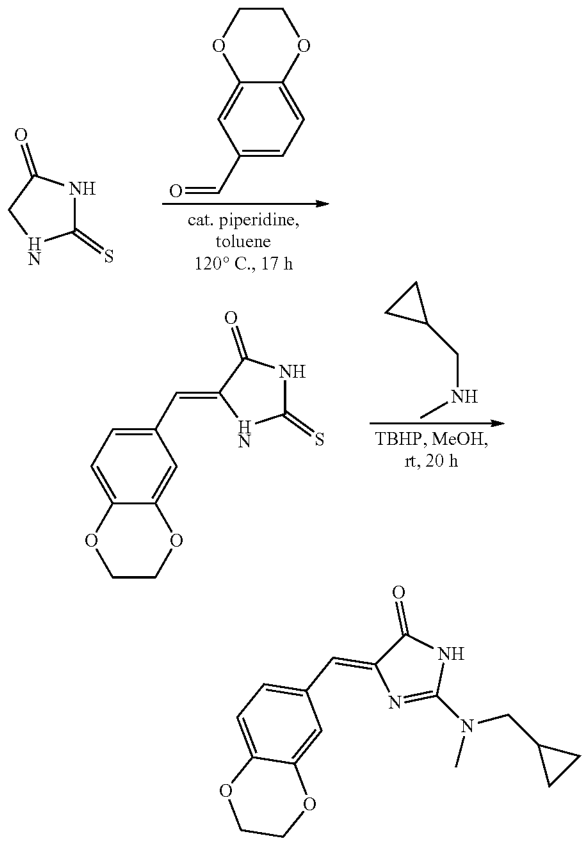

TJU-B211

(Z)-2-((cyclopropylmethyl)(methyl)amino)-5-((2,3-dihydrobenzo[b][1,4]dioxin-6-yl)methylene)-3,5-di hydro-4H-imidazol-4-one (14.2 mg) was prepared in the same procedure as described for Example 1. LRMS ($M+H^+$) m/z calculated 314.1, found 314.1. $^1H$ NMR (400 MHz, DMSO-d6) δ 11.17 (s, 1H), 7.77 (s, 1H), 7.40 (d, J=7.8 Hz, 1H), 6.82 (d, J=8.3 Hz, 1H), 6.18 (s, 1H), 4.24 (s, 4H), 3.40 (s, 2H), 3.13 (s, 3H), 1.10-1.03 (m, 1H), 0.51-0.48 (m, 2H), 0.32-0.29 (m, 2H).

Example 20

(Z)-5-(benzo[d][1,3]dioxol-5-ylmethylene)-2-(methyl(2-morpholinoethyl)amino)-3,5-dihydro-4H-imidazol-4-one

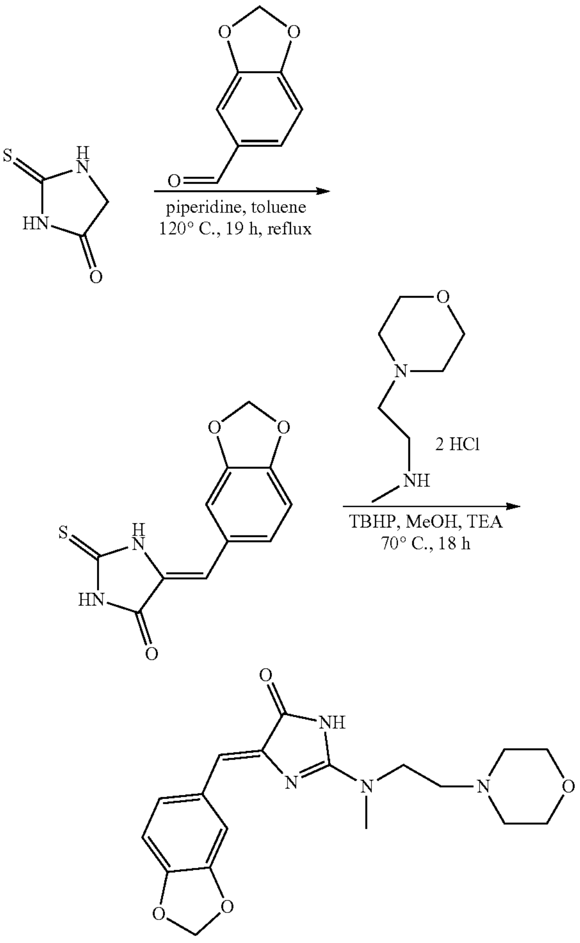

TJU-B212

(Z)-5-(benzo[d][1,3]dioxol-5-ylmethylene)-2-(methyl(2-morpholinoethyl)amino)-3,5-dihydro-4H-imidazol-4-one (4.58 mg) was prepared in the same procedure as described for Example 1. LRMS ($M+H^+$) m/z calculated 359.1, found 359.1. $^1H$ NMR (400 MHz, DMSO-d6) δ 11.22 (s, 1H), 7.95 (s, 1H), 7.35 (d, J=7.2 Hz, 1H), 6.90 (d, J=8.0 Hz, 1H), 6.23 (s, 1H), 6.02 (s, 2H), 3.54 (t, J=8.0 Hz, 6H), 3.09 (s, 3H), 2.55-2.52 (m, 2H), 2.48-2.46 (m, 4H).

Example 21

(Z)-5-(benzo[d][1,3]dioxol-5-ylmethylene)-2-((2-methoxyphenyl)(methyl)amino)-3,5-dihydro-4H-imidazol-4-one

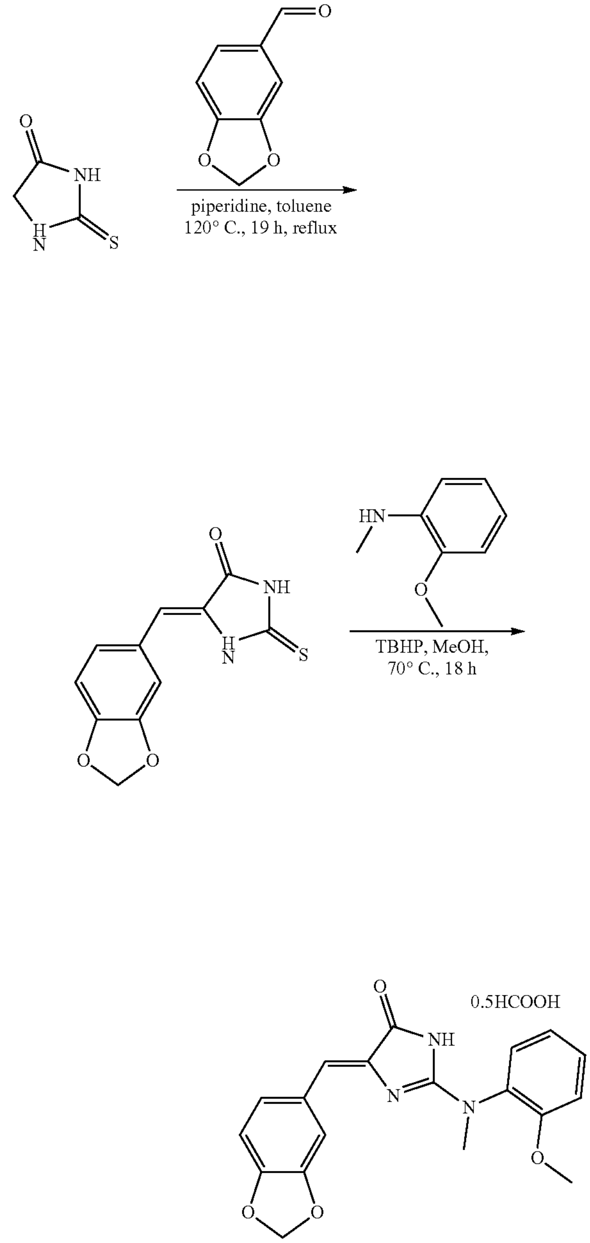

TJU-B203

(Z)-5-(benzo[d][1,3]dioxol-5-ylmethylene)-2-((2-methoxyphenyl)(methyl)amino)-3,5-dihydro-4H-imidazol-4-one (9.83 mg) was prepared in the same procedure as described for Example 1. LRMS ($M+H^+$) m/z calculated 352.1, found 352.1. $^1H$ NMR (400 MHz, DMSO-d6) δ 10.71 (br, 1H), 8.35 (s, 0.5H), 7.94 (s, 1H), 7.38-7.32 (m, 3H), 7.17-7.15 (m, 1H), 7.03-7.00 (m, 1H), 6.92 (d, J=8.1 Hz, 1H), 6.31 (s, 1H), 6.03 (s, 2H), 3.81 (s, 3H), 3.31 (s, 1H).

Example 22

(Z)-5-(benzo[d][1,3]dioxol-5-ylmethylene)-2-(benzyl(phenyl)amino)-3,5-dihydro-4H-imidazol-4-one

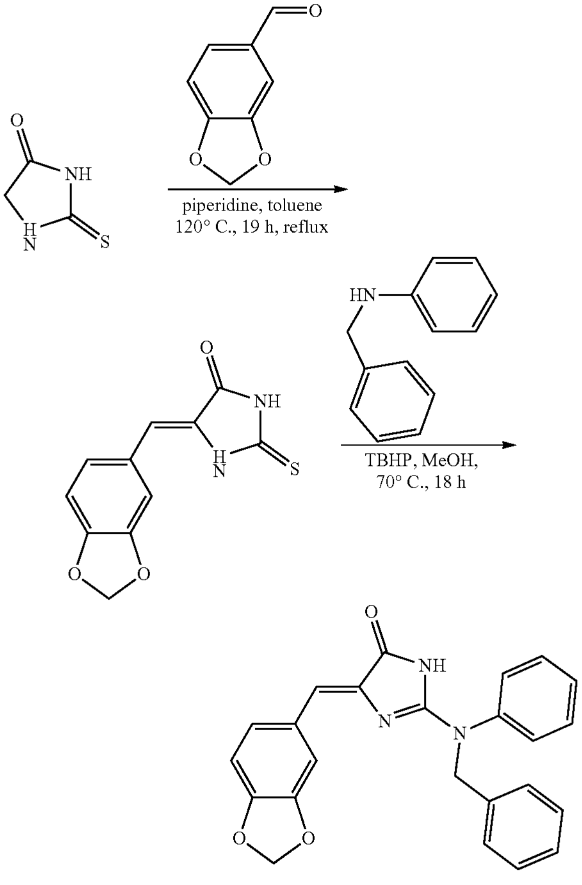

TJU-B209

(Z)-5-(benzo[d][1,3]dioxol-5-ylmethylene)-2-(benzyl(phenyl)amino)-3,5-dihydro-4H-imidazol-4-one (10.41 mg) was prepared in the same procedure as described for Example 1. LRMS ($M+H^+$) m/z calculated 398.1, found 398.1. $^1H$ NMR (400 MHz, DMSO-d6) δ 10.96 (br, 1H), 7.93 (s, 1H), 7.38-7.21 (m, 11H), 6.91 (d, J=8.1 Hz, 1H), 6.40 (s, 1H), 6.02 (s, 2H), 5.20 (s, 2H).

Example 23

(Z)-5-(benzo[d][1,3]dioxol-5-ylmethylene)-2-(benzyl(methyl)amino)-3,5-dihydro-4H-imidazol-4-one

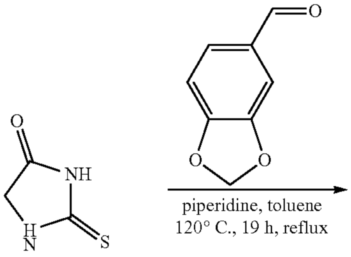

-continued

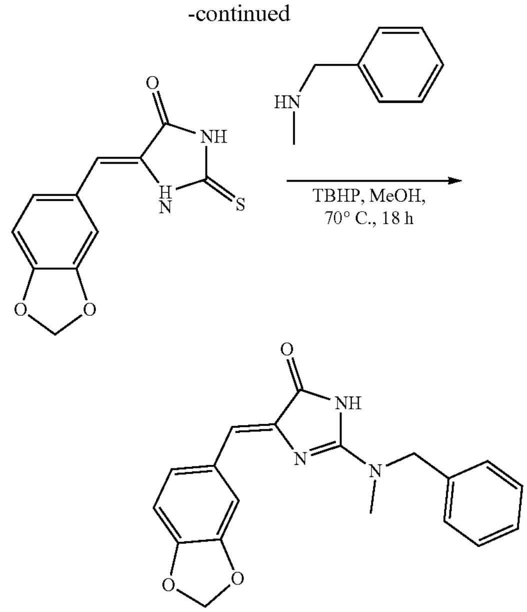

TJU-B213

(Z)-5-(benzo[d][1,3]dioxol-5-ylmethylene)-2-(benzyl(methyl)amino)-3,5-dihydro-4H-imidazol-4-one (50.57 mg) was prepared in the same procedure as described for Example 1. LRMS (M+H$^+$) m/z calculated 336.1, found 336.1. $^1$H NMR (400 MHz, DMSO-d6) δ 11.35 (br, 1H), 7.92 (d, J=4.0 Hz, 1H), 7.42-7.29 (m, 6H), 6.91 (d, J=8.1 Hz, 1H), 6.30 (s, 1H), 6.01 (s, 2H), 4.71 (s, 2H), 3.02 (s, 3H).

Example 24

(Z)-5-(benzo[d]thiazol-6-ylmethylene)-2-((4-chlorophenyl)(methyl)amino)-3,5-dihydro-4H-imidazol-4-one

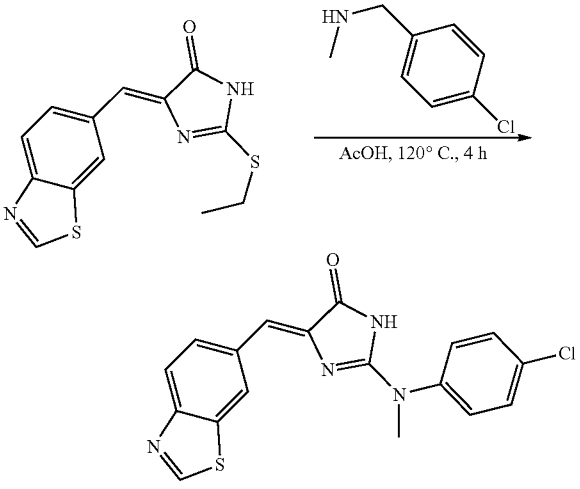

TJU-B228

A solution of (Z)-5-(benzo[d]thiazol-6-ylmethylene)-2-(ethylthio)-3,5-dihydro-4H-imidazol-4-one (150 mg, 0.52 mmol) and 1-(4-chlorophenyl)-N-methylmethanamine (121 mg, 0.78 mmol) in AcOH (8 mL) was stirred at 120° C. for 4 h. After completion, the mixture was concentrated to remove AcOH and the residue was purified by prep-HPLC (EA/PE=1/2, v/v) to give (Z)-5-(benzo[d]thiazol-6-ylmethylene)-2-((4-chlorophenyl)(methyl)amino)-3,5-dihydro-4H-imidazol-4-one as a yellow solid (79.8 mg). LRMS (M+H$^+$) m/z calculated 369.1, found 369.0. $^1$H NMR (400 MHz, DMSO-d6) δ 11.12 (s, 1H), 9.38 (s, 1H), 8.85 (s, 1H), 8.30 (d, J=8.4 Hz, 1H), 8.05 (d, J=8.5 Hz, 1H), 7.53 (s, 4H), 6.56 (s, 1H), 3.53 (s, 3H).

Example 25

(Z)-5-(benzo[d]thiazol-6-ylmethylene)-2-((4-methoxyphenyl)amino)-3,5-dihydro-4H-imidazol-4-one

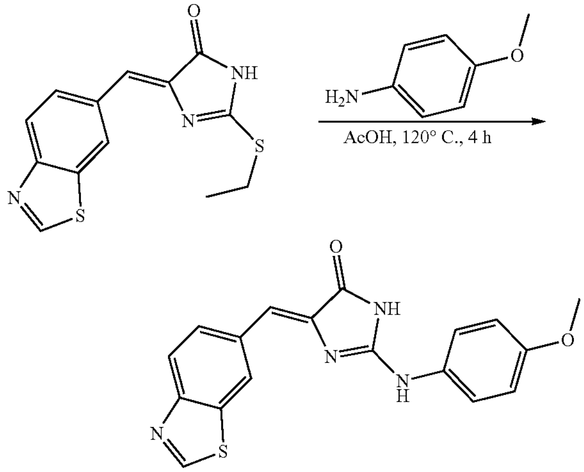

TJU-B231

(Z)-5-(benzo[d]thiazol-6-ylmethylene)-2-((4-methoxyphenyl)(methyl)amino)-3,5-dihydro-4H-imidazol-4-one (26.9 mg) was prepared in the same procedure as described for Example 24. LRMS (M+H$^+$) m/z calculated 351.0, found 351.0. $^1$H NMR (400 MHz, $CD_3OD$) δ 9.36 (s, 1H), 8.40 (s, 1H), 8.16 (d, J=8.5 Hz, 1H), 7.82 (d, J=8.3 Hz, 1H), 7.41 (d, J=8.4 Hz, 2H), 7.17 (s, 1H), 7.11-7.09 (m, 2H), 3.86 (s, 3H).

Example 26

(Z)-5-((1H-benzo[d]imidazol-5-yl)methylene)-2-(phenylamino)-3,5-dihydro-4H-imidazol-4-one

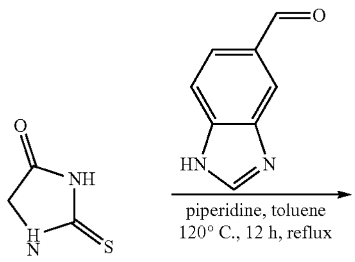

-continued

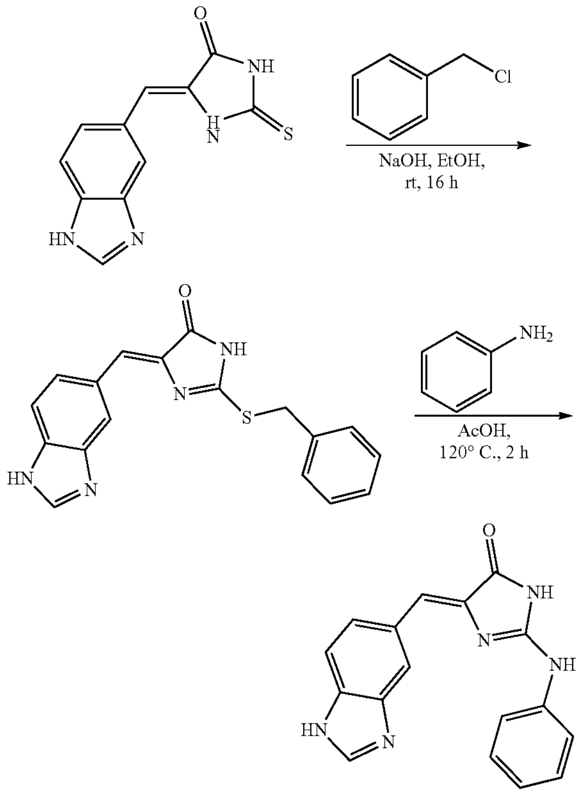

TJU-B161

(Z)-5-((1H-benzo[d]imidazol-5-yl)methylene)-2-(phenylamino)-3,5-dihydro-4H-imidazol-4-one (5.31 mg) was prepared in the same procedure as described for Example 24. LRMS (M+H+) m/z calculated 304.1, found 304.1. $^1$H NMR (DMSO-d6, 400 MHz) δ 12.57 (d, J=49.0 Hz, 1H), 10.79 (br, 1H), 9.92 (br, 1H), 8.46 (s, 1H), 8.25 (d, J=16.5 Hz, 1H), 8.04-8.00 (m, 0.5H), 7.86-7.81 (m, 2.5H), 7.64 (d, J=8.4 Hz, 0.5H), 7.53 (d, J=8.0 Hz, 0.5H), 7.44-7.37 (m, 2H), 7.10-7.06 (m, 1H), 6.65 (s, 1H).

Example 27

(Z)-3-((4-(benzo[d][1,3]dioxol-5-ylmethylene)-5-oxo-4,5-dihydro-1H-imidazol-2-yl)(phenyl)amino) propanoic acid

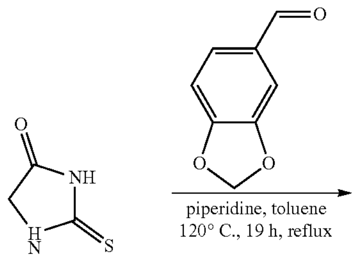

-continued

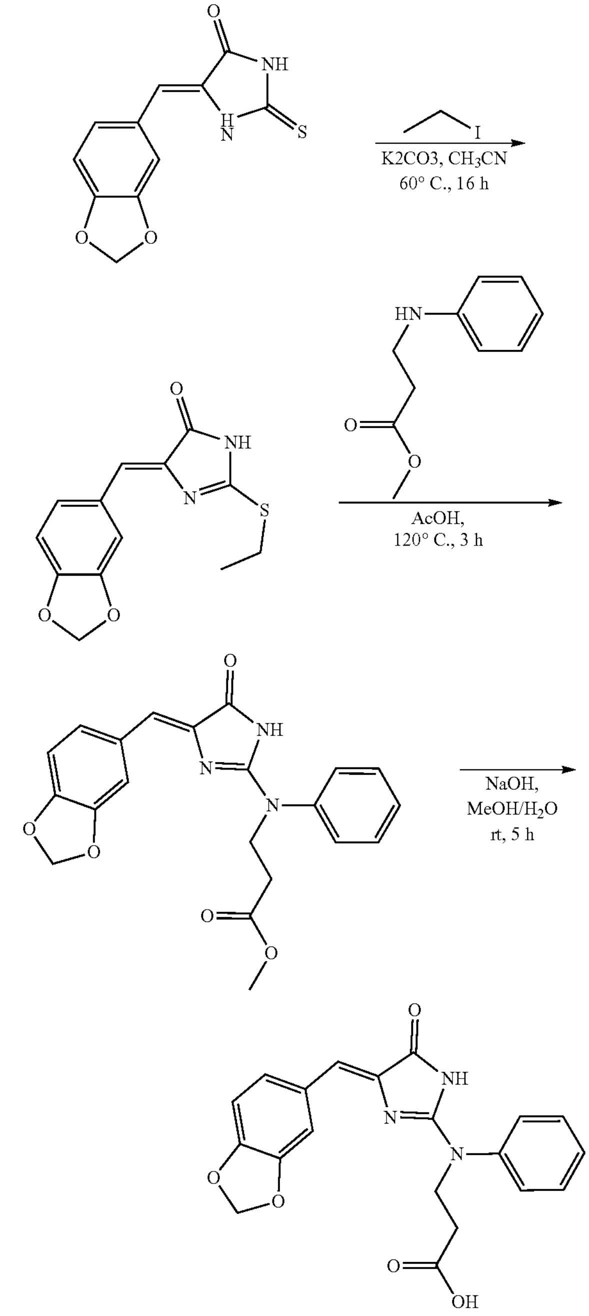

TJU-B219

(Z)-3-((4-(benzo[d][1,3]dioxol-5-ylmethylene)-5-oxo-4,5-dihydro-1H-imidazol-2-yl)(phenyl)amino)propanoic acid (7.17 mg) was prepared in the same procedure as described for Example 24. LRMS (M+H+) m/z calculated 380.1, found 380.1. $^1$H NMR (400 MHz, DMSO-d6) δ 12.35 (br, 1H), 10.89 (br, 1H), 7.94 (s, 1H), 7.47 (d, J=12.0 Hz, 2H), 7.40-7.34 (m, 4H), 6.91 (d, J=8.1 Hz, 1H), 6.37 (s, 1H), 6.03 (s, 2H), 4.12 (t, J=16.0 Hz, 2H), 2.60 (t, J=12.0 Hz, 2H).

Example 28

(Z)-5-(benzo[d]thiazol-6-ylmethylene)-2-(benzyl (methyl)amino)-3,5-dihydro-4H-imidazol-4-one

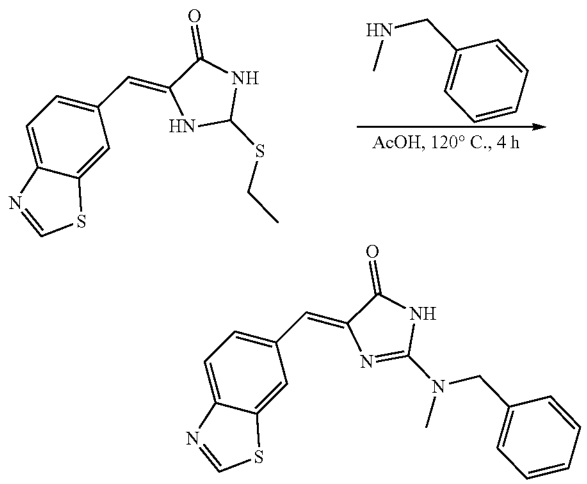

TJU-B232

(Z)-5-(benzo[d]thiazol-6-ylmethylene)-2-(benzyl (methyl)amino)-3,5-dihydro-4H-imidazol-4-one (39.7 mg) was prepared in the same procedure as described for Example 24. LRMS ($M+H^+$) m/z calculated 349.0, found 349.0. $^1$H NMR (400 MHz, DMSO-d6) δ 9.29 (s, 1H), 8.79 (s, 1H), 8.21 (dd, J=8.6 Hz, 1.2 Hz, 1H), 7.98 (d, J=8.6 Hz, 1H), 7.36-7.32 (m, 5H), 6.25 (s, 1H), 4.79 (s, 2H), 3.07 (s, 3H).

Example 29

(Z)-5-(benzo[d]thiazol-6-ylmethylene)-2-((2-morpholinoethyl)amino)-3,5-dihydro-4H-imidazol-4-one

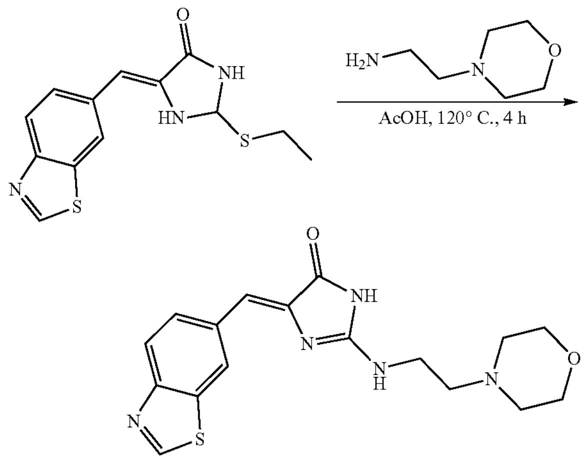

TJU-B237

(Z)-5-(benzo[d]thiazol-6-ylmethylene)-2-((2-morpholinoethyl)amino)-3,5-dihydro-4H-imidazol-4-one (23.6 mg) was prepared in the same procedure as described for Example 24. LRMS ($M+H^+$) m/z calculated 358.1, found 358.1. $^1$H NMR (400 MHz, $CD_3OD$) δ 9.24 (s, 1H), 8.52 (br, 1H), 8.04-7.80 (m, 2H), 6.64 (s, 1H), 3.72-3.70 (m, 4H), 3.62 (s, 2H), 2.66 (s, 2H), 2.56 (s, 4H).

Example 30

(Z)-5-((1H-benzo[d]imidazol-5-yl)methylene)-2-(methyl(phenyl)amino)-3,5-dihydro-4H-imidazol-4-one

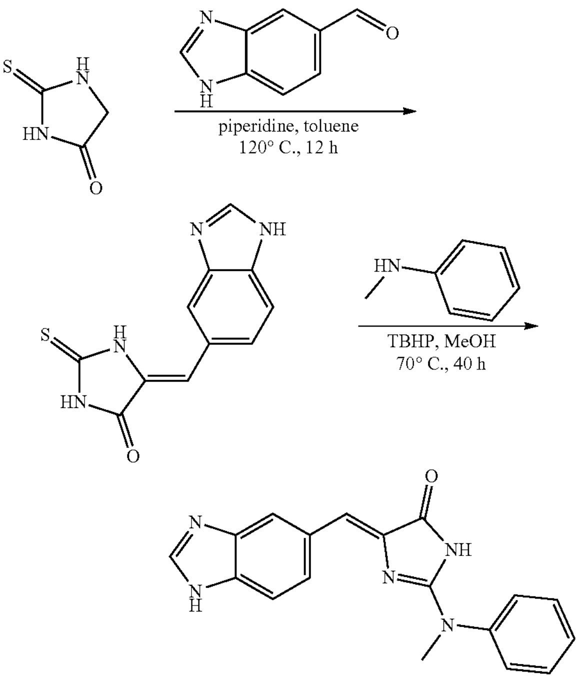

TJU-B184

(Z)-5-((1H-benzo[d]imidazol-5-yl)methylene)-2-(methyl (phenyl)amino)-3,5-dihydro-4H-imidazol-4-one (14.55 mg) was prepared in the same procedure as described for Example 1. LRMS (M+H) m/z calculated 318.2, found 318.2. $^1$H NMR (400 MHz, DMSO-d6) δ 12.73 (br, 1H), 10.94 (s, 1H), 8.46 (s, 1H), 8.31 (d, J=3.3 Hz, 1H), 7.92 (d, J=8.0 Hz, 1H), 7.56 (d, J=8.4 Hz, 1H), 7.48-7.44 (m 4H), 7.35-7.31 (m, 1H), 6.57 (s, 1H), 3.54 (s, 3H).

Example 31

(Z)-5-(benzo[d]thiazol-6-ylmethylene)-2-(benzylamino)-3,5-dihydro-4H-imidazol-4-one

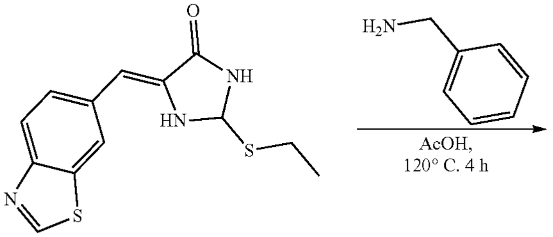

-continued

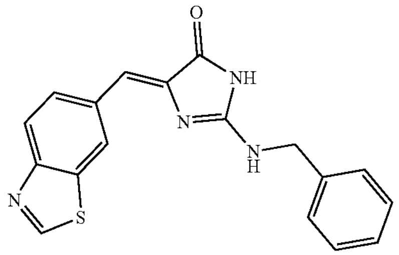

TJU-B233

(Z)-5-(benzo[d]thiazol-6-ylmethylene)-2-(benzylamino)-3,5-dihydro-4H-imidazol-4-one (27.9 mg) was prepared in the same procedure as described for Example 24. LRMS $(M+H^+)$ m/z calculated 335.1, found 335.1. $^1H$ NMR (400 MHz, DMSO-d6) δ 9.36 (s, 1H), 8.85 (s, 1H), 8.23 (d, J=8.6 Hz, 1H), 8.03 (d, J=8.5 Hz, 1H), 7.42-7.34 (m, 5H), 7.28 (d, J=7.3 Hz, 1H), 6.43 (s, 1H), 4.59 (s, 2H).

Example 32

(Z)-5-(benzo[d]thiazol-6-ylmethylene)-2-(methyl(2-morpholinoethyl)amino)-3,5-dihydro-4H-imidazol-4-one

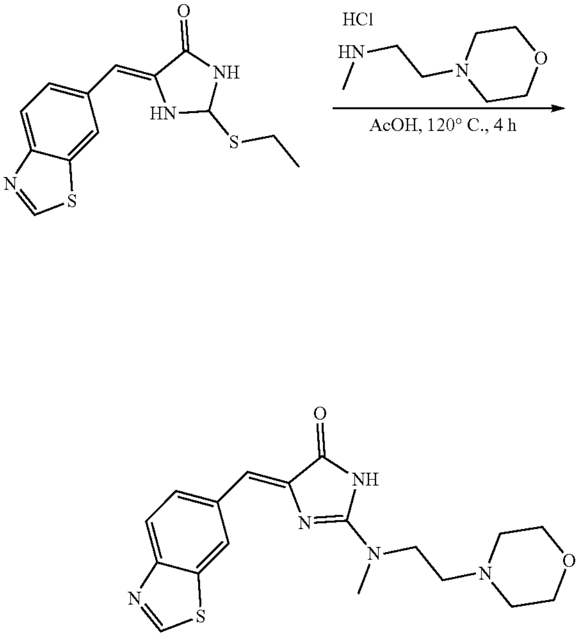

TJU-B236

(Z)-5-(benzo[d]thiazol-6-ylmethylene)-2-((cyclopropylmethyl)amino)-3,5-dihydro-4H-imidazol-4-one (7.7 mg) was prepared in the same procedure as described for Example 24. LRMS $(M+H^+)$ m/z calculated 372.1, found 372.1. $^1H$ NMR (400 MHz, $CD_3OD$) δ 9.24 (d, J=3.0 Hz, 1H), 8.80-8.72 (m, 1H), 8.02 (dd, J=7.8 Hz, 6.4 Hz, 2H), 6.62 (s, 1H), 3.75 (s, 2H), 3.66 (d, J=4.6 Hz, 4H), 3.22 (s, 3H), 2.67 (d, J=15.5 Hz, 2H), 2.59 (s, 4H).

Example 33

(Z)-5-(benzo[d]thiazol-6-ylmethylene)-2-((cyclopropylmethyl)(methyl)amino)-3,5-dihydro-4H-imidazol-4-one

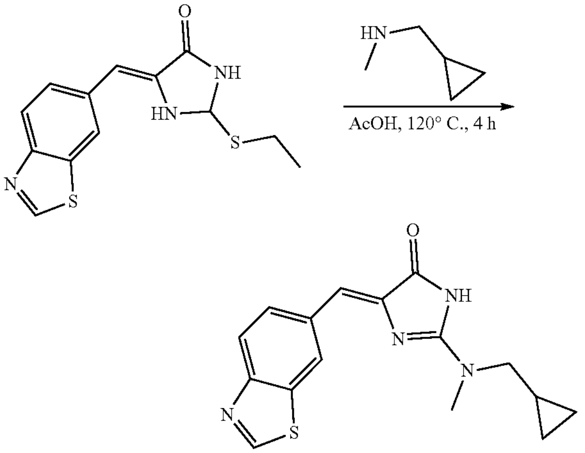

TJU-B234

(Z)-5-(benzo[d]thiazol-6-ylmethylene)-2-((cyclopropylmethyl)(methyl)amino)-3,5-dihydro-4H-imidazol-4-one (8.4 mg) was prepared in the same procedure as described for Example 24. LRMS $(M+H^+)$ m/z calculated 313.1, found 313.1. $^1H$ NMR (400 MHz, $CDCl_3$) δ 9.73 (s, 1H), 8.99 (s, 1H), 8.83 (s, 1H), 8.16 (dd, J=8.6 Hz, 1.4 Hz, 1H), 8.10 (d, J=8.5 Hz, 1H), 6.70 (s, 1H), 3.46 (s, 2H), 3.32 (s, 3H), 1.13 (s, 1H), 0.66 (q, J=5.8 Hz, 2H), 0.40 (q, J=5.0 Hz, 2H).

Example 34

(Z)-5-(benzo[d]thiazol-6-ylmethylene)-2-((cyclopropylmethyl)(methyl)amino)-3,5-dihydro-4H-imidazol-4-one

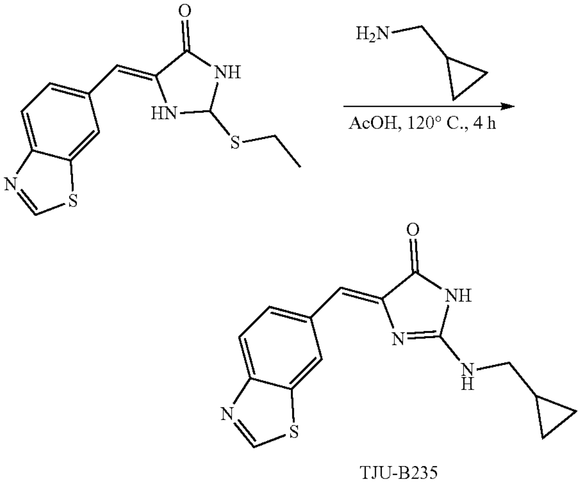

TJU-B235

(Z)-5-(benzo[d]thiazol-6-ylmethylene)-2-((cyclopropylmethyl)amino)-3,5-dihydro-4H-imidazol-4-one (23.8 mg)

was prepared in the same procedure as described for Example 24. LRMS (M+H$^+$) m/z calculated 299.1, found 299.1. $^1$H NMR (400 MHz, DMSO-d6) δ 11.22 (s, 1H), 9.36 (d, J=5.8 Hz, 1H), 8.77 (s, 1H), 8.29 (d, J=26.5 Hz, 1H), 8.03 (t, J=7.4 Hz, 1H), 6.39 (s, 1H), 3.51 (s, 2H), 1.10 (s, 1H), 0.49 (q, J=5.6 Hz, 2H), 0.29 (t, J=8.6 Hz, 2H).

Example 35

(Z)-5-((1H-benzo[d]imidazol-5-yl)methylene)-2-(benzyl(phenyl)amino)-3,5-dihydro-4H-imidazol-4-one

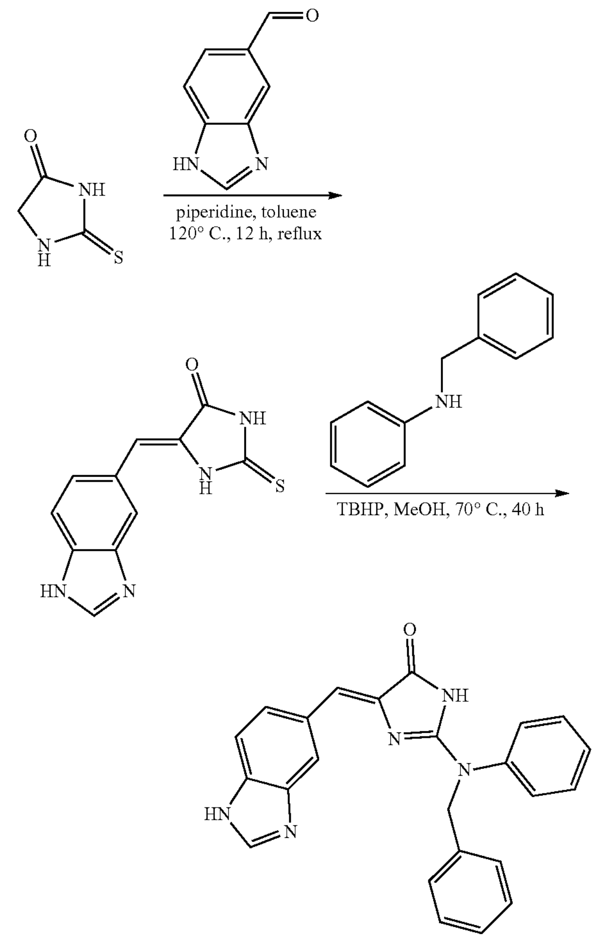

TJU-B227

(Z)-5-((1H-benzo[d]imidazol-5-yl)methylene)-2-(benzyl(phenyl)amino)-3,5-dihydro-4H-imidazol-4-one (20.74 mg) was prepared in the same procedure as described for Example 1. LRMS (M+H$^+$) m/z calculated 394.2, found 394.1. $^1$H NMR (400 MHz, DMSO-d6) δ 12.54 (s, 0.5H), 12.48 (s, 0.5H), 10.90 (br, 1H), 8.46 (d, J=8.0 Hz, 1H), 8.21 (d, J=8.0 Hz, 1H), 7.97 (d, J=8.0 Hz, 0.5H), 7.83 (d, J=12.0 Hz, 0.5H), 7.60 (d, J=8.0 Hz, 0.5H), 7.48 (d, J=8.0 Hz, 0.5H), 7.42-7.22 (m, 10H), 6.60 (s, 1H), 5.28 (d, J=12.0 Hz, 2H).

Example 36

(Z)-3-((4-(benzo[d][1,3]dioxol-5-ylmethylene)-5-oxo-4,5-dihydro-1H-imidazol-2-yl)(phenyl)amino)propanamide

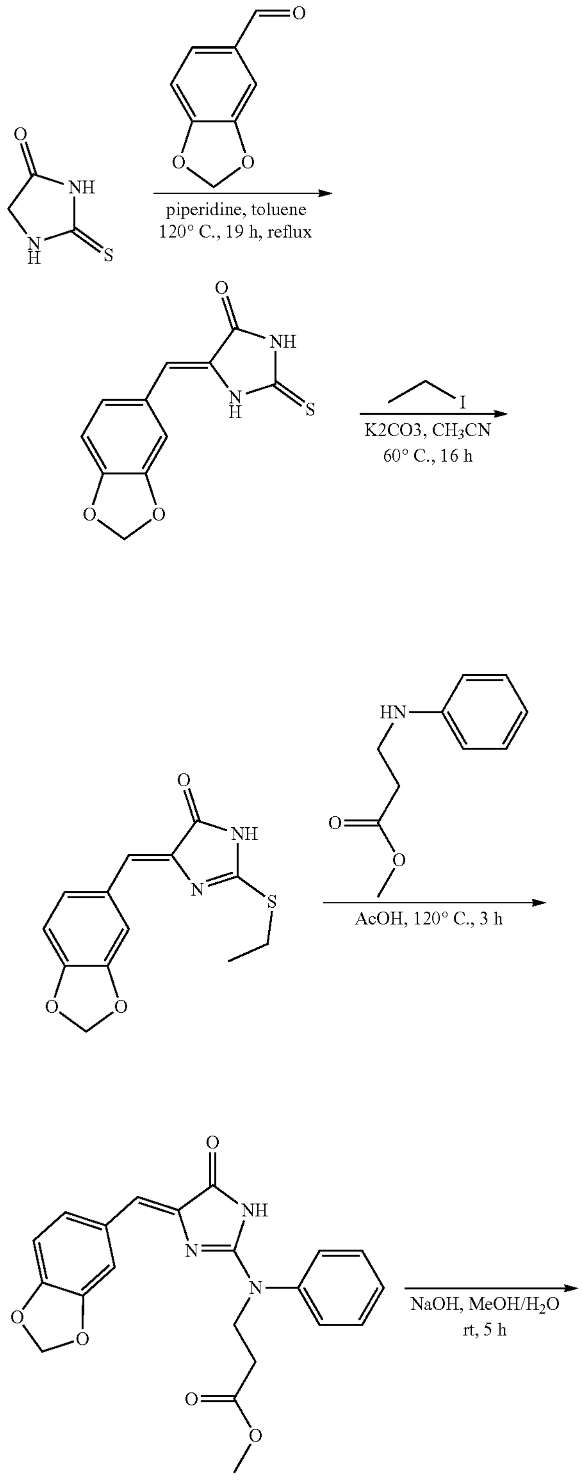

-continued

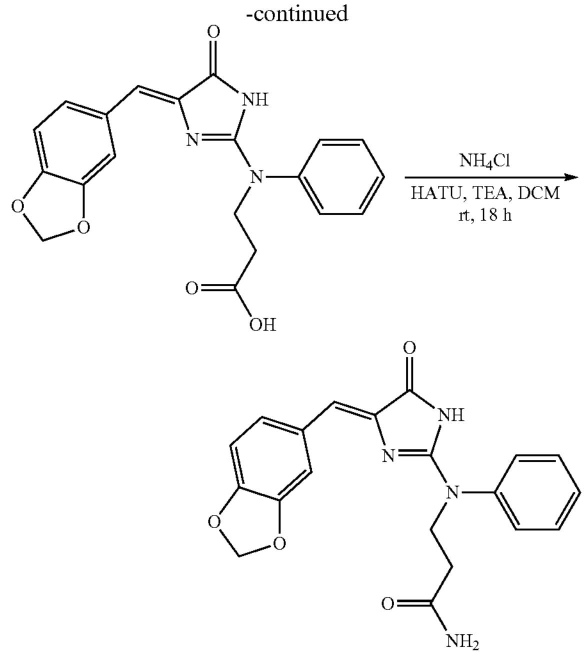

TJU-B220

(Z)-3-((4-(benzo[d][1,3]dioxol-5-ylmethylene)-5-oxo-4,5-dihydro-1H-imidazol-2-yl)(phenyl)amino)propanamide (4.38 mg) was prepared in the same procedure as described for Example 24. LRMS (M+H) m/z calculated 379.1, found 379.1. $^{1}$H NMR (400 MHz, DMSO-d6)$^{1}$H NMR (400 MHz, DMSO) δ 10.83 (s, 1H), 7.93 (d, J=1.2 Hz, 1H), 7.48-7.33 (m, 7H), 6.92-6.88 (m, 2H), 6.37 (s, 1H), 6.04 (d, J=8.0 Hz, 2H), 4.10 (t, J=8.0, 2H), 2.50-2.46 (m, 2H).

Example 37

(Z)-2-((4-aminophenyl)(methyl)amino)-5-(benzo[d][1,3]dioxol-5-ylmethylene)-3,5-dihydro-4H-imidazol-4-one

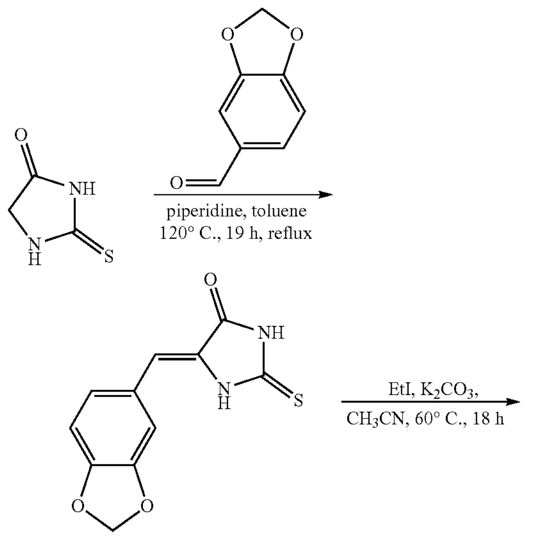

-continued

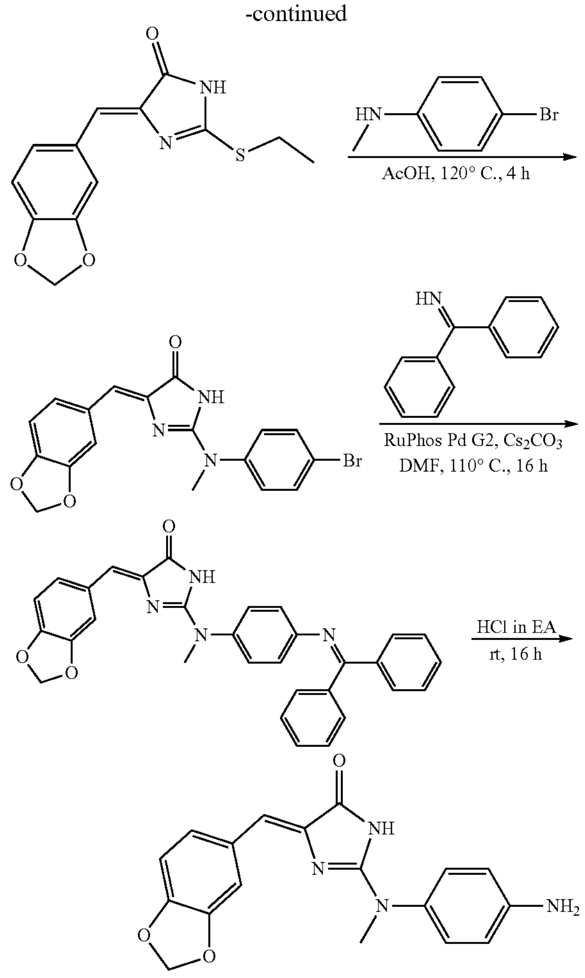

TJU-B221

(Z)-2-((4-aminophenyl)(methyl)amino)-5-(benzo[d][1,3]dioxol-5-ylmethylene)-3,5-dihydro-4H-imidazol-4-one (2.64 mg) was prepared in the same procedure as described for Example 24. LRMS (M+H$^{+}$) m/z calculated 337.1, found 337.1. $^{1}$H NMR (400 MHz, DMSO-d6) δ 10.67 (br, 1H), 7.95 (d, J=1.2 Hz, 1H), 7.39 (d, J=4.0 Hz, 1H), 7.00 (d, J=8.0 Hz, 2H), 6.91 (d, J=8.0 Hz, 1H), 6.58 (d, J=8.0 Hz, 2H), 6.28 (s, 1H), 6.03 (s, 2H), 5.26 (s, 2H), 3.37 (s, 3H).

Example 38

(Z)-5-(benzo[d]thiazol-6-ylmethylene)-2-((4-methoxyphenyl)(methyl)amino)-3,5-dihydro-4H-imidazol-4-one

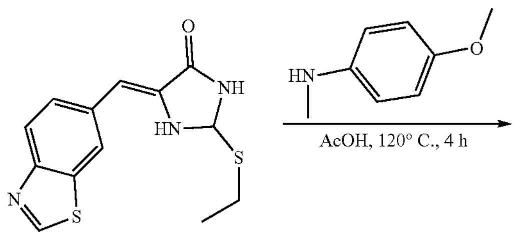

-continued

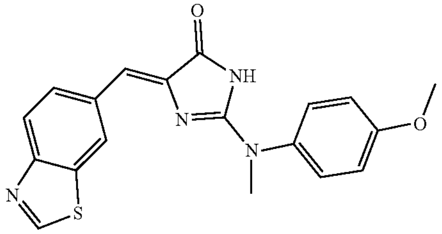

TJU-B230

(Z)-5-(benzo[d]thiazol-6-ylmethylene)-2-((4-methoxyphenyl)(methyl)amino)-3,5-dihydro-4H-imidazol-4-one (69.3 mg) was prepared in the same procedure as described for Example 24. LRMS ($M+H^+$) m/z calculated 365.1, found 365.1. $^1$H NMR (400 MHz, DMSO-d6) δ 9.37 (s, 1H), 8.84 (s, 1H), 8.28 (d, J=8.5 Hz, 1H), 8.04 (d, J=8.6 Hz, 1H), 7.37 (d, J=8.8 Hz, 2H), 7.02 (d, J=8.9 Hz, 2H), 6.49 (s, 1H), 3.80 (s, 3H), 3.50 (s, 3H).

Example 39

(Z)-2-((cyclopropylmethyl)(phenyl)amino)-5-((2,3-dihydrobenzo[b][1,4]dioxin-6-yl)methylene)-3,5-dihydro-4H-imidazol-4-one

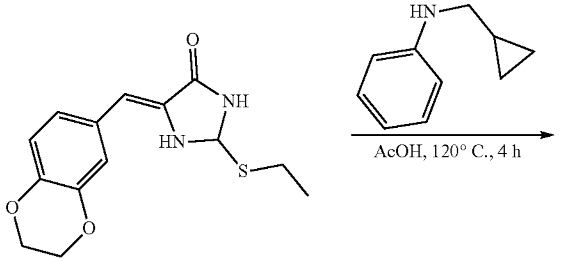

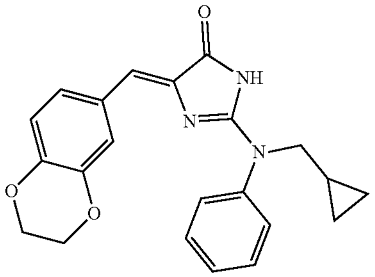

TJU-B252

(Z)-2-((cyclopropylmethyl)(phenyl)amino)-5-((2,3-dihydrobenzo[b][1,4]dioxin-6-yl)methylene)-3,5-di hydro-4H-imidazol-4-one (13.7 mg) was prepared in the same procedure as described for Example 24. LRMS ($M+H^+$) m/z calculated 376.1, found 376.1. $^1$H NMR (400 MHz, DMSO-d6) δ 7.78 (s, 1H), 7.46-7.34 (m, 6H), 6.83 (d, J=8.4 Hz, 1H), 6.29 (s, 1H), 4.25 (s, 4H), 3.82 (d, J=7.1 Hz, 2H), 1.10-1.06 (m, 1H), 0.42-0.39 (m, 2H), 0.17-0.14 (m, 2H).

Example 40

(Z)-5-(benzo[d]thiazol-6-ylmethylene)-2-((4-chlorophenyl)amino)-3,5-dihydro-4H-imidazol-4-one

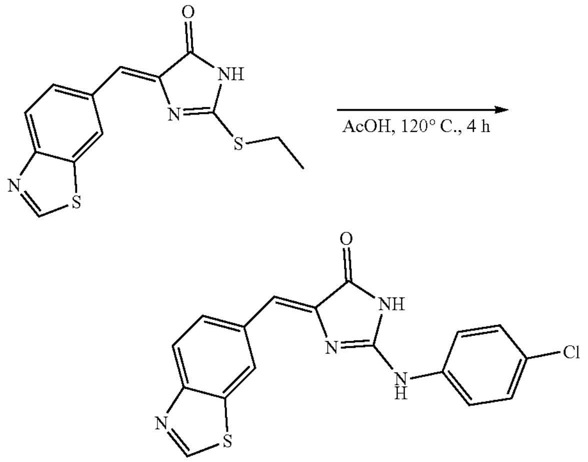

TJU-B229

(Z)-2-((cyclopropylmethyl)(phenyl)amino)-5-((2,3-dihydrobenzo[b][1,4]dioxin-6-yl)methylene)-3,5-di hydro-4H-imidazol-4-one (9.2 mg) was prepared in the same procedure as described for Example 24. LRMS ($M+H^+$) m/z calculated 355.0, found 355.0. $^1$H NMR (400 MHz, DMSO-d6) δ 9.42 (s, 1H), 8.79 (s, 1H), 8.39 (d, J=23.3 Hz, 1H), 8.13 (d, J=8.6 Hz, 1H), 7.88 (d, J=6.9 Hz, 2H), 7.47 (d, J=8.8 Hz, 2H), 6.65 (s, 1H).

Example 41

(Z)-5-(benzo[d]thiazol-6-ylmethylene)-2-(benzyl(phenyl)amino)-3,5-dihydro-4H-imidazol-4-one

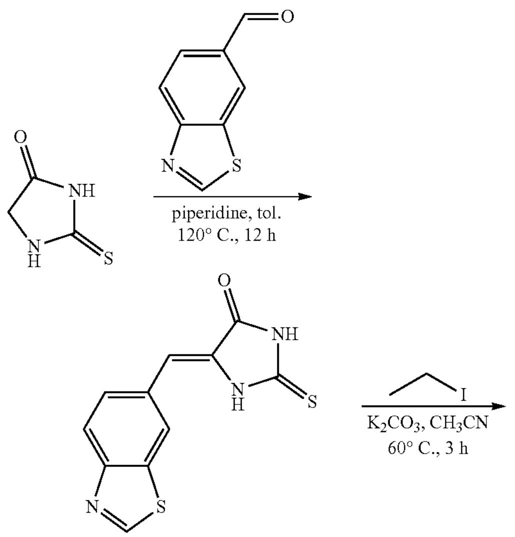

-continued

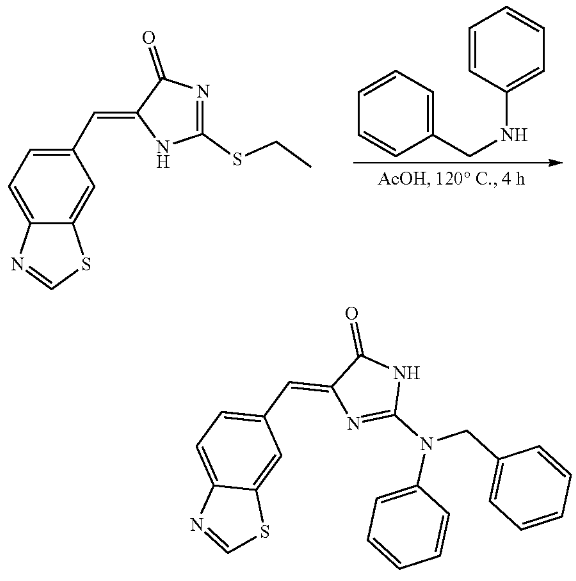

TJU-B256

(Z)-5-(benzo[d]thiazol-6-ylmethylene)-2-(benzyl(phenyl)amino)-3,5-dihydro-4H-imidazol-4-one (17.16 mg) was prepared in the same procedure as described for Example 24. LRMS (M+H$^+$) m/z calculated 411.1, found 411.1. $^1$H NMR (400 MHz, DMSO-d6) δ 11.06 (s, 1H), 9.37 (s, 1H), 8.86 (s, 1H), 8.29-8.27 (m, 1H), 8.04 (d, J=8.0 Hz, 1H), 7.44-7.22 (m, 10H), 6.57 (s, 1H), 5.26 (s, 2H).

Example 42

(Z)-5-(benzo[d]thiazol-6-ylmethylene)-3-benzyl-2-(benzyl(phenyl)amino)-3,5-dihydro-4H-imidazol-4-one

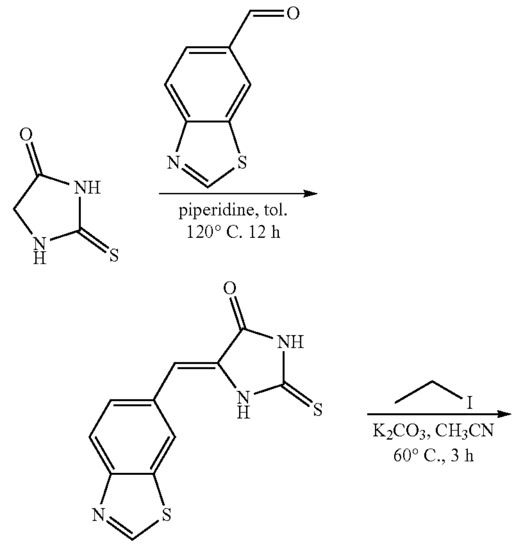

-continued

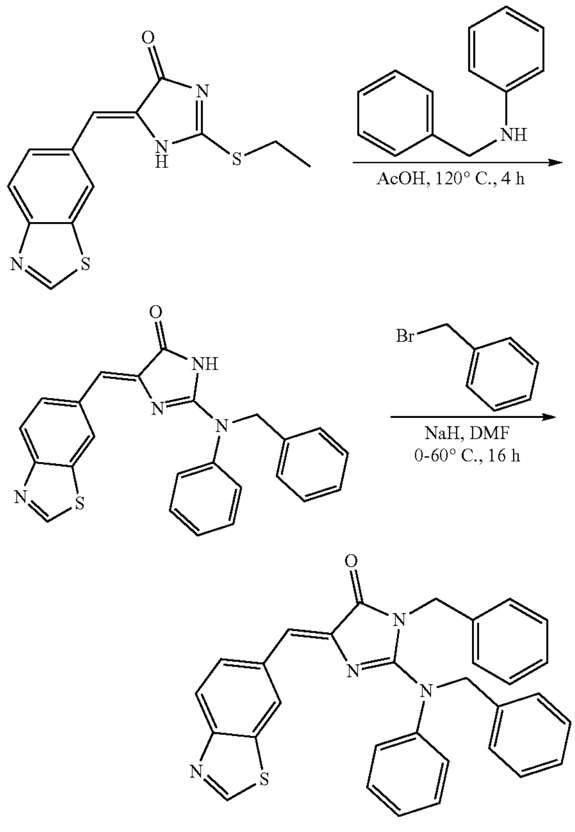

TJU-B257

(Z)-5-(benzo[d]thiazol-6-ylmethylene)-3-benzyl-2-(benzyl(phenyl)amino)-3,5-dihydro-4H-imidazol-4-one (2.22 mg) was prepared in the same procedure as described for Example 24. LRMS (M+H$^+$) m/z calculated 501.2, found 501.2. $^1$H NMR (400 MHz, DMSO-d6) δ 9.37 (s, 1H), 8.90 (s, 1H), 8.28 (d, J=8.0 Hz, 1H), 8.03 (d, J=8.0 Hz, 1H), 7.28-7.04 (m, 11H), 7.05 (d, J=8.0 Hz, 2H), 6.86 (s, 1H), 6.62 (t, J=4.0 Hz, 2H), 5.07 (s, 2H), 4.14 (s, 2H).

Example 43

(Z)-5-(benzo[d]thiazol-6-ylmethylene)-2-(methyl(4-nitrophenyl)amino)-3,5-dihydro-4H-imidazol-4-one

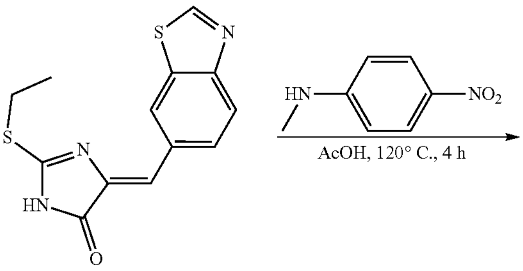

-continued

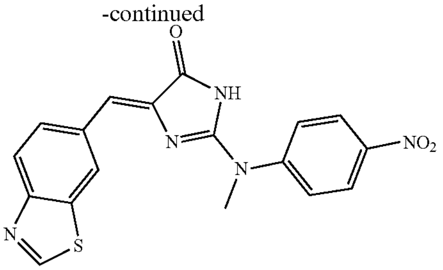

TJU-B255

(Z)-5-(benzo[d]thiazol-6-ylmethylene)-2-(methyl(4-nitrophenyl)amino)-3,5-dihydro-4H-imidazol-4-one (14.0 mg) was prepared in the same procedure as described for Example 24. LRMS (M+H$^+$) m/z calculated 380.1, found 380.1. $^1$H NMR (400 MHz, DMSO-d6) δ 9.31 (s, 1H), 8.82 (s, 1H), 8.23 (d, J=9.1 Hz, 3H), 8.00 (dd, J=8.9 Hz, 3.0 Hz, 3H), 6.31 (s, 1H), 3.69 (s, 3H).

Example 44

(Z)-2-((4-aminophenyl)(methyl)amino)-5-(benzo[d]thiazol-6-ylmethylene)-3,5-dihydro-4H-imidazol-4-one

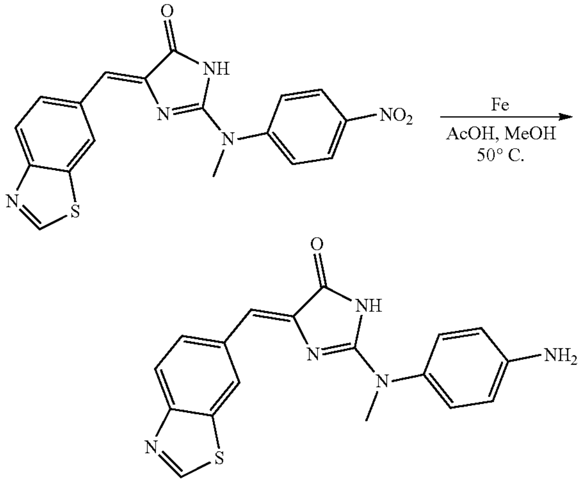

TJU-B238

To a solution of (Z)-5-(benzo[d]thiazol-6-ylmethylene)-2-(methyl(4-nitrophenyl)amino)-3,5-dihydro-4H-imidazol-4-one (150 mg, 0.39 mmol) in AcOH (8 mL) and MeOH (8 mL) was added Fe powder (214 mg, 3.9 mmol) and the mixture was stirred at 50° C. for 16 h. After completion, the mixture was filtered, the filtrate was concentrated and the residue was purified by prep-HPLC to give (Z)-2-((4-aminophenyl)(methyl)amino)-5-(benzo[d]thiazol-6-ylmethylene)-3,5-dihydro-4H-imidazol-4-one (8.4 mg) as a yellow solid. LRMS (M+H$^+$) m/z calculated 350.1, found 350.1. $^1$H NMR (400 MHz, DMSO-d6) δ 9.37 (s, 1H), 8.85 (s, 1H), 8.31 (d, J=8.3 Hz, 1H), 8.04 (d, J=8.6 Hz, 1H), 7.04 (d, J=8.5 Hz, 2H), 6.61 (d, J=8.6 Hz, 2H), 6.46 (s, 1H), 5.29 (s, 2H), 3.45 (s, 3H).

Example 45

(Z)-5-(benzo[d]thiazol-6-ylmethylene)-2-(isopropylamino)-3-methyl-3,5-dihydro-4H-imidazol-4-one

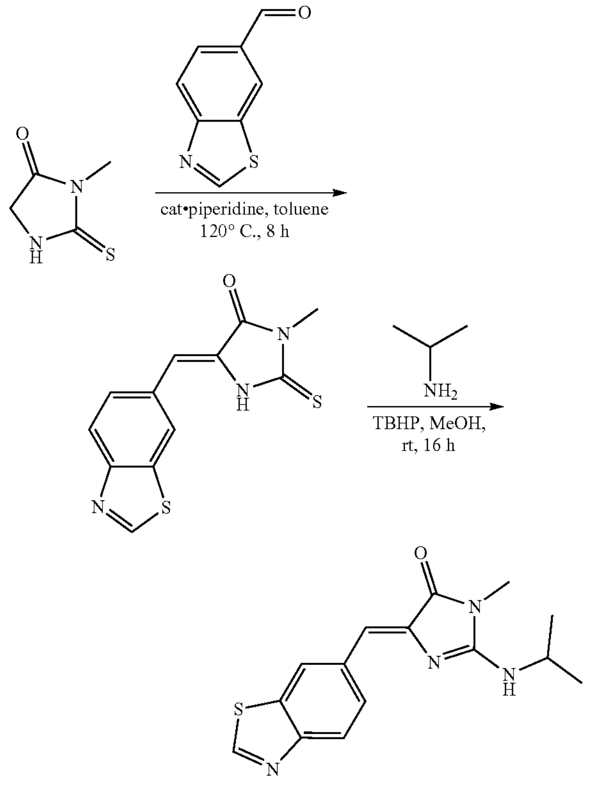

TJU-B265

(Z)-5-(benzo[d]thiazol-6-ylmethylene)-2-(isopropylamino)-3-methyl-3,5-dihydro-4H-imidazol-4-one (11.98 mg) was prepared in the same procedure as described for Example 1. LRMS (M+H) m/z calculated 301.1, found 301.1. $^1$H NMR (400 MHz, DMSO-d6) δ 9.36 (s, 1H), 8.79 (d, J=1.1 Hz, 1H), 8.35-8.33 (m, 1H), 8.05 (d, J=8.0 Hz, 1H), 7.57 (d, J=8.0 Hz, 1H), 6.52 (s, 1H), 4.35-4.30 (m, 1H), 3.08 (s, 3H), 1.30 (d, J=8.0 Hz, 6H).

Example 46

(Z)-5-((1-methyl-1H-benzo[d]imidazol-6-yl)methylene)-2-(phenylamino)-3,5-dihydro-4H-imidazol-4-one

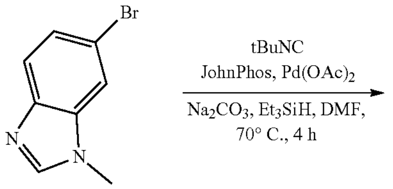

-continued

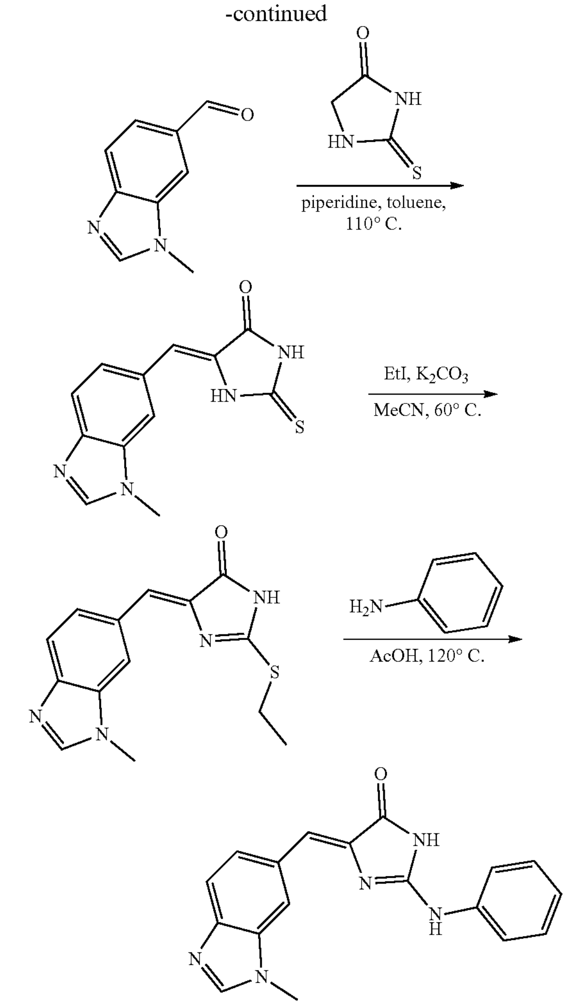

TJU-B163

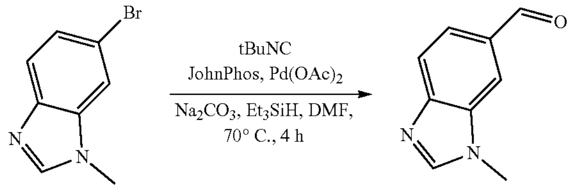

A mixture of 6-bromo-1-methyl-1H-benzo[d]imidazole (600 mg, 2.8 mmol, 1.0 eq.) and John-Phos (62 mg, 0.28 mmol, 0.1 eq.), $Pd(OAc)_2$ (65 mg, 0.28 mmol, 0.1 eq.), $Et_3SiH$ (814 mg, 7 mmol, 2.5 eq.) and $Na_2CO_3$ (742 mg, 7 mmol, 2.5 eq.) in DMF (30 mL) were stirred at 70° C. under $N_2$ for 4 hours. The mixture was diluted with $H_2O$ (20 mL) and extracted with EtOAc (10 mL×3). The organic layer was washed with brine (10 mL×3), dried over $Na_2SO_4$, concentrated to give a residue which was purified by flashing column (EA/PE=1/2, v/v) to afford 1-methyl-1H-benzo[d]imidazole-6-carbaldehyde (300 mg, 67%) as a brown solid. LRMS ($M+H^+$) m/z calculated 161.0, found 161.0.

(Z)-5-((1-methyl-1H-benzo[d]imidazol-6-yl)methylene)-2-(phenylamino)-3,5-dihydro-4H-imidazol-4-one (81.9 mg) was prepared in the same procedure as described for Example 24. LRMS ($M+H^+$) m/z calculated 318.1, found 318.1. $^1$H NMR (400 MHz, DMSO-d6) δ 8.74 (s, 1H), 8.40 (s, 1H), 8.25 (s, 1H), 7.95 (d, J=7.6 Hz, 2H), 7.72 (d, J=8.1 Hz, 1H), 7.64 (d, J=8.4 Hz, 1H), 7.40 (t, J=7.7 Hz, 3H), 7.08 (t, J=7.3 Hz, 1H), 6.65 (s, 1H), 3.92 (s, 3H).

Example 47

(Z)-5-(benzo[d][1,3]dioxol-5-ylmethylene)-2-(benzo[d]thiazol-6-ylamino)-3,5-dihydro-4H-imidazol-4-one

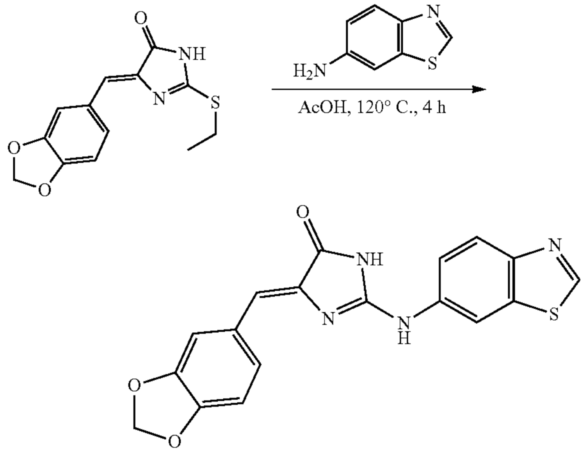

TJU-B253

(Z)-5-(benzo[d][1,3]dioxol-5-ylmethylene)-2-(benzo[d]thiazol-6-ylamino)-3,5-dihydro-4H-imidazol-4-one (156.7 mg) was prepared in the same procedure as described for Example 24. LRMS ($M+H^+$) m/z calculated 365.0, found 365.0. $^1$H NMR (400 MHz, DMSO-d6) δ 10.81 (s, 1H), 10.11 (s, 1H), 9.29 (s, 1H), 8.75 (s, 1H), 8.05 (t, J=12.0 Hz, 2H), 7.75 (d, J=8.2 Hz, 1H), 7.44 (d, J=7.3 Hz, 1H), 6.98 (d, J=8.1 Hz, 1H), 6.53 (s, 1H), 6.10 (s, 2H).

Example 48

(Z)-2-(benzo[d]thiazol-6-ylamino)-5-(benzo[d]thiazol-6-ylmethylene)-3,5-dihydro-4H-imidazol-4-one

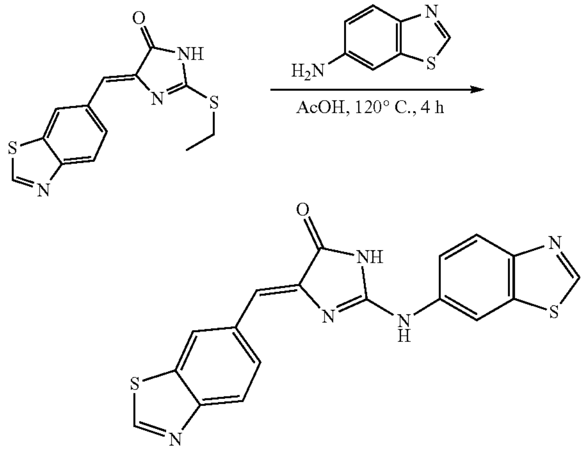

TJU-B264

(Z)-2-(benzo[d]thiazol-6-ylamino)-5-(benzo[d]thiazol-6-ylmethylene)-3,5-dihydro-4H-imidazol-4-one (74.7 mg) was prepared in the same procedure as described for Example 24. LRMS ($M+H^+$) m/z calculated 378.0, found 378.0. $^1H$ NMR (400 MHz, DMSO-d6) δ10.97 (s, 1H), 10.29 (s, 1H), 9.44 (s, 1H), 9.34 (s, 1H), 9.05 (s, 1H), 8.87 (s, 1H), 8.21 (s, 1H), 8.11 (dd, J=8.7 Hz, 2.7 Hz, 2H), 7.75 (d, J=7.9 Hz, 1H), 6.71 (s, 1H).

Example 49

(Z)-5-(benzo[d]thiazol-5-ylmethylene)-2-(isopropylamino)-3,5-dihydro-4H-imidazol-4-one

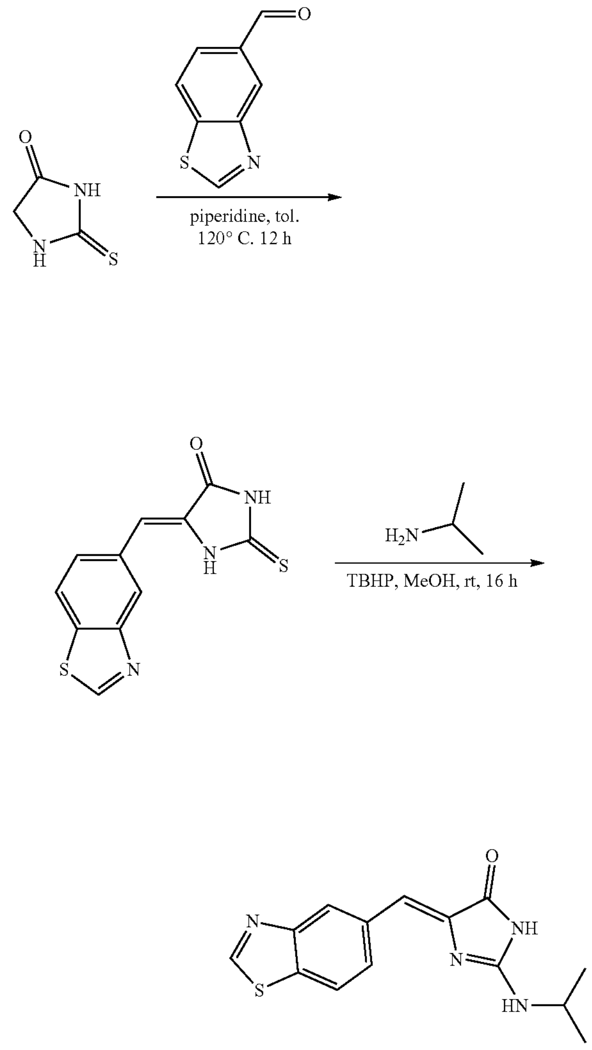

TJU-B269

(Z)-5-(benzo[d]thiazol-5-ylmethylene)-2-(isopropylamino)-3,5-dihydro-4H-imidazol-4-one (18.11 mg) was prepared in the same procedure as described for Example 1. LRMS ($M+H^+$) m/z calculated 287.1, found 287.1. $^1H$ NMR (400 MHz, DMSO-d6) δ10.95 (br, 1H), 9.37 (s, 1H), 8.85 (s, 1H), 8.43 (s, 0.33H), 8.14-8.09 (m, 2H), 7.82 (br, 1H), 6.42 (s, 1H), 4.09 (br, 1H), 1.23 (d, J=4.0 Hz, 6H).

Example 50

(Z)-2-(adamantan-1-ylamino)-5-(benzo[d]thiazol-5-ylmethylene)-3,5-dihydro-4H-imidazol-4-one

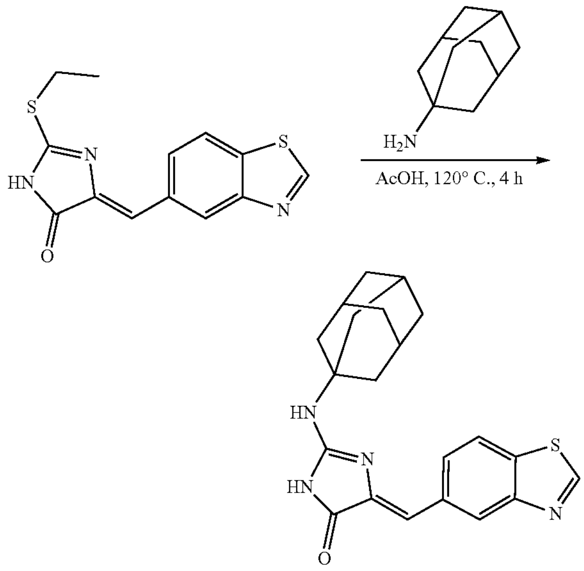

TJU=B273

(Z)-2-(adamantan-1-ylamino)-5-(benzo[d]thiazol-5-ylmethylene)-3,5-dihydro-4H-imidazol-4-one (10.2 mg) was prepared in the same procedure as described for Example 24. LRMS ($M+H^+$) m/z calculated 379.1, found 379.1. $^1H$ NMR (400 MHz, DMSO-d6) δ 9.38 (s, 1H), 9.00 (s, 1H), 8.38 (s, 1H), 8.09 (t, J=10.1 Hz, 2H), 7.40 (s, 1H), 6.43 (s, 1H), 2.19 (s, 5H), 2.10 (d, J=21.0 Hz, 5H), 1.73 (s, 4H), 1.65 (d, J=13.7 Hz, 2H).

Example 51

(Z)-5-((1H-indol-5-yl)methylene)-2-(phenylamino)-3,5-dihydro-4H-imidazol-4-one

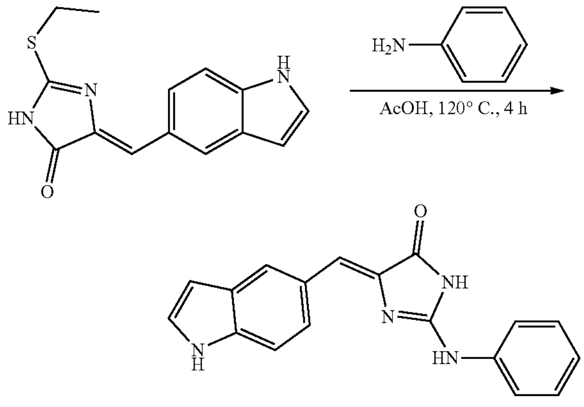

TJU-B275

(Z)-5-((1H-indol-5-yl)methylene)-2-(phenylamino)-3,5-dihydro-4H-imidazol-4-one (8.3 mg) was prepared in the same procedure as described for Example 24. LRMS (M+H$^+$) m/z calculated 303.1, found 303.1. $^1$H NMR (400 MHz, DMSO-d6) δ 11.23 (s, 1H), 10.93 (s, 1H), 10.08 (s, 1H), 8.33 (s, 1H), 7.96 (d, J=8.2 Hz, 1H), 7.87 (d, J=7.6 Hz, 2H), 7.39-7.35 (m, 5H), 7.06 (s, 1H), 6.64 (s, 1H), 6.48 (s, 1H).

Example 52

(Z)-5-(benzofuran-5-ylmethylene)-2-(phenylamino)-3,5-dihydro-4H-imidazol-4-one

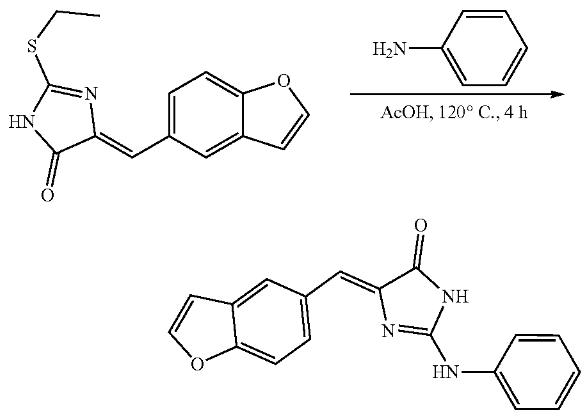

TJU-B276

(Z)-5-(benzofuran-5-ylmethylene)-2-(phenylamino)-3,5-dihydro-4H-imidazol-4-one (30.8 mg) was prepared in the same procedure as described for Example 24. LRMS (M+H$^+$) m/z calculated 305.1, found 305.1. $^1$H NMR (400 MHz, DMSO-d6) δ10.87 (s, 1H), 10.02 (s, 1H), 8.45 (s, 1H), 8.11 (s, 1H), 8.03 (d, J=2.1 Hz, 1H), 7.84 (d, J=6.9 Hz, 2H), 7.64 (d, J=8.6 Hz, 1H), 7.43 (t, J=7.8 Hz, 2H), 7.09 (t, J=7.3 Hz, 1H), 7.02 (d, J=1.5 Hz, 1H), 6.64 (s, 1H).

Example 53

(Z)-2-(phenylamino)-5-(quinolin-6-ylmethylene)-3,5-dihydro-4H-imidazol-4-one

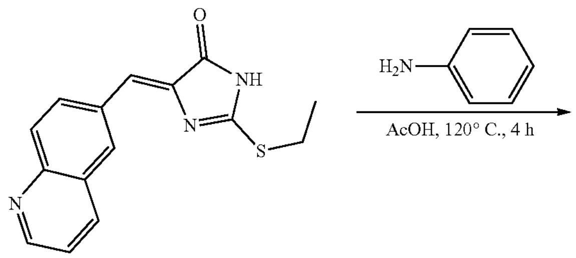

-continued

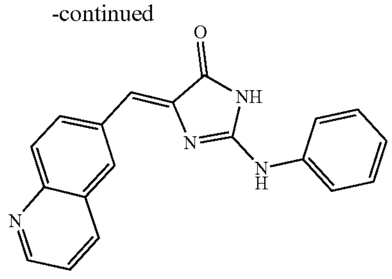

TJU-B282

(Z)-2-(phenylamino)-5-(quinolin-6-ylmethylene)-3,5-dihydro-4H-imidazol-4-one (8.4 mg) was prepared in the same procedure as described for Example 24. LRMS (M+H) m/z calculated 315.1, found 315.1. $^1$H NMR (400 MHz, DMSO-d6) δ 11.17 (s, 1H), 10.30 (s, 1H), 8.88 (dd, J=4.2 Hz, 1.6 Hz, 1H), 8.64 (s, 1H), 8.57 (d, J=8.2 Hz, 1H), 8.31 (d, J=7.8 Hz, 1H), 8.22 (s, 1H), 8.02 (d, J=8.8 Hz, 1H), 7.87 (d, J=7.6 Hz, 2H), 7.55 (dd, J=8.3 Hz, 4.2 Hz, 1H), 7.46 (t, J=7.7 Hz, 2H), 7.13 (d, J=7.4 Hz, 1H), 6.67 (s, 1H).

Example 54

(Z)-5-((1H-indazol-6-yl)methylene)-2-(phenylamino)-3,5-dihydro-4H-imidazol-4-one

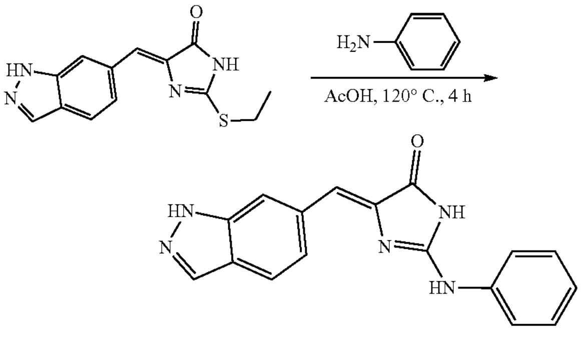

TJU-B289

(Z)-5-((1H-indazol-6-yl)methylene)-2-(phenylamino)-3,5-dihydro-4H-imidazol-4-one (8.6 mg) was prepared in the same procedure as described for Example 24. LRMS (M+H$^+$) m/z calculated 304.1, found 304.1. $^1$H NMR (400 MHz, DMSO-d6) δ13.23 (s, 1H), 11.41 (s, 1H), 8.46 (s, 2H), 8.05 (s, 1H), 7.90 (d, J=7.4 Hz, 2H), 7.75 (s, 2H), 7.44 (t, J=7.7 Hz, 2H), 7.08 (t, J=7.3 Hz, 1H), 6.60 (s, 1H).

Example 55

(Z)-5-((1H-indazol-5-yl)methylene)-2-(phenylamino)-3,5-dihydro-4H-imidazol-4-one

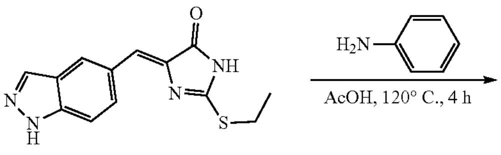

-continued

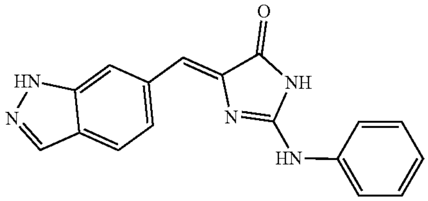

TJU-B290

(Z)-5-((1H-indazol-5-yl)methylene)-2-(phenylamino)-3,5-dihydro-4H-imidazol-4-one (32.5 mg) was prepared in the same procedure as described for Example 24. LRMS ($M+H^+$) m/z calculated 304.1, found 304.1. $^1H$ NMR (400 MHz, DMSO-d6) δ13.17 (s, 1H), 10.75 (s, 1H), 9.88 (s, 1H), 8.49 (s, 1H), 8.24 (d, J=8.6 Hz, 1H), 8.15 (s, 1H), 7.85 (d, J=8.0 Hz, 2H), 7.57 (d, J=8.7 Hz, 1H), 7.44 (s, 2H), 7.09 (t, J=7.3 Hz, 1H), 6.67 (s, 1H).

Example 56: (Z)-2-(benzo[d]thiazol-6-ylamino)-5-((2,3-dihydrobenzo[b][1,4]dioxin-6-yl)methylene)-3,5-dihydro-4H-imidazol-4-one

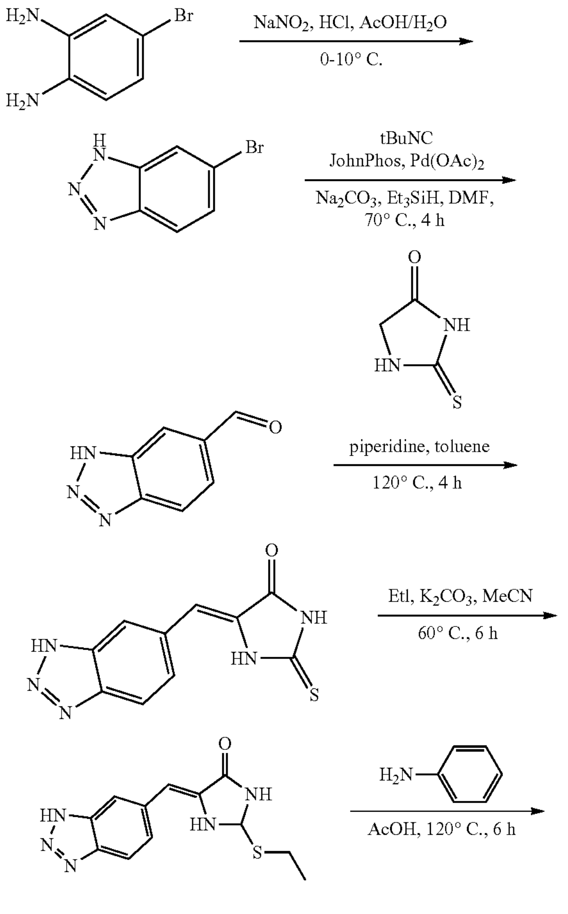

-continued

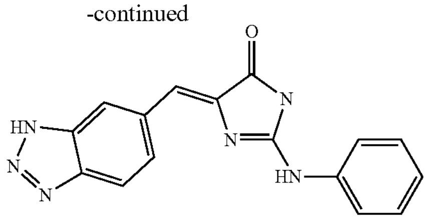

TJU-B281

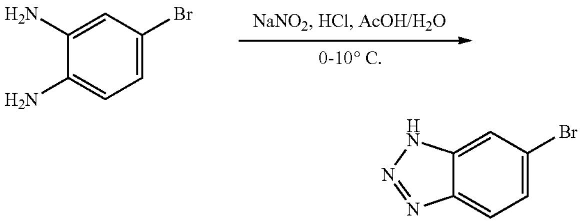

HCl (2 mL) was added to a solution of 4,5-dichlorobenzene-1,2-diamine (4.8 g, 25.7 mmol, 1 eq) in acetic acid (45 mL) and water (15 mL) at 0° C., a solution of sodium nitrite (2.8 g, 40.5 mmol, 1.5 eq) in water (15 mL) was then added. The mixture was stirred at room temperature for 30 minutes and then diluted with water. The resulting mixture was filtered, washed with water and dried in vacuo. The crude product was dissolved in hot ethanol. The solid was filtered off, then water was added to ethanol, the precipitate was filtered, washed with water and dried in vacuo to afford 6-bromo-1H-benzo[d][1,2,3]triazole (4.1 g, 81%) as a white solid. LRMS ($M+H^+$) m/z calculated 199.0, found 199.0.

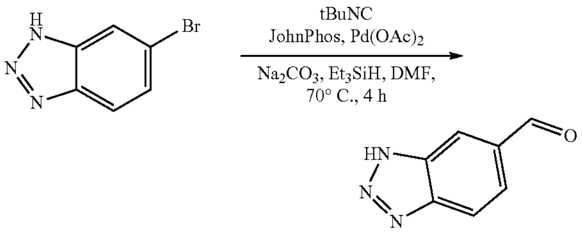

A mixture of 6-bromo-1H-benzo[d][1,2,3]triazole (600 mg, 3.1 mmol, 1.0 eq.), John-Phos (65 mg, 0.31 mmol, 0.1 eq.), $Pd(OAc)_2$ (70 mg, 0.31 mmol, 0.1 eq.), $Et_3SiH$ (980 mg, 7.8 mmol, 2.5 eq.) and $Na_2CO_3$ (827 mg, 7.8 mmol, 2.5 eq.) in DMF (30 mL) was stirred at 70° C. under $N_2$ for 4 hour. The mixture was diluted with $H_2O$ (20 mL) and extracted with EtOAc (20 mL×3). The combined organic layer was washed with brine (10 mL×3), dried over $Na_2SO_4$, concentrated to give a residue which was purified by flash-ing column (DCM/MeOH=1/0 to 10/1, v/v) to afford 1H-benzo[d][1,2,3]triazole-6-carbaldehyde (273 mg, 60%) as a brown solid. LRMS ($M+H^+$) m/z calculated 148.0, found 148.0.

(Z)-5-((1H-benzo[d][1,2,3]triazol-6-yl)methylene)-2-(phenylamino)-3,5-dihydro-4H-imidazol-4-one (8.9 mg) was prepared following the same procedure of Example 1. LRMS ($M+H^+$) m/z calculated 305.1, found 305.1. $^1H$ NMR (400 MHz, $CD_3OD$) δ 10.86 (s, 1H), 8.69 (s, 1H), 8.15 (s, 1H), 7.89 (dd, J=33.0 Hz, 8.1 Hz, 3H), 7.44 (t, J=7.9 Hz, 2H), 7.13 (t, J=7.4 Hz, 1H), 6.71 (s, 1H).

Example 57

(Z)-5-(benzo[d]thiazol-5-ylmethylene)-2-(benzo[d]thiazol-6-ylamino)-3,5-dihydro-4H-imidazol-4-one

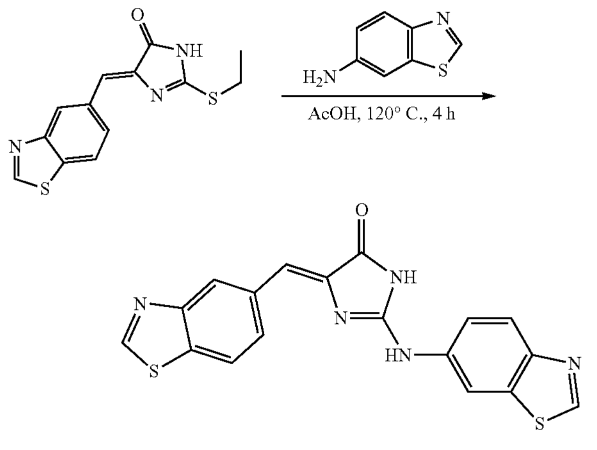

TJU-B303

(Z)-5-(benzo[d]thiazol-5-ylmethylene)-2-(benzo[d]thiazol-6-ylamino)-3,5-dihydro-4H-imidazol-4-one (152.7 mg) was prepared in the same procedure as described for Example 24. LRMS (M+H) m/z calculated 378.0, found 378.0. $^1$H NMR (400 MHz, DMSO-d6) δ 10.77 (s, 2H), 9.44 (s, 1H), 9.33 (s, 1H), 9.05 (s, 1H), 8.87 (s, 1H), 8.20 (s, 1H), 8.10 (dd, J=8.7 Hz, 3.2 Hz, 2H), 7.75 (d, J=8.0 Hz, 1H), 6.70 (s, 1H).

Example 58

(Z)-5-(1H-indol-5-yl)methylene)-2-(benzo[d]thiazol-6-ylamino)-3,5-dihydro-4H-imidazol-4-one

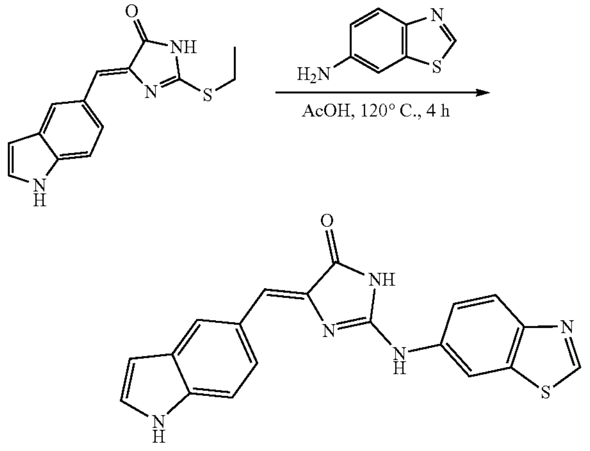

TJU-B304

(Z)-5-((1H-indol-5-yl)methylene)-2-(benzo[d]thiazol-6-ylamino)-3,5-dihydro-4H-imidazol-4-one (30.9 mg) was prepared in the same procedure as described for Example 24. LRMS (M+H$^+$) m/z calculated 360.0, found 360.0. $^1$H NMR (400 MHz, DMSO-d6) δ 12.61 (s, 1H), 11.87 (s, 1H), 11.24 (s, 1H), 9.28 (s, 1H), 9.04 (s, 1H), 8.51 (d, J=12.6 Hz, 2H), 8.08 (d, J=8.8 Hz, 1H), 7.81-7.75 (m, 2H), 7.44-7.40 (m, 2H), 6.64 (s, 1H), 6.51 (s, 1H).

Example 59

(Z)-2-(benzo[d]thiazol-6-ylamino)-5-(benzofuran-5-ylmethylene)-3,5-dihydro-4H-imidazol-4-one

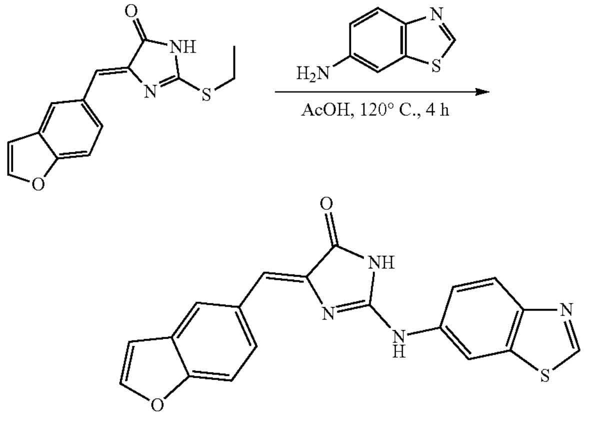

TJU-B305

(Z)-2-(benzo[d]thiazol-6-ylamino)-5-(benzofuran-5-ylmethylene)-3,5-dihydro-4H-imidazol-4-one (46.4 mg) was prepared in the same procedure as described for Example 24. LRMS (M+H$^+$) m/z calculated 361.1, found 361.1. $^1$H NMR (400 MHz, DMSO-d6) δ 10.85 (s, 1H), 10.16 (s, 1H), 9.31 (s, 1H), 8.82 (s, 1H), 8.57 (s, 1H), 8.08-8.02 (m, 3H), 7.84 (s, 1H), 7.64 (d, J=8.6 Hz, 1H), 7.00 (d, J=1.4 Hz, 1H), 6.69 (s, 1H).

Example 60

(Z)-2-(benzo[d]thiazol-6-ylamino)-5-(quinolin-7-ylmethylene)-3,5-dihydro-4H-imidazol-4-one

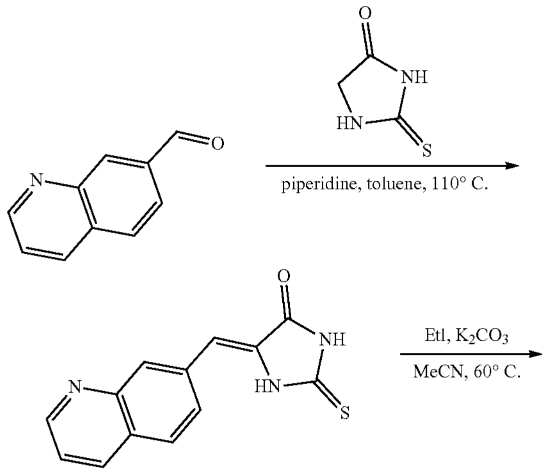

-continued

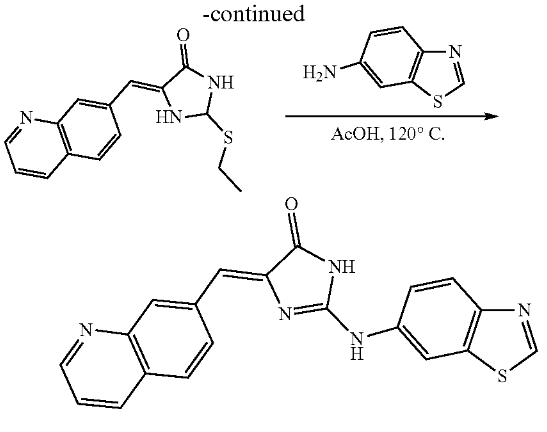

TJU-B307

(Z)-2-(benzo[d]thiazol-6-ylamino)-5-(quinolin-7-ylmethylene)-3,5-dihydro-4H-imidazol-4-one (25.9 mg) was prepared in the same procedure as described for Example 24. LRMS ($M+H^+$) m/z calculated 371.4, found 371.4. $^1H$ NMR (400 MHz, DMSO-d6) δ 11.00 (s, 1H), 10.38 (s, 1H), 9.34 (s, 1H), 8.90 (dd, J=4.2 Hz, 1.6 Hz, 2H), 8.74 (s, 1H), 8.47 (d, J=27.3 Hz, 1H), 8.33 (d, J=7.7 Hz, 1H), 8.14 (d, J=8.8 Hz, 1H), 8.03 (d, J=8.8 Hz, 1H), 7.86 (s, 1H), 7.58 (dd, J=8.3 Hz, 4.2 Hz, 1H), 6.72 (s, 1H).

Example 61

(Z)-5-(benzo[d]thiazol-6-ylmethylene)-2-((1-methyl-1H-benzo[d]imidazol-5-yl)amino)-3,5-dihydro-4H-imidazol-4-one

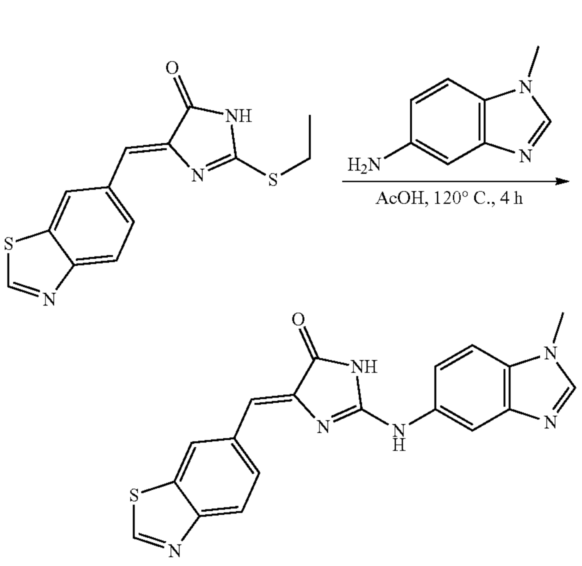

TJU-B293

(Z)-5-(benzo[d]thiazol-6-ylmethylene)-2-((1-methyl-1H-benzo[d]imidazol-5-yl)amino)-3,5-dihydro-4H-imidazol-4-one (56.1 mg) was prepared in the same procedure as described for Example 24. LRMS (M+H) m/z calculated 374.2, found 374.2. $^1H$ NMR (400 MHz, DMSO-d6) δ 12.18 (s, 1H), 11.16 (s, 1H), 9.40 (s, 1H), 8.96 (s, 1H), 8.31 (s, 3H), 8.19 (s, 1H), 8.08 (d, J=8.5 Hz, 1H), 7.59 (d, J=6.9 Hz, 2H), 6.58 (s, 1H), 3.86 (s, 3H).

Example 63

(Z)-5-((1H-indol-6-yl)methylene)-2-(benzo[d]thiazol-6-ylamino)-3,5-dihydro-4H-imidazol-4-one

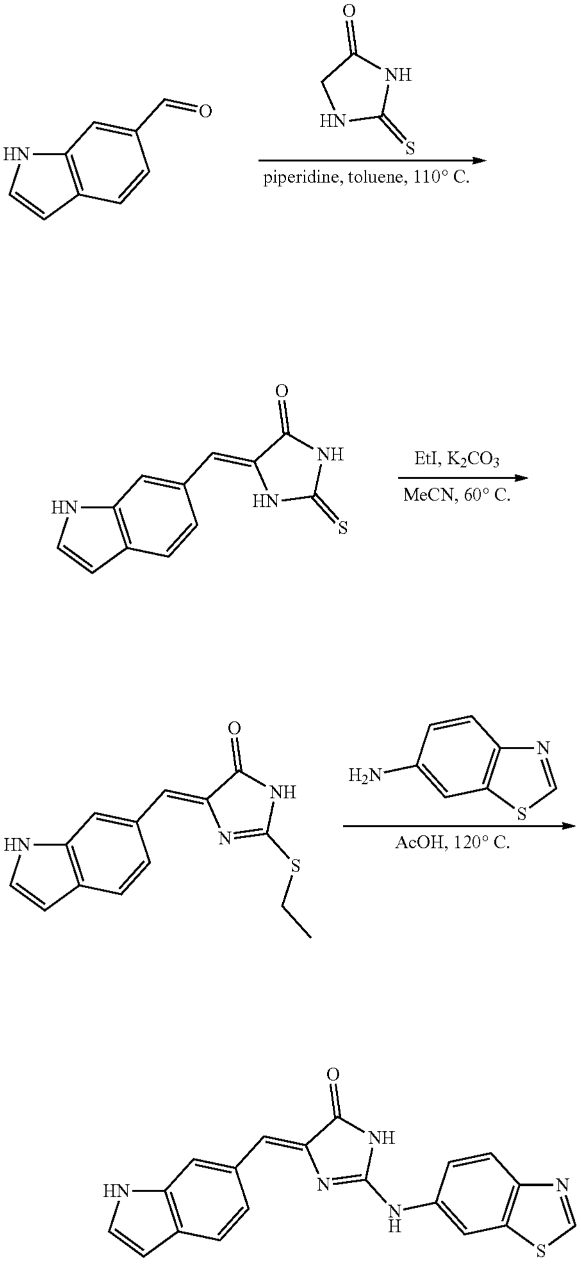

TJU-B306

(Z)-5-((1H-indol-6-yl)methylene)-2-(benzo[d]thiazol-6-ylamino)-3,5-dihydro-4H-imidazol-4-one (8.1 mg) was prepared in the same procedure as described for Example 24. LRMS ($M+H^+$) m/z calculated 360.0, found 360.0. $^1H$ NMR (400 MHz, DMSO-d6) δ 11.22 (s, 1H), 9.51 (s, 1H), 8.24 (d, J=2.0 Hz, 2H), 8.19 (d, J=15.0 Hz, 1H), 7.83-7.81 (m, 1H), 7.53-7.51 (m, 2H), 7.41 (dd, J=6.5 Hz, 3.8 Hz, 1H), 7.22 (s, 1H), 6.65 (s, 1H), 6.43 (s, 1H).

Example 65

(Z)-5-((4-methyl-3,4-dihydro-2H-benzo[b][1,4]oxazin-7-yl)methylene)-2-(phenylamino)-3,5-dihydro-4H-imidazol-4-one

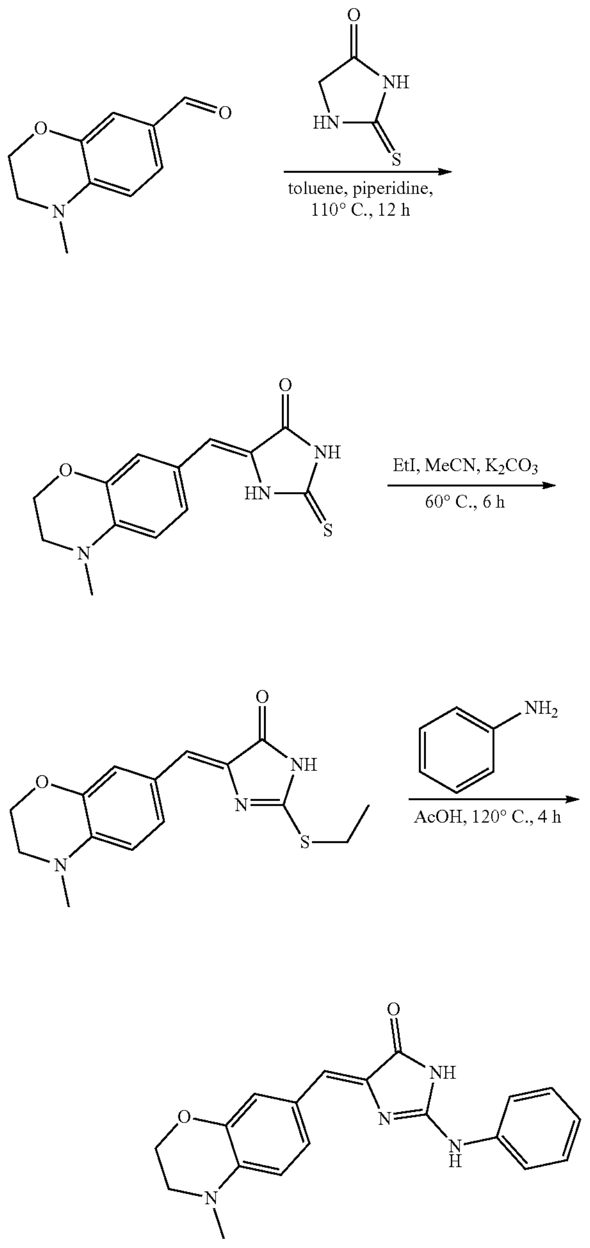

TJU-B318

(Z)-5-((4-methyl-3,4-dihydro-2H-benzo[b][1,4]oxazin-7-yl)methylene)-2-(phenylamino)-3,5-dihydro-4H-imidazol-4-one (16.0 mg) was prepared in the same procedure as described for Example 24. LRMS ($M+H^+$) m/z calculated 335.2, found 335.2. $^1$H NMR (400 MHz, DMSO-d6) δ 9.87 (s, 1H), 8.50 (s, 1H), 7.81 (d, J=7.6 Hz, 2H), 7.61 (s, 1H), 7.44 (s, 1H), 7.34-7.32 (m, 2H), 7.02 (s, 1H), 6.71 (d, J=8.5 Hz, 1H), 6.34 (s, 1H), 4.24 (s, 2H), 3.40 (s, 2H), 2.90 (s, 3H).

Example 69

(Z)-2-((1H-indol-5-yl)amino)-5-(benzo[d]thiazol-6-ylmethylene)-3,5-dihydro-4H-imidazol-4-one

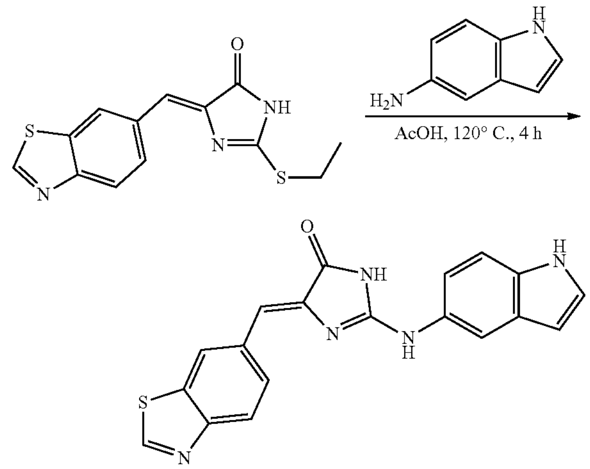

TJU-B328

(Z)-2-((1H-indol-5-yl)amino)-5-(benzo[d]thiazol-6-ylmethylene)-3,5-dihydro-4H-imidazol-4-one (8.5 mg) was prepared in the procedure as described in Example 24. LRMS (M+H) m/z calculated 360.1, found 360.0. $^1$H NMR (400 MHz, DMSO-$d_6$) δ 11.11 (s, 1H), 10.69 (s, 1H), 9.78 (s, 1H), 9.40 (s, 1H), 9.05 (s, 1H), 8.25 (d, J=8.6 Hz, 1H), 8.17 (s, 1H), 8.10 (d, J=8.6 Hz, 1H), 7.41 (d, J=8.6 Hz, 2H), 7.32 (d, J=8.1 Hz, 1H), 6.58 (s, 1H), 6.49 (s, 1H).

Example 70

(Z)-5-(benzo[d][1,3]dioxol-5-ylmethylene)-2-(benzo[d]thiazol-6-yl(methyl)amino)-3,5-dihydro-4H-imidazol-4-one

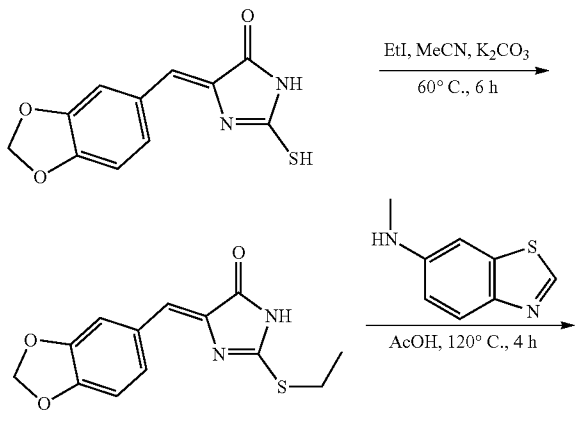

-continued

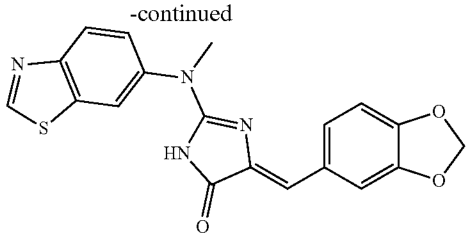

TJU-B330

(Z)-5-(benzo[d][1,3]dioxol-5-ylmethylene)-2-(benzo[d]thiazol-6-yl(methyl)amino)-3,5-dihydro-4H-imidazol-4-one one (64.6 mg) was prepared in the procedure as described in Example 24. LRMS (M+H$^+$) m/z calculated 379.1, found 379.0. $^1$H NMR (400 MHz, DMSO-$d_6$) δ 10.95 (s, 1H), 9.44 (s, 1H), 8.26 (d, J=2.1 Hz, 1H), 8.14 (d, J=8.7 Hz, 1H), 7.95 (d, J=1.2 Hz, 1H), 7.61 (dd, J=8.7 Hz, 2.2 Hz, 1H), 7.42 (dd, Hz=8.2 Hz, 1.2 Hz, 1H), 6.92 (d, J=8.1 Hz, 1H), 6.40 (s, 1H), 6.03 (s, 2H), 3.56 (s, 3H).

Example 71

(Z)-5-((1-methyl-1H-benzo[d]imidazol-5-yl)methylene)-2-(phenylamino)-3,5-dihydro-4H-imidazol-4-one (TJU-B274)

TJU-B274

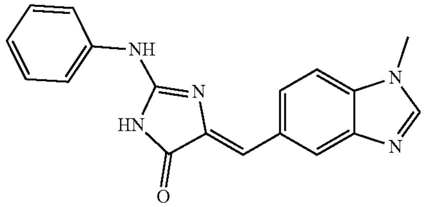

(Z)-5-((1-methyl-1H-benzo[d]imidazol-5-yl)methylene)-2-(phenylamino)-3,5-dihydro-4H-imidazol-4-one was prepared in the same procedure as described for Example 24. LRMS (M+H+) m/z calculated 318.1, found 318.1. 1H NMR (400 MHz, DMSO-d6) δ 8.44 (s, 0.5H), 8.37 (s, 1H), 8.13 (m, 1H), 7.89 (d, J=7.3 Hz, 1H), 7.57 (dd, J=31.6, 7.6 Hz, 2H), 7.37 (dd, J=21.0, 13.1 Hz, 3H), 7.06 (d, J=7.3 Hz, 1H), 6.63 (s, 1H), 3.82 (m, 2H).

Example 72

(Z)-5-(benzo[b]thiophen-5-ylmethylene)-2-(phenylamino)-3,5-dihydro-4H-imidazol-4-one (TJU-277)

TJU-277

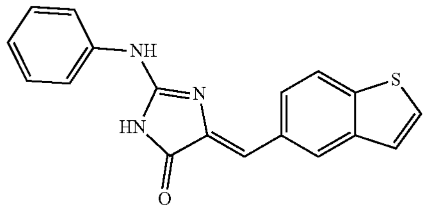

(Z)-5-(benzo[b]thiophen-5-ylmethylene)-2-(phenylamino)-3,5-dihydro-4H-imidazol-4-one was prepared in the same procedure as described for Example 24. LRMS (M+H+) m/z calculated 320.1, found 320.1. 1H NMR (400 MHz, DMSO-d6) δ 10.73 (s, 1H), 9.87 (s, 1H), 8.62 (s, 1H), 8.17 (d, J=8.2 Hz, 1H), 8.04 (d, J=8.5 Hz, 1H), 7.83-7.79 (m, 3H), 7.49-7.41 (m, 3H), 7.10 (t, J=7.4 Hz, 1H), 6.65 (s, 1H).

Example 73

(Z)-5-((1H-indol-6-yl)methylene)-2-(phenylamino)-3,5-dihydro-4H-imidazol-4-one (TJU-278)

TJU-278

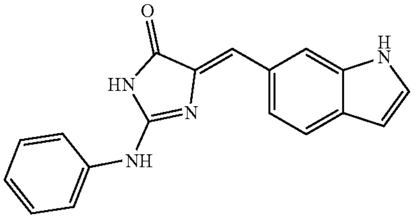

(Z)-5-((1H-indol-6-yl)methylene)-2-(phenylamino)-3,5-dihydro-4H-imidazol-4-one was prepared in the same procedure as described for Example 24. LRMS (M+H$^+$) m/z calculated 303.1, found 303.1. $^1$H NMR (400 MHz, DMSO-$d_6$) δ 11.31 (s, 2H), 10.33 (s, 1H), 8.31 (s, 1H), 7.89 (d, J=7.9 Hz, 2H), 7.68 (d, J=8.4 Hz, 1H), 7.55 (d, J=8.3 Hz, 1H), 7.45-7.42 (m, 3H), 7.07 (t, J=7.3 Hz, 1H), 6.63 (s, 1H), 6.44 (s, 1H).

Example 74

(Z)-2-(benzo[d]thiazol-6-ylamino)-5-((2,3-dihydrobenzo[b][1,4]dioxin-6-yl)methylene)-3,5-dihydro-4H-imidazol-4-one

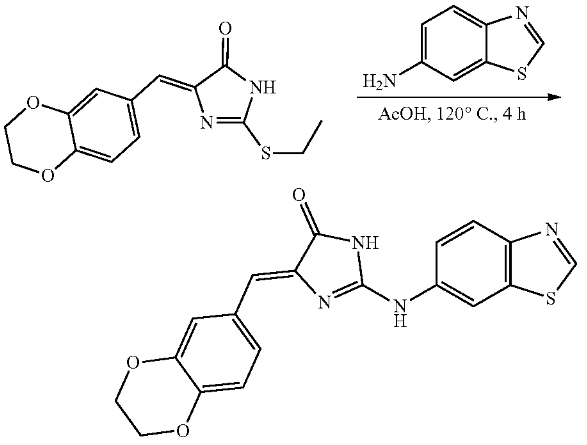

TJU-B296

(Z)-2-(benzo[d]thiazol-6-ylamino)-5-((2,3-dihydrobenzo[b][1,4]dioxin-6-yl)methylene)-3,5-dihydro-4H-imidazol-4-one (40.0 mg) was prepared as described for Example 24. LRMS (M+H$^+$) m/z calculated 379.0, found 379.0. $^1$H NMR (400 MHz, DMSO-d6) δ 10.78 (s, 1H), 10.11 (s, 1H), 9.30

(s, 1H), 8.79 (s, 1H), 8.06 (d, J=8.8 Hz, 1H), 7.91 (s, 1H), 7.75 (d, J=8.4 Hz, 1H), 7.45 (s, 1H), 6.89 (d, J=8.4 Hz, 1H), 6.48 (s, 1H), 4.30 (s, 4H).

Example 75

(Z)-2-(benzo[d]thiazol-6-ylamino)-5-((1-methyl-1H-benzo[d]imidazol-6-yl)methylene)-3,5-dihydro-4H-imidazol-4-one

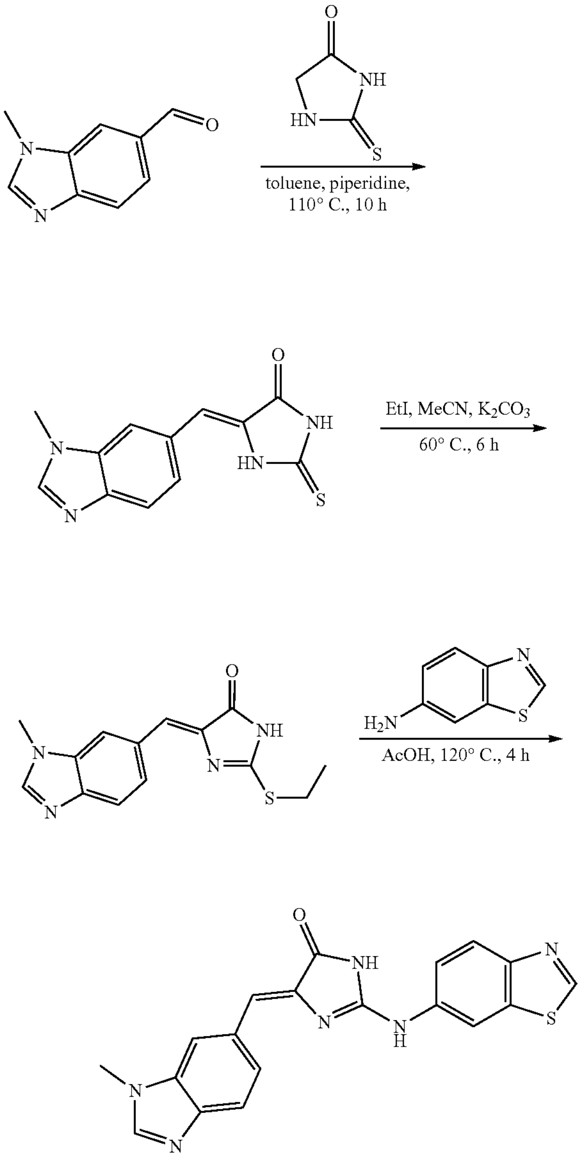

TJU-B299

(Z)-2-(benzo[d]thiazol-6-ylamino)-5-((1-methyl-1H-benzo[d]imidazol-6-yl)methylene)-3,5-dihydro-4H-imidazol-4-one (9.4 mg) was prepared as described for Example 24. LRMS (M+H$^+$) m/z calculated 375.1, found 375.1. $^1$H NMR (400 MHz, DMSO-d6) δ 11.07 (s, 2H), 9.32 (s, 1H), 9.26 (d, J=5.8 Hz, 1H), 8.83-8.81 (m, 2H), 8.11 (d, J=8.8 Hz, 1H), 8.01 (d, J=7.9 Hz, 1H), 7.84-7.80 (m, 2H), 6.75 (s, 1H), 4.11 (s, 3H).

Example 76

(Z)-5-((1H-benzo[d]imidazol-6-yl)methylene)-2-(benzo[d]thiazol-6-ylamino)-3,5-dihydro-4H-imidazol-4-one

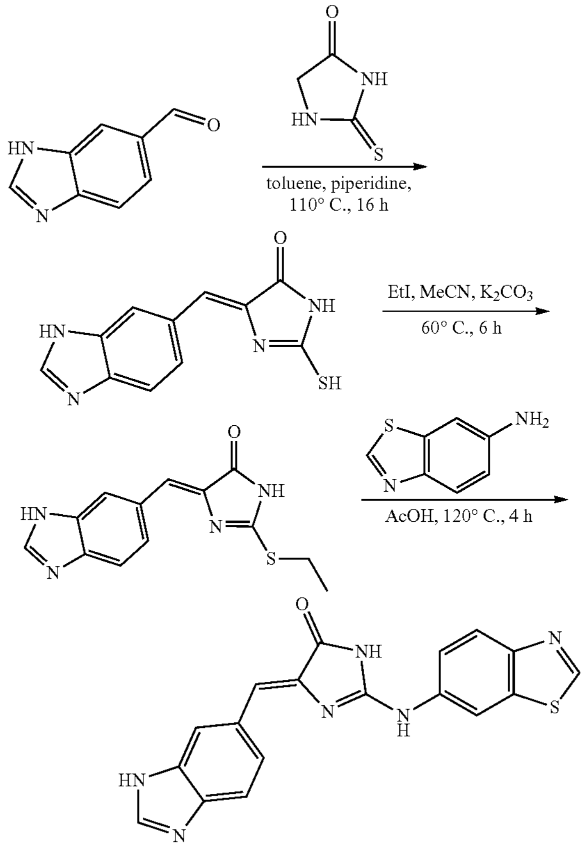

TJU-B300

(Z)-5-((1H-benzo[d]imidazol-6-yl)methylene)-2-(benzo[d]thiazol-6-ylamino)-3,5-dihydro-4H-imidazol-4-one (86.20 mg) was prepared as described for Example 24. LRMS (M+H$^+$) m/z calculated 361.1, found 361.0. $^1$H NMR (400 MHz, DMSO-d6) δ 10.79 (s, 1H), 9.31 (s, 1H), 8.68 (s, 1H), 8.47 (s, 1H), 8.33 (s, 1H), 8.12 (d, J=12.0 Hz, 1H), 8.06-7.89 (m, 2H), 7.62 (d, J=8.0 Hz, 1H), 6.72 (s, 1H).

Example 77

(Z)-5-((1-methyl-1H-indazol-5-yl)methylene)-2-(phenylamino)-3,5-dihydro-4H-imidazol-4-one

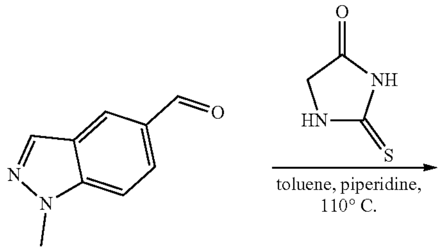

-continued

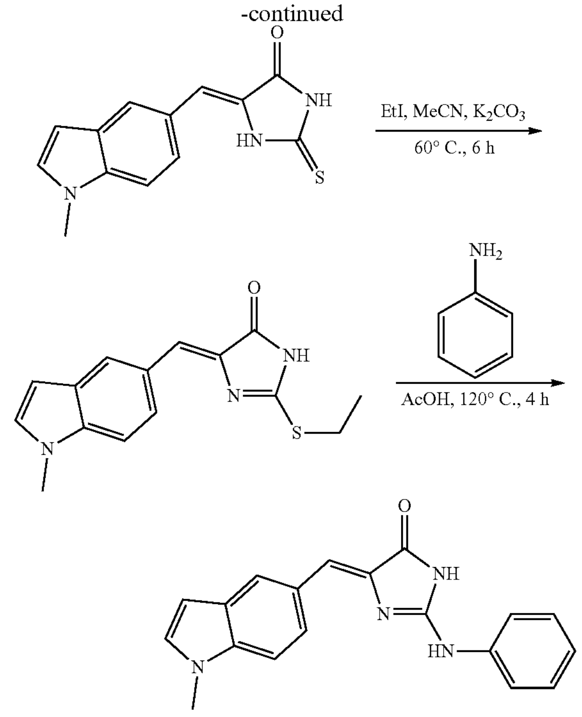

TJU-B321

(Z)-5-((1-methyl-1H-indazol-5-yl)methylene)-2-(phenylamino)-3,5-dihydro-4H-imidazol-4-one (39.1 mg) was prepared as described for Example 24. LRMS (M+H$^+$) m/z calculated 318.1, found 318.1. $^1$H NMR (400 MHz, DMSO-d6) δ 10.65 (s, 1H), 9.78 (s, 1H), 8.47 (s, 1H), 8.31 (d, J=8.7 Hz, 1H), 8.12 (s, 1H), 7.84 (d, J=7.8 Hz, 2H), 7.69 (d, J=8.8 Hz, 1H), 7.43 (t, J=7.9 Hz, 2H), 7.10 (t, J=7.3 Hz, 1H), 6.68 (s, 1H), 4.06 (s, 3H).

Example 78

(Z)-2-(benzo[d]thiazol-6-ylamino)-5-((1-methyl-1H-indazol-5-yl)methylene)-3,5-dihydro-4H-imidazol-4-one

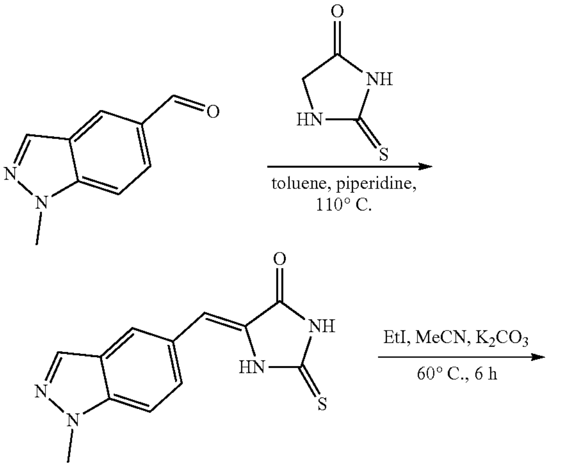

-continued

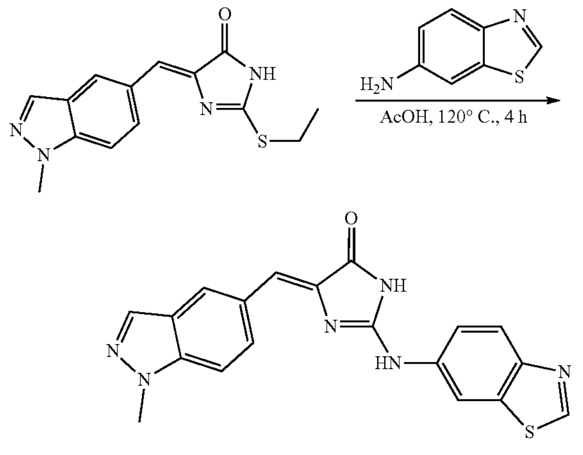

TJU-B322

(Z)-2-(benzo[d]thiazol-6-ylamino)-5-((1-methyl-1H-indazol-5-yl)methylene)-3,5-dihydro-4H-imidazol-4-one (81.7 mg) was prepared as described for Example 24. LRMS (M+H) m/z calculated 375.1, found 375.1. $^1$H NMR (400 MHz, DMSO-d6) δ 10.83 (s, 1H), 10.14 (s, 1H), 9.32 (s, 1H), 8.80 (s, 1H), 8.58 (s, 1H), 8.24 (d, J=8.7 Hz, 1H), 8.12 (d, J=8.7 Hz, 2H), 7.84 (d, J=8.6 Hz, 1H), 7.69 (d, J=8.8 Hz, 1H), 6.72 (s, 1H), 4.08 (s, 3H).

Example 79

5-((1-methyl-1H-indazol-6-yl)methylene)-2-(phenylamino)-3,5-dihydro-4H-imidazol-4-one

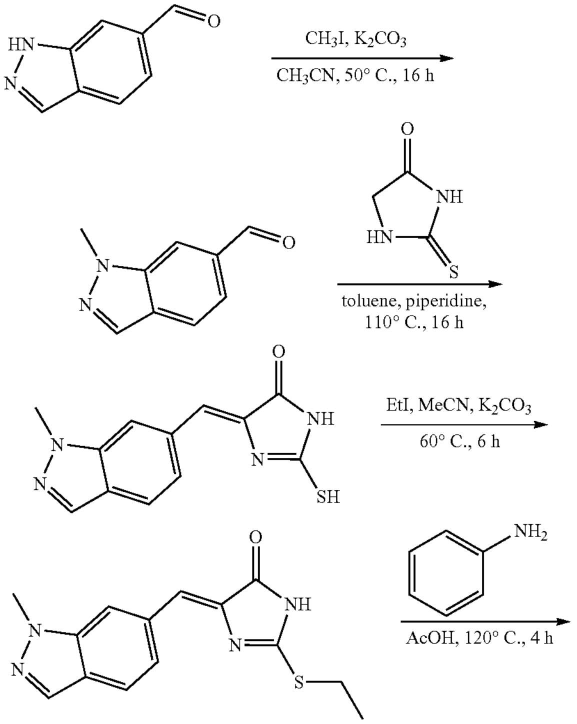

-continued

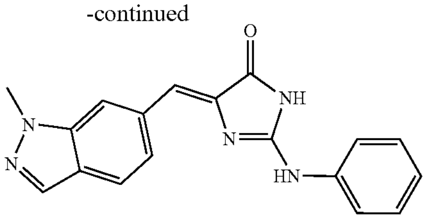

TJU-B323

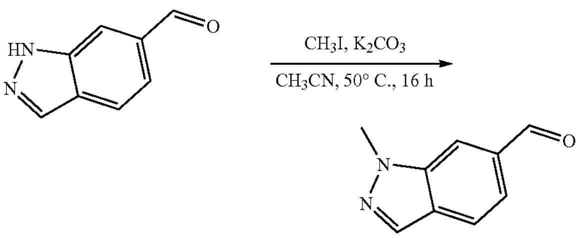

To a solution of 1H-indazole-6-carbaldehyde (1.22 g, 8.36 mmol) in MeOH (15 mL) were added iodomethane (1.30 g, 9.15 mmol) and Potassium carbonate (2.31 g, 16.74 mmol) at room temperature under $N_2$. The mixture was stirred at 50° C. for 16 h. Then the mixture was quenched with water (40 mL) and extracted with EtOAc (40 mL×3). The combined organic layer was washed with brine (40 mL), dried over anhydrous $Na_2SO_4$ and concentrated. The residue was purified by column chromatography on silica gel (EA/PE=1/3, v/v) to afford the 1-methyl-1H-indazole-6-carbaldehyde (1.2 g, 89%) as a yellow solid. LRMS (M+H$^+$) m/z calculated 161.1, found 161.1.

5-((1-methyl-1H-indazol-6-yl)methylene)-2-(phenylamino)-3,5-dihydro-4H-imidazol-4-one (8.50 mg) was prepared as described for Example 24. LRMS (M+H$^+$) m/z calculated 318.1, found 318.1. $^1$H NMR (400 MHz, DMSO-d6) δ 10.74 (s, 1H), 9.88 (s, 1H), 8.31 (d, J=8.0 Hz, 2H), 7.86-7.84 (m, 3H), 7.69 (d, J=12.0 Hz, 1H), 7.40 (t, J=8.0 Hz, 2H), 7.10 (t, J=8.0 Hz, 1H), 6.62 (s, 1H), 4.18 (s, 3H).

Example 80

(Z)-2-(benzo[d]thiazol-6-ylamino)-5-((1-methyl-1H-indazol-6-yl)methylene)-3,5-dihydro-4H-imidazol-4-one

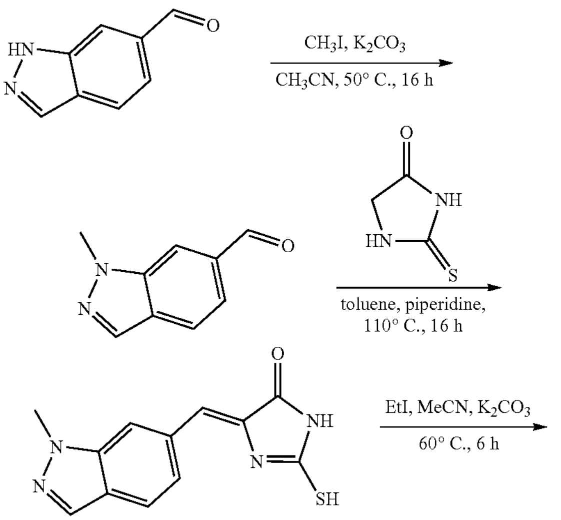

-continued

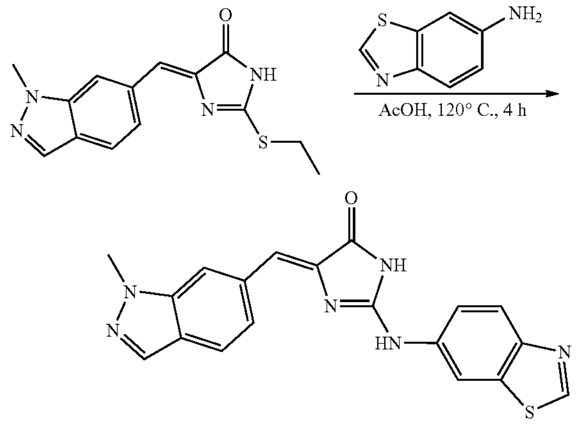

TJU-B324

(Z)-2-(benzo[d]thiazol-6-ylamino)-5-((1-methyl-1H-indazol-6-yl)methylene)-3,5-dihydro-4H-imidazol-4-one (42.40 mg) was prepared as described for Example 24. LRMS (M+H$^+$) m/z calculated 375.1, found 375.1. $^1$H NMR (400 MHz, DMSO-d6) δ 10.93 (s, 1H), 10.25 (s, 1H), 9.31 (s, 1H), 8.80 (s, 1H), 8.32 (s, 2H), 8.08 (d, J=8.0 Hz, 1H), 7.89 (d, J=16.0 Hz, 2H), 7.71 (d, J=8.0 Hz, 1H), 6.66 (s, 1H), 4.19 (s, 3H).

Example 81

(Z)-5-(benzo[d]thiazol-6-ylmethylene)-2-((2,3-dihydrobenzo[b][1,4]dioxin-6-yl)amino)-3,5-dihydro-4H-imidazol-4-one

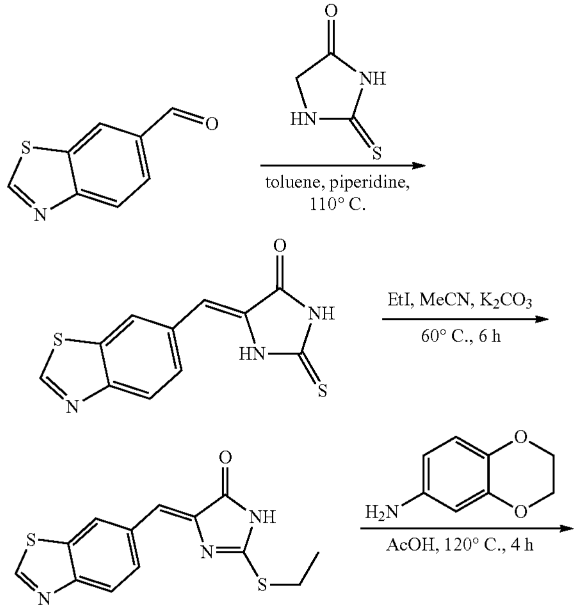

-continued

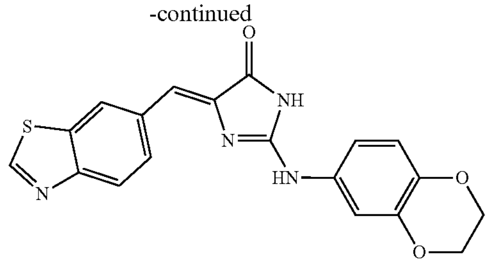

TJU-B325

(Z)-5-(benzo[d]thiazol-6-ylmethylene)-2-((2,3-dihydrobenzo[b][1,4]dioxin-6-yl)amino)-3,5-dihydro-4H-imidazol-4-one (4.6 mg) was prepared as described for Example 24. LRMS ($M+H^+$) m/z calculated 379.1, found 379.0. $^1H$ NMR (400 MHz, DMSO-d6) δ 10.79 (s, 1H), 9.81 (s, 1H), 9.41 (s, 1H), 8.94 (s, 1H), 8.25 (d, J=9.2 Hz, 1H), 8.06 (d, J=8.6 Hz, 1H), 7.57 (s, 1H), 7.13 (d, J=7.1 Hz, 1H), 6.88 (d, J=8.7 Hz, 1H), 6.61 (s, 1H), 4.37-4.15 (m, 4H).

Example 82

(Z)-5-(benzo[d]thiazol-6-ylmethylene)-2-(quinoxalin-6-ylamino)-3,5-dihydro-4H-imidazol-4-one

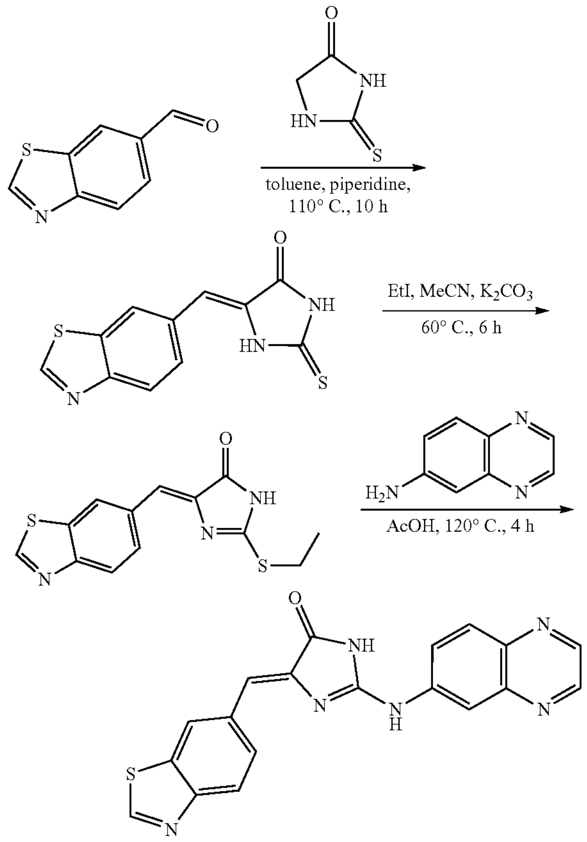

TJU-B326

(Z)-5-(benzo[d]thiazol-6-ylmethylene)-2-(quinoxalin-6-ylamino)-3,5-dihydro-4H-imidazol-4-one (40.1 mg) was prepared as described for Example 24. LRMS ($M+H^+$) m/z calculated 373.1, found 373.0. $^1H$ NMR (400 MHz, DMSO-d6) δ 11.21 (s, 1H), 10.68 (s, 1H), 9.45 (s, 1H), 9.17-8.78 (m, 4H), 8.34 (s, 1H), 8.12 (d, J=9.5 Hz, 3H), 6.78 (s, 1H).

Example 83

(Z)-2-(benzo[d]thiazol-6-yl(methyl)amino)-5-(benzo[d]thiazol-6-ylmethylene)-3,5-dihydro-4H-imidazol-4-one

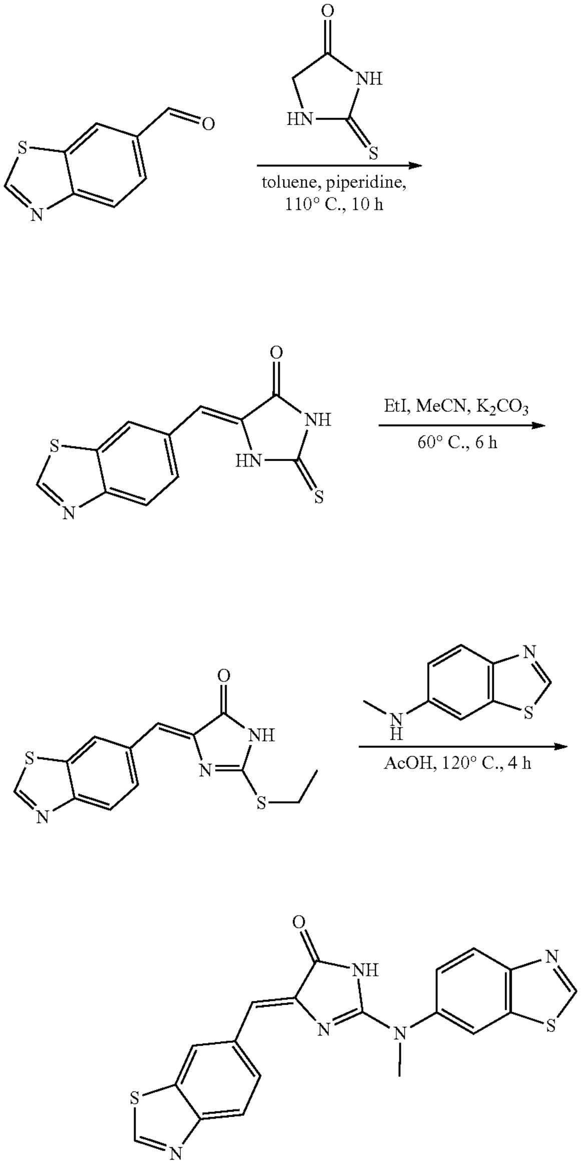

TJU-B329

(Z)-2-(benzo[d]thiazol-6-yl(methyl)amino)-5-(benzo[d]thiazol-6-ylmethylene)-3,5-dihydro-4H-imidazol-4-one (33.1 mg) was prepared as described for Example 24. LRMS ($M+H^+$) m/z calculated 392.1, found 392.0. $^1H$ NMR (400 MHz, DMSO-d6) δ 11.23 (s, 1H), 9.45 (s, 1H), 9.36 (s, 1H), 8.87 (s, 1H), 8.33 (d, J=2.1 Hz, 1H), 8.27 (d, J=8.1 Hz, 1H), 8.15 (d, J=8.7 Hz, 1H), 8.03 (d, J=8.6 Hz, 1H), 7.66 (dd, J=8.7 Hz, 2.2 Hz, 1H), 6.50 (s, 1H), 3.63 (s, 3H).

Example 84

(Z)-2-(benzo[d]thiazol-6-yl(methyl)amino)-5-((2,3-dihydrobenzo[b][1,4]dioxin-6-yl)methylene)-3,5-dihydro-4H-imidazol-4-one

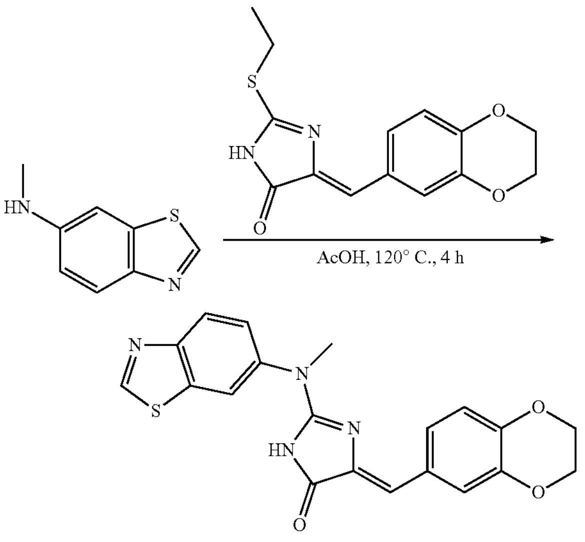

TJU-B331

(Z)-2-(benzo[d]thiazol-6-yl(methyl)amino)-5-((2,3-dihydrobenzo[b][1,4]dioxin-6-yl)methylene)-3,5-dihydro-4H-imidazol-4-one (17.6 mg) was prepared as described for Example 24. LRMS (M+H$^+$) m/z calculated 393.0, found 393.0. $^1$H NMR (400 MHz, DMSO-d6) δ 10.92 (s, 1H), 9.44 (s, 1H), 8.26 (s, 1H), 8.14 (d, J=8.0 Hz, 1H), 7.78 (s, 1H), 7.61 (d, J=8.0 Hz, 1H), 7.46 (d, J=8. Hz, 1H), 6.84 (d, J=8.0 Hz, 1H), 6.35 (s, 1H), 4.25-4.23 (m, 4H), 3.55 (s, 3H).

Example 85

(Z)-2-(benzo[d]thiazol-6-yl)methyl)amino)-5-(quinolin-6-ylmethylene)-3,5-dihydro-4H-imidazol-4-one

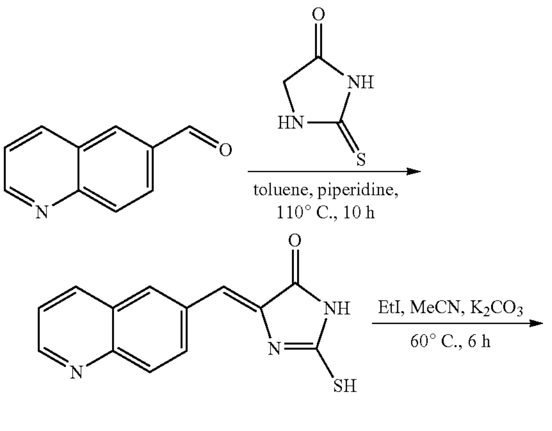

-continued

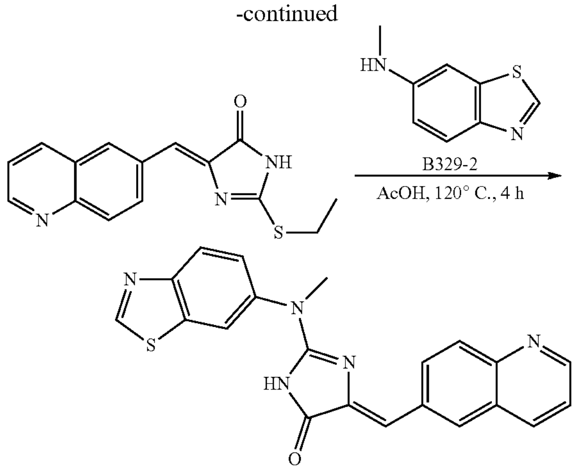

TJU-B332

(Z)-2-(benzo[d]thiazol-6-yl(methyl)amino)-5-(quinolin-6-ylmethylene)-3,5-dihydro-4H-imidazol-4-one (55.8 mg) was prepared as described for Example 24. LRMS (M+H$^+$) m/z calculated 386.1, found 386.0. $^1$H NMR (400 MHz, DMSO-d6) δ 11.10 (s, 1H), 9.47 (s, 1H), 8.85 (dd, J=4.2 Hz, 1.7 Hz, 1H), 8.62 (dd, J=8.9 Hz, 1.8 Hz, 2H), 8.58 (s, 1H), 8.33 (d, J=2.1 Hz, 1H), 8.28 (d, J=7.6 Hz, 1H), 8.18 (d, J=8.7 Hz, 1H), 7.96 (d, J=8.8 Hz, 1H), 7.67 (dd, J=8.7 Hz, 2.2 Hz, 1H), 7.52 (dd, J=8.3 Hz, 4.2 Hz, 1H), 6.59 (s, 1H), 3.65 (s, 3H).

Example 86

(Z)-5-(benzo[d]thiazol-6-ylmethylene)-2-(methyl(1-methyl-1H-benzo[d]imidazol-5-yl)amino)-3,5-dihydro-4H-imidazol-4-one

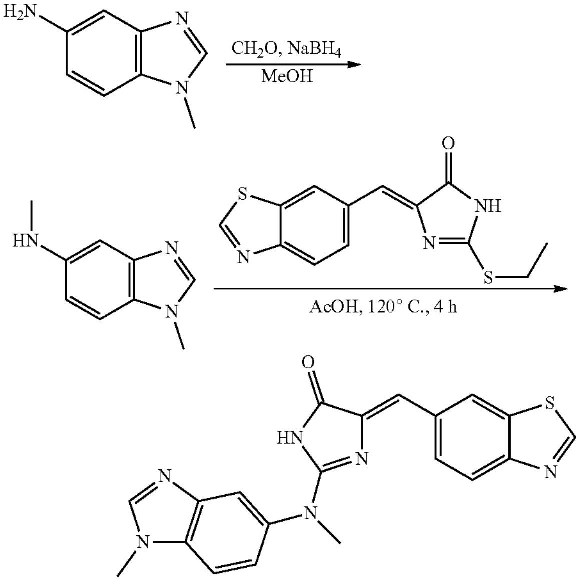

TJU-B334

(Z)-5-(benzo[d]thiazol-6-ylmethylene)-2-(methyl(1-methyl-1H-benzo[d]imidazol-5-yl)amino)-3,5-dihydro-4H- imidazol-4-one (7.2 mg) was prepared in the same procedure as described for Example 24. LRMS ($M+H^+$) m/z calculated 389.1, found 389.1. $^1H$ NMR (400 MHz, DMSO-d6) δ 10.84 (s, 1H), 9.37 (s, 1H), 8.87 (s, 1H), 8.34-8.30 (m, 2H), 8.05 (d, J=8.6 Hz, 1H), 7.73 (d, J=1.6 Hz, 1H), 7.67 (d, J=8.6 Hz, 1H), 7.36-7.33 (m, 1H), 6.50 (s, 1H), 3.89 (s, 3H), 3.59 (s, 3H).

Example 87

(Z)-5-((1H-indol-5-yl)methylene)-2-(benzo[d]thiazol-6-yl)methyl)amino)-3,5-dihydro-4H-imidazol-4-one

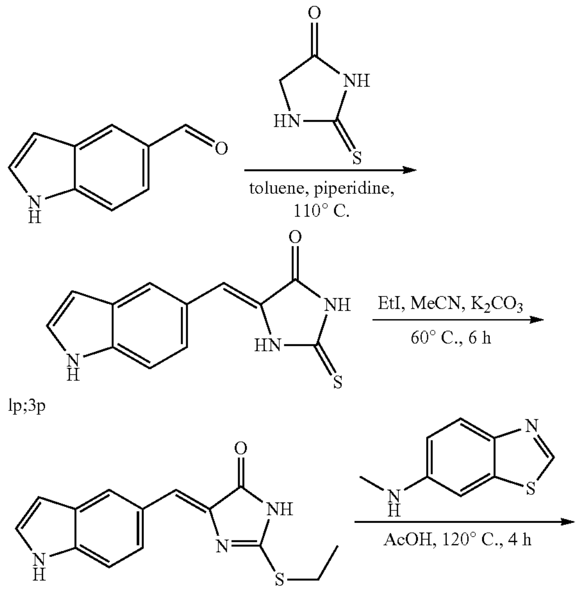

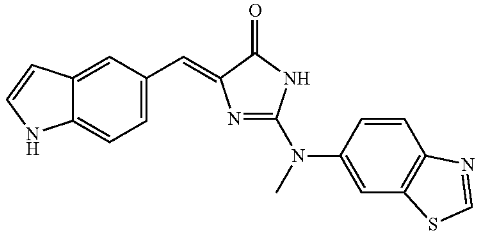

TJU-B333

(Z)-5-((1H-indol-5-yl)methylene)-2-(benzo[d]thiazol-6-yl(methyl)amino)-3,5-dihydro-4H-imidazol-4-one (12.8 mg) was prepared as described for Example 24. LRMS ($M+H^+$) m/z calculated 374.1, found 374.1. $^1H$ NMR (400 MHz, DMSO-d6) δ 11.18 (s, 1H), 10.88 (s, 1H), 9.44 (s, 1H), 8.30 (s, 2H), 8.15 (d, J=8.6 Hz, 1H), 7.96 (d, J=8.6 Hz, 1H), 7.63 (d, J=8.7 Hz, 1H), 7.41-7.29 (m, 2H), 6.57 (s, 1H), 6.43 (s, 1H), 3.60 (s, 3H).

Example 88

(Z)-2-(benzo[d]thiazol-6-ylamino)-5-(benzo[d]thiazol-6-ylmethylene)-3-methyl-3,5-dihydro-4H-imidazol-4-one

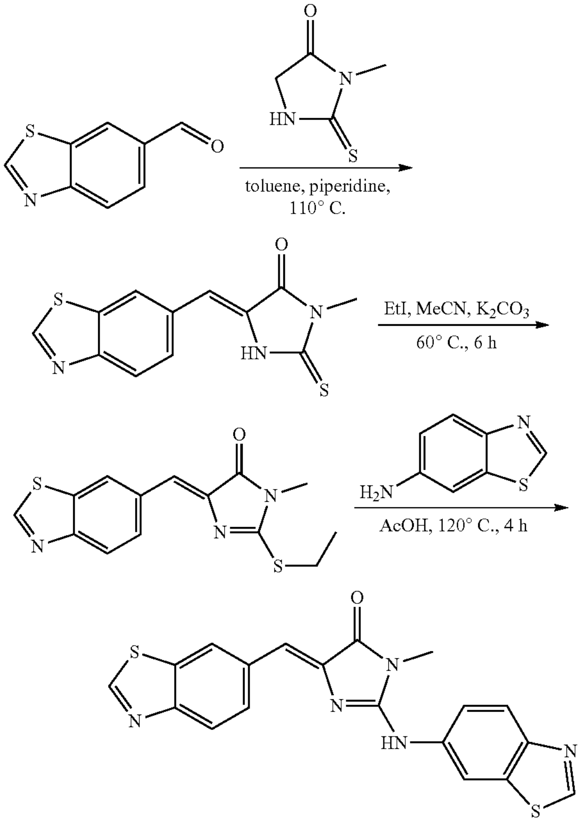

TJU-B344

(Z)-2-(benzo[d]thiazol-6-ylamino)-5-(benzo[d]thiazol-6-ylmethylene)-3-methyl-3,5-dihydro-4H-imidazol-4-one (62.4 mg) was prepared as described for Example 24. LRMS (M+H) m/z calculated 392.1, found 392.0. $^1H$ NMR (400 MHz, DMSO-d6) δ 9.84 (s, 1H), 9.44 (s, 1H), 9.37 (s, 1H), 9.10 (s, 1H), 9.06 (d, J=1.9 Hz, 1H), 8.21 (d, J=8.6 Hz, 1H), 8.14 (d, J=8.9 Hz, 1H), 8.09 (d, J=8.5 Hz, 1H), 7.93 (dd, J=8.9 Hz, J=2.0 Hz, 1H), 6.82 (s, 1H), 3.29 (s, 3H).

Example 89

(Z)-2-(benzo[d]thiazol-6-yl(2-methoxyethyl)amino)-5-(benzo[d]thiazol-6-ylmethylene)-3,5-dihydro-4H-imidazol-4-one

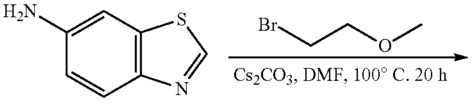

-continued

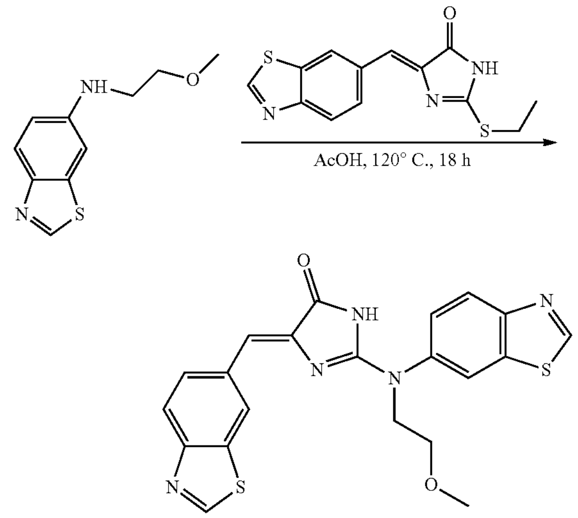

TJU-B347

(Z)-2-(benzo[d]thiazol-6-yl(2-methoxyethyl)amino)-5-(benzo[d]thiazol-6-ylmethylene)-3,5-dihydro-4H-imidazol-4-one (8.5 mg) was prepared as described for Example 24. LRMS ($M+H^+$) m/z calculated 436.1, found 436.1. $^1H$ NMR (400 MHz, DMSO-d6) δ 10.95 (s, 1H), 9.47 (s, 1H), 9.38 (s, 1H), 8.86 (s, 1H), 8.31-8.27 (m, 2H), 8.17 (d, J=8.7 Hz, 1H), 8.05 (d, J=8.6 Hz, 1H), 7.60 (dd, J=8.7 Hz, 2.1 Hz, 1H), 6.56 (s, 1H), 4.23 (t, J=5.6 Hz, 2H), 3.63 (t, J=5.6 Hz, 2H), 3.28 (s, 3H).

Example 90

(Z)-5-(benzo[d]thiazol-6-ylmethylene)-2-((2-methyl-benzo[d]thiazol-6-yl)amino)-3,5-dihydro-4H-imidazol-4-one

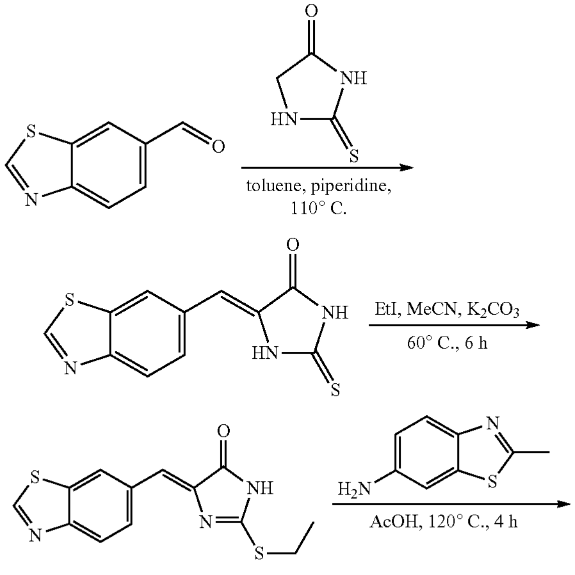

-continued

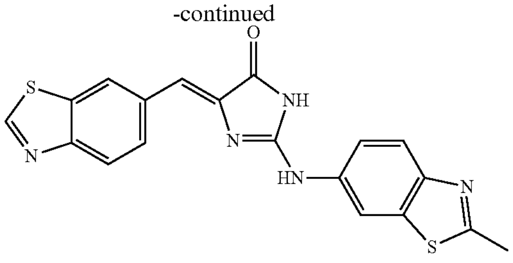

TJU-B353

(Z)-5-(benzo[d]thiazol-6-ylmethylene)-2-((2-methyl-benzo[d]thiazol-6-yl)amino)-3,5-dihydro-4H-imidazol-4-one (11.2 mg) was prepared as described for Example 24. LRMS ($M+H^+$) m/z calculated 392.1, found 392.1. $^1H$ NMR (400 MHz, DMSO-d6) δ 10.95 (s, 1H), 10.26 (s, 1H), 9.43 (s, 1H), 9.06 (s, 1H), 8.78 (s, 1H), 8.19 (s, 1H), 8.09 (d, J=8.5 Hz, 1H), 7.91 (d, J=8.7 Hz, 1H), 7.67 (s, 1H), 6.69 (s, 1H), 2.81 (s, 3H).

Example 91: Preparation of (Z)-5-((1H-benzo[d][1,2,3]triazol-6-yl)methylene)-2-(phenylamino)-3,5-dihydro-4H-imidazol-4-one

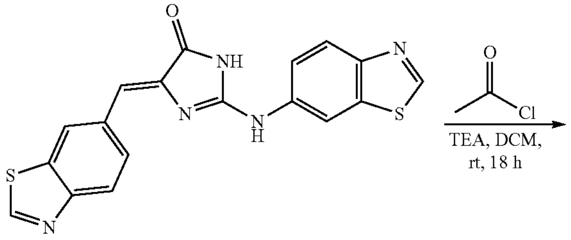

TJU-B264

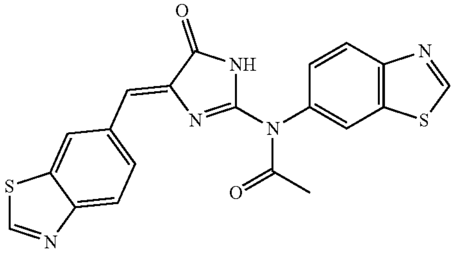

TJU-B356

To a mixture of (Z)-2-(benzo[d]thiazol-6-ylamino)-5-(benzo[d]thiazol-6-ylmethylene)-3,5-dihydro-4H-imidazol-4-one (75.0 mg, 0.2 mmol, 1 eq.) in DCM (5 mL) were added TEA (60.0 mg, 0.6 mmol, 3 eq.) and acetyl chloride (31.0 mg, 0.4 mmol, 2 eq.). The mixture was stirred at room temperature for 18 h. The mixture was concentrated and the residue was purified by prep-HPLC to afford (Z)—N-(benzo[d]thiazol-6-yl)-N-(4-(benzo[d]thiazol-6-ylmethylene)-5-oxo-4,5-dihydro-1H-imidazol-2-yl)acetamide as a yellow solid (23.5 mg, 29%). LRMS ($M+H^+$) m/z calculated 420.1, found 420.0. $^1H$ NMR (400 MHz, DMSO-d6) δ 10.41 (s, 1H), 9.47-9.39 (m, 2H), 9.01-8.95 (m, 2H), 8.23-8.13 (m, 3H), 7.87 (s, 1H), 6.96 (s, 1H), 2.65 (s, 3H).

Example 92

(Z)-2-(benzo[d]thiazol-6-ylamino)-5-(thiazol-5-ylmethylene)-3,5-dihydro-4H-imidazol-4-one

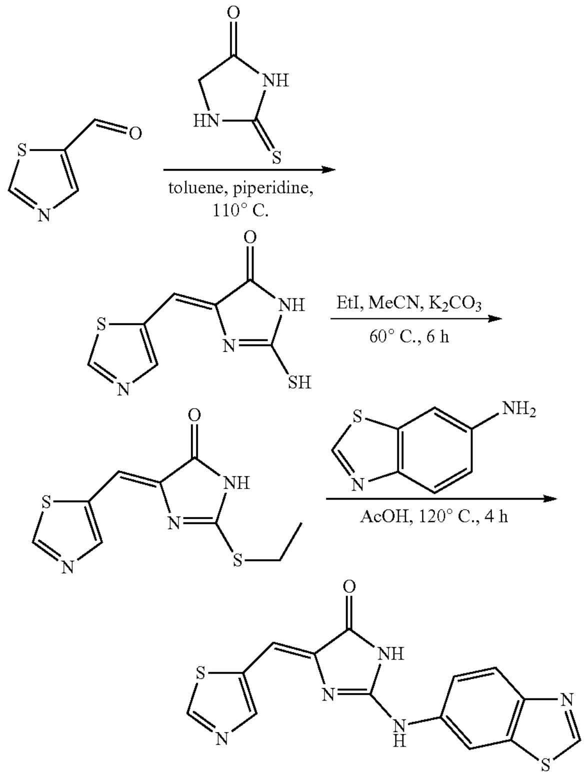

TJU-B308

(Z)-2-(benzo[d]thiazol-6-ylamino)-5-(thiazol-5-ylmethylene)-3,5-dihydro-4H-imidazol-4-one (11.0 mg) was prepared as described for Example 24. LRMS ($M+H^+$) m/z calculated 328.0, found 328.0. $^1$H NMR (400 MHz, DMSO-d6) δ 9.31 (s, 1H), 9.21 (s, 1H), 8.90 (s, 1H), 8.35 (s, 0.5H), 8.24 (s, 1H), 8.09 (d, J=7.4 Hz, 1H), 7.90 (s, 1H), 7.00 (s, 1H).

Example 93

(Z)-5-(benzo[d]thiazol-6-ylmethylene)-24(1-methyl-1H-benzo[d]imidazol-6-yl)amino)-3,5-dihydro-4H-imidazol-4-one

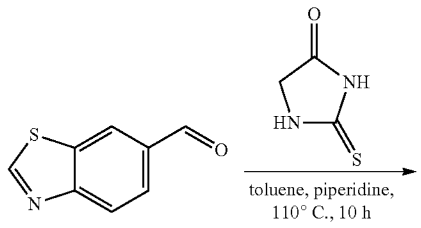

-continued

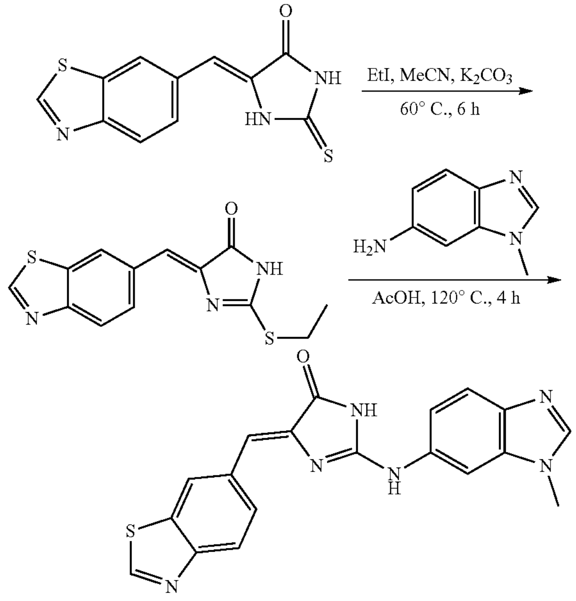

TJU-B292

(Z)-5-(benzo[d]thiazol-6-ylmethylene)-2-((1-methyl-1H-benzo[d]imidazol-6-yl)amino)-3,5-dihydro-4H-imidazol-4-one (23.1 mg) was prepared as described for Example 24. LRMS ($M+H^+$) m/z calculated 375.1, found 375.1. $^1$HNMR (400 MHz, DMSO-d6) δ 12.55 (s, 1H), 11.48 (s, 1H), 9.40 (s, 1H), 8.98 (s, 1H), 8.38-8.35 (m, 3H), 8.19 (s, 1H), 8.08 (d, J=8.3 Hz, 1H), 7.61-7.56 (m, 2H), 6.58 (s, 1H), 3.86 (s, 3H).

Example 94

(Z)-2-(benzo[d]thiazol-6-ylamino)-5-(quinoxalin-6-ylmethylene)-3,5-dihydro-4H-imidazol-4-one

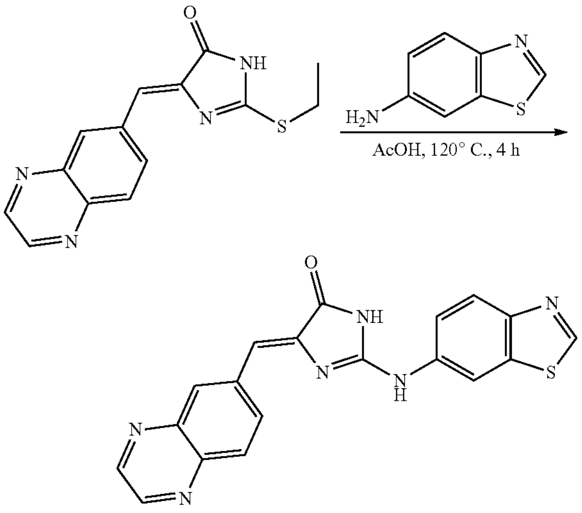

TJU-B297

(Z)-2-(benzo[d]thiazol-6-ylamino)-5-(quinoxalin-6-ylmethylene)-3,5-dihydro-4H-imidazol-4-one (9.2 mg) was prepared as described for Example 24. LRMS (M+H) m/z calculated 374.2, found 374.2. $^{1}$H NMR (400 MHz, DMSO-d6) δ 9.52 (d, J=2.5 Hz, 1H), 8.92 (d, J=1.8 Hz, 1H), 8.88 (dd, J=3.7 Hz, 1.8 Hz, 2H), 8.62 (dd, J=8.8 Hz, 1.8 Hz, 1H), 8.28 (d, J=2.0 Hz, 1H), 8.24 (d, J=8.6 Hz, 1H), 8.18 (s, 1H), 8.07 (d, J=8.8 Hz, 1H), 7.56 (dd, J=8.6 Hz, 2.1 Hz, 1H), 6.73 (s, 1H).

Example 95

(Z)-5-((1H-indazol-6-yl)methylene)-2-(benzo[d]thiazol-6-ylamino)-3,5-dihydro-4H-imidazol-4-one

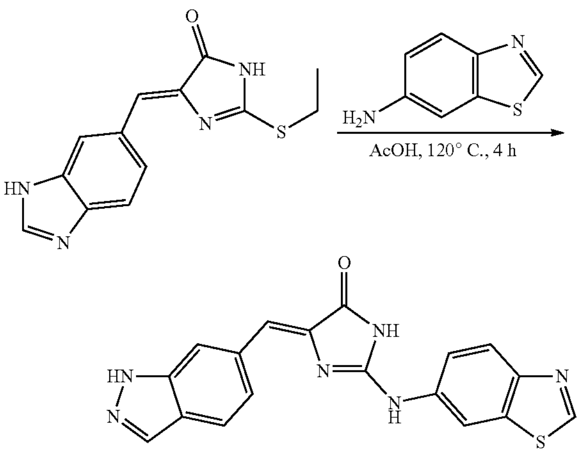

TJU-B302

(Z)-5-((1H-indazol-6-yl)methylene)-2-(benzo[d]thiazol-6-ylamino)-3,5-dihydro-4H-imidazol-4-one (9.7 mg) was prepared as described for Example 24. LRMS (M+H$^{+}$) m/z calculated 361.1, found 361.1. $^{1}$H NMR (400 MHz, DMSO-d6) δ 12.78 (s, 1H), 9.14 (s, 1H), 8.75 (s, 1H), 8.19 (s, 1H), 7.97 (s, 3H), 7.74 (s, 1H), 7.63 (d, J=8.4 Hz, 1H), 6.12 (s, 1H).

Example 96: (Z)-5-(benzo[b]thiophen-5-ylmethylene)-2-thioxoimidazolidin-4-one

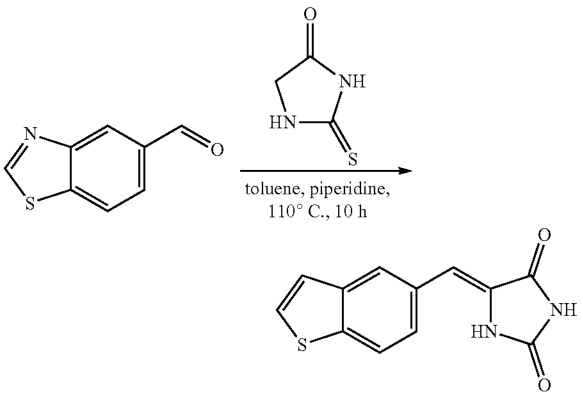

TJU-B315

(Z)-5-(benzo[b]thiophen-5-ylmethylene)-2-thioxoimidazolidin-4-one (2.0 mg) was prepared as described for Example 24. LRMS (M+H$^{+}$) m/z calculated 261.0, found 261.0. $^{1}$H NMR (400 MHz, DMSO-d6) δ 12.24 (s, 2H), 8.36 (s, 1H), 8.04 (d, J=8.4 Hz, 1H), 7.83 (d, J=5.4 Hz, 1H), 7.72 (dd, J=8.5 Hz, 1.3 Hz, 1H), 7.48 (d, J=5.4 Hz, 1H), 6.59 (s, 1H).

Example 97

(Z)-2-((1H-benzo[d]imidazol-6-yl)amino)-5-(benzo[d]thiazol-6-ylmethylene)-3,5-dihydro-4H-imidazol-4-one

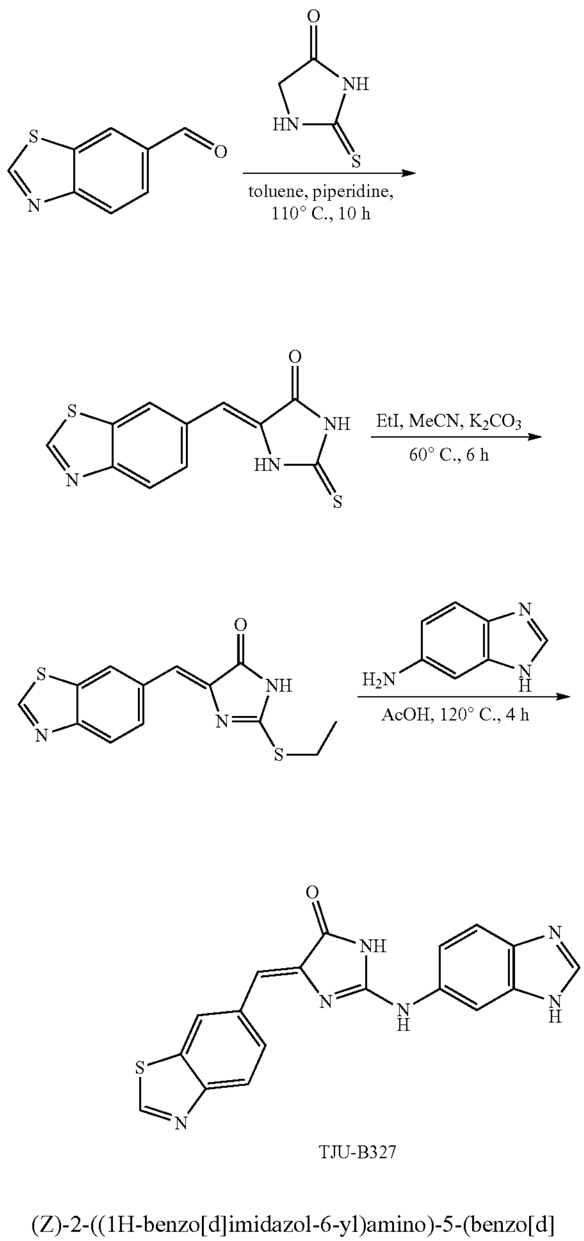

TJU-B327

(Z)-2-((1H-benzo[d]imidazol-6-yl)amino)-5-(benzo[d]thiazol-6-ylmethylene)-3,5-dihydro-4H-imidazol-4-one (35.7 mg) was prepared as described for Example 24. LRMS (M+H$^{+}$) m/z calculated 361.1, found 361.0. $^{1}$H NMR (400 MHz, DMSO-d6) δ 12.48 (s, 1H), 10.91 (d, J=10.7 Hz, 1H), 10.12 (s, 1H), 9.41 (s, 1H), 8.82 (s, 1H), 8.47 (s, 1H), 8.24 (d, J=11.3 Hz, 2H), 8.17 (s, 2H), 7.60 (d, J=7.2 Hz, 1H), 7.40 (s, 1H), 6.62 (s, 1H).

Example 98

(Z)-2-((4-aminophenyl)amino)-5-(benzo[d]thiazol-6-ylmethylene)-3,5-dihydro-4H-imidazol-4-one

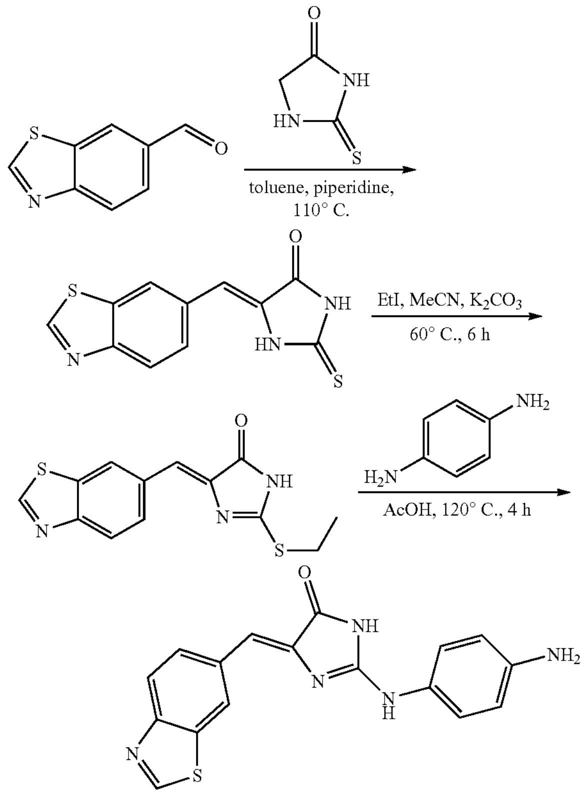

TJU-B239

(Z)-2-((4-aminophenyl)amino)-5-(benzo[d]thiazol-6-ylmethylene)-3,5-dihydro-4H-imidazol-4-one (14.4 mg) was prepared as described for Example 24. LRMS ($M+H^+$) m/z calculated 336.1, found 336.1. $^1H$ NMR (400 MHz, DMSO-d6) δ 10.66 (s, 1H), 9.54 (br, 1H), 9.38 (s, 1H), 8.88 (s, 1H), 8.27-8.25 (m, 1H), 8.14 (s, 0.5H), 8.06 (d, J=8.6 Hz, 1H), 7.40 (d, J=6.7 Hz, 2H), 6.61 (d, J=8.7 Hz, 2H), 6.52 (s, 1H), 5.08 (s, 2H).

Example 99

(Z)-2-(benzo[d]thiazol-6-yl(benzyl)amino)-5-(benzo[d]thiazol-6-ylmethylene)-3,5-dihydro-4H-imidazol-4-one

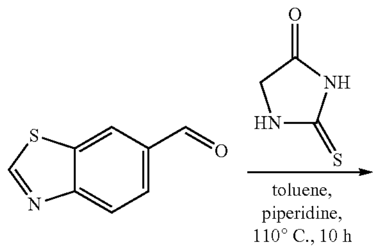

-continued

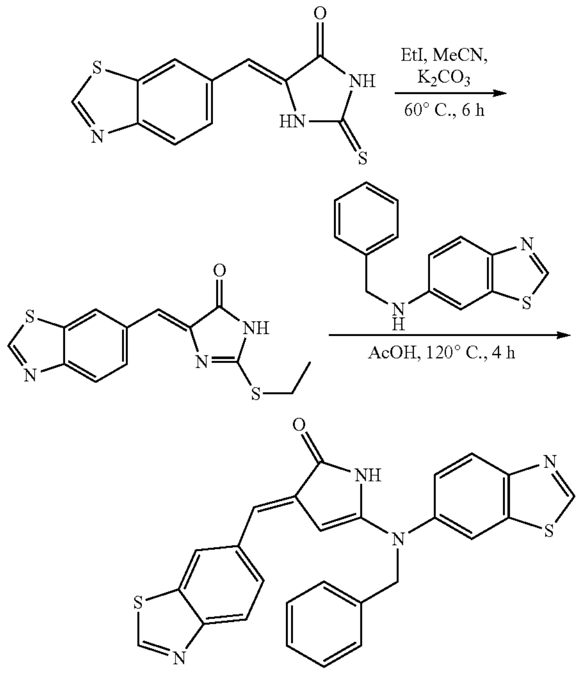

TJU-B352

(Z)-2-(benzo[d]thiazol-6-yl(benzyl)amino)-5-(benzo[d]thiazol-6-ylmethylene)-3,5-dihydro-4H-imidazol-4-one (21.4 mg) was prepared as described for Example 24. LRMS ($M+H^+$) m/z calculated 468.1, found 468.0. $^1H$ NMR (400 MHz, DMSO-d6) δ 11.04 (s, 1H), 9.43 (s, 1H), 9.38 (s, 1H), 8.88 (s, 1H), 8.30 (dd, J=8.6 Hz, 1.2 Hz, 1H), 8.23 (d, J=2.0 Hz, 1H), 8.10 (d, J=8.7 Hz, 1H), 8.05 (d, J=8.6 Hz, 1H), 7.52 (dd, J=8.7 Hz, 2.2 Hz, 1H), 7.40 (d, J=7.2 Hz, 2H), 7.32 (t, J=7.4 Hz, 2H), 7.25 (d, J=8.0 Hz, 1H), 6.60 (s, 1H), 5.35 (s, 2H).

Example 100

(Z)-5-(benzo[d]thiazol-6-ylmethylene)-2-((2-(isopropylamino)benzo[d]thiazol-6-yl)amino)-3,5-dihydro-4H-imidazol-4-one

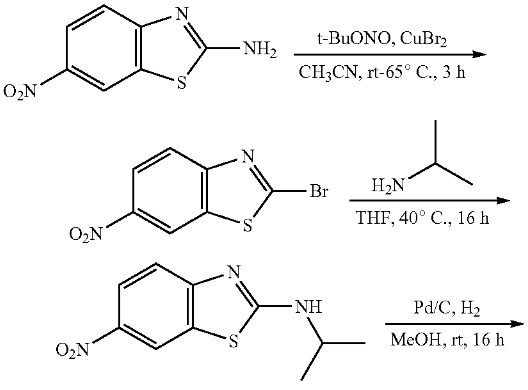

-continued

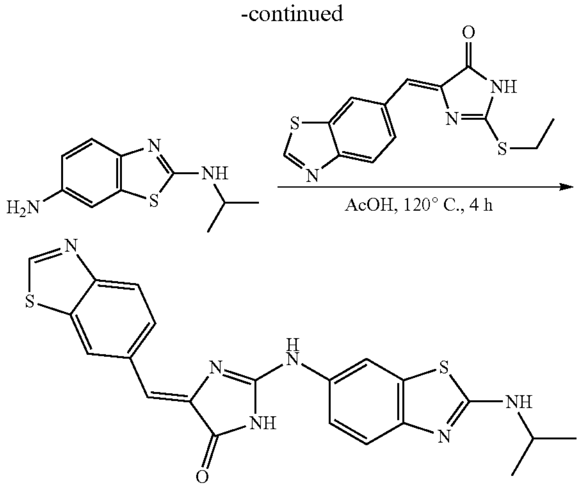

TJU-B358

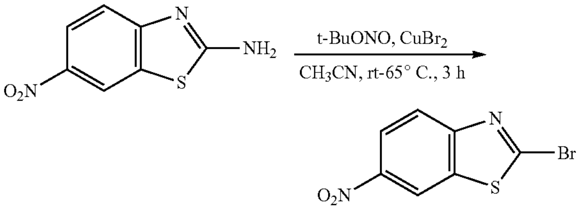

A mixture of t-BuONO (4.95 g, 48.0 mmol) and $CuBr_2$ (8.71 g, 39.0 mmol) in $CH_3CN$ (70 mL) was stirred at 65° C. for 1 hour under $N_2$. 6-Nitrobenzo[d]thiazol-2-amine (5.85 g, 30.0 mmol) was added to the above mixture at room temperature under $N_2$. The mixture was stirred at 65° C. for 2 h. The mixture was diluted with DCM (50 mL) and added 0.1 N HCl to precipitate the product. The filter cake was collected and dried in a vacuum to afford 2-bromo-6-nitrobenzo[d]thiazole (5.5 g, 71%) as a brown solid. LRMS ($M+H^+$) m/z calculated 258.9/260.9, found 259.0/261.0.

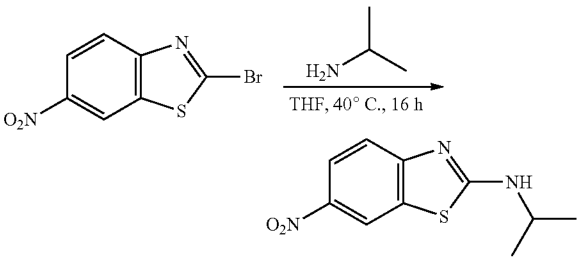

A mixture of 2-bromo-6-nitrobenzo[d]thiazole (77.0 mg, 0.3 mmol) and propan-2-amine (177.0 mg, 3.0 mmol) in THF (5 mL) was stirred at 40° C. for 16 h. The mixture was concentrated, and the residue was purified by pre-TLC (PE/EA=3/1, v/v) to afford N-isopropyl-6-nitrobenzo[d]thiazol-2-amine (64.0 mg, 90%) as a yellow solid. LRMS ($M+H^+$) m/z calculated 238.1, found 238.1.

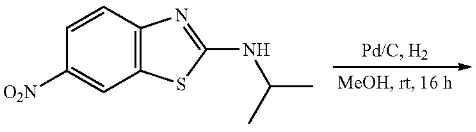

-continued

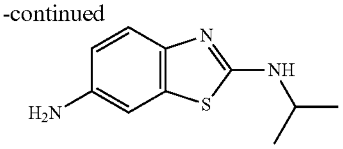

To a solution of N-isopropyl-6-nitrobenzo[d]thiazol-2-amine (64.0 mg, 0.27 mmol) in MeOH (5 mL) was added Pd/C (19.0 mg, 30%). The mixture was stirred for 16 h at rt. After completion, DCM (50 mL) was added to the reaction mixture and the mixture was stirred for 20 min at rt. The mixture was filtered with DCM/MeOH (12/1, 50 mL). The organic phase was concentrated to give $N^2$-isopropylbenzo[d]thiazole-2,6-diamine (53.0 mg, 95%) which was used for the next step without further purification. LRMS ($M+H^+$) m/z calculated 208.1, found 208.1.

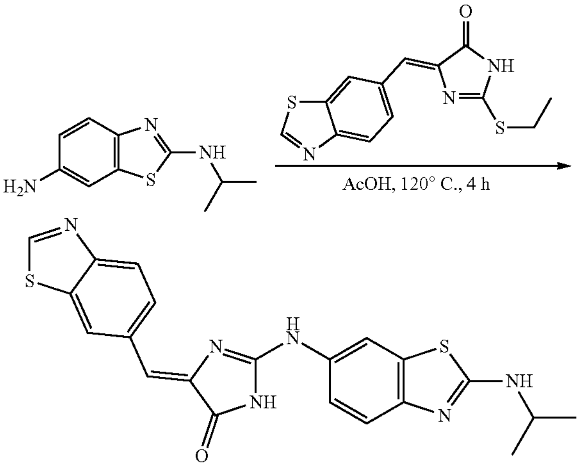

TJU-B358

A mixture of (Z)-5-(benzo[d]thiazol-6-ylmethylene)-2-(ethylthio)-3,5-dihydro-4H-imidazol-4-one (62.0 mg, 0.21 mmol) and $N^2$-isopropylbenzo[d]thiazole-2,6-diamine (53.0 mg, 0.26 mmol). in AcOH (1.5 mL) was stirred at 120° C. for 4 h under $N_2$. The reaction mixture was concentrated and the residue was purified by prep-HPLC to give (Z)-5-(benzo[d]thiazol-6-ylmethylene)-2-((2-(isopropylamino)benzo[d]thiazol-6-yl)amino)-3,5-dihydro-4H-imidazol-4-one (25.0 mg, 27%) as a yellow solid. LRMS ($M+H^+$) m/z calculated 435.1, found 435.0. $^1$H NMR (400 MHz, DMSO-d6) δ 11.38 (br, 1H), 10.47 (br, 1H), 9.43 (s, 1H), 9.05 (s, 1H), 8.38 (s, 1H), 8.27 (s, 0.5H), 8.17 (d, J=7.8 Hz, 1H), 8.07 (d, J=8.5 Hz, 1H), 7.91 (d, J=7.3 Hz, 1H), 7.44-7.37 (m, 2H), 6.60 (s, 1H), 4.04-3.96 (m, 1H), 1.23 (d, J=4.0 Hz, 6H).

Example 101

(Z)-2-(benzo[b]thiophen-5-ylamino)-5-(benzo[d]thiazol-6-ylmethylene)-3,5-dihydro-4H-imidazol-4-one

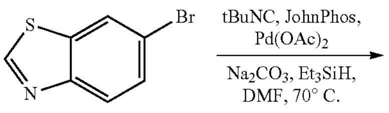

-continued

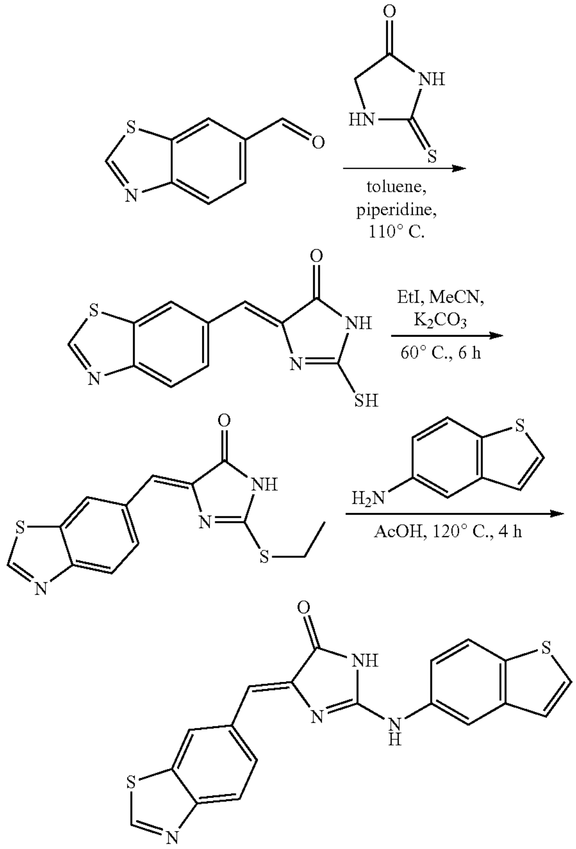

TJU-B363

(Z)-2-(benzo[b]thiophen-5-ylamino)-5-(benzo[d]thiazol-6-ylmethylene)-3,5-dihydro-4H-imidazol-4-one (103.0 mg) was prepared as described for Example 24. LRMS ($M+H^+$) m/z calculated 376.4, found 377.0. $^1H$ NMR (400 MHz, DMSO-d6) δ 10.87 (s, 1H), 10.09 (s, 1H), 9.42 (s, 1H), 9.01 (s, 1H), 8.60 (s, 1H), 8.29 (s, 1H), 8.14 (d, J=8.5 Hz, 1H), 8.01 (d, J=8.7 Hz, 1H), 7.84 (d, J=5.2 Hz, 1H), 7.61 (d, J=8.1 Hz, 1H), 7.51 (d, J=5.2 Hz, 1H), 6.67 (s, 1H).

Example 102

2-(benzo[d]thiazol-6-ylamino)-5-(benzo[d]thiazol-6-ylmethyl)-3,5-dihydro-4H-imidazol-4-one

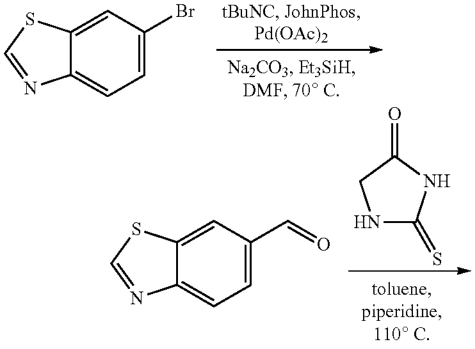

-continued

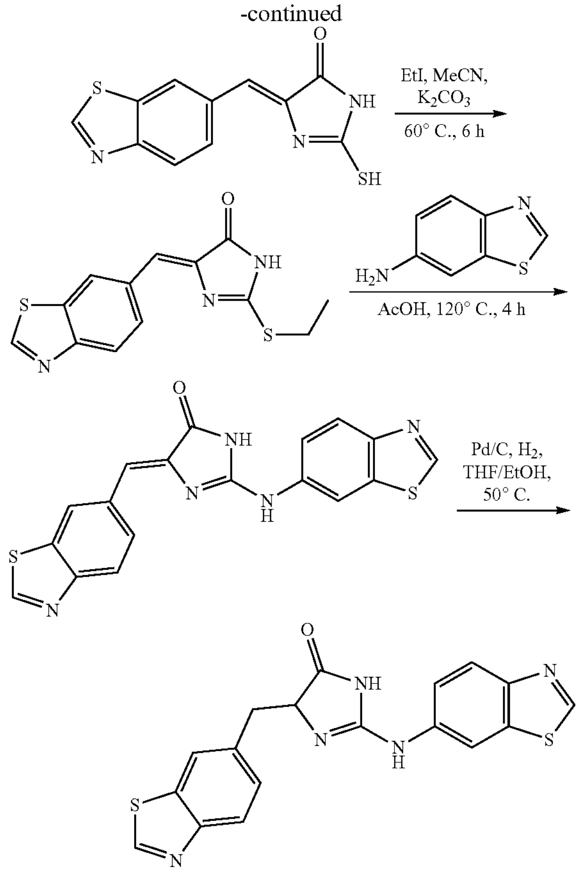

TJU-B355

2-(Benzo[d]thiazol-6-ylamino)-5-(benzo[d]thiazol-6-ylmethyl)-3,5-dihydro-4H-imidazol-4-one (8.1 mg) was prepared as described for Example 24. LRMS ($M+H^+$) m/z calculated 380.1, found 380.0. $^1H$ NMR (400 MHz, $CD_3OD$) δ 9.38 (s, 1H), 9.30 (s, 1H), 8.18 (s, 1H), 8.08 (d, J=8.4 Hz, 1H), 7.94 (s, 2H), 7.43 (d, J=7.6 Hz, 1H), 7.33 (d, J=8.2 Hz, 1H), 4.76 (s, 1H), 3.38 (m, 2H).

Example 103

(Z)-2-amino-5-(benzo[d]thiazol-6-ylmethylene)-3,5-dihydro-4H-imidazol-4-one

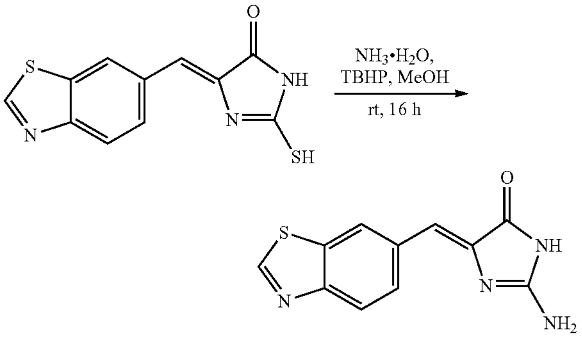

TJU-B357

(Z)-2-amino-5-(benzo[d]thiazol-6-ylmethylene)-3,5-dihydro-4H-imidazol-4-one (9.3 mg) was prepared as described for Example 1. LRMS (M+H) m/z calculated 245.0, found 245.1. $^1$H NMR (400 MHz, DMSO-d6) δ 9.36 (s, 1H), 8.77 (s, 1H), 8.16 (s, 1H), 8.04 (d, J=8.4 Hz, 1H), 7.38 (s, 2H), 6.40 (s, 1H).

Example 104

(Z)-5-(benzo[d]thiazol-6-ylmethylene)-2-((2-(phenylamino)benzo[d]thiazol-6-yl)amino)-3,5-dihydro-4H-imidazol-4-one

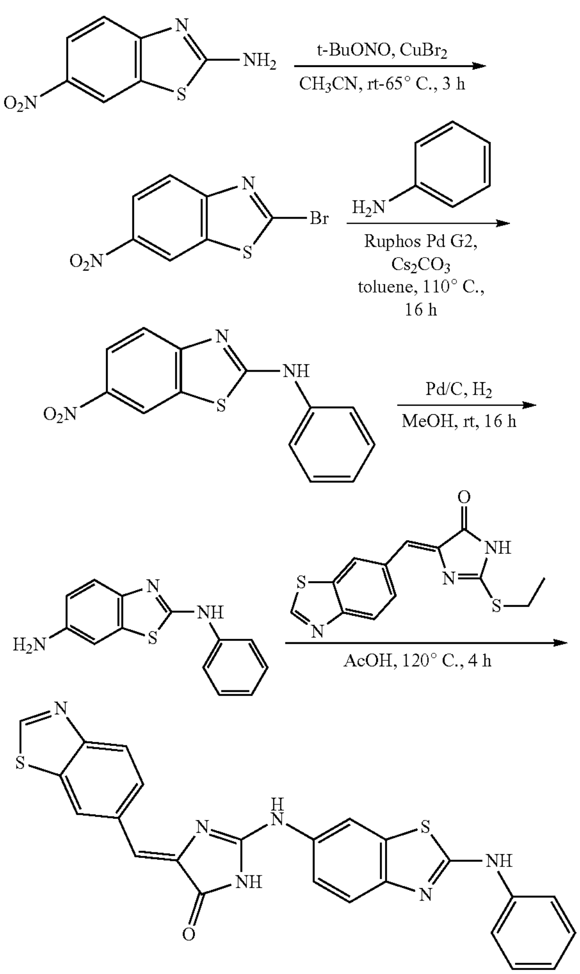

TJU-B361

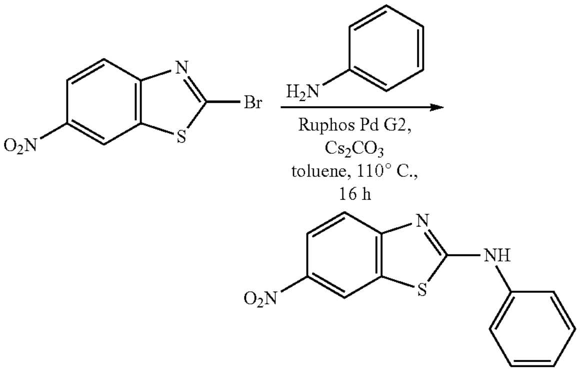

A mixture of 2-bromo-6-nitrobenzo[d]thiazole (387.0 mg, 1.5 mmol) and aniline (210.0 mg, 2.25 mmol), Ruphos Pd G2 (117.0 mg, 0.15 mmol) and $Cs_2CO_3$ (1466.0 mg, 4.5 mmol) in toluene (15 mL) was stirred at 110° C. for 16 h under $N_2$. The mixture was concentrated, the residue was diluted with $H_2O$ (50 mL) and extracted with DCM (40 mL×3). The organic layer was dried over $Na_2SO_4$, concentrated, the residue was by prep-TLC (PE/EA=5/1, v/v) to afford 6-nitro-N-phenylbenzo[d]thiazol-2-amine (120.0 mg, 30%) as a brown solid. LRMS (M+H$^+$) m/z calculated 272.0, found 272.0.

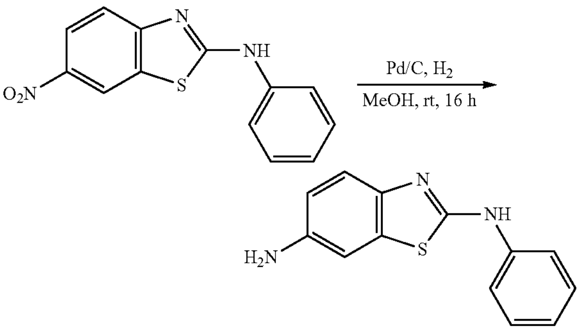

To a solution of 6-nitro-N-phenylbenzo[d]thiazol-2-amine (120.0 mg, 0.44 mmol) in MeOH/DCM (12/4 mL) were added Pd/C (36.0 mg, 30%). The mixture was stirred for 16 h at rt. After completion, DCM (50 mL) was added to the reaction mixture and the mixture was stirred for 20 min at rt. The mixture was filtered with DCM/MeOH (12/1, 50 mL). The organic phase was concentrated to give N$^2$-phenylbenzo[d]thiazole-2,6-diamine (100.0 mg, 93%) which was used for the next step without further purification. LRMS (M+H$^+$) m/z calculated 242.1, found 242.0.

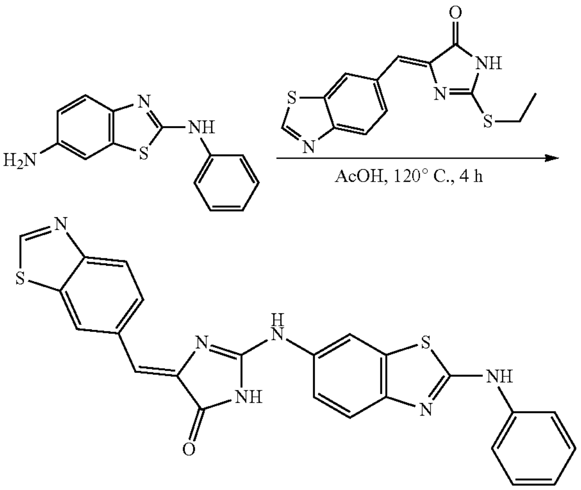

TJU-B361

A mixture of (Z)-5-(benzo[d]thiazol-6-ylmethylene)-2-(ethylthio)-3,5-dihydro-4H-imidazol-4-one (75.0 mg, 0.26 mmol) and N$^2$-phenylbenzo[d]thiazole-2,6-diamine (100.0 mg, 0.41 mmol) in AcOH (2.0 mL) was stirred at 120° C. for 4 h under $N_2$. The reaction mixture was concentrated, the residue was recrystallized from MeOH (15 mL). The filter cake was purified by prep-HPLC to give (Z)-5-(benzo[d]

thiazol-6-ylmethylene)-2-((2-(phenylamino)benzo[d]thiazol-6-yl)amino)-3,5-dihydro-4H-imidazol-4-one (5.0 mg, 4%) as an orange solid. LRMS ($M+H^+$) m/z calculated 469.1, found 469.0. $^1H$ NMR (400 MHz, DMSO-d6) δ 11.03 (br, 1H), 10.49 (s, 1H), 10.20 (br, 1H), 9.44 (s, 1H), 9.07 (s, 1H), 8.51 (s, 1H), 8.18 (d, J=7.4 Hz, 1H), 8.09 (d, J=8.4 Hz, 1H), 7.81 (d, J=8.4 Hz, 2H), 7.62 (d, J=8.7 Hz, 1H), 7.54 (d, J=5.7 Hz, 1H), 7.38 (t, J=7.7 Hz, 2H), 7.05-7.00 (m, 1H), 6.64 (s, 1H).

Example 105

(Z)-2-(benzo[d]thiazol-6-yl(cyclopropylmethyl)amino)-5-(benzo[d]thiazol-6-ylmethylene)-3,5-dihydro-4H-imidazol-4-one

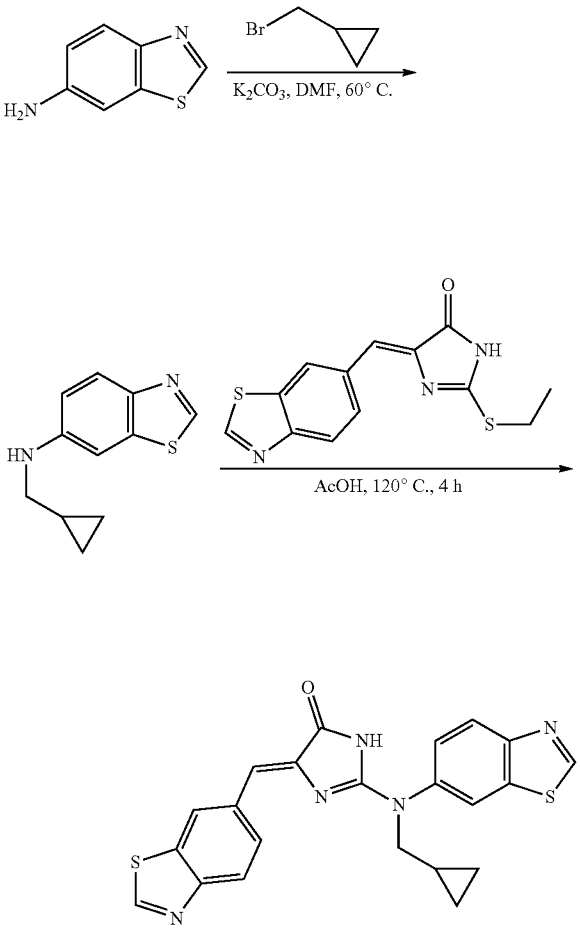

TJU-B364

(Z)-2-(benzo[d]thiazol-6-yl(cyclopropylmethyl)amino)-5-(benzo[d]thiazol-6-ylmethylene)-3,5-dihydro-4H-imidazol-4-one (9.1 mg) was prepared as described for Example 24. LRMS ($M+H^+$) m/z calculated 432.1, found 432.1. $^1H$ NMR (400 MHz, DMSO-d6) 9.81 (s, 1H), 9.44 (s, 1H), 9.38 (s, 1H), 9.08 (d, J=15.6 Hz, 2H), 8.22 (d, J=8.4 Hz, 1H), 8.15 (d, J=8.9 Hz, 1H), 8.09 (d, J=8.4 Hz, 1H), 7.95 (d, J=8.6 Hz, 1H), 6.82 (s, 1H), 3.76 (d, J=7.0 Hz, 2H), 1.23 (s, 1H), 0.52 (d, J=7.1 Hz, 2H), 0.42 (d, J=4.2 Hz, 2H).

Test Example 1

(1) Assay Protocols

1. Isolation of and Culture Neonatal Rat Ventricular Myocytes (NRVMs)

Ventricles from neonatal rats were separated from the atria, cut into small pieces (about 2×2 $mm^2$) and then dissociated in Ca2+-free HBSS containing 0.125 mg ml-1 trypsin (Gibco), 10 μg ml-1 DNase II (Sigma) and 0.1 mg ml-1 collagenase type IV (Sigma). The digestion was carried out under constant stirring at 37° C. for 5 min. The supernatant was collected with FBS (Gibco) after each digestion period. After digestion, the collected supernatant was centrifuged at 1000 g for 10 min at room temperature, and then cell pellets were resuspended in DMEM (Gibco) supplemented with 10% FBS and with 100 uM 5-bromo-2'-deoxyuridine (Sigma). The resuspended cells were passed through a cell strainer (100 mm, BD Falcon) and seeded onto 100-mm plastic dishes for 2 h at 37° C. in a 5% CO2 to remove fibroblasts, the supernatant was then collected and plated onto 1% gelatin (Sigma)-coated dishes. 24 h after the seeding, the medium was changed to DMEM (Gibco) containing 2% FBS (Gibco), 1% insulin-transferrin-selenium (ITS; Gibco), 1% Penicillin-Streptomycin (Gibco). After 24 hours of low serum culture, remove the medium with DMEM (Gibco) containing 6% FBS (Gibco), 1% insulin-transferrin-selenium (ITS; Gibco), 1% Penicillin-Streptomycin (Gibco), different concentrations of compounds (the compounds were pre-diluted in the medium and the drug concentration was 10 uM, 3 uM, 1 uM, fully mixed). After 36 h add Edu substrate (Invitrogen) according to the manufacturer's guidelines, and then after 12 h cell can be used.

2. EdU Assay 2.1. Immobilization: Remove the medium and fix the cells with 4 ul of PFA in 200 ul (whichever is covered) for 15 min and wash the cells twice with 500 ul of PBS for 5 min each time.

2.2. Broken membrane: Add 200 ul of 0.3% Triton-X 100 (diluted in PBS) to each well, incubate for 10-15 min at room temperature (the time should not be too long), and wash the cells twice with 500 ul of PBS for 5 min each time.

2.3. Blocking: Add 200 ul of 10% normal goat serum (diluted with 0.1% PBST) to each well, incubate for 1 h at room temperature, and wash twice with 500 ul of 0.1% PBST for 5 min each time.

2.4. Primary antibody: dilute the primary antibody (abcam, ab8295) to blocking solution at a ratio of 1:200, add 100 ul per well, incubate for 1 h at room temperature (may be slightly longer than 2-3 h), wash the cells twice with 500 ul 0.1% PBST for 5 min each time.

2.5. Secondary antibody: Dilute the fluorescently labeled secondary antibody (abcam, ab150117) into blocking solution at a ratio of 1:200, add 100 ul per well, incubate for 1 h at room temperature (the time should not be too long), wash the cells twice with 0.1% PBST for 5 min each time, pay attention to the whole process. Protected from light.

2.6. Edu staining (Invitrogen C10338)

2.6.1 Prepare Click-iT® reaction cocktail according to Table 3. It was important to add the ingredients in the order listed in the table; otherwise, the reaction would not proceed optimally. Use the Click-iT® reaction cocktail within 15 minutes of preparation.

TABLE 3

| Click-iT ® reaction cocktails. | | | | | | | |
|---|---|---|---|---|---|---|---|
| Reaction | Number of coverslips | | | | | | |
| components* | 1 | 2 | 4 | 5 | 10 | 25 | 50 |
| 1X Click-iT ® reaction buffer (prepared in step 1.4) | 430 µL | 850 µL | 1.6 mL | 22 mL | 43 mL | 10.7 mL | 21.4 mL |
| $CuSO_4$ (Component E) | 20 µL | 40 µL | 80 µL | 100 µL | 200 µL | 500 µL | 1 mL |
| Alexa Fluor ® azide (prepared in step 1.3] | 1.2 µL | 2.5 µL | 5 µL | 6 µL | 12.5 µL | 31 µL | 62 µL |
| Reaction buffer additive (prepared in step 4.1) | 50 µL | 100 µL | 200 µL | 250 µL | 500 µL | 1.25 mL | 2.5 mL |
| Total volume | 500 µL | 1 mL | 2 mL | 2.5 ml | 5 mL | 12.5 mL | 25 mL |

*Note:
Add the ingredients in the order listed in the table.

2.6.2 Add 0.1 mL of Click-iT® reaction cocktail to each well containing a coverslip. Rock the plate briefly to ensure that the reaction cocktail is distributed evenly over the coverslip.

2.6.3 Incubate the plate for 30 minutes at room temperature, protected from light.

2.6.4 Remove the reaction cocktail, then wash the cells twice with 0.1% PBST for 5 min each time.

2.7. DAPI staining: DAPI stain was diluted to PBS at a ratio of 1:1000, 100 ul per well, incubated for 30 min at room temperature, and the cells were washed twice with PBS for 5 min each.

3. Data Analysis

We used Molecular Devices' Image Xpress Micro Confocal for high-throughput photo and data analysis.

Buffer Solution

1. PBS buffer: Take a volume of 500 ml as an example, 25 ml PBS buffer (20×) (Sangon Biotech, B548117-0500)+475 ml ddH2O
2. 0.1% PBST: Take a volume of 500 ml as an example, 25 ml PBS buffer (20×) (Sangon Biotech, B548117-0500)+475 ml ddH2O+500 ul Tween 20 (Sinopharm Chemical Reagent Co Ltd, 30189328)

References used for the cardiomyocyte proliferation assay:

1. Chen, J. et al. mir-17-92 cluster is required for and sufficient to induce cardiomyocyte proliferation in postnatal and adult hearts. Circ Res 112, 1557-1566, doi:10.1161/CIRCRESAHA.112.300658 (2013).
2 Andersson, O. et al. Adenosine signaling promotes regeneration of pancreatic beta cells in vivo. Cell Metab 15, 885-894, doi:10.1016/j.cmet.2012.04.018 (2012).
3 Dogra, D. et al. Opposite effects of Activin type 2 receptor ligands on cardiomyocyte proliferation during development and repair. Nat Commun 8, 1902, doi:10.1038/s41467-017-01950-1 (2017).
4 Hirose, K. et al. Evidence for hormonal control of heart regenerative capacity during endothermy acquisition. Science 364, 184-188, doi:10.1126/science.aar2038 (2019).
5 Lin, Z. et al. Pi3kcb links Hippo-YAP and PI3K-AKT signaling pathways to promote cardiomyocyte proliferation and survival. Circ Res 116, 35-45, doi:10.1161/CIRCRESAHA.115.304457 (2015).
6 Wang, J., Cao, J., Dickson, A. L. & Poss, K. D. Epicardial regeneration is guided by cardiac outflow tract and Hedgehog signalling. Nature 522, 226-230, doi:10.1038/nature14325 (2015).
7 Salic, A. & Mitchison, T. J. A chemical method for fast and sensitive detection of DNA synthesis in vivo. Proc Natl Acad Sci USA 105, 2415-2420, doi:10.1073/pnas.0712168105 (2008).
8 Wang, Q. et al. Bioconjugation by copper(I)-catalyzed azide-alkyne [3+2] cycloaddition. J Am Chem Soc 125, 3192-3193, doi:10.1021/ja021381e (2003).

(2) Results

The results of Test Example 1 are shown in Table 1

TABLE 1

| Average myocyte proliferation assay data | | | | |
|---|---|---|---|---|
| Example | Compound ID | Avg 1 uM | Avg 3 uM | Avg 10 uM |
| 1 | TJU-B115 | * | *** | ** |
| 2 | TJU-B076 | * | * | *** |
| 3 | TJU-B116 | * | * | * |
| 4 | TJU-B182 | ** | ** | ** |
| 5 | TJU-B183 | ** | ** | *** |
| 6 | TJU-B170 | *** | ** | * |
| 7 | TJU-B185 | * | ** | * |
| 8 | TJU-B180 | ** | * | ** |
| 9 | TJU-B181 | * | ** | ** |
| 10 | TJU-B207 | ** | * | *** |
| 11 | TJU-B210 | ** | ** | *** |
| 12 | TJU-B215 | * | ** | |
| 13 | TJU-B218 | * | ** | |
| 14 | TJU-B171 | * | ** | |
| 15 | TJU-B179 | * | ** | |
| 16 | TJU-B200 | * | * | |
| 17 | TJU-B205 | * | * | * |
| 18 | TJU-B214 | * | * | ** |
| 19 | TJU-B211 | * | * | * |
| 20 | TJU-B212 | * | * | ** |
| 21 | TJU-B203 | *** | *** | ** |
| 22 | TJU-B209 | ** | ** | ** |
| 23 | TJU-B213 | ** | ** | ** |
| 24 | TJU-B228 | * | * | * |
| 25 | TJU-B231 | ** | * | * |
| 26 | TJU-B161 | * | * | * |
| 27 | TJU-B219 | * | * | ** |
| 28 | TJU-B232 | * | * | * |
| 29 | TJU-B237 | ** | * | *** |
| 30 | TJU-B184 | * | * | |
| 31 | TJU-B233 | ** | ** | |
| 32 | TJU-B236 | * | * | |
| 33 | TJU-B234 | * | * | |
| 34 | TJU-B235 | ** | *** | |
| 35 | TJU-B227 | * | * | |
| 36 | TJU-B220 | * | ** | |
| 37 | TJU-B221 | *** | ** | ** |
| 38 | TJU-B230 | *** | ** | *** |
| 39 | TJU-B252 | *** | ** | * |
| 40 | TJU-B229 | *** | *** | *** |
| 41 | TJU-B256 | * | * | ** |
| 42 | TJU-B257 | ** | ** | *** |
| 43 | TJU-B255 | ** | ** | ** |
| 44 | TJU-B238 | *** | ** | ** |
| 45 | TJU-B265 | ** | ** | ** |
| 46 | TJU-B163 | *** | ** | *** |
| 47 | TJU-B263 | *** | *** | *** |

TABLE 1-continued

| Average myocyte proliferation assay data | | | | |
|---|---|---|---|---|
| Example | Compound ID | Avg 1 uM | Avg 3 uM | Avg 10 uM |
| 48 | TJU-B264 | *** | *** | *** |
| 49 | TJU-B269 | * | ** | *** |
| 50 | TJU-B273 | * | * | |
| 51 | TJU-B275 | ** | ** | ** |
| 52 | TJU-B276 | ** | ** | ** |
| 53 | TJU-B282 | ** | *** | ** |
| 54 | TJU-B289 | * | * | |
| 55 | TJU-B290 | * | * | |
| 56 | TJU-B281 | * | * | |
| 57 | TJU-B303 | * | * | |
| 58 | TJU-B304 | * | * | |
| 59 | TJU-B305 | * | * | |
| 60 | TJU-B307 | * | * | |
| 61 | TJU-B293 | * | ** | |
| 63 | TJU-B306 | * | * | |
| 69 | TJU-B328 | ** | * | |
| 70 | TJU-B330 | ** | ** | |
| 71 | TJU-B274 | * | * | |
| 72 | TJU-B277 | * | * | |
| 73 | TJU-B278 | * | * | |
| 74 | TJU-B296 | * | *** | |
| 75 | TJU-B299 | ** | ** | |
| 76 | TJU-B300 | * | ** | |
| 77 | TJU-B321 | * | * | |
| 78 | TJU-B322 | * | * | |
| 79 | TJU-B323 | * | * | |
| 80 | TJU-B324 | * | * | |
| 81 | TJU-B325 | * | * | |
| 82 | TJU-B326 | ** | ** | |
| 83 | TJU-B329 | ** | ** | |
| 84 | TJU-B331 | * | ** | |
| 85 | TJU-B332 | * | ** | |
| 86 | TJU-B334 | ** | ** | |
| 87 | TJU-B333 | ** | ** | |
| 88 | TJU-B344 | * | * | |
| 89 | TJU-B347 | ** | * | |
| 90 | TJU-B353 | ** | ** | |
| 91 | TJU-B356 | * | * | |
| 92 | TJU-B308 | * | * | |
| 93 | TJU-B292 | * | ** | |
| 94 | TJU-B297 | * | * | |
| 95 | TJU-B302 | * | * | |
| 96 | TJU-B315 | * | * | |
| 97 | TJU-B327 | * | * | |
| 98 | TJU-B239 | ** | ** | |
| 99 | TJU-B352 | ** | * | |
| 100 | TJU-B358 | ** | ** | |
| 101 | TJU-B363 | ** | * | |
| 102 | TJU-B355 | * | ** | |
| 103 | TJU-B357 | ** | ** | |
| 104 | TJU-B361 | * | ** | |
| 105 | TJU-B364 | ** | ** | |

Note:
*** = >50%,
** = 10%-50%,
* = <10% growth relative to blank myocyte growth without compound added.

Test Example 2: Kinase Assay Methods

Compounds in the present invention have been evaluated for inhibition of human kinase activities in the following assays.

1. GSK3 Beta Enzyme Assay

The ability of compounds to inhibit human GSK3 beta kinase activities was determined using a commercially available ADP-Glo™ Kinase Assay kit (Promega, Cat #V9102) according to the manufacturer's protocol. The ADP-Glo™ Kinase Assay is a luminescent ADP detection assay that provides a universal, homogeneous, high-throughput screening method to measure kinase activity by quantifying the amount of ADP produced during a kinase reaction. The ADP-Glo™ Kinase Assay can be used to monitor the activity of virtually any ADP-generating enzymes (e.g., kinases or ATPases).

Recombinant full-length human GSK3 beta (expressed in Sf9 insect cells with an N-terminal His tag) was purchased from SignalChem (Cat #G09-10H). The GSK3 substrate peptide (sequence: YRRAAVPPSPSLSRHSSPHQ(pS) EDEEE) was purchased from SignalChem (Cat #G50-58). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the GSK3 substrate peptide are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, GSK3 beta (4 nM) in the enzymatic buffer solutions (40 mM Tris, pH 7.5, 20 mM MgCl2, 0.1 mg/ml BSA, 50 µM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 13 µM and 25 µM, respectively. The final reaction mixture of enzyme-substrate-ATP-compound was incubated for 60 minutes at 25° C.

Afterwards ADP-Glo™ Reagent was added and the mixture was incubated at 25° C. for 60 minutes. Then Kinase Detection Reagent was added and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

2. DYRK1A Enzyme Assay

The ability of compounds to inhibit human DYRK1A kinase activities was determined using a commercially available ADP-Glo™ Kinase Assay kit (Promega, Cat #V9102) according to the manufacturer's protocol.

Recombinant full-length DYRK1A (expressed in *E. Coli* cells with an N-terminal GST tag) was purchased from SignalChem (Cat #D09-10G). The DYRK substrate peptide (DYRKtide, sequence: RRRFRPASPLRGPPK) was purchased from SignalChem (Cat #D96-58). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the DYRKtide are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, DYRK1A (3 nM) in the enzymatic buffer solutions (40 mM Tris, pH 7.5, 20 mM MgCl2, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 20 μM and 60 μM, respectively. The final reaction mixture of enzyme-substrate-ATP-compound was incubated for 60 minutes at 25° C.

Afterwards ADP-Glo™ Reagent was added and the mixture was incubated at 25° C. for 60 minutes. Then Kinase Detection Reagent was added and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

3. DYRK2 Enzyme Assay

The ability of compounds to inhibit human DYRK2 kinase activities was determined using a commercially available ADP-Glo™ Kinase Assay kit (Promega, Cat #V9102) according to the manufacturer's protocol.

Recombinant full-length human DYRK2 (expressed in *E. Coli* cells with an N-terminal GST tag) was purchased from SignalChem (Cat #D10-10G). The DYRKtide peptide (sequence: RRRFRPASPLRGPPK) was purchased from SignalChem (Cat #D96-58). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the DYRKtide are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, DYRK2 (6 nM) in the enzymatic buffer solutions (40 mM Tris, pH 7.5, 20 mM MgCl2, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 25 μM and 10 μM, respectively. The final reaction mixture of enzyme-substrate-ATP-compound was incubated for 60 minutes at 25° C.

Afterwards ADP-Glo™ Reagent was added and the mixture was incubated at 25° C. for 60 minutes. Then Kinase Detection Reagent was added and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

4. CLK1 Enzyme Assay

The ability of compounds to inhibit human CLK1 kinase activities was determined using a commercially available ADP-Glo™ Kinase Assay kit (Promega, Cat #V9102) according to the manufacturer's protocol.

Recombinant human CLK1 (129-end) (expressed in Sf9 insect cells with an N-terminal GST tag) was purchased from SignalChem (Cat #C57-11G). Recombinant full length human MBP (expressed in *E. Coli* cells with an N-terminal GST tag.) was purchased from SignalChem (Cat #M42-54G). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the MBP protein are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, CLK1 (16 nM) in the enzymatic buffer solutions (40 mM Tris, pH 7.5, 20 mM MgCl2, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 2 μM and 10 μM, respectively. The final reaction mixture of enzyme-substrate-ATP-compound was incubated for 60 minutes at 25° C.

Afterwards ADP-Glo™ Reagent was added and the mixture was incubated at 25° C. for 60 minutes. Then Kinase Detection Reagent was added and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

5. CIT Enzyme Assay

The ability of compounds to inhibit human CIT kinase activities was determined using a commercially available ADP-Glo™ Kinase Assay kit (Promega, Cat #V9102) according to the manufacturer's protocol.

Recombinant human CIT (1-499) (expressed in Sf9 insect cells with an N-terminal GST tag) was purchased from SignalChem (Cat #C52-11G). Recombinant full length human MBP (expressed in *E. Coli* cells with an N-terminal GST tag) was purchased from SignalChem (Cat #M42-54G). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the MBP protein are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, CIT (20 nM) in the enzymatic buffer solutions (40 mM Tris, pH 7.5, 20 mM MgCl2, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 0.05 mg/ml and 5 μM, respectively. The final reaction mixture of enzyme-substrate-ATP-compound was incubated for 90 minutes at 25° C.

Afterwards ADP-Glo™ Reagent was added and the mixture was incubated at 25° C. for 60 minutes. Then Kinase Detection Reagent was added, and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

6. HIPK1 Enzyme Assay

The ability of compounds to inhibit human HIPK1 kinase activities was determined using a commercially available ADP-Glo™ Kinase Assay kit (Promega, Cat #V9102) according to the manufacturer's protocol.

Recombinant human HIPK1 (156-555) (expressed in Sf9 insect cells with an N-terminal GST tag) was purchased from SignalChem (Cat #H03-11G). Recombinant full length human MBP (expressed in *E. Coli* cells with an N-terminal GST tag) was purchased from SignalChem (Cat #M42-54G). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the MBP protein are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, HIPK1 (4 nM) in the enzymatic buffer solutions (40 mM Tris, pH 7.5, 20 mM MgCl2, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 0.05 mg/ml and 5 μM, respectively. The final reaction mixture of enzyme-substrate-ATP-compound was incubated for 90 minutes at 25° C.

Afterwards ADP-Glo™ Reagent was added and the mixture was incubated at 25° C. for 60 minutes. Then Kinase Detection Reagent was added, and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

7. HIPK2 Enzyme Assay

The ability of compounds to inhibit human HIPK2 kinase activities was determined using a commercially available ADP-Glo™ Kinase Assay kit (Promega, Cat #V9102) according to the manufacturer's protocol.

Recombinant human HIPK2 (1-640) (expressed in Sf9 insect cells with an N-terminal GST tag) was purchased from SignalChem (Cat #H04-11BG). Recombinant full length human MBP (expressed in *E. Coli* cells with an N-terminal GST tag) was purchased from SignalChem (Cat #M42-54G). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the MBP protein are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, HIPK2 (1 nM) in the enzymatic buffer solutions (40 mM Tris, pH 7.5, 20 mM MgCl2, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 0.05 mg/ml and 5 μM, respectively. The final reaction mixture of enzyme-substrate-ATP-compound was incubated for 90 minutes at 25° C.

Afterwards ADP-Glo™ Reagent was added and the mixture was incubated at 25° C. for 60 minutes. Then Kinase Detection Reagent was added, and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

8. CK2a2 (CSNK2a2) Enzyme Assay

The ability of compounds to inhibit human CK2a2 (CSNK2a2) kinase activities was determined using a commercially available ADP-Glo™ Kinase Assay kit (Promega, Cat #V9102) according to the manufacturer's protocol.

Recombinant human CK2a2 (CSNK2a2) (full length) (expressed in Sf9 insect cells with an N-terminal GST tag) was purchased from SignalChem (Cat #C71-10G). CK2 substrate (sequence: RRRADDSDDDDD) was purchased from SignalChem (Cat #C08-58). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the MBP protein are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, CK2a2 (CSNK2a2) (7 nM) in the enzymatic buffer solutions (40 mM Tris, pH 7.5, 20 mM $MgCl_2$, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 0.04 mg/ml and 15 μM, respectively. The final reaction mixture of enzyme-substrate-ATP-compound was incubated for 90 minutes at 25° C.

Afterwards ADP-Glo™ Reagent was added and the mixture was incubated at 25° C. for 60 minutes. Then Kinase Detection Reagent was added, and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

9. Results

The results of test example 2 are shown in Table 2.

TABLE 2

Kinase activity of compounds

| Synthesis ID | Example | GSK3b IC50 (nM) | DYRK1A IC50 (nM) | CLK1 IC50 (nM) | HIPK1 IC50 (nM) | HIPK2 IC50 (nM) | CK2 alpha 2 IC50 (nM) | CIT IC50 (nM) |
|---|---|---|---|---|---|---|---|---|
| TJU-B115 | 1 | ++++ | ++ | ++ | ++++ | ++++ | ++ | ++++ |
| TJU-B076 | 2 | ++++ | +++ | +++ | ++++ | ++++ | | ++++ |
| TJU-B116 | 3 | ++++ | +++ | +++ | ++++ | ++++ | | |
| TJU-B182 | 4 | ++++ | ++ | ++ | ++++ | ++++ | ++ | ++++ |
| TJU-B183 | 5 | ++++ | + | ++ | ++ | +++ | + | ++++ |
| TJU-B170 | 6 | ++ | + | + | ++ | ++ | + | ++ |
| TJU-B185 | 7 | +++ | ++ | ++ | +++ | +++ | ++ | ++ |
| TJU-B180 | 8 | ++++ | +++ | +++ | ++++ | ++++ | | |
| TJU-B181 | 9 | ++++ | ++ | ++ | ++++ | ++++ | | |
| TJU-B207 | 10 | ++++ | ++ | ++ | ++++ | ++++ | | |
| TJU-B210 | 11 | ++++ | ++ | ++ | ++++ | ++++ | ++ | ++++ |
| TJU-B215 | 12 | ++++ | ++ | ++ | ++++ | ++++ | | |
| TJU-B218 | 13 | +++ | ++ | ++ | +++ | +++ | ++ | ++++ |
| TJU-B171 | 14 | ++++ | ++++ | ++++ | ++++ | ++++ | | |
| TJU-B179 | 15 | ++++ | ++++ | ++++ | ++++ | ++++ | | |
| TJU-B200 | 16 | +++ | + | + | +++ | +++ | | |
| TJU-B205 | 17 | ++++ | ++++ | ++++ | ++++ | ++++ | | |
| TJU-B214 | 18 | ++++ | ++ | ++ | ++++ | ++++ | | |
| TJU-B211 | 19 | ++++ | ++ | +++ | ++++ | ++++ | | |
| TJU-B212 | 20 | +++ | ++ | ++ | ++++ | ++++ | | |
| TJU-B203 | 21 | ++++ | ++ | +++ | ++++ | ++++ | +++ | ++++ |
| TJU-B209 | 22 | ++++ | ++++ | +++ | ++++ | ++++ | ++++ | ++++ |
| TJU-B213 | 23 | ++++ | ++ | ++ | ++++ | ++++ | ++++ | ++++ |
| TJU-B228 | 24 | ++++ | ++ | ++ | ++++ | ++ | | |
| TJU-B231 | 25 | ++++ | + | + | ++ | ++ | | |
| TJU-B161 | 26 | ++ | + | + | ++ | ++ | | |
| TJU-B219 | 27 | ++++ | +++ | +++ | +++ | +++ | | |
| TJU-B232 | 28 | +++ | ++ | ++ | +++ | +++ | | |
| TJU-B237 | 29 | +++ | ++ | ++ | +++ | +++ | | |
| TJU-B184 | 30 | ++++ | +++ | ++ | ++++ | ++++ | | |
| TJU-B233 | 31 | +++ | + | + | ++ | ++ | | |
| TJU-B236 | 32 | +++ | +++ | ++ | ++++ | ++++ | | |
| TJU-B234 | 33 | ++++ | +++ | ++ | ++++ | +++ | | |
| TJU-B235 | 34 | +++ | ++ | + | +++ | +++ | | |
| TJU-B227 | 35 | ++++ | +++ | ++ | ++++ | ++++ | | |
| TJU-B220 | 36 | ++++ | ++ | ++ | ++++ | ++++ | | |
| TJU-B221 | 37 | ++++ | +++ | +++ | ++++ | ++++ | ++ | ++++ |
| TJU-B230 | 38 | ++++ | ++ | ++ | +++ | +++ | ++ | +++ |

TABLE 2-continued

| Kinase activity of compounds | | | | | | | | |
|---|---|---|---|---|---|---|---|---|
| Synthesis ID | Example | GSK3b IC50 (nM) | DYRK1A IC50 (nM) | CLK1 IC50 (nM) | HIPK1 IC50 (nM) | HIPK2 IC50 (nM) | CK2 alpha 2 IC50 (nM) | CIT IC50 (nM) |
| TJU-B252 | 39 | ++++ | +++ | ++++ | ++++ | ++++ | | |
| TJU-B229 | 40 | ++++ | +++ | + | +++ | +++ | ++++ | ++ |
| TJU-B256 | 41 | +++ | ++ | + | ++++ | +++ | | |
| TJU-B257 | 42 | ++++ | ++++ | ++++ | ++++ | ++++ | ++++ | ++++ |
| TJU-B255 | 43 | ++++ | +++ | +++ | ++++ | ++++ | | |
| TJU-B238 | 44 | +++ | ++ | ++ | +++ | +++ | ++ | ++ |
| TJU-B265 | 45 | +++ | ++ | + | +++ | +++ | +++ | ++ |
| TJU-B163 | 46 | ++ | + | + | ++ | ++ | + | ++ |
| TJU-B263 | 47 | ++++ | ++++ | ++++ | ++++ | ++++ | ++++ | ++++ |
| TJU-B264 | 48 | ++++ | + | + | ++ | + | + | ++ |
| TJU-B269 | 49 | ++++ | ++++ | ++++ | ++++ | ++++ | | |
| TJU-B273 | 50 | ++++ | +++ | ++++ | ++++ | ++++ | | |
| TJU-B275 | 51 | ++++ | ++++ | ++++ | ++++ | ++++ | | |
| TJU-B276 | 52 | ++++ | ++++ | ++ | ++++ | ++++ | ++++ | ++++ |
| TJU-B282 | 53 | ++++ | + | + | ++++ | ++ | ++++ | ++++ |
| TJU-B289 | 54 | ++++ | ++++ | ++++ | ++++ | ++++ | | |
| TJU-B290 | 55 | ++ | + | + | ++++ | ++ | | |
| TJU-B281 | 56 | +++ | + | + | ++++ | +++ | | |
| TJU-B303 | 57 | ++++ | + | + | + | ++ | | |
| TJU-B304 | 58 | ++++ | ++++ | ++++ | ++++ | ++++ | | |
| TJU-B305 | 59 | ++++ | ++++ | ++++ | ++++ | ++++ | | |
| TJU-B307 | 60 | ++++ | ++++ | ++++ | ++++ | ++++ | | |
| TJU-B293 | 61 | ++ | + | ++ | ++ | ++ | | |
| TJU-B306 | 63 | ++++ | ++++ | ++++ | ++++ | ++++ | | |
| TJU-B328 | 69 | ++ | + | + | ++ | + | | |
| TJU-330 | 70 | ++++ | ++++ | + | ++++ | ++++ | ++ | ++++ |
| TJU-B274 | 71 | ++++ | ++++ | ++++ | ++++ | ++++ | | |
| TJU-B277 | 72 | ++++ | ++++ | ++++ | ++++ | ++++ | | |
| TJU-B278 | 73 | ++++ | ++++ | ++++ | ++++ | ++++ | | |
| TJU-B296 | 74 | ++++ | ++++ | ++++ | ++++ | ++++ | | |
| TJU-B299 | 75 | ++ | + | + | + | + | | |
| TJU-B300 | 76 | ++ | + | + | ++ | ++ | | |
| TJU-B321 | 77 | ++++ | + | ++ | ++++ | ++++ | | |
| TJU-B322 | 78 | ++++ | ++++ | ++++ | ++++ | ++++ | | |
| TJU-B323 | 79 | ++++ | ++++ | ++++ | ++++ | ++++ | | |
| TJU-B324 | 80 | ++++ | ++++ | ++++ | ++++ | ++++ | | |
| TJU-B325 | 81 | ++ | + | + | ++ | + | | |
| TJU-B326 | 82 | ++ | + | + | ++++ | ++ | + | ++++ |
| TJU-B329 | 83 | +++ | ++ | + | ++++ | ++++ | ++ | ++ |
| TJU-B331 | 84 | +++ | ++ | ++ | ++++ | +++ | ++ | ++++ |
| TJU-B332 | 85 | +++ | ++ | ++ | ++++ | ++++ | | |
| TJU-B334 | 86 | +++ | +++ | +++ | +++ | +++ | | |
| TJU-B333 | 87 | ++++ | ++++ | ++++ | ++++ | ++++ | | |
| TJU-B344 | 88 | ++++ | + | + | ++++ | ++++ | | |
| TJU-B347 | 89 | +++ | ++ | + | +++ | ++ | | |
| TJU-B353 | 90 | ++++ | + | + | ++++ | + | + | ++++ |
| TJU-B356 | 91 | ++++ | + | + | ++ | + | | |
| TJU-B308 | 92 | ++ | ++ | + | ++ | ++ | | |
| TJU-B292 | 93 | ++ | + | + | ++ | ++ | | |
| TJU-B297 | 94 | ++++ | ++++ | ++++ | ++++ | ++++ | | |
| TJU-B302 | 95 | ++++ | ++++ | ++++ | ++++ | ++++ | | |
| TJU-B315 | 96 | +++ | ++++ | ++++ | ++++ | ++++ | | |
| TJU-B327 | 97 | +++ | ++ | ++ | ++ | + | | |
| TJU-B239 | 98 | ++ | + | + | ++ | ++ | + | ++ |
| TJU-B352 | 99 | ++++ | ++ | + | ++++ | ++ | | |
| TJU-B358 | 100 | ++ | ++ | +++ | ++++ | ++ | | |
| TJU-B363 | 101 | ++++ | + | ++ | ++++ | ++++ | | |
| TJU-B355 | 102 | ++++ | +++ | ++ | ++ | ++ | | |
| TJU-B357 | 103 | +++ | + | + | ++ | ++ | ++ | ++ |
| TJU-B361 | 104 | ++++ | +++ | + | ++++ | +++ | | |
| TJU-B364 | 105 | ++++ | ++++ | ++++ | ++++ | ++++ | | |

Data definition:
++++: >10000 nM,
+++: 1000-10000 nM,
++: 100-1000 nM,
+: <100 nM;
–: NA Test Example 3: In Vivo Protocol 1. Myocardial Infarction 6-week-old C57/BL6 mice were anesthetized with 1% isoflurane in a chamber. The mice were placed in a left supine position on a heating pad (37° C.), and the heart was exposed via thoracotomy at the fourth left intercostal space. The pericardium was then opened, and the left coronary artery was permanently ligated with a 7-0 suture. Ligation was considered successful when the left ventricle became pale. From one week after surgery, the compound prepared in Examples 1-105 or control solvent were injected via tail vein every other day. The mice were then euthanized after 6 weeks of injection, and the hearts were subjected to histology.

2. Injury Region Division

The cardiac tissue regions used for image characterization are described as the whole heart, infarct zone (left ventricle free wall), border zone (left ventricle anterior and posterior walls), or distal zone (interventricular septum).

3. Histology

For histology studies, hearts were collected at the indicated time points. After removing the blood by retrograde perfusion from the heart apex with cold PBS, the whole hearts were fixed with 4% paraformaldehyde (PFA, Sigma) at 4° C. overnight. Next, the hearts were dehydrated in increasing concentrations of ethanol and embedded in paraffin. Hematoxylin and eosin staining and Masson's trichrome staining were performed according to previously published methods [Development 140, 4683-4690 (2013)]

Hearts were sectioned at a thickness of 8 μm, and slides were created with 5 sections per slide. The sections started at the ligation site and ended at the heart apex (approximately 50 slides). Slides were stained with Masson's trichrome stain to identify areas of fibrosis. Scar size was quantified by examining serial sections from the apex to the ligation site and calculating the average percent fibrotic area of the total area using Image J software based on Masson's trichrome staining.

4. Results

In vivo test showed that the compounds prepared in Examples 1-105 can promote cardiomyocyte proliferation in the heart Infarct model and reduced infarct size.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

What is claimed:

1. A compound of formula (I), or a pharmaceutically acceptable salt, a solvate, a stereoisomer or a prodrug thereof:

(I)

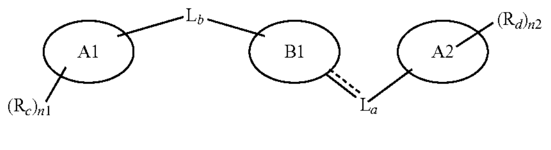

wherein ring A1 is selected from the group consisting of substituted or unsubstituted C3-C10 heterocyclic group, C4-C10 heteroaryl, and C6-C10 aryl, wherein the heterocyclic group and heteroaryl each have 1-4 heteroatoms selected from N, O, S;

ring A2 is

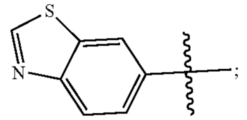 [SMILES: *c1ccc2ncsc2c1]

ring B1 has a structure of:

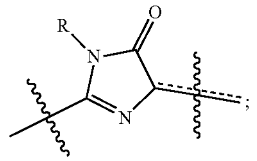

wherein R is H, C1-C4 alkyl, C3-C4 cycloalkyl or C1-C4 haloalkyl;

---- is a double bond;

La is =$CR_b$—; wherein $R_b$ is H or C1-C8 alkyl;

Lb is —NRa—; wherein $R_a$ is selected from the group consisting of: H, substituted of unsubstituted C1-C8 alkyl, substituted or unsubstituted C2-C6 alkenyl, substituted or unsubstituted C2-C8 alkynyl, substituted or unsubstituted C3-C10 cycloalkyl, substituted or unsubstituted C3-C10 heterocycloalkyl, substituted or unsubstituted C6-C10 aryl, substituted or unsubstituted C3-C7 heteroaryl, substituted or unsubstituted C1-C3 alkylene-C6-C10 aryl, substituted or unsubstituted C1-C3 alkylene-C3-C10 cycloalkyl, and substituted or unsubstituted C1-C3 alkylene-C3-C10 heterocycloalkyl;

each $R_c$ is independently selected from the group consisting of halogen, —OH, nitro, cyano, sulfonyl, R", —N(R")$_2$—, R"—O—, R"—S—, R"—S(O)$_2$—, R"—S(O)—, R"—C(O), R"—C(O)O—, and R"—OC(O)—; wherein R" is each independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, —C1-C4 alkylene-C3-C6 cycloalkyl, —C1-C4 alkylene-C6-C10 aryl, —C1-C4 alkylene-4 to 7-membered heterocycloalkyl, and —C1-C4 alkylene-5 to 7-membered heteroaryl;

or two adjacent Rc together form a substituted or unsubstituted C4-C8 heterocyclic ring, substituted or unsubstituted C4-C7 heteroaryl, or substituted or unsubstituted C6 aryl;

$R_d$ is H or C1-C6 alkyl n1 is 1, 2, 3, 4 or 5;

n2 is 0, 1, or 2;

the term "substituted" refers to one or more hydrogens in the group is replaced with an R' group;

each R' is independently selected from the group consisting of D, halogen, —OH, nitro, cyano, sulfonyl, R", —N(R"), R"—O—, R"—S—, R"—S(O)$_2$—, R"—S(O)—, R"—C(O), R"—C(O)O—, R"—OC (O)—, where R" is each independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, C1-C4 alkylene-C3-C6 cycloalkyl, —C1-C4 alkylene-C6-C10 aryl, —C1-C4 alkylene-(4 to 7-membered heterocycloalkyl), and —C1-C4 alkylene-(5 to 7-membered heteroaryl).

2. The compound of claim 1, or a pharmaceutically acceptable salt, a solvate, a stereoisomer or a prodrug thereof, wherein ring A1 is C6-C10 aryl; or ring A1 is selected from the group consisting of:

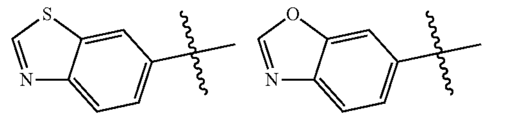
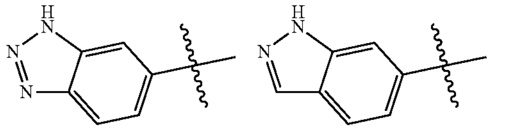
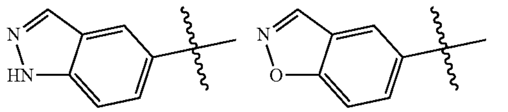
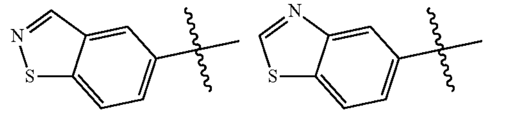
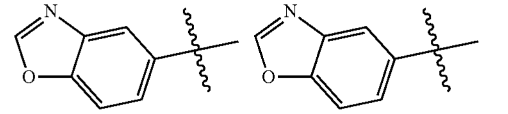
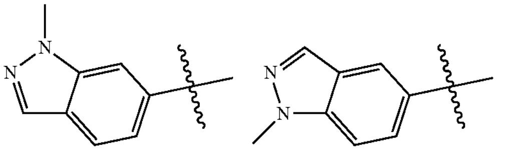
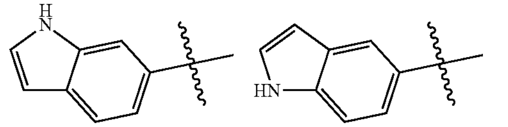
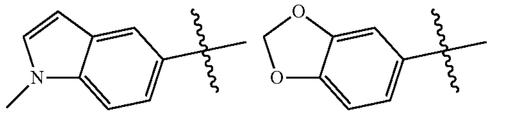
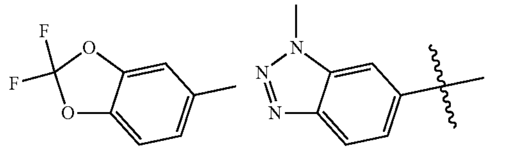
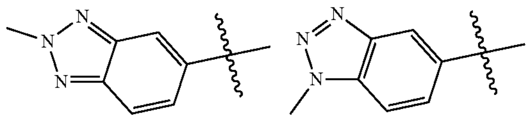
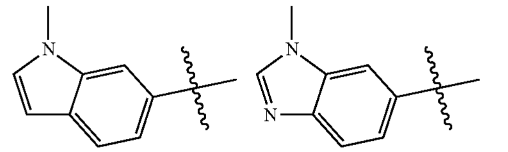

-continued

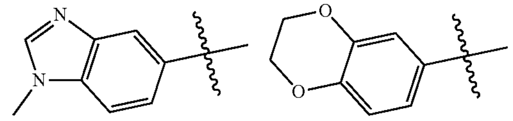
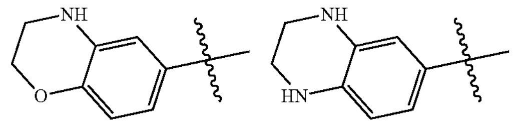
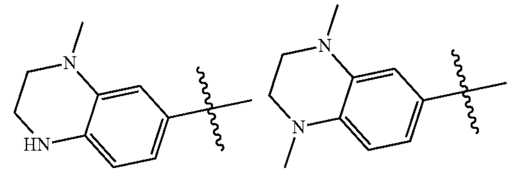
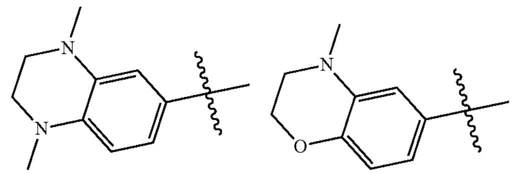
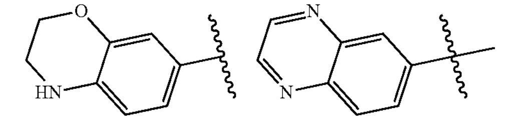
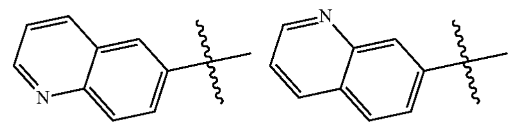
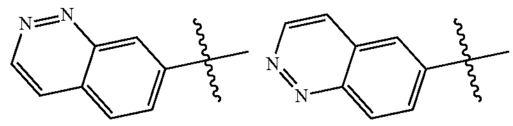
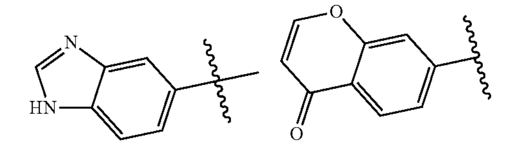
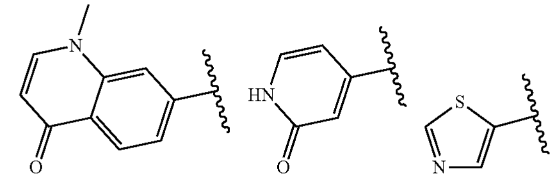
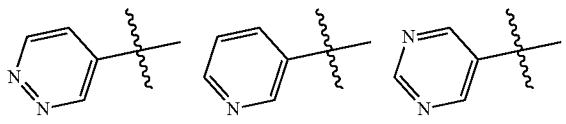
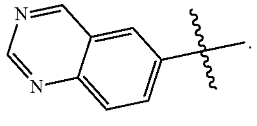

3. A compound, or a pharmaceutically acceptable salt, a solvate, a stereoisomer or a prodrug thereof, wherein the compound is selected from below table

| Compound | Structure | Name |
|---|---|---|
| Example 6: | 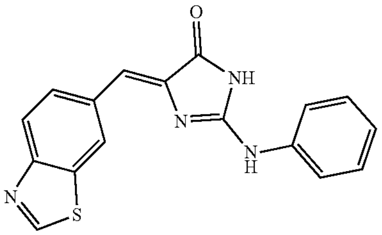 [SMILES: O=C1NC(Nc2ccccc2)=N/C1=C\c1ccc2ncsc2c1] | (4Z)-4-[(1,3-benzothiazol-6-yl)methylidene]-2-(phenylamino)-4,5-dihydro-1H-imidazol-5-one |
| Example 7: | 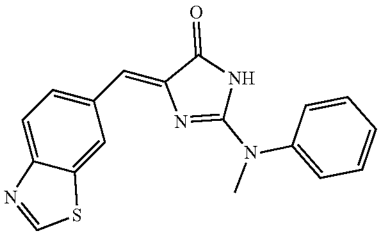 [SMILES: CN(C1=N/C(=C\c2ccc3ncsc3c2)C(=O)N1)c1ccccc1] | (4Z)-4-[(1,3-benzothiazol-6-yl)methylidene]-2-[methyl(phenyl)amino]-4,5-dihydro-1H-imidazol-5-one |
| Example 24: | 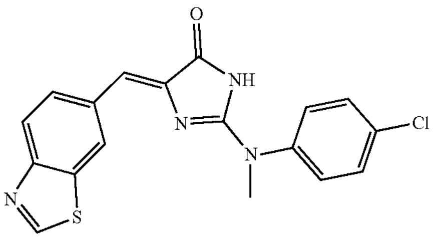 [SMILES: CN(C1=N/C(=C\c2ccc3ncsc3c2)C(=O)N1)c1ccc(Cl)cc1] | (4Z)-4-[(1,3-benzothiazol-6-yl)methylidene]-2-[(4-chlorophenyl)(methyl)amino]-4,5-dihydro-1H-imidazol-5-one |
| Example 25: | 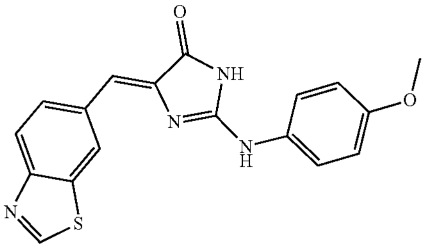 [SMILES: COc1ccc(NC2=N/C(=C\c3ccc4ncsc4c3)C(=O)N2)cc1] | (4Z)-4-[(1,3-benzothiazol-6-yl)methylidene]-2-[(4-methoxyphenyl)amino]-4,5-dihydro-1H-imidazol-5-one |
| Example 28: | 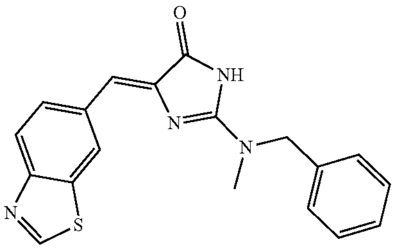 [SMILES: CN(Cc1ccccc1)C1=N/C(=C\c2ccc3ncsc3c2)C(=O)N1] | (4Z)-4-[(1,3-benzothiazol-6-yl)methylidene]-2-[benzyl(methyl)amino]-4,5-dihydro-1H-imidazol-5-one |
| Example 29: | 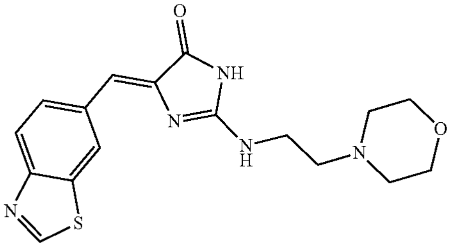 [SMILES: O=C1NC(NCCN2CCOCC2)=N/C1=C\c1ccc2ncsc2c1] | (4Z)-4-[(1,3-benzothiazol-6-yl)methylidene]-2-{[2-(morpholin-4-yl)ethyl]amino}-4,5-dihydro-1H-imidazol-5-one |

-continued

| Compound | Structure | Name |
|---|---|---|
| Example 31: | 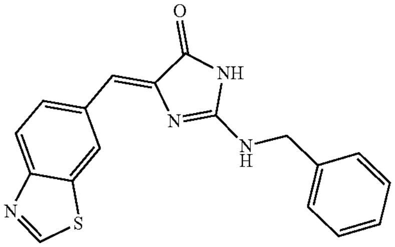 [SMILES: O=C1NC(NCc2ccccc2)=N/C1=C\c1ccc2ncsc2c1] | (4Z)-4-[(1,3-benzothiazol-6-yl)methylidene]-2-(benzylamino)-4,5-dihydro-1H-imidazol-5-one |
| Example 32: | 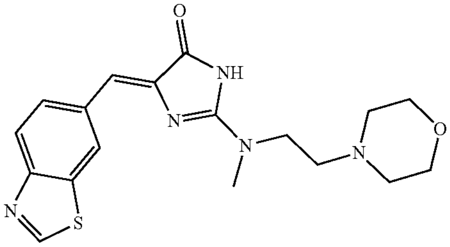 [SMILES: CN(CCN1CCOCC1)C1=N/C(=C\c2ccc3ncsc3c2)C(=O)N1] | (4Z)-4-[(1,3-benzothiazol-6-yl)methylidene]-2-{methyl[2-(morpholin-4-yl)ethyl]amino}-4,5-dihydro-1H-imidazol-5-one |
| Example 33: | 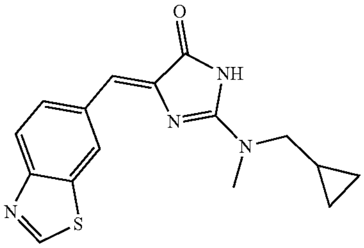 [SMILES: CN(CC1CC1)C1=N/C(=C\c2ccc3ncsc3c2)C(=O)N1] | (4Z)-4-[(1,3-benzothiazol-6-yl)methylidene]-2-[(cyclopropylmethyl)(methyl)amino]-4,5-dihydro-1H-imidazol-5-one |
| Example 34: | 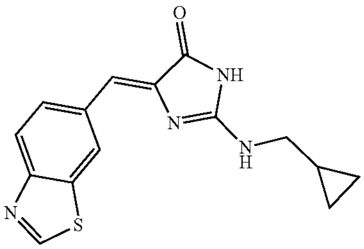 [SMILES: O=C1NC(NCC2CC2)=N/C1=C\c1ccc2ncsc2c1] | (4Z)-4-[(1,3-benzothiazol-6-yl)methylidene]-2-[(cyclopropylmethyl)amino]-4,5-dihydro-1H-imidazol-5-one |
| Example 38: | 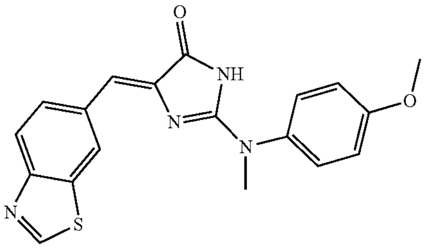 [SMILES: COc1ccc(N(C)C2=N/C(=C\c3ccc4ncsc4c3)C(=O)N2)cc1] | (4Z)-4-[(1,3-benzothiazol-6-yl)methylidene]-2-[(4-methoxyphenyl)(methyl)amino]-4,5-dihydro-1H-imidazol-5-one |
| Example 40: | 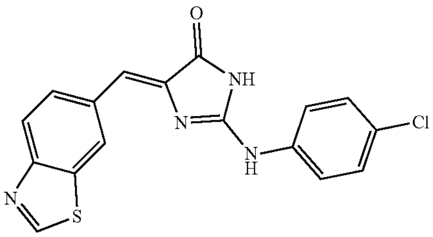 [SMILES: O=C1NC(Nc2ccc(Cl)cc2)=N/C1=C\c1ccc2ncsc2c1] | (4Z)-4-[(1,3-benzothiazol-6-yl)methylidene]-2-[(4-chlorophenyl)amino]-4,5-dihydro-1H-imidazol-5-one |

-continued

| Compound | Structure | Name |
|---|---|---|
| Example 41: | 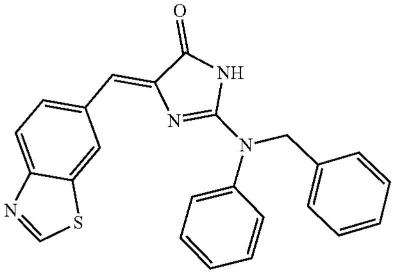 [SMILES: O=C1NC(N(Cc2ccccc2)c2ccccc2)=N/C1=C\c1ccc2ncsc2c1] | (4Z)-4-[(1,3-benzothiazol-6-yl)methylidene]-2-[benzyl(phenyl)amino]-4,5-dihydro-1H-imidazol-5-one |
| Example 42: | 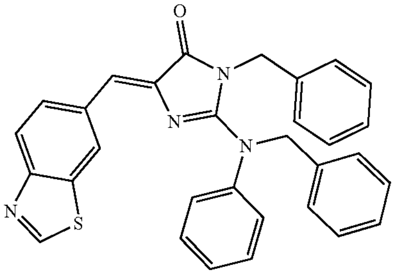 [SMILES: O=C1/C(=C/c2ccc3ncsc3c2)N=C(N(Cc2ccccc2)c2ccccc2)N1Cc1ccccc1] | (4Z)-4-[(1,3-benzothiazol-6-yl)methylidene]-1-benzyl-2-[benzyl(phenyl)amino]-4,5-dihydro-1H-imidazol-5-one |
| Example 43: | 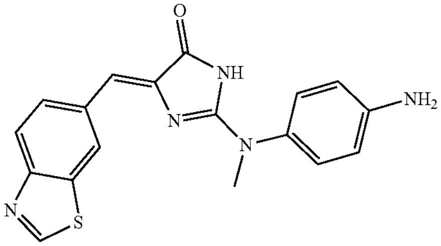 [SMILES: CN(C1=N/C(=C\c2ccc3ncsc3c2)C(=O)N1)c1ccc(N)cc1] | (4Z)-4-[(1,3-benzothiazol-6-yl)methylidene]-2-[methyl(4-nitrophenyl)amino]-4,5-dihydro-1H-imidazol-5-one |
| Example 44: | 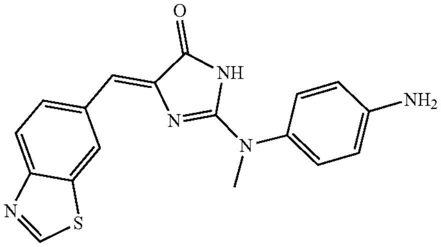 [SMILES: CN(C1=N/C(=C\c2ccc3ncsc3c2)C(=O)N1)c1ccc(N)cc1] | (4Z)-2-[(4-aminophenyl)(methyl)amino]-4-[(1,3-benzothiazol-6-yl)methylidene]-4,5-dihydro-1H-imidazol-5-one |
| Example 45: | 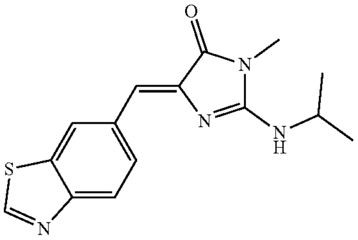 [SMILES: CC(C)NC1=N/C(=C\c2ccc3ncsc3c2)C(=O)N1C] | (4Z)-4-[(1,3-benzothiazol-6-yl)methylidene]-1-methyl-2-[(propan-2-yl)amino]-4,5-dihydro-1H-imidazol-5-one |
| Example 48: | 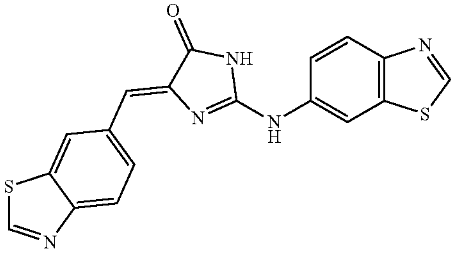 [SMILES: O=C1NC(Nc2ccc3ncsc3c2)=N/C1=C\c1ccc2ncsc2c1] | (4Z)-2-[(1,3-benzothiazol-6-yl)amino]-4-[(1,3-benzothiazol-6-yl)methylidene]-4,5-dihydro-1H-imidazol-5-one |

-continued

| Compound | Structure | Name |
| --- | --- | --- |
| Example 61: | 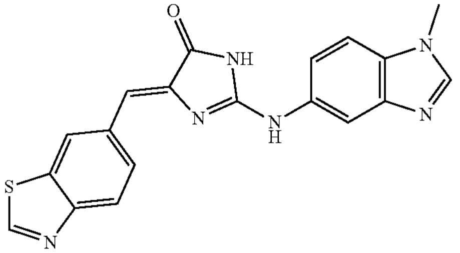 [SMILES: Cn1cnc2cc(NC3=N/C(=C\c4ccc5ncsc5c4)C(=O)N3)ccc21] | (4Z)-4-[(1,3-benzothiazol-6-yl)methylidene]-2-[(1-methyl-1H-1,3-benzodiazol-5-yl)amino]-4,5-dihydro-1H-imidazol-5-one; formic acid |
| Example 69: | 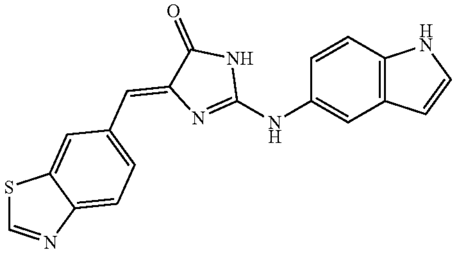 [SMILES: O=C1NC(Nc2ccc3[nH]ccc3c2)=N/C1=C\c1ccc2ncsc2c1] | (4Z)-4-[(1,3-benzothiazol-6-yl)methylidene]-2-[(1H-indol-5-yl)amino]-4,5-dihydro-1H-imidazol-5-one |
| Example 81: | 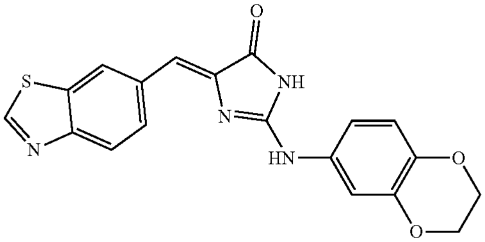 [SMILES: O=C1NC(Nc2ccc3c(c2)OCCO3)=N/C1=C\c1ccc2ncsc2c1] | (4Z)-4-[(1,3-benzothiazol-6-yl)methylidene]-2-[(2,3-dihydro-1,4-benzodioxin-6-yl)amino]-4,5-dihydro-1H-imidazol-5-one |
| Example 82: | 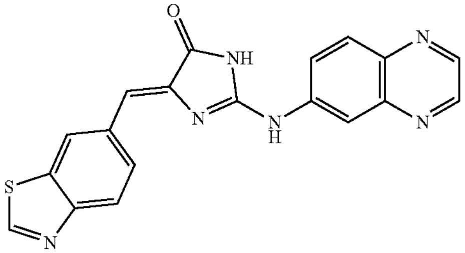 [SMILES: O=C1NC(Nc2ccc3nccnc3c2)=N/C1=C\c1ccc2ncsc2c1] | (4Z)-4-[(1,3-benzothiazol-6-yl)methylidene]-2-[(quinoxalin-6-yl)amino]-4,5-dihydro-1H-imidazol-5-one |
| Example 83: | 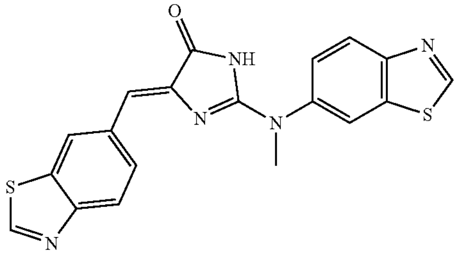 [SMILES: CN(C1=N/C(=C\c2ccc3ncsc3c2)C(=O)N1)c1ccc2ncsc2c1] | (4Z)-2-[(1,3-benzothiazol-6-yl)(methyl)amino]-4-[(1,3-benzothiazol-6-yl)methylidene]-4,5-dihydro-1H-imidazol-5-one |
| Example 86: | 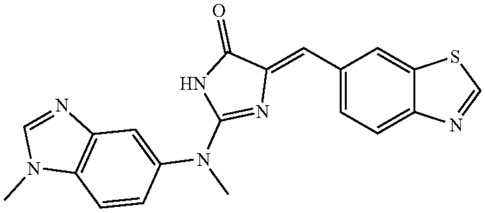 [SMILES: CN(C1=N/C(=C\c2ccc3ncsc3c2)C(=O)N1)c1ccc2c(c1)ncn2C] | (4Z)-4-[(1,3-benzothiazol-6-yl)methylidene]-2-[methyl(1-methyl-1H-1,3-benzodiazol-5-yl)amino]-4,5-dihydro-1H-imidazol-5-one |

-continued

| Compound | Structure | Name |
|---|---|---|
| Example 88: | 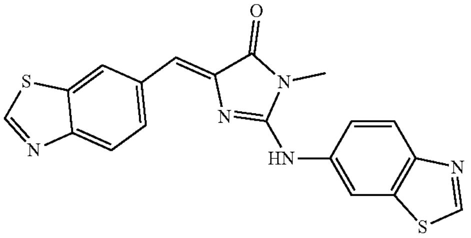 [SMILES: CN1C(=O)/C(=C/c2ccc3ncsc3c2)N=C1Nc1ccc2ncsc2c1] | (4Z)-2-[(1,3-benzothiazol-6-yl)amino]-4-[(1,3-benzothiazol-6-yl)methylidene]-1-methyl-4,5-dihydro-1H-imidazol-5-one |
| Example 89: | 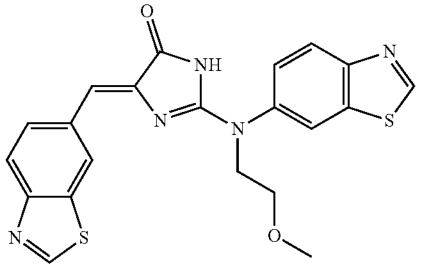 [SMILES: COCCN(C1=N/C(=C\c2ccc3ncsc3c2)C(=O)N1)c1ccc2ncsc2c1] | (4Z)-2-[(1,3-benzothiazol-6-yl)(2-methoxyethyl)amino]-4-[(1,3-benzothiazol-6-yl)methylidene]-4,5-dihydro-1H-imidazol-5-one |
| Example 90: | 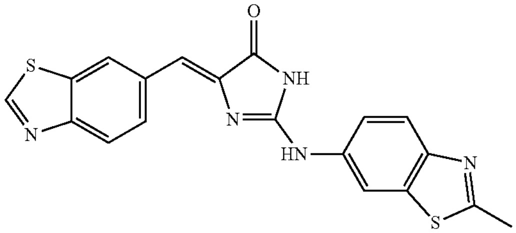 [SMILES: Cc1nc2ccc(NC3=N/C(=C\c4ccc5ncsc5c4)C(=O)N3)cc2s1] | (4Z)-4-[(1,3-benzothiazol-6-yl)methylidene]-2-[(2-methyl-1,3-benzothiazol-6-yl)amino]-4,5-dihydro-1H-imidazol-5-one |
| Example 91: | 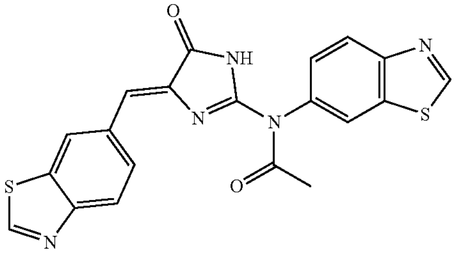 [SMILES: CC(=O)N(C1=N/C(=C\c2ccc3ncsc3c2)C(=O)N1)c1ccc2ncsc2c1] | N-(1,3-benzothiazol-6-yl)-N-[(4Z)-4-[(1,3-benzothiazol-6-yl)methylidene]-5-oxo-4,5-dihydro-1H-imidazol-2-yl]acetamide |
| Example 93: | 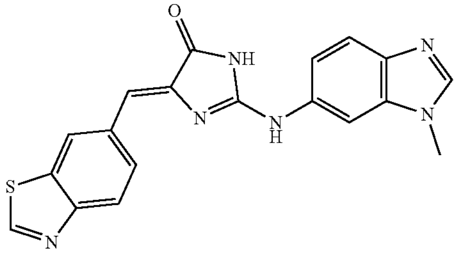 [SMILES: Cn1cnc2ccc(NC3=N/C(=C\c4ccc5ncsc5c4)C(=O)N3)cc21] | (4Z)-4-[(1,3-benzothiazol-6-yl)methylidene]-2-[(1-methyl-1H-1,3-benzodiazol-6-yl)amino]-4,5-dihydro-1H-imidazol-5-one |
| Example 97: | 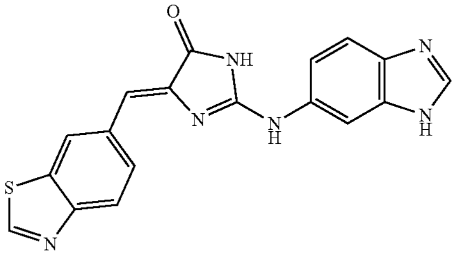 [SMILES: O=C1NC(Nc2ccc3nc[nH]c3c2)=N/C1=C\c1ccc2ncsc2c1] | (4Z)-2-[(1H-1,3-benzodiazol-6-yl)amino]-4-[(1,3-benzothiazol-6-yl)methylidene]-4,5-dihydro-1H-imidazol-5-one |

-continued

| Compound | Structure | Name |
| --- | --- | --- |
| Example 98: | 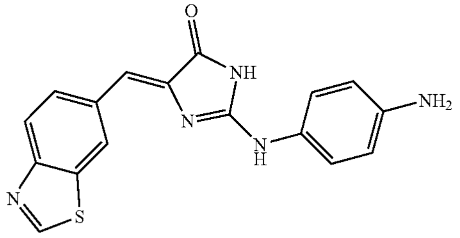 [SMILES: Nc1ccc(NC2=N/C(=C\c3ccc4ncsc4c3)C(=O)N2)cc1] | (4Z)-2-[(4-aminophenyl)amino]-4-[(1,3-benzothiazol-6-yl)methylidene]-4,5-dihydro-1H-imidazol-5-one |
| Example 99: | 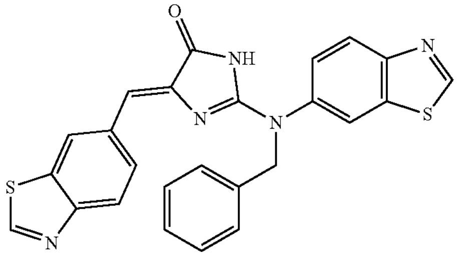 [SMILES: O=C1NC(N(Cc2ccccc2)c2ccc3ncsc3c2)=N/C1=C\c1ccc2ncsc2c1] | (4Z)-2-[(1,3-benzothiazol-6-yl)(benzyl)amino]-4-[(1,3-benzothiazol-6-yl)methylidene]-4,5-dihydro-1H-imidazol-5-one |
| Example 100: | 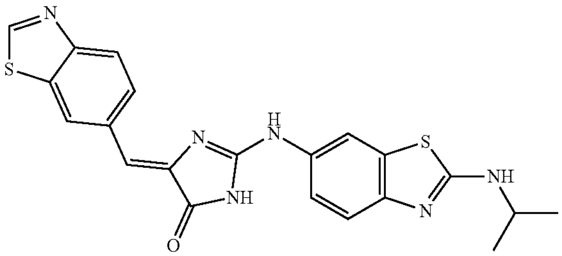 [SMILES: CC(C)Nc1nc2ccc(NC3=N/C(=C\c4ccc5ncsc5c4)C(=O)N3)cc2s1] | (4Z)-4-[(1,3-benzothiazol-6-yl)methylidene]-2-({2-[(propan-2-yl)amino]-1,3-benzothiazol-6-yl}amino)-4,5-dihydro-1H-imidazol-5-one |
| Example 101: | 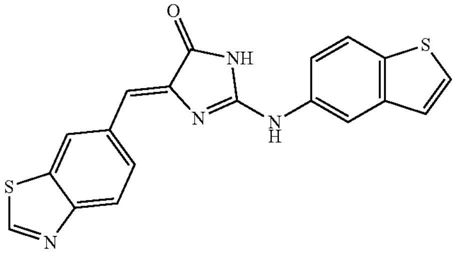 [SMILES: O=C1NC(Nc2ccc3sccc3c2)=N/C1=C\c1ccc2ncsc2c1] | (4Z)-4-[(1,3-benzothiazol-6-yl)methylidene]-2-[(1-benzothiophen-5-yl)amino]-4,5-dihydro-1H-imidazol-5-one |
| Example 103: | 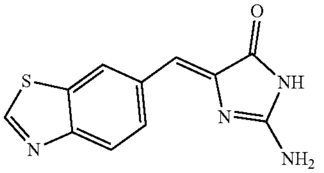 [SMILES: NC1=N/C(=C\c2ccc3ncsc3c2)C(=O)N1] | (4Z)-2-amino-4-[(1,3-benzothiazol-6-yl)methylidene]-4,5-dihydro-1H-imidazol-5-one |
| Example 104: | 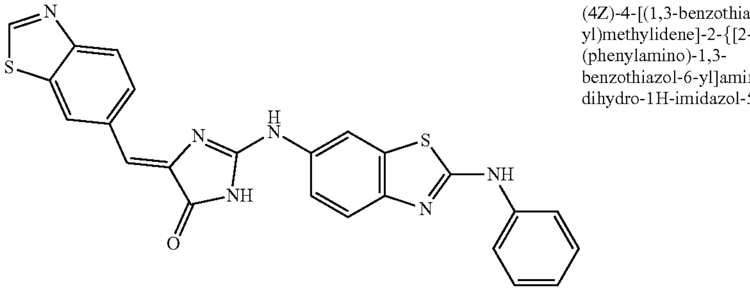 | (4Z)-4-[(1,3-benzothiazol-6-yl)methylidene]-2-{[2-(phenylamino)-1,3-benzothiazol-6-yl]amino}-4,5-dihydro-1H-imidazol-5-one |

-continued

| Compound | Structure | Name |
|---|---|---|
| Example 105: | 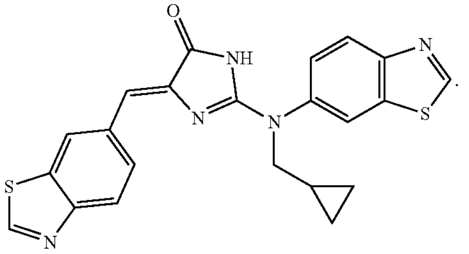 [SMILES: O=C1NC(N(CC2CC2)c2ccc3ncsc3c2)=N/C1=C\c1ccc2ncsc2c1] | (4Z)-2-[(1,3-benzothiazol-6-yl)(cyclopropylmethyl)amino]-4-[(1,3-benzothiazol-6-yl)methylidene]-4,5-dihydro-1H-imidazol-5-one |

4. A pharmaceutical composition comprising the compound of claim 1, or a pharmaceutically acceptable salt, a solvate, a stereoisomer or a prodrug thereof; and a pharmaceutically acceptable carrier.

5. A method for promoting growth of cardiomyocytes in vitro, which comprises a step of:

culturing cardiomyocyte in the presence of the compound of claim 1, or a pharmaceutically acceptable salt, a solvate, a stereoisomer or a prodrug.

6. A method for promoting cardiomyocyte proliferation and/or regeneration in vitro, which comprises a step of:

contacting cardiomyocyte with the compound of claim 1, or a pharmaceutically acceptable salt, a solvate, a stereoisomer or a prodrug, thereby promoting cardiomyocyte proliferation and/or regeneration.

7. A method for treating or preventing a cardiovascular disease, which comprises a step of: administering the compound according to claim 1 or a pharmaceutically acceptable salt, a solvate, a stereoisomer or a prodrug to a subject in need.

8. The compound of claim 1, or a pharmaceutically acceptable salt, a solvate, a stereoisomer or a prodrug thereof, wherein Lb is —NRa—; wherein $R_a$ is selected from the group consisting of: H, substituted or unsubstituted C1-C8 alkyl, substituted or unsubstituted C1-C3 alkylene-C6-C10 aryl, and substituted or unsubstituted C1-C3 alkylene-C3-C10 cycloalkyl;

$R_c$ is selected from the group consisting of —OH, nitro, cyano, R", —N(R")$_2$—, R"—O—, R"—S—, R"—S(O)$_2$—, R"—S(O)—, R"—C(O), R"—C(O)O—, R"—OC(O)—; wherein R" is each independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, —C1-C4 alkylene-C3-C6 cycloalkyl, —C1-C4 alkylene-C6-C10 aryl, —C1-C4 alkylene-4 to 7-membered heterocycloalkyl, and —C1-C4 alkylene-5 to 7-membered heteroaryl;

$R_d$ is H;

n1 is 1, 2, 3, 4 or 5;

n2 is 0;

wherein the term "substituted" refers to one or more hydrogens in the group is replaced with an R' group; and each R' is independently selected from the group consisting of D, —OH, R", R"—O—, where R" is C1-C6 alkyl.

9. The compound of claim 1, or a pharmaceutically acceptable salt, a solvate, a stereoisomer or a prodrug thereof, wherein $R_a$ is H or C1-C8 alkyl.

10. The compound of claim 1, or a pharmaceutically acceptable salt, a solvate, a stereoisomer or a prodrug thereof, wherein $R_b$ is H or C1 alkyl.

11. The compound of claim 1, or a pharmaceutically acceptable salt, a solvate, a stereoisomer or a prodrug thereof, wherein $R_c$ is selected from the group consisting of nitro, R", —N(R")$_2$—, R"—O—, and R"—S—; wherein each R" is independently selected from the group consisting of H, C1-C6 alkyl, C3-C8 cycloalkyl, C6-C10 aryl, 4- to 7-membered heterocycloalkyl, 5- to 7-membered heteroaryl, —C1-C4 alkylene-C3-C6 cycloalkyl, —C1-C4 alkylene-C6-C10 aryl, —C1-C4 alkylene-4 to 7-membered heterocycloalkyl, and —C1-C4 alkylene-5 to 7-membered heteroaryl.

* * * * *